United States Patent
Cee et al.

(10) Patent No.: US 8,022,221 B2
(45) Date of Patent: *Sep. 20, 2011

(54) AURORA KINASE MODULATORS AND METHOD OF USE

(75) Inventors: Victor J. Cee, Thousand Oaks, CA (US); Holly L. Deak, Brookline, MA (US); Bingfan Du, Cambridge, MA (US); Stephanie D. Geuns-Meyer, Medford, MA (US); Brian L. Hodous, Cambridge, MA (US); Hanh Nho Nguyen, Arlington, MA (US); Philip R. Olivieri, Medford, MA (US); Vinod F. Patel, Acton, MA (US); Karina Romero, Cambridge, MA (US); Laurie Schenkel, Boston, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/378,426

(22) Filed: Feb. 12, 2009

(65) Prior Publication Data

US 2009/0163501 A1 Jun. 25, 2009

Related U.S. Application Data

(63) Continuation of application No. 11/655,642, filed on Jan. 18, 2007, now Pat. No. 7,560,551.

(60) Provisional application No. 60/761,675, filed on Jan. 23, 2006.

(51) Int. Cl.
| | |
|---|---|
| C07D 401/14 | (2006.01) |
| C07D 403/14 | (2006.01) |
| A61K 31/53 | (2006.01) |
| A61K 31/4427 | (2006.01) |
| A61K 31/506 | (2006.01) |
| A61P 19/02 | (2006.01) |
| A61P 35/00 | (2006.01) |

(52) U.S. Cl. ............... 546/268.1; 546/288; 514/345; 514/341; 514/242; 514/272; 514/274; 514/241; 514/245; 514/252.01; 514/252.02; 514/252.1; 514/256; 514/269; 514/275; 514/277; 514/336; 514/340; 514/348; 544/182; 544/320; 544/322; 544/408; 544/180; 544/209; 544/219; 544/238; 544/239; 544/240; 544/295; 544/297; 544/310; 544/317; 544/324; 544/328; 544/331; 544/405

(58) Field of Classification Search ............... 546/268.1, 546/288; 514/345, 341; 544/180, 209, 219, 544/238, 239, 240, 295, 297, 310, 317, 320, 544/324, 328, 331, 405, 408

See application file for complete search history.

(56) References Cited

U.S. PATENT DOCUMENTS 6,919,338 B2  7/2005  Mortlock

FOREIGN PATENT DOCUMENTS

| EP | 1702919 A1 | 9/2006 |
|---|---|---|
| WO | 9412505 A1 | 6/1994 |
| WO | 0146196 A1 | 6/2001 |
| WO | 03055491 A1 | 7/2003 |
| WO | 03082289 A1 | 10/2003 |
| WO | 04000833 A1 | 12/2003 |
| WO | 2004016612 A1 | 2/2004 |
| WO | 2004037814 A1 | 5/2004 |
| WO | 2004039774 A2 | 5/2004 |
| WO | 2005113494 A2 | 12/2005 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*

(Continued)

Primary Examiner — Venkataraman Balasubramanian
(74) Attorney, Agent, or Firm — G. Prabhakar Reddy

(57) ABSTRACT

The present invention relates to chemical compounds having a general formula I

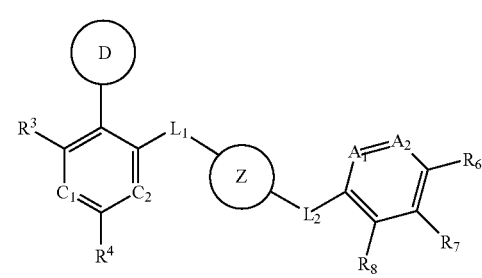

wherein $A^1$, $A^2$, $C^1$, $C^2$, D, $L^1$, $L^2$, Z and $R^3$, $R^4$, $R^6$, $R^7$ and $R^8$ are defined herein, which are capable of modulating Aurora kinase protein activity, thereby influencing various disease states and conditions related to the activities of Aurora kinase proteins. For example, the compounds are capable of influencing the process of cell cycle and cell proliferation to treat cancer and cancer-related diseases. The invention also includes pharmaceutical compositions, processes of preparing compounds of the invention, synthetic intermediates and methods of treatment of conditions related to the activity of Aurora kinase.

28 Claims, No Drawings

OTHER PUBLICATIONS

Powell et al., British Journal of Dermatology, 141 802-810, 1999.*
Golub et al., Science, 286, 531-537, 1999.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Chun, et al., Syn. Comm. 34(7)1301-1308 (2004).
Church, et al., J. Org. Chem., 60:3750-3758 (1995).
Diaz, Org. Lett., 6:43 (2004).
Elworthy, et al., J. Med. Chem., 40(17):2674-2687 (1997).
Garnier, et al., J. Org. Chem., 69:7809 (2004).
Giet, et al., J. Cell. Sci., 112:3591-3601 (1999).
Miyoshi, et al., Int. J. Cancer, 92:370-373 (2001).
Paul, D.B., Aust. J. Chem., 27:1331 (1974).
Sakamoto, Chem. Pharm. Bull., 34:2719-2724 (1986).
Samaritoni, J.G., Org. Prep. Proced. Int. 20:117-121 (1988).
Sircar, I., J. Het. Chem., 20:1473-1476 (1983).
Blood First Edition Paper, prepublished online Feb. 11, 2008; DOI 10.1182/blood-2007-09-113175.
Cancer Res 2006; 66: (15). Aug. 1, 2006.
Clin Cancer Res 2006;12(13) Jul. 1, 2006.
Expert Opin. Ther. Patents (2005) 15(9).
Expert Opin. Investig. Drugs (2009) 18(4).
Expert Opin. Ther. Patents (2009) 19(3).
Mol Cancer Ther 2007;6(12). Dec. 2007.
Nature Medicine vol. 10 No. 3 Mar. 2004.
Nature Reviews Cancer vol. 4 Dec. 2004 929.
Nerviano Medical Sciences Article, Jun. 18, 2010.
Scientificblogging.com, Jun. 22, 2010.

* cited by examiner

AURORA KINASE MODULATORS AND METHOD OF USE

This application is a continuation patent application, and claims the benefit, of U.S. non-provisional patent application Ser. No. 11/655,642 filed Jan. 18, 2007, now U.S. Pat. No. 7,560,551, which in turn claims the benefit of U.S. Provisional Application No. 60/761,675, filed Jan. 23, 2006, both of which are hereby incorporated herein by reference in their entireties.

FIELD OF THE INVENTION

The invention relates to the field of pharmaceutical agents and, more specifically, is directed to compounds and compositions useful for modulating Aurora kinase, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different types of cancer, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation. Various kinase proteins have been identified, which play roles in the cell cycling cascade and in protein phosphorylation in particular.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 2, Aurora 1, and Aurora 3, respectively.

The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarion cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Thus, the inhibition of Aurora kinases has been regarded as a promising approach for the development of novel anticancer agents. For example, WO 04/039774 describes aza-quinazolinones for treating cancer via inhibition of Aurora kinase, WO 04/037814 describes indazolinones for treating cancer via inhibition of Aurora-2 kinase, WO 04/016612 describes 2, 6, 9-substituted purine derivatives for treating cancer via inhibition of Aurora kinase, WO 04/000833 describes tri- and tetra-substituted pyrimidine compounds useful for treating Aurora-meiated diseases, WO 04/092607 describes crystals useful for screening, designing and evaluating compounds as agonists or antagonists of Aurora kinase and U.S. Pat. No. 6,919,338 and WO 03/055491 each describe substituted quinazoline derivatives as inhibitors of Aurora-2 kinase.

BRIEF DESCRIPTION OF THE INVENTION

The present invention provides a new class of compounds useful for modulating one or more of the Aurora kinase enzymes and for treating Aurora kinase-mediated conditions and/or diseases, including cancer. In one embodiment of the invention, the compounds, including pharmaceutically acceptable salts thereof, are generally defined by Formula I

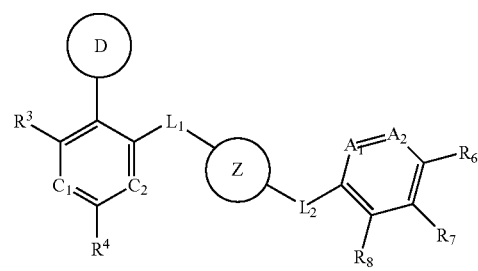

I wherein $A^1$, $A^2$, $C^1$, $C^2$, D, $L^1$, $L^2$, Z and $R^{3-8}$ are defined herein.

In another embodiment, the invention provides compounds of Formulas II and III, which are similar in structure to Formula I above.

The invention also provides processes for making compounds of Formulas I-III, as well as intermediates useful in such processes.

The compounds provided by the invention have kinase modulatory activity and, in particular, inhibitory activity, including, without limitation, Aurora kinase inhibitory activity.

To this end, the invention further provides the use of these compounds, as well as their pharmaceutically acceptable salts, in the preparation and manufacture of a medicament for therapeutic, prophylactic, acute or chronic treatment of cancer. Thus, these compounds are useful in the manufacture of anti-cancer medicaments. More particularly, these compounds are useful in the manufacture of a medicament to attenuate or prevent disorders through inhibition of Aurora kinase activity. For example, in one embodiment, the invention provides a pharmaceutical composition (also referred to herein as a medicament) comprising a therapeutically-effective amount of a compound of Formula I, II or III in association with at least one pharmaceutically-acceptable carrier, adjuvant or diluent.

DETAILED DESCRIPTION OF THE INVENTION

In one embodiment of the invention, compounds useful for treating Aurora kinase and related disorders, including cancer and inflammation, are defined by Formula I:

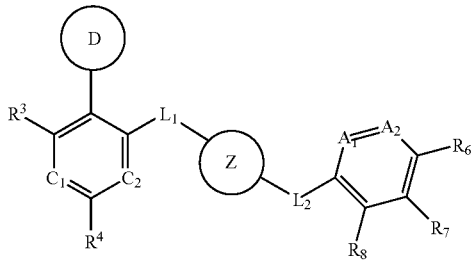

I or stereoisomer, tautomer, solvate, pharmaceutically acceptable salt, derivative or prodrug thereof, wherein each of $A^1$ and $A^2$, independently, is N or $CR^9$, provided that at least one of $A^1$ and $A^2$ is N;

$C^1$ is N or $CR^{10}$;
$C^2$ is N or CH;
D is

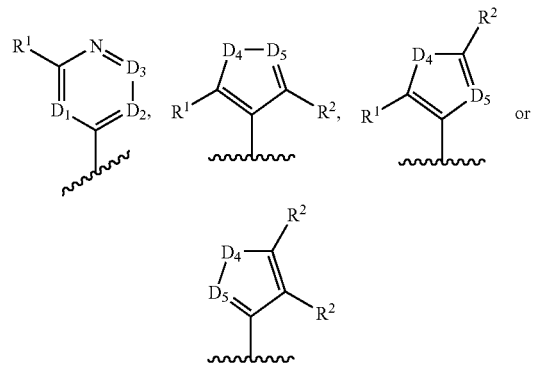

wherein $D^1$ is N or $CR^{11}$;
$D^2$ is N or $CR^{12}$;
$D^3$ is N or $CR^2$;
$D^4$ is $NR^{1a}$, O, S or $CR^{12}$;
$D^5$ is N or $CR^2$;
$R^1$ is H, $OR^{14}$, $SR^{14}$, $OR^{15}$, $SR^{15}$, $NR^{14}R^{15}$, $NR^{15}R^{15}$ $(CHR^{15})_nR^{14}$, $(CHR^{15})_nR^{15}$ or $R^{15}$;
$R^{1a}$ is H, CN or $C_{1-10}$alkyl;
alternatively $R^1$ taken together with either of $R^{11}$ and $R^{1a}$ and the carbon or nitrogen atoms to which they are attached form a partially or fully unsaturated 5- or 6-membered ring of carbon atoms optionally including 1-3 heteroatoms selected from O, N and S, and the ring optionally substituted independently with 1-3 substituents of oxo, $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$; and $R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

$L^1$ is $NR^3$, O, S, C(O), S(O), $SO_2$ or $CR^3R^3$;
$L^2$ is $NR^3$, O, S, C(O), S(O), $SO_2$ or $CR^3R^3$;

Z is a fully unsaturated 5-6 membered first monocyclic ring, said first ring (1) formed of carbon atoms optionally including 1-3 heteroatoms selected from O, N, or S, (2) optionally fused to a partially or fully saturated or fully unsaturated 5-6 membered second monocyclic ring formed of carbon atoms optionally including 1-3 heteroatoms selected from O, N, or S, and (3) wherein 0, 1, 2 or 3 atoms of each of said first and second ring is optionally substituted independently with 1-3 substituents of $R^5$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{14}R^{15}$, NR $C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}NR^{15}C(O)C(O)NR^{15}R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

each of $R^6$, $R^7$ and $R^8$, independently, is $R^{13}$, $R^{14}$ or $R^{15}$;

alternatively, either of $R^6$ or $R^8$, independently, taken together with $R^7$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R$ $NR^{15}C(O)R^{15}$, $NR^{15}C(O)$ $NR^{14}R^{15}NR^{15}C(O)NR^{15}$, $R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)$

R$^{15}$, C(O)C(O)R$^{15}$, NR$^{15}$C(O)NR$^{14}$R$^{15}$, NR$^{15}$C(O)NR$^{15}$R$^{15}$, NR$^{15}$C(O)C(O)R$^{15}$, NR$^{15}$(COOR$^{14}$), NR$^{15}$(COOR$^{15}$), NR$^{15}$C(O)C(O)NR$^{14}$R$^{15}$, NR$^{15}$C(O)C(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{15}$S(O)$_2$R$^{14}$, NR$^{15}$S(O)$_2$R$^{15}$, NR$^{15}$S(O)$_2$NR$^{14}$R$^{15}$ or NR$^{15}$S(O)$_2$NR$^{15}$R$^{15}$;

R$^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of R$^{15}$;

R$^{15}$ is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3 or 4;

provided that (1) no more than one of D$^1$ and D$^2$ is N, and (2) each of L$^1$ and L$^2$ is, independently, bound to the first ring of Z.

Accordingly, the above embodiment of the present invention included pyridine and pyrimidine D ring compounds while not encompassing triazine D-ring compounds (wherein both D$^1$ and D$^2$ are N, respectively). Triazine D-ring compounds (Formula III) are described in another embodiment herein below. In addition, the above embodiment includes compounds wherein both of L$^1$ and L$^2$ linkers are attached to the first Z ring, and not one of L$^1$ and L$^2$ substituted on the first ring while the other of L$^1$ and L$^2$ is substituted on a second ring of Z (where Z is a fused ring system for example).

In another embodiment, Formula I includes compounds wherein each of A$^1$ and A$^2$, independently, is N or CR$^9$, provided that at least one of A$^1$ and A$^2$ is N, in conjunction with any of the above or below embodiments.

In another embodiment, Formula I includes compounds wherein A$^1$ is N, in conjunction with any of the above or below embodiments.

In another embodiment, Formula I includes compounds wherein A$^1$ is CR$^9$, in conjunction with any of the above or below embodiments.

In another embodiment, Formula I includes compounds wherein A$^2$ is N, in conjunction with any of the above or below embodiments.

In another embodiment, Formula I includes compounds wherein each of A$^1$ and A$^2$, independently, is N, in conjunction with any of the above or below embodiments.

In another embodiment, Formula I includes compounds wherein A$^2$ is CR$^9$, in conjunction with any of the above or below embodiments.

In another embodiment, Formula I includes compounds wherein D is

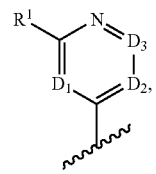

in conjunction with any of the above or below embodiments.

In another embodiment, Formula I includes compounds wherein D is

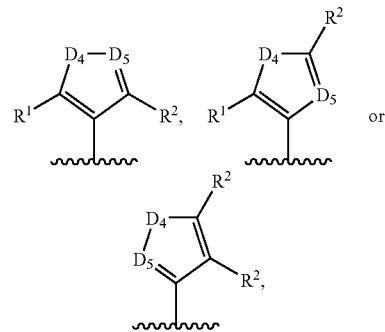

in conjunction with any of the above or below embodiments.

In another embodiment, Formula I includes compounds wherein D1 is N and D$^2$ is CR$^{12}$, in conjunction with any of the above or below embodiments.

In another embodiment, Formula I includes compounds wherein D$^2$ is N and D$^1$ is CR$^{11}$, in conjunction with any of the above or below embodiments.

In another embodiment, Formula I includes compounds wherein D$^1$ is CR$^{11}$ and D$^2$ is CR$^{12}$, in conjunction with any of the above or below embodiments.

In another embodiment, Formula I includes compounds wherein D is

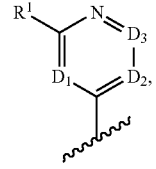

wherein D$^1$ is N, D$^2$ is CR$^{12}$ and D$^3$ is CH, in conjunction with any of the above or below embodiments.

In another embodiment, Formula I includes compounds wherein D is

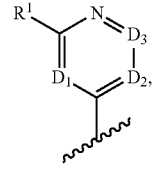

wherein D$^1$ is CR$^{11}$, D$^2$ is N and D$^3$ is CH, in conjunction with any of the above or below embodiments.

In another embodiment, Formula I includes compounds wherein $C^1$ is N or $CR^{10}$, in conjunction with any of the above or below embodiments.

In another embodiment, Formula I includes compounds wherein $C^1$ is $CR^{10}$, in conjunction with any of the above or below embodiments.

In another embodiment, Formula I includes compounds wherein $C^2$ is N or CH, in conjunction with any of the above or below embodiments.

In another embodiment, Formula I includes compounds wherein $C^2$ is N, in conjunction with any of the above or below embodiments.

In another embodiment, Formula I includes compounds wherein $C^1$ is $CR^{10}$, $C^2$ is N and $R^2$ is H, halo, $NO_2$, CN, $C_{1-10}$alkyl or $C_{1-10}$alkoxyl, in conjunction with any of the above or below embodiments.

In another embodiment, Formula I includes compounds wherein $C^1$ is $CR^{10}$ and $R^{10}$ is H, halo, haloalkyl, haloalkoxyl, CN, OH, SH, $NO_2$, $NH_2$, acetyl, $C_{1-10}$-alkyl or $C_{1-10}$-alkoxyl, $C^2$ is N and $R^2$ is H, halo, $NO_2$, CN, $C_{1-10}$alkyl or $C_{1-10}$alkoxyl, in conjunction with any of the above or below embodiments.

In another embodiment, Formula I includes compounds wherein $L^1$ is $NR^3$, O, S, C(O), S(O), $SO_2$ or $CR^3R^3$, in conjunction with any of the above or below embodiments.

In another embodiment, Formula I includes compounds wherein $L^1$ is O or S, in conjunction with any of the above or below embodiments.

In another embodiment, Formula I includes compounds wherein $L^1$ is $NR^3$, in conjunction with any of the above or below embodiments.

In another embodiment, Formula I includes compounds wherein $L^1$ is $NR^{15}$, in conjunction with any of the above or below embodiments.

In another embodiment, Formula I includes compounds wherein $L^1$ is NH, in conjunction with any of the above or below embodiments.

In another embodiment, Formula I includes compounds wherein $L^1$ is C(O), S(O) or $SO_2$, in conjunction with any of the above or below embodiments.

In another embodiment, Formula I includes compounds wherein $L^1$ is $CR^3R^3$, in conjunction with any of the above or below embodiments.

In another embodiment, Formula I includes compounds wherein $L^2$ is $NR^3$, O, S, C(O), S(O), $SO_2$ or $CR^3R^3$, in conjunction with any of the above or below embodiments.

In another embodiment, Formula I includes compounds wherein $L^2$ is O or S, in conjunction with any of the above or below embodiments.

In another embodiment, Formula I includes compounds wherein $L^2$ is $NR^3$, in conjunction with any of the above or below embodiments.

In another embodiment, Formula I includes compounds wherein $L^2$ is $NR^{15}$, in conjunction with any of the above or below embodiments.

In another embodiment, Formula I includes compounds wherein $L^2$ is NH, in conjunction with any of the above or below embodiments.

In another embodiment, Formula I includes compounds wherein $L^2$ is C(O), S(O) or $SO_2$, in conjunction with any of the above or below embodiments.

In another embodiment, Formula I includes compounds wherein $L^2$ is $CR^3R^3$, in conjunction with any of the above or below embodiments.

In another embodiment, Formula I includes compounds wherein $L^1$ is $NR^{13}$, O, $CHR^{13}$, S, C(O), S(O) or $SO_2$ and $R^2$ is H, halo, $NO_2$, CN, $C_{1-10}$alkyl or $C_{1-10}$alkoxyl, in conjunction with any of the above or below embodiments.

In another embodiment, Formula I includes compounds wherein the first monocyclic ring of Z is phenyl, pyridyl, pyrimidinyl, pyridazinyl, pyazinyl, triazinyl, thiophenyl, furyl, pyrrolyl, pyrazolyl, imidazolyl, triazolyl, tetrazolyl, thiazolyl, thiadiazolyl, oxazolyl, oxadiazolyl, isoxazolyl, or isothiazolyl, in conjunction with any of the above or below embodiments.

In another embodiment, Formula I includes compounds wherein the first monocyclic ring of Z is a fully unsaturated 6-membered ring, and $L^1$ and $L^2$ are para oriented to one another on the first monocyclic ring of Z, in conjunction with any of the above or below embodiments.

In another embodiment, Formula I includes compounds wherein $L^2$ is $NR^{15}$, O or S; each of $R^3$, $R^4$ and $R^9$, independently, is H; $C^1$ is $CR^{10}$; and Z is phenyl, pyridyl, pyrimidinyl, pyridazinyl, pyrazinyl, triazinyl, thiophenyl, furyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl or isothiazolyl, wherein $L^1$ and $L^2$, together, are para-oriented to one another on ring Z, wherein ring Z is optionally substituted with 1-5 substitutions of $R^{15}$, in conjunction with any of the above or below embodiments.

In another embodiment, Formula I includes compounds wherein each of $L^1$ and $L^2$, independently, is $CHR^{15}$, $NR^{15}$, O, S, or C(O), $R^2$ is H, halo, $NO_2$, CN, $C_{1-10}$alkyl or $C_{1-10}$alkoxyl,
each of $R^3$, $R^4$ and $R^9$, independently, is H, and $C^1$ is $CR^{10}$, in conjunction with any of the above or below embodiments.

In another embodiment, Formula I includes compounds wherein $R^1$ is H, $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$, in conjunction with any of the above or below embodiments.

In another embodiment, Formula I includes compounds wherein $R^1$ is H, in conjunction with any of the above or below embodiments.

In another embodiment, Formula I includes compounds wherein $R^1$ is $OR^{14}$, $SR^{14}$, $OR^{15}$ or $SR^{15}$, in conjunction with any of the above or below embodiments.

In another embodiment, Formula I includes compounds wherein $R^1$ is $NR^{14}R^{15}$ or $NR^{15}R^{15}$, in conjunction with any of the above or below embodiments.

In another embodiment, Formula I includes compounds wherein $R^1$ is $R^5$, in conjunction with any of the above or below embodiments.

In another embodiment, Formula I includes compounds wherein $R^1$ is $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- or heteroaryl-alkyl-amino-, in conjunction with any of the above or below embodiments.

In another embodiment, Formula I includes compounds wherein $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of $R^5$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$, in conjunction with any of the above or below embodiments.

In another embodiment, Formula I includes compounds wherein $R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}$, $R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C$ (O)R$^{15}$, NR$^{15}$(COOR$^{15}$), OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{15}$S(O)$_2$ NR$^{14}$R$^{15}$, NR$^{15}$S(O)$_2$NR$^{15}$R$^{15}$, NR$^{15}$S(O)$_2$R$^{14}$, NR$^{15}$S(O)$_2$R$^{15}$ or R$^{15}$, in conjunction with any of the above or below embodiments.

In another embodiment, Formula I includes compounds wherein R$^2$ is H, in conjunction with any of the above or below embodiments.

In another embodiment, Formula I includes compounds wherein R$^2$ is OR$^{14}$, SR$^{14}$, OR$^{15}$, SR$^{15}$, C(O)R$^{14}$ or C(O)R$^{15}$, in conjunction with any of the above or below embodiments.

In another embodiment, Formula I includes compounds wherein R$^2$ is NR$^{14}$R$^{15}$ or NR$^{15}$R$^{15}$, in conjunction with any of the above or below embodiments.

In another embodiment, Formula I includes compounds wherein R$^2$ is C$_{1-10}$alkyl, C$_{1-10}$alkoxyl, C$_{1-10}$alkyl-amino-, aryl-amino-, aryl, heteroaryl, heterocyclyl, heteroaryl-amino-, aryl-alkyl-amino-, heterocyclyl-alkyl-amino- or heteroaryl-alkyl-amino-, in conjunction with any of the above or below embodiments.

In another embodiment, Formula I includes compounds wherein each of R$^3$ and R$^4$, independently, is SR$^{14}$, OR$^{14}$SR$^{15}$, OR$^{15}$, NR$^{14}$R$^{15}$, NR$^{15}$R$^{15}$, C(O)R$^{14}$, C(O)R$^{15}$, COOR$^{15}$, OC(O)R$^{15}$, C(O)C(O)R$^{15}$, C(O)NR$^{14}$R$^{15}$, C(O)NR$^{15}$R$^{15}$, NR$^{15}$C(O)R$^{14}$, NR$^{15}$C(O)R$^{15}$, NR$^{15}$C(O)NR$^{14}$R$^{15}$, NR$^{15}$C(O)NR$^{15}$R$^{15}$, NR$^{15}$C(O)C(O)R$^{15}$, NR$^{15}$(COOR$^{15}$), OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{15}$S(O)$_2$NR$^{15}$R$^{15}$, NR$^{15}$S(O)$_2$R$^{14}$, NR$^{15}$S(O)$_2$R$^{15}$, NR$^{15}$S(O)$_2$NR$^{14}$R$^{15}$, NR$^{15}$C(O)C(O)NR$^{14}$R$^{15}$, NR$^{15}$C(O)C(O)NR$^{15}$R$^{15}$ or R$^{15}$, in conjunction with any of the above or below embodiments.

In another embodiment, Formula I includes compounds wherein each of R$^3$ and R$^4$, independently, is H, in conjunction with any of the above or below embodiments.

In another embodiment, Formula I includes compounds wherein each of R$^3$ and R$^4$, independently, is R$^{15}$, in conjunction with any of the above or below embodiments.

In another embodiment, Formula I includes compounds wherein each of R$^3$ and R$^4$, independently, is C$_{1-10}$alkyl, C$_{1-10}$alkoxyl, C$_{1-10}$alkyl-amino-, aryl-amino-, aryl, heteroaryl, heterocyclyl, heteroaryl-amino-, aryl-alkyl-amino-, heterocyclyl-alkyl-amino- or heteroaryl-alkyl-amino-, in conjunction with any of the above or below embodiments.

In another embodiment, Formula I includes compounds wherein either of R$^3$ or R$^4$, independently, taken together with R$^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of R$^{13}$, R$^{14}$ or R$^{15}$, in conjunction with any of the above or below embodiments.

In another embodiment, Formula I includes compounds wherein each R$^5$, independently, is SR$^{14}$, OR$^{14}$, SR$^{15}$, OR$^{15}$, NR$^{14}$R$^{15}$, NR$^{15}$R$^{15}$, C(O)R$^{15}$, C(O)R$^{15}$, COOR$^{15}$, OC(O)R$^{15}$, C(O)C(O)R$^{15}$, C(O)NR$^{14}$R$^{15}$, C(O)NR$^{15}$R$^{15}$, NR$^{15}$C(O)R$^{14}$, NR$^{15}$C(O)R$^{15}$, NR$^{15c}$(O)NR$^{14}$R$^{15}$, NR$^{15}$C(O)NR$^{15}$R$^{15}$, NR$^{15}$C(O)C(O)R$^{15}$, NR$^{15}$(COOR$^{15}$), OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{15}$S(O)$_2$NR$^{15}$R$^{15}$, NR$^{15}$S(O)$_2$R$^{14}$, NR$^{15}$S(O)$_2$R$^{15}$, NR$^{15}$S(O)$_2$NR$^{14}$R$^{15}$, NR$^{15}$C(O)C(O)NR$^{14}$R$^{15}$, NR$^{15}$C(O)C(O)NR$^{15}$R$^{15}$ or R$^{15}$, in conjunction with any of the above or below embodiments.

In another embodiment, Formula I includes compounds wherein each R$^5$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, in conjunction with any of the above or below embodiments.

In another embodiment, Formula I includes compounds wherein each R$^5$, independently, is H, halo, haloalkyl, CN, OH, SH, NO$_2$, NH$_2$, acetyl, C$_{1-10}$-alkyl, C$_{3-10}$-cycloalkyl, C$_{1-10}$-alkylamino-, C$_{1-10}$-dialkylamino-, C$_{1-10}$-alkoxyl or C$_{1-10}$-thioalkoxyl, in conjunction with any of the above or below embodiments.

In another embodiment, Formula I includes compounds wherein each R$^5$, independently, is H, Cl, Br, F, I, CF$_3$, CF$_2$CF$_3$, NO$_2$, CN, acetyl, oxo, haloalkyl, haloalkoxyl, CN, OH, SH, NO$_2$, NH$_2$, acetyl, C$_{1-10}$-alkylamino-, benzyl or phenyl, in conjunction with any of the above or below embodiments.

In another embodiment, Formula I includes compounds wherein R$^6$ is R$^{13}$, in conjunction with any of the above or below embodiments.

In another embodiment, Formula I includes compounds wherein R$^6$ is R$^{14}$, in conjunction with any of the above or below embodiments.

In another embodiment, Formula I includes compounds wherein R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of R$^{15}$, in conjunction with any of the above or below embodiments.

In another embodiment, Formula I includes compounds wherein R$^6$ is R$^{15}$, in conjunction with any of the above or below embodiments.

In another embodiment, Formula I includes compounds wherein R$^7$ is R$^3$, in conjunction with any of the above or below embodiments.

In another embodiment, Formula I includes compounds wherein R$^7$ is R$^{14}$, in conjunction with any of the above or below embodiments.

In another embodiment, Formula I includes compounds wherein R$^7$ is R$^{15}$, in conjunction with any of the above or below embodiments.

In another embodiment, Formula I includes compounds wherein R$^7$ is H, halo, haloalkyl, haloalkoxyl, CN, OH, NO$_2$, NH$_2$, SH, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, in conjunction with any of the above or below embodiments.

In another embodiment, Formula I includes compounds wherein R$^7$ is H, halo, haloalkyl, C$_{1-10}$-alkyl, C$_{1-10}$-alkylamino-, C$_{1-10}$-dialkylamino- or C$_{1-10}$-alkoxyl, in conjunction with any of the above or below embodiments.

In another embodiment, Formula I includes compounds wherein R$^8$ is R$^3$, in conjunction with any of the above or below embodiments.

In another embodiment, Formula I includes compounds wherein R$^8$ is R$^{14}$, in conjunction with any of the above or below embodiments.

In another embodiment, Formula I includes compounds wherein $R^8$ is $R^{15}$, in conjunction with any of the above or below embodiments.

In another embodiment, Formula I includes compounds wherein $R^8$ is H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, in conjunction with any of the above or below embodiments.

In another embodiment, Formula I includes compounds wherein $R^8$ is H, halo, haloalkyl, $C_{1-10}$-alkyl, $C_{1-10}$-alkylamino-, $C_{1-10}$-dialkylamino- or $C_{1-10}$-alkoxyl, in conjunction with any of the above or below embodiments.

In another embodiment, Formula I includes compounds wherein either of $R^1$ or $R^8$, independently, taken together with $R^7$ and the carbon atoms to which they are attached form a fully saturated or partially or fully unsaturated 5- or 6-membered ring of carbon atoms optionally including 1-4 heteroatoms selected from O, N, or S, and the ring optionally substituted independently with 1-3 substituents of $R^{13}$, $R^{14}$ or $R^{15}$, in conjunction with any of the above or below embodiments.

In another embodiment, Formula I includes compounds wherein $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$, in conjunction with any of the above or below embodiments.

In another embodiment, Formula I includes compounds wherein $R^7$ and $R^8$ taken together with the carbon atoms to which they are attached form a phenyl, pyridine or pyrimidine ring, the ring optionally substituted independently with 1-4 substituents of $R^{13}$, $R^{14}$ or $R^{15}$, in conjunction with any of the above or below embodiments.

In a further embodiment, the immediately preceeding embodiment includes compounds of Formula I wherein each of $A^1$ and $A^2$, independently, is N and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of $R^{15}$.

In another embodiment, Formula I includes compounds wherein each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)N^{15}R^{15}$, $NR^{15}C(O)R^{14}$, $NR^{15}C(O)R^{15}$, $NR^{15}C(O)NR^{14}R^{15}NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$, in conjunction with any of the above or below embodiments.

In another embodiment, Formula I includes compounds wherein each of $R^9$, $R^{10}$, $R^{11}$ and $R^{12}$, independently, is H, halo, haloalkyl, CN, OH, SH, $NO_2$, $NH_2$, acetyl, $C_{1-10}$-alkyl, $C_{3-10}$-cycloalkyl, $C_{1-10}$-alkylamino-, $C_{1-10}$-dialkylamino-, $C_{1-10}$-alkoxyl or $C_{1-10}$-thioalkoxyl, in conjunction with any of the above or below embodiments.

In another embodiment, Formula I includes compounds wherein each of $R^9$, $R^{10}$, $R^{11}$ and $R^{12}$, independently, is H, in conjunction with any of the above or below embodiments.

In another embodiment, Formula I includes compounds wherein as $R^{14}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally independently substituted with 1-3 substituents of $R^{15}$, in conjunction with any of the above or below embodiments.

In yet another embodiment, the invention provides compounds generally defined by Formula II:

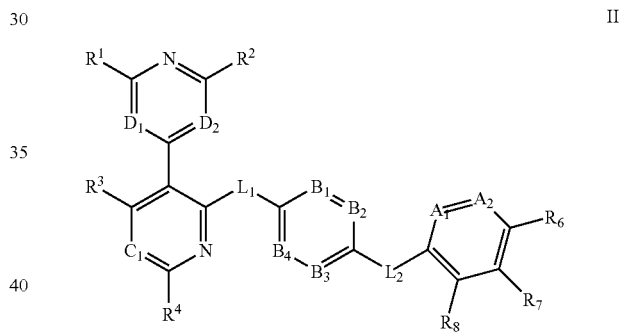

II or stereoisomer, tautomer, solvate, pharmaceutically acceptable salt, derivative or prodrug thereof, wherein each of $A^1$ and $A^2$, independently, is N or $CR^9$, provided that at least one of $A^1$ and $A^2$ is N;

each of $B^1$, $B^2$, $B^3$ and $B^4$, independently, is N or $CR^5$, provided that no more than two of $B^1$, $B^2$, $B^3$ and $B^4$ is N;

$C^1$ is N or $CR^{10}$;

$D^1$ is N or $CR^{11}$;

$D^2$ is N or $CR^{12}$;

$L^1$ is $NR^3$, O, S or $CR^3R^3$;

$L^2$ is $NR^3$, O, S or $CR^3R^3$;

$R^1$ is $OR^{14}SR^{14}$, $OR^{15}SR^5$, $NR^{14}R^{15}$, $NR^{15}R^{15}$, $(CHR^{15})_n R^{14}$, $(CHR^{15})_n R^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of oxo, $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$;

$R^2$ is $SR^{14}$, $OR^{14}SR^{15}$, $OR^{15}$, $NR^{14}R^{15}$, $NR^{15}R^{15}$, $C(O)R^{15}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)$ $R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}C(O)C(O)R^{15}$, $C(O)NR^{14}R^{15}$, $C(O)NR^{15}R^{15}$, $NR^{15}C(O)R^{14}$, $NR^{15}C(O)^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^6$ is $R^{13}$ or $R^{14}$;

each of $R^7$ and $R^8$, independently, is $R^{13}$, $R^{14}$ or $R^{15}$;

alternatively, either of $R^7$ and $R^8$ taken together with the carbon atoms to which they are attached form a fully saturated or partially or fully unsaturated 5- or 6-membered ring of carbon atoms optionally including 1-4 heteroatoms selected from O, N, or S, and the ring optionally substituted independently with 1-3 substituents of $R^{13}$, $R^{14}$ or $R^{15}$;

each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}C(O)R^{15}$, $OC(O)R^{14}C(O)R^{15}COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of $R^{15}$;

$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3 or 4;

provided that no more than one of $D^1$ and $D^2$ is N.

In another embodiment, Formula II includes compounds wherein each of $A^1$ and $A^2$, independently, is N;

each of $B^1$, $B^2$, $B^3$ and $B^4$, independently, is N or $CR^5$, provided that no more than one of $B^1$, $B^2$, $B^3$ and $B^4$ is N;

$C^1$ is $CR^{10}$;

$D^1$ is N or $CR^{11}$;

$D^2$ is N or $CR^{12}$;

$L^1$ is NH, O or S;

$L^2$ is NH, O or S;

$R^1$ is H, halo, haloalkyl, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl, $NR^{14}$, $NHR^{15}$, $OR^{15}$, $SR^{15}$ or $CH_2R^{15}$;

$R^2$ is H, halo, $NO_2$, CN, $C_{1-10}$alkyl or $C_{1-10}$alkoxyl;

each of $R^3$ and $R^4$, independently, is $SR^{15}$, $OR^{15}$, $NR^{14}R^{15}$, $NR^{15}R^{15}$, $C(O)R^{14}$, $C(O)R^{15}$ or $R^{15}$;

each $R^5$ is, independently, is $SR^{15}$, $OR^{15}$, $NR^{15}R^{15}$, $C(O)R^{15}$, $C(O)NR^{15}R^{15}$, $NR^{15}C(O)R^{15}$, $NR^{15}C(O)NR^{15}R^{15}$, $NR^{15}(COOR^{15})$, $S(O)_2R^{15}$, $S(O)_2NR^{15}R^{15}$, $NR^{15}S(O)_2NR^{15}R^{15}$, $NR^{15}S(O)_2R^{15}$, $NR^{15}C(O)C(O)NR^{14}R^{15}$ or $R^{15}$;

$R^6$ is $R^{14}$;

each of $R^7$ and $R^8$, independently, is $R^{15}$;

alternatively, either of $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$ or $R^{15}$; and each of $R^9$, $R^{10}$, $R^{11}$ and $R^{12}$, independently, is $R^{15}$.

In another embodiment, Formula II includes compounds wherein $R^1$ is $NR^{14}R^{15}$, $NR^{15}R^{15}$, $(CHR^{15})_nR^{14}$, $(CHR^{15})_nR^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of $R^{15}$;

$R^2$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

each of $R^3$ and $R^4$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

each $R^5$ is, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylaamine, dipropylamine or diisopropylamine;

$R^6$ is $R^{13}$ or $R^{14}$;

each of $R^7$ and $R^8$, independently, is $R^{15}$;

alternatively, either of $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$; and each of $R^9$, $R^{10}$, $R^{11}$ and $R^{12}$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine.

In another embodiment, Formula II includes compounds wherein each of $A^1$ and $A^2$, independently, is N; and
$R^7$ and $R^8$ taken together with the carbon atoms to which they are attached form a fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$, in conjunction with any of the above or below embodiments.

In another embodiment, Formula II includes compounds wherein $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of $R^{15}$, in conjunction with any of the above or below embodiments.

In another embodiment, Formula II includes compounds wherein $C_1$ is CH;
$D^1$ is N;
$D^2$ is $CR^{12}$ wherein $R^{12}$ is H, halo, $NO_2$, CN, $C_{1-10}$alkyl or $C_{1-10}$alkoxyl;
$L^1$ is NH, O or S;
$L^2$ is NH;
$R^1$ is H, halo, haloalkyl, acetyl, $C_{1-10}$-alkyl or $NHR^{15}$;
each of $R^2$, $R^3$ and $R^4$, independently, is H, halo, $C_{1-10}$alkyl or $C_{1-10}$alkoxyl;
$R^6$ is $R^{14}$; and
$R^7$ and $R^8$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$ or $R^5$, in conjunction with any of the above or below embodiments.

The embodiments for various of the elements described herein above with respect to compounds of Formula I also apply to compounds of Formula II, where appropriate, as will be appreciated by those skilled in the art.

In another embodiment, the invention provides compounds generally defined by Formula III or stereoisomer, tautomer, solvate, pharmaceutically acceptable salt, derivative or prodrug thereof, wherein
each of $A^1$ and $A^2$, independently, is N or $CR^9$, provided that at least one of $A^1$ and $A^2$ is N;
each of $B^1$, $B^2$, $B^3$ and $B^4$, independently, is N or $CR^5$, provided that no more than two of $B^1$, $B^2$, $B^3$ and $B^4$ is N;
$C^1$ is N or $CR^{10}$;
$L^1$ is O, S, C(O), S(O), $SO_2$ or $CR^3R^3$;
$L^2$ is $NR^3$, O, S or $CR^3R^3$;
$R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of $R^5$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$;
$R^2$ is $SR^{14}$, $OR^{14}$, $SR^5$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;
each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;
alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;
each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;
$R^6$ is $R^{13}$ or $R^{14}$;
each of $R^7$ and $R^8$, independently, is $R^3$, $R^{14}$ or $R^{15}$;
alternatively, either of $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^3$, $R^{14}$ or $R^{15}$;
each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;
$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}C(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{14}$, $NR^{15}S(O)_2NR^{14}R^{15}$ or $NR^{15}S(O)_2NR^{15}R^{15}$;
$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of $R^{15}$;

$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3 or 4.

The embodiments for various of the elements described herein above with respect to compounds of Formula I also apply to compounds of Formula III, where appropriate, as will be appreciated by those skilled in the art.

In yet another embodiment, Formulas I, II and III include the exemplary compounds and derivatives, prodrugs, solvates, tautomers and pharmaceutically acceptable salt forms thereof, intermediates related thereto, which are described in the Examples herein.

Definitions

The following definitions should further assist in understanding the scope of the invention described herein.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Aurora kinase(s) in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), any prodrug such as a phospshate or an ester of a compound of this invention, or any other compound which upon administration to a patient is capable of providing (directly or indirectly) a compound of this invention, or a metabolite or residue thereof, characterized by the ability to inhibit Aurora kinase.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies.

The terms "ring" and "ring system" refer to a one or more rings, typically fused together where more than one ring, comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is not fully unsaturated.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated.

The term "alkenyl", alone or in combination, embraces linear or branched radicals having at least one carbon-carbon double bond and having two or more carbon atoms. Examples of alkenyl radicals include, without limitation, ethenyl, propenyl, allyl, propenyl, butenyl and 4-methylbutenyl. The term "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine, chlorine, bromine or iodine atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "hydroxyalkyl", alone or in combination, embraces linear or branched alkyl radicals having one or more carbon atoms any one of which may be substituted with one or more hydroxyl radicals. Examples of such radicals include hydroxymethyl, hydroxyethyl, hydroxypropyl, hydroxybutyl and hydroxyhexyl.

The term "alkoxy", alone or in combination, embraces linear or branched oxy-containing radicals each having alkyl portions of alpha to beta number of carbon atoms. For example, a $C_{1-10}$ alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "partially or fully saturated" as used herein, refers to a moiety, linear, branched or cyclic in nature, having no atom-atom double or triple bonds (fully saturated) or having one or more atom-atom double or triple bonds which are arranged such that where the structural moiety is cyclic, the cycle is not fully unsaturated (non-aromatic), as appreciated by those skilled in the art.

The term "fully unsaturated" as used herein, refers to a moiety having double or triple bonds, arranged in a manner such that the structure is aromatic in nature, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have I or more substituents such as lower alkyl, hydroxyl, halo, haloalkyl, nitro, cyano, alkoxy and lower alkylamino, and the like. Phenyl substituted with —O—CH$_2$—O— forms an aryl benzodioxolyl substituent. Aryl as used herein, implies a fully unsaturated ring.

The term "heterocycles" or "heterocyclic radicals", alone or in combination, embraces saturated, partially saturated and partially unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 or more substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl].

Examples of partially saturated (or partially unsaturated) heterocyclyl radicals include dihydrothienyl, dihydropyranyl, dihydrofuryl and dihydrothiazolyl.

The term "heteroaryl" radicals, alone or in combination, embraces fully unsaturated heteroatom-containing ring radicals, where the heteroatoms may be selected from nitrogen, sulfur and oxygen. Examples of heteroaryl radicals include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The terms "heterocycle" and "heteroaryl" also embraces radicals which are fused/condensed with aryl radicals: unsaturated condensed heterocyclic or heteroaryl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially and fully saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The term "carbonyl", whether used alone or with other terms, such as "aminocarbonyl", denotes —(C=O)—.

The term "alkylthio" embraces radicals containing a linear or branched alkyl radical, of one to ten carbon atoms, attached to a divalent sulfur atom. An example of "alkylthio" is methylthio, ($CH_3S-$).

The term "aminoalkyl" and "diaminoalkyl" embraces "N-alkylamino" and "N,N-dialkylamino", respectively, where amino groups are independently substituted with one alkyl radical and with two alkyl radicals, respectively. Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "$C_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidyl-methylamino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "comprising" is meant to be open ended, including the indicated component(s) but not excluding other elements.

The terms "Formula I", "Formula II" and "Formula III" include any sub formulas.

The present invention comprises processes for the preparation of a compound of Formulae I and II.

Also included in the family of compounds of Formulas I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-III may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-III include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound of Formulas I-III. When a basic group and an acid group are present in the same molecule, a compound of Formulas I-III may also form internal salts.

General Synthetic Procedures

The compounds of the invention can be synthesized according to the following procedures of Schemes 1-8, wherein the substituents are as defined for Formulas I-III, above, except where further noted. The synthetic methods described below are merely exemplary, and the compounds of the invention may be synthesized by alternate routes as appreciated by persons of ordinary skill in the art.

The following list of abbreviations used throughout the specification represent the following:

| | |
|---|---|
| ACN, AcCN, MeCN | acetonitrile |
| BSA | bovine serum albumin |
| $Cs_2CO_3$ | cesium carbonate |
| $CHCl_3$ | chloroform |
| $CH_2Cl_2$, DCM | dichloromethane, methylene chloride |
| DIBAL | diisobutylaluminum hydride |
| DIEA,($iPr_2Net$) | diisopropylethylamine |
| DME | dimethoxyethane |
| DMF | dimethylformamide |
| DMAP | 4-dimethylaminopyridine |
| DMSO | dimethylsulfoxide |
| dppa | diphenylphosphoryl azide |
| EDC | 1-(3-dimethylaminopropyl)-3-ethylcarbodiimide hydrochloride |
| $Et_2O$ | diethyl ether |
| EtOAc | ethyl acetate |
| FBS | fetal bovine serum |

| | |
|---|---|
| g, gm | gram |
| h, hr | hour |
| HBr | hydrobromic acid |
| HCl | hydrochloric acid |
| HOBt | 1-hydroxybenzotriazole hydrate |
| $H_2$ | hydrogen |
| $H_2O_2$ | hydrogen peroxide |
| HATU | O-(7-azabenzotriazol-1-yl)-N,N,N',N'-tetramethyluroniumhexafluorophosphate |
| HPLC | high pressure liquid chromatography |
| IPA, IpOH | isopropyl alcohol |
| $K_2CO_3$ | potassium carbonate |
| MCPBA | meta-chloroperbenzoic acid |
| $MgSO_4$ | magnesium sulfate |
| MeOH | methanol |
| $N_2$ | nitrogen |
| $NaHCO_3$ | sodium bicarbonate |
| NaOH | sodium hydroxide |
| NaH | sodium hydride |
| $Na_2SO_4$ | sodium sulfate |
| $NH_4Cl$ | ammonium chloride |
| $NH_4OH$ | ammonium chloride |
| NMP | N-methylpyrrolidinone |
| $P(t-bu)_3$ | tri(tert-butyl)phosphine |
| PBS | phospate buffered saline |
| Pd/C | palladium on carbon |
| $Pd(PPh_3)_4$ | palladium(0)triphenylphosphine tetrakis |
| $Pd(PhCN)_2Cl_2$ | palladium di-cyanophenyl dichloride |
| $Pd(OAc)_2$ | palladium acetate |
| $Pd_2(dba)_3$ | bis(dibenzylideneacetone) palladium |
| PyBop | benzotriazol-1-yl-oxy-tripyrrolidino-phosphonium hexafluorophosphate |
| RT, rt | room temperature |
| RBF | round bottom flask |
| rac-BINAP | 2,2'-Bis(diphenylphosphine)-1,1'-binaphthyl |
| TBTU | O-benzotriazol-1-yl-N,N,N',N'-tetramethyluronium tetrafluoroborate |
| TEA, $Et_3N$ | triethylamine |
| TFA | trifluoroacetic acid |
| THF | tetrahydrofuran |

Scheme 1

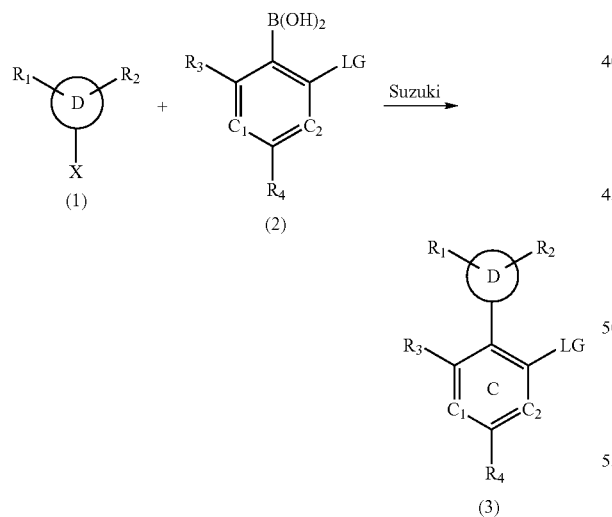

The biaryl ring system (3), including substituted or unsubstituted pyridyl-pyridines (where ring C and D are both pyridines), pyridyl-pyrimidines (where one of rings C and D is a pyridine and the other is a pyrimidine), pyridyl triazines (where D is a triazine), pyrimidyl-pyrimidines and pyrimidyl-triazines (where ring D is a triazine) and 5-membered D ring-C rings, generally referred to herein as the C-D ring portion of the compounds of Formulas I-III, can be prepared according to the method generally described in Scheme 1. As shown, Suzuki coupling methodology utilizing an aryl halide (1) where X is a halide such as iodide, bromide or chloride, and an aryl borinate (2) in the presence of palladium, such as $Pd(PPh_3)_4$, and a weak base, such as a $Na_2CO_3$, $K_2CO_3$ or $NaHCO_3$ in a polar solvent such as DME can be used to synthesize compound (3). LG is a known leaving group, such as F, Br, I or Cl. Similarly, other known aryl coupling methods, such as use of stannanes, zincates and copper coupling techniques are also suitable to prepare compound (3).

In a similar manner, phenyl-pyridines, phenyl-pyrimidines and phenyl-triazine C-D rings of the compounds of Formulas I-III, can also be prepared according to the Suzuki or other metallation chemistry methods, wherein the aryl borinate (2) is a desirably substituted phenyl borinate, as described in Scheme 1.

Alternatively, amino-substituted pyridyl pyrimidines C-D ring systems (8) can be prepared according to the method shown in scheme 2.

Scheme 2

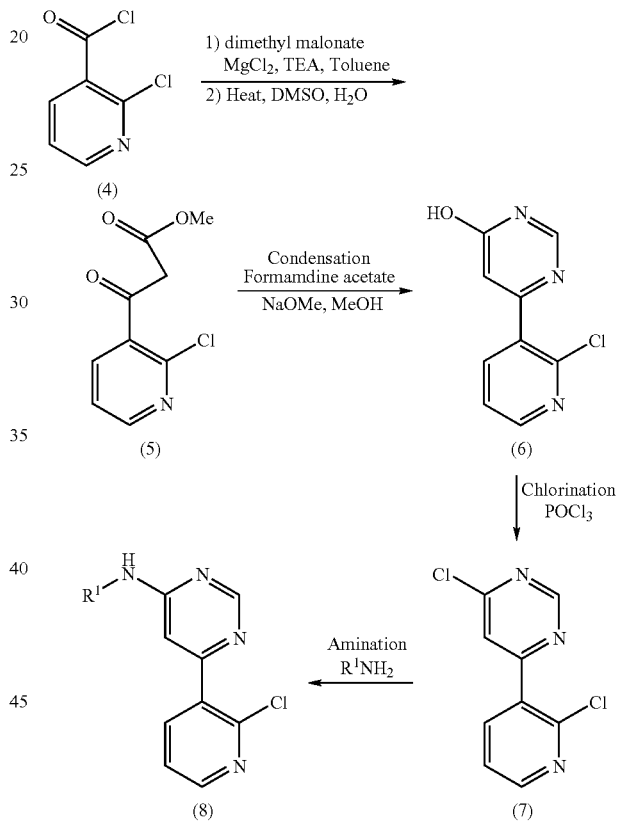

Chloro-nicotinic acid chlorides (4) can be treated with dimethylmalonate in the presence of a suitable base and MgCl to form intermediate (5). Compound (5) can be cyclized to form the hydroxyl-substituted pyrimidyl-pyridine compound (6), in the presence of suitable base and formamidine acetate. Desirable amino-$R^1$ groups can be installed at the 3 position of the 4,6-pyrimidine D-ring by simply treating compound (7) with a primary or secondary amine, having the desired substitution, with heat under conditions milder than those required to displace the pyridyl chloride of compound (6). Further, compound (6) can be treated with p-toluene sulfonyl chloride, or other similar activating reagents to render the pyrimidine hydroxyl group into a suitable leaving group (LG) for displacement with a desired, sufficiently reactive nucleophile, including amines, sulfur, and oxygen nucleophiles. Also, compound (6) may be treated with a base sufficiently strong to deprotonate the hydroxylproton in order to alkylate the hydroxyl group, thereby forming an ether, alkoxy moiety, and the like. Further, compound (6) can be converted to the corresponding thiol utilizing reactions and techniques known in the art. This thiol (not shown0 may then be converted to corresponding thio-linked $R^1$ groups. In addition, compound (7) can be treated with ammonia to give the amino adduct, which then can be alkylated, acylated, or otherwise substituted with a desired group. Such methods are known to those skilled in the art, and are described in Jerry March's Advanced Organic Chemistry, $4^{th}$ edition (1992), which disclosure is hereby incorporated by reference in its entirety.

The 2,4-regioisomer of the above pyridyl-pyrimidines can also be made using the following Scheme 3.

Alternatively, compound (9c) can be treated with guanidine.HCl in the presence of NaOH in isopropanol to afford the corresponding 3-amino-pyrimidine D ring (not shown, where $R^1$ is $NH_2$). The $R^1$ position of this intermediated can be modified using reductive alkylation methods with corresponding aldehydes, acylation methods, and other groups, by methods appreciated by persons of ordinary skill in the art, to install the desired groups at this position on the D ring of compounds of Formulas I-III. Alternatively, the 3-aminopyrimidine may be converted to 3-fluoropyrimidine with use of t-butyl nitrate and HF-pyridine, and the fluoride then displaced with a desired $R^1$ group such as $NH_2R$, OR and SR. This latter technique may also be used to convert aminotriazines to the corresponding fluoro-triazines.

Similarly, pyridyl-triazines C-D biaryl ring systems can be made using the method of scheme 4.

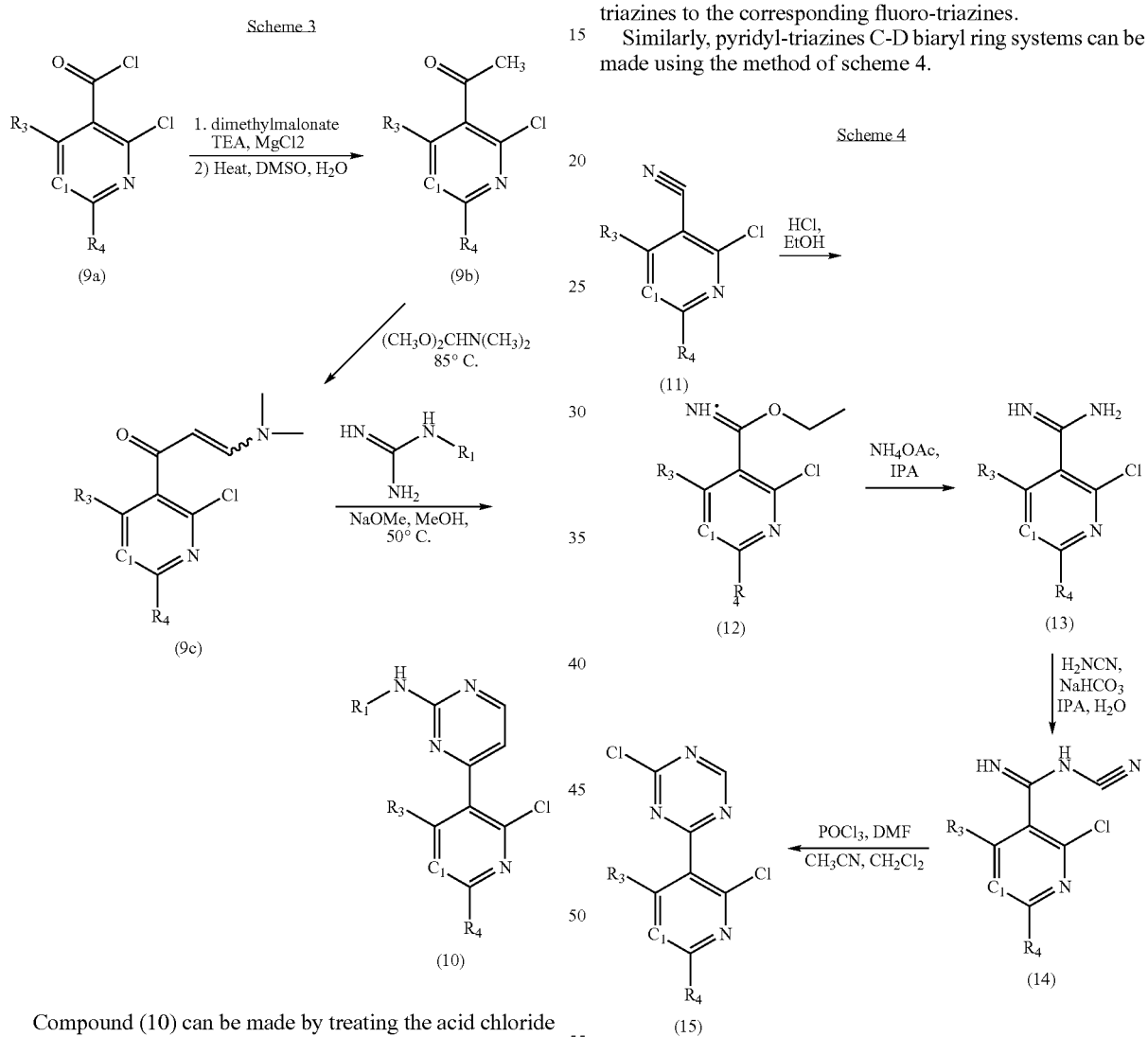

Compound (10) can be made by treating the acid chloride of compound (9a) (ring C) and converting it to the corresponding methyl ketone (9b) followed by treatment with dimethyl formamide dimethylacetal to obtain the corresponding enaminone (9c). Then substituted guanidine.HCl can be treated with a suitable base, such as sodium methoxide, for a time period prior to exposing the guanidine mixture to the enaminone (9c) to form the pyridyl pyrimidine (10). This method allows desired $R^1$ groups to be installed prior to ring closure. Care must be taken to restrict the $R^1$ groups in this method to those, which would not interfere with or react during formation of intermediates 9a-9c and also ring closure to form compound (10), as appreciated by persons of ordinary skill in the art.

In a manner similar to the method illustrated and described in Scheme 2, desirable amino-$R^1$ groups can be installed at the 3 position of a triazine D ring by treating compound (15) with a primary or secondary amine, having the desired substitution, with heat under conditions less strenuous than required to displace the pyridyl chloride of compound (15).

The C-D ring portion of the compounds of Formulas I-III can be attached to the B ring of compound (17—see scheme 5 below) by a number of conventional methods known in the art, as disclosed in March. Suitable methods are illustrated in schemes 5 and 6 below.

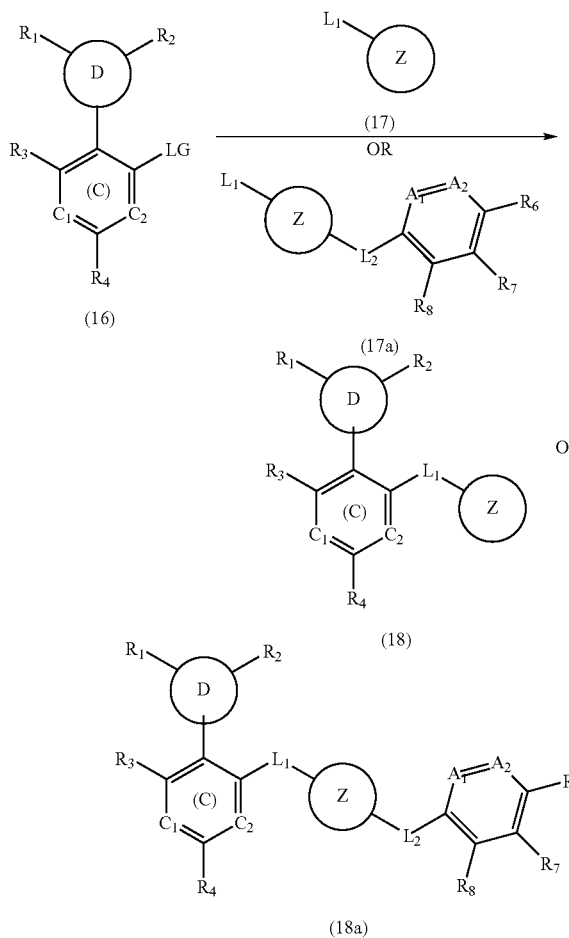

As shown in Scheme 5, compound (18 or 18a) comprising biaryl ethers and thiols (where $L^1$=O and S, respectively) can be prepared by reacting compound (16) (where LG is a leaving group, such as a halide, like a chlorine or bromine) with a nucleophilic phenyl compound (17) wherein $L^1$ is a suitable nucleophile, such as NHR or $NH_2$ (Scheme 6), OH, SH or carbon nucleophile, sufficient to displace the chloride from ring C of compound (16). For example, phenols ($L^1$=O) and thiols ($L^1$=S) can be coupled with activated aryl chlorides to form the biaryl ethers and thiols (compound 18) using weak bases such as TEA, or inorganic bases such as $Cs_2CO_3$, in DMSO at elevated temperatures, such as ranging form about 70° C. to about 130° C. Similarly, this transformation can also be carried out in NMP at about 200° C. in a microwave.

Anilines (compound 17 or 17a) can be coupled with activated aryl chlorides (compound 16) to form biaryl anilines (compound 18 or 18a) using Pd catalysis or $NEt_3$.TFA under suitable conditions, which may or may not require the input of heat.

Alternatively, and with reference to Scheme 2, where certain $R^1$ and/or $R^2$ groups hinder or limit the ability to couple ring C to ring B via the nucleophilic displacement method described above, the B-C ring coupling can be accomplished from intermediate compound (6) in Scheme 2 as follows in Scheme 7.

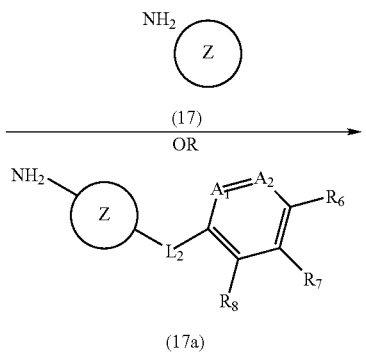

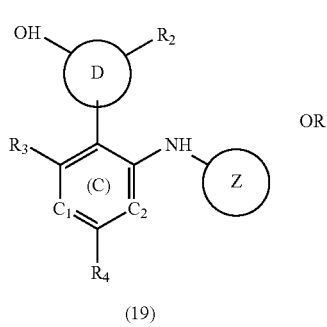
(19)

OR

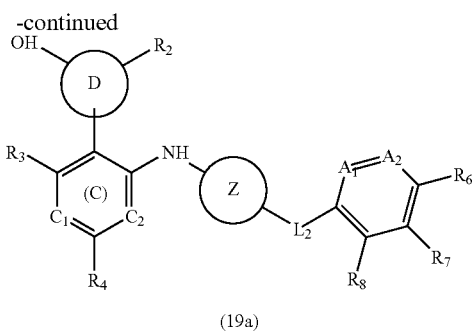
(19a)

1) POCl₃
2) RNH₂

1) POCl₃
2) RNH₂

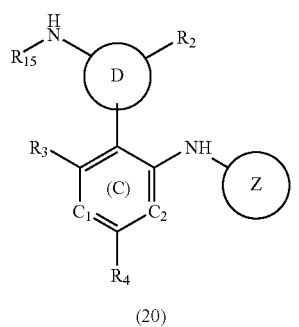
(20)

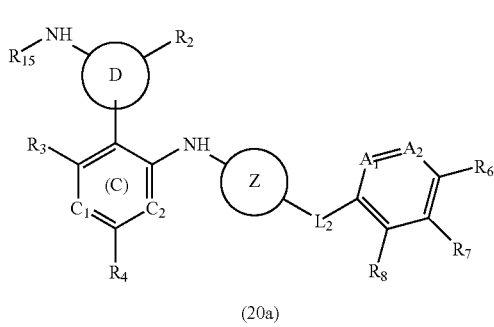
(20a)

As shown, compound (16) can first be reacted with the desired B ring nucleophilic species prior to converting the D-ring hydroxyl group to the corresponding chloride for subsequent displacement with an amine, or other desired R⁵ group.

Compounds of the invention (Formulas I-III) wherein D is $CR^{12}$ can be prepared by the general method shown in scheme 8.

Compounds of the invention (Formulas I-III) wherein $C^1$ is $CR^{10}$ can be prepared by the general method shown in scheme 8.

Scheme 8

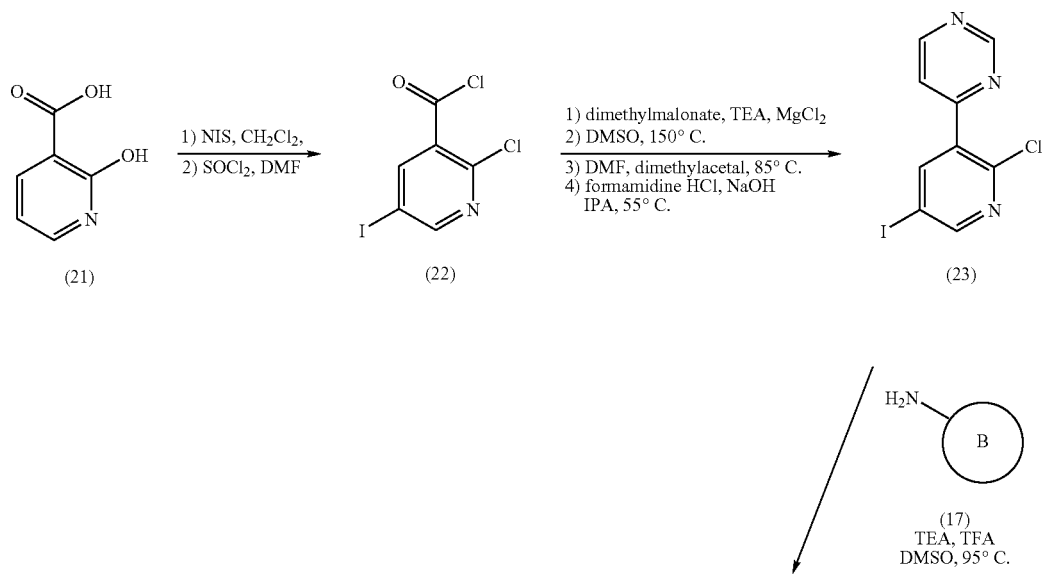

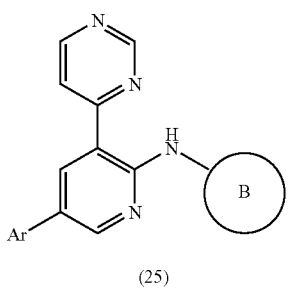 → 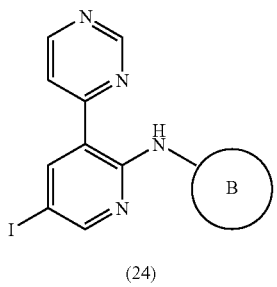

ArylB(OH)₂, K₂CO₃
Pd(PPh3)4
toluene, H₂O, heat

(25)  (24)

As shown, commercially available 2-hydroxynicotinic acid can be iodinated and subjected to thionyl chloride according to the procedure disclosed in Elworthy et al., J. Med. Chem., 40(17):2674-2687 (1997), which disclosure is incorporated herein by reference in its entirety. Conversion of the iodinated intermediate (compound 22) to the corresponding pyrimidine (compound 23) proceeds as described above in Scheme 2. After displacement of the pyridyl chloride (compound 23) with an aniline (compound 17) to form compound (24), Pd(0) mediated-coupling with an aryl boronate in the presence of mild base, such as sodium or potassium carbonate or bicarbonate, in toluene affords compound (25), an aryl pyridyl pyrimidine. Compound (25) can also be prepared using corresponding stannanes or zincates, as known in the art. Alternatively, desired $R^{10}$ groups may be installed onto the C-ring via the iodide, using conventional methods (not shown), as appreciated by those skilled in the art.

Alternatively, the desired aryl group can be installed on ring C (compound 20) even before building the D-C ring piece of compounds of Formulas I-III. For example, Church et al. describes the synthesis of 5-aryl-2-chloropyridines from phenylacetic acids in J. Org. Chem., 60:3750-3758 (1995), which disclosure is incorporated herein by reference in its entirety.

The examples described hereinafter represent exemplary methods of synthesizing or preparing desired compounds of Formulas I-III, intermediates and starting building blocks thereof, including exemplary A rings, B rings, A-B rings, C-D rings, B-C-D rings and fragments thereof. It should be appreciated that these methods are merely representative examples and other conventional, known or developed alternative methods may also be utilized. It should also be appreciated that the exemplary compounds are merely for illustrative purposes only and are not to be construed as limiting the scope of this invention in any manner.

Analytical Methods:

Unless otherwise indicated, all HPLC analyses were run on a Agilent Model 1100 system with an Agilent Technologies Zorbax SB-C₈(5μ) reverse phase column (4.6×150 mm; Part no. 883975-906) run at 30° C. with a flow rate of about 1.50 mL/min. The mobile phase used solvent A (H₂O/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-C₈ (3.5 g) reverse phase column (4.6×75 mm) at 30° C. The flow rate was constant and ranged from about 0.75 mL/min to about 1.0 mL/min.

The mobile phase used a mixture of solvent A (H₂O/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 20×50 mm column at 20 mL/min. The mobile phase used a mixture of solvent A (H₂O/0.1% TFA) and solvent B (AcCN/0.1% TFA) with a 10 min gradient from 5% to 100% solvent B. The gradient is followed by a 2 min return to 5% AcCN.

Proton NMR Spectra:

Unless otherwise indicated, all ¹H NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

Example 1

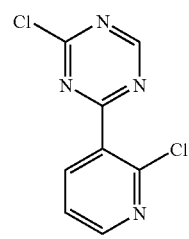

Synthesis of
2-chloro-4-(2-chloro-pyridin-3-yl)-[1,3,5]triazine

Step 1: Preparation of 2-chloro-nicotinamidine

2-Chloro-3-cyanopyridine (5.0 g, 36 mmol) was dissolved in dry EtOH (100 mL) at 0° C. HCl was bubbled through the mixture for 3 h and the mixture was sealed and refrigerated (about 8° C.) overnight. After concentration, the residue was stirred with ammonium acetate (5.5 g) in 100 mL IpOH. After 12 h, the pH was adjusted to 9 (from 4) using concentrated NH₄OH solution, and stirring continued two more days. The mixture was concentrated and purified by flash chromatography (10:1:0.1 CH₂Cl₂/MeOH/NH₄OH). Trituration in hot tBuOMe/IpOH removed some residual amide side-product to provide the product as a white solid.

Step 2: Preparation of amino-(2-chloro-pyridin-3-yl)-methylcyanamide

2-Chloro-nicotinamidine was suspended in 10 mL IpOH with 500 mg solid cyanamide and the stirring solids were dissolved by addition of 5% aqueous NaHCO$_3$ (30 mL). After two days stirring, the amino-(2-chloro-pyridin-3-yl)-methyl-cyanamide was isolated by EtOAc extraction of the aqueous reaction mixture followed by flash chromatography using 95:5:0.5 CH$_2$Cl$_2$/MeOH/NH$_4$OH. MS m/z=181 [M+H]$^+$. Calc'd for C$_7$H$_6$N$_4$Cl: 181.03.

Step 3: Preparation of 2-chloro-4-(2-chloro-pyridin-3-yl)-[1,3,5]triazine

Amino-(2-chloro-pyridin-3-yl)-methylcyanamide (3.5 g) was added as a solid to a stirring, 0° C. solution of POCl$_3$ (2.3 ml, 25 mmol) and DMF (1.9 mL, 25 mmol) in 100 mL AcCN. The clear solution was stirred at RT for 1 h. Toluene (40 mL) was added and the mixture was concentrated. The residue was immediately filtered through a 200 g plug of silica (loading in 10:1 CH$_2$Cl$_2$/IpOH, eluting with 10:1->4:1 hexane/t-BuOMe). Concentration provided 2-chloro-4-(2-chloro-pyridin-3-yl)-[1,3,5]triazine as a white solid. MS m/z=227 [M+H]$^+$. Calc'd for C$_8$H$_4$Cl$_2$N$_4$: 225.98.

Example 2

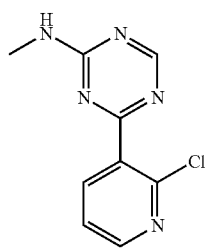

Synthesis of [4-(2-Chloro-pyridin-3-yl)-[1,3,5]triazin-2-yl]-methyl-amine

To 2-chloro-4-(2-chloro-pyridin-3-yl)-[1,3,5]triazine (10.0 g, 44.0 mmol) in 55 ml of methylene chloride was added methylamine (45 ml, 88.0 mmol) as a 2.0 M solution in THF at 0° C. After stirring at room temperature for 18 h, the mixture was diluted with acetone and filtered through a plug of silica gel and concentrated to yield the desired product. MS m/z=222 [M+H]$^+$. Calc'd for C$_9$H$_8$ClN$_5$: 221.65.

Example 3

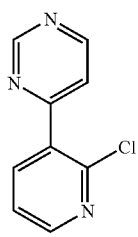

Synthesis of 4-(2-Chloro-pyridin-3-yl)-pyrimidine

Step 1. Preparation of 1-(2-Chloro-pyridin-3-yl)-3-dimethylamino-propenone 1-(2-Chloro-pyridin-3-yl)-ethanone (21.7 g, 139 mmol) in 46 mL N,N-dimethylformamide, dimethyl acetal (42 g, 350 mmol) was heated under a drying tube at 85° C. for 1.5 h and concentrated. The residue was purified by suction filtration chromatography (using 150 g silica in a Buchner funnel, with rapid collection of fractions eluting with 10:1 and then 5:1 CH$_2$Cl$_2$/IpOH) to provide yellow solid product. MS m/z=211 [M+H]$^+$. Calc'd for C$_{10}$H$_{11}$ClN$_2$O: 210.66.

Step 2. Preparation of 4-(2-Chloro-pyridin-3-yl)-pyrimidine

Sodium methoxide was generated over a period of 1.5 h by the intermittent addition of small chunks of sodium metal (8.3 g total, 360 mmol) to 400 mL dry methanol under N$_2$ at room temperature, using a bath of 500 mL IpOH at room temperature as a heat sink. Formamidine acetate (42.7 g, 410 mmol) was added, followed ten minutes later by the enaminone (30.6 g, 146 mmol). The reaction was stirred overnight under a N$_2$-filled balloon at an internal temperature of 40° C. After 20 h, the mixture was stirred at 48° C. for 4 h. Additional formamidine acetate (7.0 g) was added and the mixture was stirred overnight at 44° C. The mixture was concentrated by rotary evaporator, taken up in ethyl acetate and extracted with saturated aqueous NaHCO$_3$. The aqueous layer was back-extracted with EtOAc. The combined organic layers (1.2 L) were dried over Na$_2$SO$_4$ and concentrated. The residue was purified by flash vacuum filtration chromatography (300 g silica) in 3:1 to 2:1 hexane/EtOAc to provide white solid product. MS m/z=192 [M+H]$^+$. Calc'd for C$_9$H$_6$ClN$_3$: 191.62.

Example 4

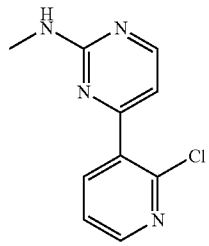

Synthesis of 4-(2-chloropyridin-3-yl)-N-methylpyrimidin-2-amine

Step 1. Preparation of 1-(2-Chloro-pyridin-3-yl)-3-dimethylamino-propenone

The title compound was prepared according to the procedure in Example 3, step 1.

Step 2. Preparation of 4-(2-chloropyridin-3-yl)-N-methylpyrimidin-2-amine

Sodium metal (3.40 g, 148 mmol) was added over -10 minutes to 180 mL of MeOH at RT and allowed to stir for an additional 30 minutes to generate sodium methoxide. Methyl guanidine HCl (200.0 g, 182 mmol) was added and the resulting mixture was stirred for 30 minutes before 1-(2-Chloro-pyridin-3-yl)-3-dimethylamino-propenone (12.0 g, 57 mmol) was added. An air condenser was attached and the mixture was heated to 50° C. for 23 hours. Part of the MeOH was removed by rotary evaporation and the resulting solid was filtered and washed with saturated sodium bicarbonate

Example 5

4-(2,5-dichloropyridin-3-yl)-N-methylpyrimidin-2-amine

The title compound was prepared in a manner analogous to that described in Example 4. MS m/z=255, 257 [M+H]$^+$; Calc'd for $C_{10}H_8Cl_2N_4$: 255.11.

Example 6

4-(2-chloropyridin-3-yl)-5-fluoro-N-methylpyrimidin-2-amine

The title compound was prepared in a manner analogous to that described in Example 4. MS m/z=238 [M+H]$^+$. Calc'd for $C_{10}H_8ClFN_4$: 238.65.

Example 7

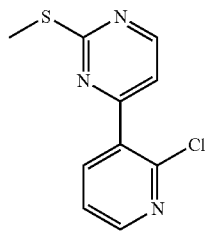

Synthesis of 4-(2-Chloropyridin-3-yl)-2-(methylthio)pyrimidine

The 5 L reactor was purged with Argon then charged with 4-chloro-2-methyl-thiopyrimidine (111 mL, 953 mmol) and 2-choropyridine-3-boronic acid (100 g, 635 mmol). The reactor was put under vacuum and filled with Argon. This was repeated two more times. Ethylene glycol dimethyl ether (500 mL) was added to the mixture followed by Pd(PPh$_3$)$_4$ (58.7 g, 50.8 mmol). The reactor was put under vacuum and filled with Argon. This was repeated two more times then more ethylene glycol dimethyl ether (1500 mL) was added. A solution of sodium bicarbonate (1M soln, 1300 mL) was added to the stirred reaction mixture. A small exotherm was observed. The reaction mixture was stirred and refluxed for 2.75 h then gradually cooled to 25° C. The mixture was diluted with ethyl acetate (1500 mL) and vigorously stirred. The layers were allowed to separate and the aqueous phase was removed. The organic phase was washed with water (1000 mL), then brine (1000 mL), dried over magnesium sulfate and filtered. The solvents were removed under vacuum to afford the crude product as a light yellow solid. The crude product was separated by column chromatography using a mixture of ethanol and dichloromethane. The product was obtained as a white solid and was slurried in ethyl acetate to remove traces of an impurity. The title compound was obtained as a white fluffy solid. MS m/z=238 [M+H]$^+$. Calc'd for $C_{10}H_8ClN_3S$: 237.71.

Example 8

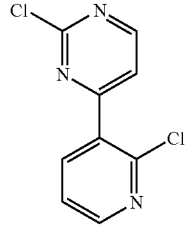

Synthesis of 2-Chloro-4(2-chloropyridin-3-yl)pyrimidine

To 2,4-dichloropyrimidine (2.00 g, 13.4 mmol), 2-choropyridine-3-boronic acid (3.16 g, 20.1 mmol) and Pd(PPh$_3$)$_4$ (1.55 g, 1.30 mmol), was added DME (30.0 mL) and 1 M NaHCO$_3$ (13.0 mL). The resulting mixture was heated to 90° C. for 17 hours, then diluted with EtOAc and extracted with saturated sodium carbonate, water, and brine. The organics were dried over sodium sulfate, filtered and concentrated. The resulting solid was triturated with ether and dried to yield the desired product. MS m/z=226 [M+H]$^+$. Calc'd for $C_9H_5Cl_2N_4$: 225.12.

Example 9

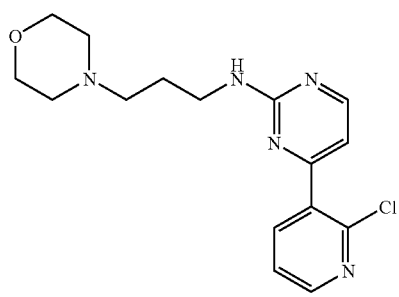

Synthesis of 4(2-chloropyridin-3-yl)-N-(3-morpholinopropyl)pyrimidin-2-amine To 2-chloro-4-(2-chloropyridin-3-yl)pyrimidine (100 mg, 0.44 mmol) and potassium carbonate (122 mg, 0.88 mmol) was added DMSO (1.0 mL) and 3-morpholinopropan-1-amine (77 mg, 0.53 mmol). The resulting mixture was heated for 15 hours at 80° C. The cooled reaction was diluted with EtOAc and extracted with water. The organic layer was dried over sodium sulfate, filtered and concentrated to yield the desired product as a yellow oil. MS m/z=334 [M+H]$^+$. Calc'd for $C_{16}H_{20}ClN_5O$: 333.84.

Example 10

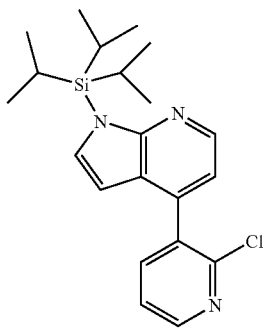

Synthesis of 4-(2-chloropyridine-3-yl)-1-(triisopropylsilyl)-1H-pyrrolo[2,3,b]pyridine Step 1. Preparation of 4-chloro-1-(triisopropylsilyl)-1H-pyrrolo[2,3-b]pyridine Sodium hydride (880 mg, 22 mmol, 1.1 equiv, 60% in mineral oil) was washed with 15 mL of dry hexanes under an argon atmosphere. The hexanes was removed and replaced with 40 mL of THF. 4-Chloro-7-azaindole was added portionwise into the sodium hydride suspension. The suspension was stirred until the gas evolution ceased. Triisopropylchlorosilane (3 g, 20 mmol, 1 equiv) was added via syringe. The reaction was placed in a preheated oil bath at 80° C. and monitored by LC-MS and TLC. After 3 hours, the reaction was cooled to room temperature. The reaction was quenched slowly with saturated $NH_4Cl$. The product was extracted with hexanes and $Et_2O$. The organic layers were combined, washed with brine, dried over $MgSO_4$, and concentrated. The residue was passed through a plug of silica gel with an aid of hexanes to remove the baseline spots. The filtrate was concentrated to afford 4-chloro-1-(triisopropylsilyl)-1H-pyrrolo[2,3-b]pyridine as a viscous colorless oil. $^1$H NMR (Varian, 300 MHz, $CDCl_3$) ppm: 8.14 (d, J=5 Hz, 1H), 7.32 (d, J=3.6 Hz, 1H), 7.05 (dd, J=5, 0.8 Hz, 1H), 6.64 (dd, J=3.5, 0.8 Hz, 1H), 1.87 (sept, J=7.3 Hz, 3H), 1.10 (d, J=7.3 Hz, 18H).

Step 2. Preparation of 4-(2-chloropyridine-3-yl)-1-(triisopropylsilyl)-1H-pyrrolo[2,3,b]pyridine 4-Chloro-1-(triisopropylsilyl)-1H-pyrrolo[2,3-b]pyridine (5.03 g, 16.3 mmol, 1 equiv), 2-chlorpyridine-3-boronic acid (4.36 g, 27.7 mmol, 1.7 equiv), palladium acetate (183 mg, 0.815 mmol, 5 mol %), 2-(dicyclohexylphosphino)biphenyl (571 mg, 1.63 mmol, 10 mol %), and finely ground anhydrous $K_3PO_4$ (10.4 g, 48.9 mmol, 3 equiv) were added into a sealed tube. The tube was purged with argon for 5 minutes. Dioxane (30 mL) was added via syringe under a positive argon flow. The tube was sealed and the reaction was stirred at RT for 5 minutes. Then the tube was placed in a preheated oil bath at 110° C. for 2 h. The reaction was cooled down to room temperature. The content was filtered through a plug of celite with an aid of diethyl ether. The filtrated was concentrated under reduced pressure. The product was purified by column chromatography using a mixture of 95:5 $Hex:Et_2O$ as eluent. The product, 4-(2-chloropyridine-3-yl)-1-(triisopropylsilyl)-1H-pyrrolo[2,3,b]pyridine was obtained as a light yellow solid. $^1$H NMR (Varian, 300 MHz, $CDCl_3$) ppm: 8.35 (d, J=4.7 Hz, 1H), 8.30-8.28 (m, 1H), 8.10-8.03 (m, 1H), 7.40-7.30 (m, 2H), 7.15 (dd, J=4.3, 1.7 Hz, 1H), 6.54 (dd, J=3.6, 1.9 Hz, 1H), 1.89 (sept, J=7.4 Hz, 3H), 1.15 (d, J=7.4 Hz, 18H).

Example 11

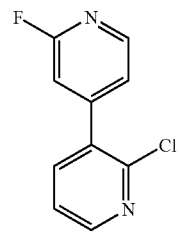

Synthesis of 2-Chloro-2'-fluoro-[3,4']bipyridinyl

To 2-fluoro-4-iodopyridine (9.45 g, 42.4 mmol), 2-chloropyridine-3-boronic acid (10.0 g, 63.5 mmol), $Na_2CO_3$ (13.5 g, 127 mmol), $Pd(OAc)_2$ (480 mg, 2.12 mmol) and $P(tBu)_3 \cdot HBF_4$ (1.23 g, 4.24 mmol) was added dioxane (125 mL) and water (45 mL). The mixture was heated overnight at 100° C. in a sealed tube. The resulting mixture was diluted with EtOAc and extracted with water and brine. The organic layer was dried over $Na_2SO_4$, filtered and concentrated. The resulting solid was triturated with n-Hexanes and dried to yield 2-chloro-2'-fluoro-[3,4']bipyridinyl. MS m/z=209 [M+1]$^+$. Calc'd for $C_{10}H_6ClFN_2$: 208.62.

Example 12

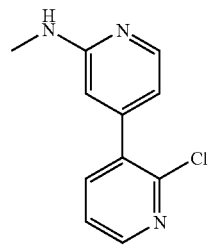

Synthesis of (2-Chloro-[3,4']bipyridinyl-2'-yl)-methyl-amine

To 2-chloro-2'-fluoro-[3,4']bipyridinyl (5.30 g, 25.4 mmol), methylamine hydrochloride (9.00 g, 133 mmol) and $K_2CO_3$ (28.1 g, 203 mmol) was added DMSO (70 mL). The mixture was heated overnight at 80° C. in a sealed tube. The cooled mixture was diluted with water (300 mL) and the resulting solid was filtered, washed with water and dried to yield (2-chloro-[3,4']bipyridinyl-2'-yl)-methyl-amine. MS m/z=220 [M+1]$^+$. Calc'd for $C_{11}H_{10}ClN_3$: 219.68.

Example 13

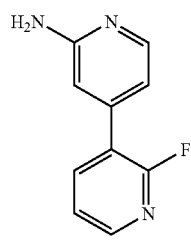

Synthesis of 4-(2-fluoropyridin-3-yl)pyridin-2-amine

A pressure vessel was charged with 6.35 mL of water and degassed with nitrogen for 0.5 h. To this vessel was added potassium acetate (2.31 g, 23.5 mmol), 2-fluoropyridine-3-boronic acid (2.48 g, 17.6 mmol), 4-chloropyridin-2-amine (1.51 g, 11.7 mmol), dichloro-bis(di-tert-butylphenylphosphino)Pd(II) (0.146 g, 0.235 mmol) and 58.5 mL CH$_3$CN. The mixture was purged under nitrogen for several additional minutes, and the pressure bottle was sealed. The reaction mixture was heated to 85° C. for 15 h. Upon cooling the layers were separated, and the organic portion was dried with Na$_2$SO$_4$ and concentrated. The resulting solid was triturated with ethyl acetate/diethyl ether to provide 4-(2-fluoropyridin-3-yl)pyridin-2-amine as a tan solid. MS m/z=190 [M+H]$^+$. Calc'd for C$_{10}$H$_8$FN$_3$: 189.19.

Example 14

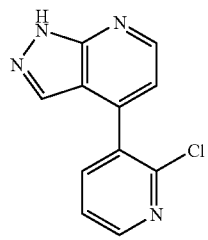

Synthesis of 4-(2-chloropyridin-3-yl)-1H-pyrazolo[3,4-b]pyridine

Step 1. Preparation of 4-iodo-1H-pyrazolo[3,4-b]pyridine

To 2-fluoro-4-iodonicotinaldehyde (11.33 g, 45.1 mmol) in THF (200 mL) was added hydrazine (5.67 ml, 181 mmol) dropwise. The resulting mixture was stirred at RT under a nitrogen atmosphere for 5 h. The reaction was concentrated, diluted with 10:1 acetone/MeOH and filtered through a pad of silica gel. Removed most of the solvent in vacuo, then diluted with some hexanes and filtered resulting solid. Dried to yield 4-iodo-1H-pyrazolo[3,4-b]pyridine as an off-white solid. MS m/z=246 [M+1]$^+$. Calc'd for C$_6$H$_4$IN$_3$: 245.02.

Step 2. Preparation of tert-butyl 4-iodo-1H-pyrazolo[3,4-b]pyridine-1-carboxylate To 4-iodo-1H-pyrazolo[3,4-b]pyridine (1.110 g, 4.53 mmol), di-t-butyl dicarbonate (1.09 g, 4.98 mmol), and N,N-dimethylpyridin-4-amine (0.277 g, 2.27 mmol) was added methylene chloride (15 mL). The resulting mixture was stirred at RT under a nitrogen atmosphere for 15 h, diluted with methylene chloride and extracted with saturated sodium bicarbonate. Dried organics over sodium sulfate, filtered through a pad of silica gel using 1:1 EtOAc/CH$_2$Cl$_2$ and concentrated to yield tert-butyl 4-iodo-1H-pyrazolo[3,4-b]pyridine-1-carboxylate as a light yellow solid. $^1$H NMR (Bruker, 400 MHz, DMSO-d$_6$) ppm: 8.42 (m, 2H), 7.98 (m, 1H), 1.72 (s, 9H).

Step 3. Preparation of 4-(2-chloropyridin-3-yl)-1H-pyrazolo[3,4-b]pyridine

To tert-butyl 4-iodo-1H-pyrazolo[3,4-b]pyridine-1-carboxylate (1.00 g, 2.90 mmol), 2-chloropyridin-3-ylboronic acid (1.14 g, 7.24 mmol), and sodium carbonate (1.23 g, 11.6 mmol) was added dioxane (10 mL) and water (4 mL). The mixture was stirred at RT for 5 minutes, then tri-t-butylphosphonium tetrafluoroborate (0.084 g, 0.290 mmol) and palladium(II) acetate (0.033 g, 0.145 mmol) were added and the mixture was heated to 100° C. in a sealed tube for 23 hours. The reaction was diluted with EtOAc and extracted with 1N sodium bicarbonate. The organics were dried over sodium sulfate, filtered and concentrated. The crude was purified by ISCO silica gel chromatography (10-90% EtOAc/hexanes; 80 g column) and product fractions were concentrated to yield 4-(2-chloropyridin-3-yl)-1H-pyrazolo[3,4-b]pyridine as a white solid. MS m/z=231 [M+1]$^+$. Calc'd for C$_{11}$H$_7$ClN$_4$: 230.66.

Example 15

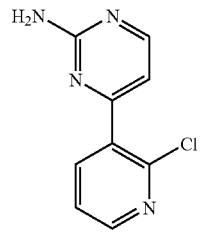

Synthesis of 4(2-chloropyridin-3-yl)pyrimidin-2-amine

In an argon purged 500 mL round bottom flask placed in an isopropanol bath, was added sodium metal (3.40 g, 148 mmol) slowly to methanol (180 mL). The mixture was stirred at RT for about 30 minutes. To this was added guanidine hydrochloride (12.0 mL, 182 mmol) and the mixture was stirred at RT for 30 minutes, followed by addition of (E)-1-(2-chloropyridin-3-yl)-3-(dimethylamino)prop-2-en-1-one (12.0 g, 57.0 mmol), attached air condenser, moved reaction to an oil bath, where it was heated to about 50° C. for 24 h. Approximately half of the methanol was evaporated under reduced pressure and the solids were filtered under vacuum, then washed with saturated NaHCO$_3$ and H$_2$O, air dried to yield 4-(2-chloropyridin-3-yl)pyrimidin-2-amine as off white solid. MS m/z=207 [M+1]$^+$. Calc'd for C$_9$H$_7$ClN$_4$: 206.63.

Example 16

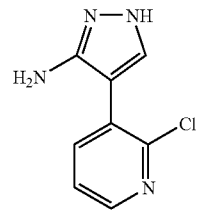

Synthesis of 4(2-chloropyridin-3-yl)-1H-pyrazol-3-amine

Step 1. Preparation of (2-chloropyridin-3-yl)methanol

To a stirred solution of 2-chloronicotinic acid (8.00 g, 51.0 mmol) in THF (120 mL) at 0° C. under nitrogen was slowly added lithium tetrahydroaluminate (51 mL, 51 mmol) over five minutes. The reaction was allowed to warm to RT over 2 h and was monitored by TLC. The reaction was quenched by addition of small amounts of ice followed by water. Extracted product into EtOAc, washed 2×H$_2$O, 1×NaCl, dried with Mg$_2$SO$_4$, filtered through fritted funnel, and concentrated the solution to yield (2-chloropyridin-3-yl)methanol as an orange oil. Used without further purification.

Step 2. Preparation of 3-(bromomethyl)-2-chloropyridine

In a 250 mL round bottom flask was dissolved (2-chloropyridin-3-yl)methanol (6.7 g, 47 mmol) in $CH_2Cl_2$ (100 mL). The reaction was cooled to 0° C., to which was slowly added tribromophosphine (4.8 mL, 51 mmol), and allowed to warm to RT overnight. The reaction was quenched by addition of ice, extracted into $CH_2Cl_2$, washed 1×$NaHCO_3$, 2×$H_2O$, dried with $Mg_2SO_4$, filtered through fritted funnel and filtrate was concentrated. The crude was purified by silica gel chromatography eluting with 15-45% EtOAc/Hex. The product fraction were concentrated down to yield 3-(bromomethyl)-2-chloropyridine as off-white solid. MS m/z=206, 208 [M+1]$^+$. Calc'd for $C_6H_5BrClN$: 206.47.

Step 3. Preparation of 2-(2-chloropyridin-3-yl)acetonitrile

In a 250 mL round bottom flask was dissolved 3-(bromomethyl)-2-chloropyridine (7.2 g, 35 mmol) in MeOH (70 mL). To the solution was added sodium cyanide (3.4 g, 70 mmol), then attached a reflux condenser, stirred the mixture at 80° C., while monitoring the reaction by LCMS. After about 1.5 h, the reaction was cooled to RT, concentrated, diluted with EtOAc, upon which a white solid crashed out. The solids were filtered and rinsed with EtOAc. The organic filtrate was concentrated to yield a crude reddish brown solid. The solid was dissolved in EtOAc, and purified by silica gel chromatography eluting with 40-70% EtOAc/Hexanes. The product fractions were concentrated to yield 2-(2-chloropyridin-3-yl)acetonitrile as an off-white solid. MS m/z=153 [M+1]$^+$. Calc'd for $C_7H_5ClN_2$: 152.58.

Step 4. Preparation of 2-(2-chloropyridin-3-yl)-3-oxopropanenitrile

A solution of 2-(2-chloropyridin-3-yl)acetonitrile (2.0 g, 13 mmol) in THF (5 mL) was slowly added to a suspension of sodium hydride, 60% in mineral oil (1.31 g, 33.0 mmol) in THF (10 mL) at 0° C. The mixture was stirred for 15 minutes, and ethyl formate (1.1 mL, 13 mmol) was slowly added. The mixture was stirred at RT, and monitored by LCMS. Upon completion, the reaction was extracted into EtOAc, washed organics 2×$H_2O$, dried with $Mg_2SO_4$, filtered through fritted funnel, and lyophilized to yield 2-(2-chloropyridin-3-yl)-3-oxopropanenitrile as reddish brown solid. The crude was used without further purification. MS m/z=181 [M+1]$^+$. Calc'd for $C_8H_5ClN_2O$: 180.59.

Step 5. Preparation of 4-(2-chloropyridin-3-yl)-1H-pyrazol-3-amine

In a 150 mL sealed tube, added 2-(2-chloropyridin-3-yl)-3-oxopropanenitrile (2.5 g, 14 mmol), water (2.0 mL, 14 mmol), acetic acid (14 mL, 14 mmol), ethanol (28 mL, 14 mmol), 1,4-dioxane (14 mL), and anhydrous hydrazine (0.40 ml, 14 mmol). The mixture was stirred at 70° C. for 20 minutes. The reaction was cooled to RT and concentrated. The concentrate was extracted into EtOAc, washed 1×$NaHCO_3$, 1×$H_2O$, dried over $Mg_2SO_4$, filtered through fritted funnel and concentrated. The crude was purified using reverse phase chromatography. The product was extracted into $CH_2Cl_2$, washed 1×$NaHCO_3$ 1×$H_2O$, dried with $Na_2SO_4$, filtered through fritted funnel, concentrated to yield 4-(2-chloropyridin-3-yl)-1H-pyrazol-3-amine as tan solid. MS m/z=195 [M+1]$^+$. Calc'd for $C_8H_7ClN_4$: 194.62.

Example 17

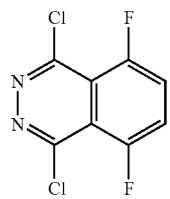

Synthesis of 1,4-dichloro-5,8-difluorophthalazine

Step 1: Preparation of 5,8-difluoro-2,3-dihydrophthalazine-1,4-dione

To 4,7-difluoroisobenzofuran-1,3-dione (1.00 g, 5.43 mmol) and sodium acetate (0.535 g, 6.52 mmol) was added water (14 mL), acetic acid (7.15 ml, 125 mmol) and hydrazine (0.205 ml, 6.52 mmol) (slowly). A water condenser was attached and the mixture was heated to reflux for 20 hours. Cooled to RT and filtered the resulting solid. Washed with water and dried to yield 5,8-difluoro-2,3-dihydrophthalazine-1,4-dione as a white solid. MS m/z=199 [M+1]$^+$. Calc'd for $C_8H_4F_2N_2O_2$: 198.13.

Step 2: Preparation of 1,4-dichloro-5,8-difluorophthalazine

To 5,8-difluoro-2,3-dihydrophthalazine-1,4-dione (0.860 g, 4.34 mmol) was added phosphorus oxychloride (4.05 ml, 43.4 mmol). A water condenser was attached and the resulting mixture was heated to reflux for 15.5 hours. Cooled the reaction and concentrated in vacuo. Diluted the reaction with methylene chloride and ice water, then quenched with solid sodium bicarbonate until pH was basic. The layers were separated and organics dried over sodium sulfate, filtered and concentrated to yield 1,4-dichloro-5,8-difluorophthalazine as a light yellow solid. MS m/z=235, 237 [M+1]$^+$. Calc'd for $C_8H_2Cl_2F_2N_2$: 235.02.

The following intermediates were prepared by a method analogous to that described in Example 17 above.

Example 18

1,4-dichloro-6,7-difluorophthalazine

MS m/z=235, 237 [M+1]$^+$. Calc'd for $C_8H_2Cl_2F_2N_2$: 235.02.

Example 19

5,8-dichloropyrido[3,2-d]pyridazine

MS m/z=200, 202 [M+1]$^+$. Calc'd for $C_7H_3Cl_2N_3$: 200.03.

Example 20

1,4-dichloro-6,7-dihydro-5H-cyclopenta[d]pyridazine. MS m/z=189, 191 [M+1]$^+$. Calc'd for $C_7H_6Cl_2N_2$: 189.05.

Example 21

1,4-dichloro-5,6,7,8-tetrahydrophthalazine

MS m/z=203, 205 [M+1]$^+$. Calc'd for $C_8H_8Cl_2N_2$: 203.07.

Example 22

3,6-dichloro-4,5-dimethylpyridazine

MS m/z=177, 179 [M+1]$^+$. Calc'd for $C_6H_6Cl_2N_2$: 177.03.

Example 23

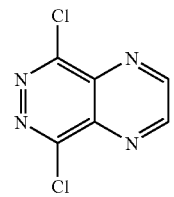

Synthesis of 5,8-dichloropyrazino[2,3-d]pyridazine

Step 1. Preparation of 6.7-Dihydropyrazino[2,3-d]pyridazine-5,8-dione

The title compound was prepared according to a literature procedure (Paul, D. B. *Aust. J. Chem.* 1974, 27, 1331). As described therein, 2,3-pyrazinedicarboxylic anhydride (5.00 g, 33.3 mmol), hydrazine hydrate (2.8 g, 56 mmol), and acetic acid (40.4 ml, 33.3 mmol) were mixed at RT. White precipitated crashed out. The reaction was heated under reflux for approximately 20 min. The reaction was cooled to RT and the solids were filtered, washed with water, and dried under vacuum. The product, 6,7-dihydropyrazino[2,3-d]pyridazine-5,8-dione was obtained as white solid. $^1$H NMR (Bruker, 400 MHz, D$_2$O) ppm: 8.87 (s, 2H).

Step 2. Preparation of 5,8-Dichloropyrazino[2,3-d]pyridazine

The title compound was prepared according to a literature procedure (Patel, N. R.; Castle, R. N. *J. Heterocyclic Chem.* 1966, 3, 512). A mixture of 6,7-dihydropyrazino[2,3-d]pyridazine-5,8-dione (2.50 g, 15.2 mmol), phosphorus pentachloride (6.98 g, 33.5 mmol), and phosphorus oxychloride (39.8 ml, 42.7 mmol) were added into a round bottom flask equipped with a magnetic stir bar. A drying tube was attached on top of the condenser. The reaction was heated to reflux for 8 h. The orange suspension was formed. The reaction was cooled to RT. The solvent was azeotropically (toluene) removed under reduced pressure to remove excess POCl$_3$. The black resulting residue was treated with ice and basified slowly with solid Na$_2$CO$_3$. The aqueous solution was extracted several times with chloroform, the combined extracts were dried over MgSO$_4$, filtered, and concentrated to give product, 5,8-dichloropyrazino[2,3-d]pyridazine. $^1$H NMR (Bruker, 400 MHz, CDCl$_3$) ppm: 9.24 (s, 2H).

Example 24

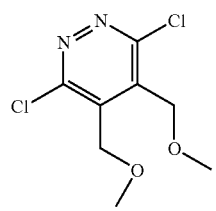

Synthesis of 3,6-dichloro-4,5-bis(methoxymethyl)pyridazine

The title compound was made following the literature reference: Samaritoni, J G, *Org. Prep. Proced Int.* 20, 117-121, 1988. To a slightly heterogeneous mixture of methoxyacetic acid (3.6 ml, 47 mmol), silver nitrate (0.57 g, 3.4 mmol), 3,6-dichloropyridazine (2.0 g, 13 mmol), and concentrated sulfuric acid (1.7 ml, 20 mmol) in 30 mL water at 70° C. was added a solution of ammonium persulfate (7.7 g, 34 mmol) in 15 mL water dropwise over ca. 10 min. The heterogeneous mixture was allowed to stir for 30 min, at which point it was poured onto ice. A gummy gray solid was present. The aqueous material was filtered, and the cold filtrate was basified with conc. ammonium hydroxide. At pH 10, the solution became dark yellow. The aqueous material was extracted three times with dichloromethane, dried over anhyd sodium sulfate, filtered, and concentrated in vacuo. The resulting yellow oil was purified by silica gel chromatography (0-40% EtOAc/hexanes) to give 3,6-dichloro-4,5-bis(methoxymethyl)pyridazine as a white solid. MS m/z=237 [M+H]$^+$. Calc'd for C$_8$H$_{10}$Cl$_2$N$_2$O$_2$: 237.1.

Example 25

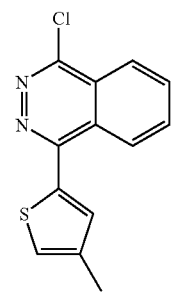

Synthesis of 1-Chloro-4-(4-methylthiophen-2-yl)phthalazine 1,4-Dichlorophthalazine (1.40 g, 7.03 mmol), 4-methylthiophen-2-ylboronic acid (999 mg, 7.03 mmol), and PdCl$_2$ (DPPF) (721 mg, 985 μmol) were added into a sealed tube. The tube was purged with Argon. Then sodium carbonate (2.0 M in water) (7.74 ml, 15.5 mmol) and 1,4-dioxane (35.2 ml, 7.03 mmol) were added. The tube was sealed, stirred at rt for 5 min, and placed in a preheated oil bath at 110° C. After 1 h, LC-MS showed product and byproduct (double coupling), and SM dichlorophthalazine. The reaction was cooled to rt, filtered through a pad of celite with an aid of EtOAc, concentrated, and loaded onto column. The product was purified by column chromatography using Hex to remove the top spot, then 80:20 Hex:EtOAc to collect the product. The product, 1-chloro-4-(4-methylthiophen-2-yl)phthalazine was obtained as yellow solid. LC-MS showed that the product was contaminated with a small amount of SM dichlorophthalazine and biscoupling byproduct. MS m/z=261 [M+1]$^+$. Calcd for C$_{13}$H$_9$ClN$_2$S: 260.12.

Example 26

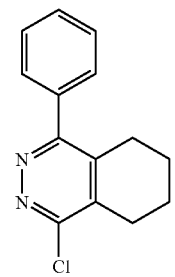

Synthesis of 1-chloro-4-phenyl-5,6,7,8-tetrahydrophthalazine 1,1'-bis(diphenylphosphino)ferrocene-palladium dichloride (0.270 g, 0.369 mmol), phenylboronic acid (0.900 g, 7.38 mmol) and 1,4-dichloro-5,6,7,8-tetrahydrophthalazine (2.25 g, 11.1 mmol) were combined in a 150 mL sealable vessel under argon. 15 mL dioxane and 2.0 M Sodium carbonate, aqueous (7.38 ml, 14.8 mmol) were added. The vessel was sealed and heated to 80° C. to give a homogenous brown reaction. After 30 min, the reaction was cooled to ambient temperature and was diluted with EtOAc, water, and brine. The layers were separated, and the organic layer was dried over anhydrous sodium sulfate, filtered, and concentrated in vacuo to give a red solid. This was taken up in dichloromethane and purified by silica gel chromatography (0-60% EtOAc in hexanes) to give 1-chloro-4-phenyl-5,6,7,8-tetrahydrophthalazine as an off-white solid. MS m/z=245 [M+H]+. Calc'd for $C_{14}H_{13}ClN_2$: 244.7.

Example 27

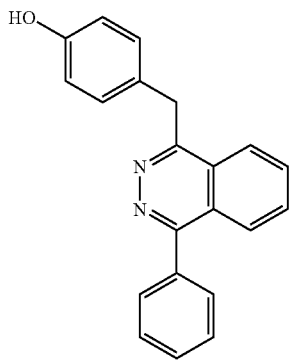

Synthesis of
4-((4-phenylphthalazin-1-yl)methyl)phenol

Step 1. Preparation of 2-(2-(4-methoxyphenyl)acetyl)-N-methylbenzamide

At 0° C., (4-methoxybenzyl)magnesium chloride (0.25 M in THF) (37 ml, 9.3 mmol) was added to 2-methylisoindoline-1,3-dione (1.00 g, 6.2 mmol) in THF (3.0 mL) (Reference: Synthetic Comm. 2004, 34(7), 1301-1308). The mixture was stirred at 0° C. for 5 minutes, then quenched with 10 mL of water. The reaction was warmed to RT and concentrated to yield 2-(2-(4-methoxyphenyl)acetyl)-N-methylbenzamide as a white solid (crude). The material was carried on to next step without further purification. MS m/z=284 [M+1]+. Calc'd for $C_{17}H_{17}NO_3$: 283.33.

Step 2: Preparation of 4-(4-methoxybenzyl)phthalazin-1 (2H)-one

To 2-(2-(4-methoxyphenyl)acetyl)-N-methylbenzamide (1.76 g, 6.20 mmol) in EtOH (20 mL) was added hydrazine (3.50 ml, 112 mmol). A water condenser was attached and the mixture was heated to reflux under a nitrogen atmosphere for 5 days. After concentration, the reaction was diluted with EtOAc and extracted with water. The organics were dried over sodium sulfate, filtered and concentrated. The crude was purified by washing the resulting solid with diethyl ether and filtering to yield 4-(4-methoxybenzyl)phthalazin-1(2H)-one as a white solid. MS m/z=267[M+1]+. Calc'd for $C_{16}H_{14}N_2O_2$: 266.30.

Step 3. Preparation of 1-(4-methoxybenzyl)-4-chlorophthalazine

To 4-(4-methoxybenzyl)phthalazin-1 (2H)-one (1.18 g, 4.43 mmol) was added phosphorus oxychloride (4.13 ml, 44.3 mmol). A water condenser was attached and the mixture was heated to reflux under a nitrogen atmosphere for 15 hours. The reaction was concentrated in vacuo, diluted with methylene chloride and ice water, then quenched with solid sodium bicarbonate until pH was basic and gas evolution ceased. The layers were separated and the organic layers were dried over sodium sulfate, filtered through a pad of silica gel using EtOAc and concentrated to yield 1-(4-methoxybenzyl)-4-chlorophthalazine as a light orange solid. MS m/z=285 [M+1]+. Calc'd for $C_{16}H_{13}ClN_2O$: 284.75.

Step 4. Preparation of 1-(4-methoxybenzyl)-4-phenylphthalazine

To 1,1'-bis(diphenylphosphoino)ferrocene-palladium dichloride (0.046 g, 0.063 mmol), 1-(4-methoxybenzyl)-4-chlorophthalazine (0.360 g, 1.3 mmol), and phenylboronic acid (0.39 g, 3.2 mmol) was added dioxane (4.0 mL) and sodium carbonate (2.0M, aq) (1.9 ml, 3.8 mmol). The resulting mixture was heated to 100° C. in a sealed tube for 1 hour. The reaction was diluted with EtOAc and extracted with water and brine. The organic layers were dried over sodium sulfate, filtered, concentrated, and the crude was purified by ISCO silica gel chromatography (10-100% EtOAc/hexanes, 40 g column). Concentrated the product fractions to yield 1-(4-methoxybenzyl)-4-phenylphthalazine as a light yellow solid. MS m/z=327 [M+1]+. Calc'd for $C_{22}H_{18}N_2O$: 326.40.

Step 5. Preparation of 4-((4-phenylphthalazin-1-yl)methyl) phenol

To 1-(4-methoxybenzyl)-4-phenylphthalazine (0.240 g, 0.735 mmol) was added acetic acid (1.5 mL) followed by hydrobromic acid 48% (1.50 ml, 27.6 mmol). A water condenser was attached and the mixture was heated to reflux for 3 hours. The reaction was diluted with water and neutralized with 6 N NaOH until pH~6. Filtered the resulting solid, washed with water and dried to yield 4-((4-phenylphthalazin-1-yl)methyl)phenol as an off-white solid. MS m/z=313 [M+1]+. Calc'd for $C_{21}H_{16}N_2O$: 312.37.

Example 28

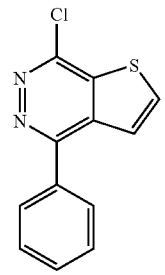

Synthesis of
7-chloro-4-phenylthieno[3,2-d]pyridazine

Step 1. Preparation of 4-phenylthieno[2,3-d]pyridazin-7 (6H)-one

To 3-benzoylthiophene-2-carboxylic acid (1.00 g, 4.31 mmol) and EtOH (15 mL) was added hydrazine (1.35 ml, 43.1 mmol). A water condenser was attached to the reaction flask and the mixture was heated to reflux under nitrogen for 3.5 hours. The reaction was cooled to RT, the resulting solids filtered and washed with water, and dried to yield 4-phenylthieno[2,3-d]pyridazin-7(6H)-one as a white solid. MS m/z=229 [M+1]+. Calc'd for $C_{12}H_8N_2OS$: 228.27.

Step 2. Preparation of 7-chloro-4-phenylthieno[3,2-d]pyridazine

To 4-phenylthieno[2,3-d]pyridazin-7(6H)-one (0.714 g, 3.13 mmol) was added POCl₃ (2.92 ml, 31.3 mmol). A water condenser was attached to the reaction flask and the mixture was heated to reflux for 15.5 hours. The reaction was concentrated and diluted with CH₂Cl₂ and ice water. The mixture was basified with solid sodium bicarbonate. The organic layers were separated and dried over sodium sulfate. To the residual crude after concentration, 50% EtOAc was added and the solution was filtered through a pad of silica gel. The product fraction were concentrated to yield 7-chloro-4-phenylthieno[3,2-d]pyridazine as a light yellow solid. MS m/z=247 [M+1]⁺. Calc'd for $C_{12}H_7N_2S$: 246.71.

Example 29

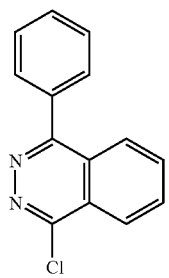

Synthesis of 1-chloro-4-phenylphthalazine

A mixture of phosphoryl trichloride (28.4 ml, 310 mmol) and 4-phenylphthalazin-1(2H)-one (13.8 g, 62.0 mmol) was heated overnight with reflux condensor and drying tube in a 130° C. bath. The light orange, homogeneous solution was cooled to ambient temperature and allowed to stand for several days. The reaction was poured onto stirring ice carefully. The resulting mixture was brought to pH 8 by addition of 6N NaOH carefully with addition of ice to control the temperature. The resulting off-white solid was collected by filtration, air dried, and dried in vacuo to give as a light yellow solid. 1-chloro-4-phenylphthalazine. MS m/z=241 [M+H]⁺. Calc'd for $C_{14}H_9ClN_2$: 240.7.

Example 30

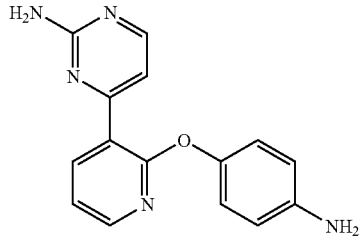

Synthesis of 4-(2-(4-aminophenoxy)pyridin-3-yl) pyrimidin-2-amine

To a resealable tube was added 4-aminophenol (1.3 g, 12 mmol), cesium carbonate (7.8 g, 24 mmol), and DMSO (16 ml, 0.75 M). The mixture was heated to 100° C. for 5 minutes, and then 4-(2-chloropyridin-3-yl)pyrimidin-2-amine (2.5 g, 12 mmol) was added, and the reaction mixture was heated to 130° C. overnight. Upon completion, as judged by LCMS, the reaction mixture was allowed to cool to RT and diluted with water. The resulting precipitate was filtered, and the solid washed with water and diethyl ether. The solid was then taken up in 9:1 CH₂Cl₂:MeOH and passed through a pad of silica gel with 9:1 CH₂Cl₂:MeOH as eluent. The solvent was concentrated in vacuo to provide the desired product, 4-(2-(4-aminophenoxy)pyridin-3-yl)pyrimidin-2-amine. MS m/z=280 [M+1]⁺. Calc'd for $C_{15}H_{13}N_5O$: 279.30.

Example 31

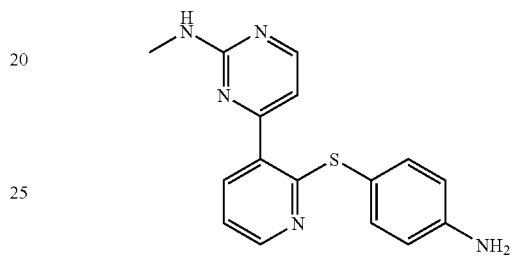

Synthesis of 4-(2-((4-aminophenyl)sulfanyl)-3-pyridinyl)-N-methyl-2-pyrimidinamine To 4-aminothiophenol (1.70 g, 13.6 mmol) and Cs₂CO₃ (8.90 g, 27.2 mmol) was added DMSO (18 mL). The mixture was stirred for 5 minutes at 100° C. before 4-(2-chloropyridin-3-yl)-N-methylpyrimidin-2-amine (3.00 g, 13.6 mmol) was added. The resulting mixture was stirred for 16 hours at 130° C., then diluted with water and the resulting solid filtered. After washing the solid with water and Et₂O it was dried under vacuum to yield the desired product as a tan solid. MS m/z=310 [M+1]⁺. Calc'd for $C_{16}H_{15}N_3S$: 309.40.

Example 32

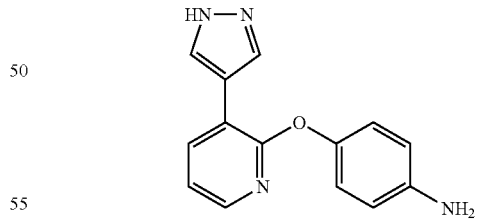

Synthesis of 4-(3-(1H-pyrazol-4-yl)pyridin-2-yloxy) benzenamine

Step 1. Preparation of 4-bromo-1-trityl-1H-pyrazole

In a 75 mL sealed tube, 4-bromopyrazole (1.0 g, 6.8 mmol), pyridine (21.0 mL, 258 mmol), triphenylmethyl chloride (2.1 g, 7.5 mmol), and 4-dimethylaminopyridine (0.17 g, 1.4 mmol) were added. The mixture was stirred at 80° C. for 24 hours. The mixture was diluted with water, and the solids which crashed out were filtered, rinsed with water and air-dried to yield 4-bromo-1-trityl-1H-pyrazole as a white solid.

Step 2. Preparation of 2-chloro-3-(1-trityl-1H-pyrazol-4-yl)pyridine

To an argon purged 48 mL sealed pressure vessel was added 1,4-dioxane (2.6 mL), 4-bromo-1-trityl-1H-pyrazole (1.00 g, 2.60 mmol), potassium fluoride (0.492 g, 8.48 mmol), 2-chloropyridine-3-boronic acid (0.808 g, 5.14 mmol), tris(dibenzylideneacetone)dipalladium (0) (0.176 g, 0.193 mmol) and tri-t-butylphosphonium tetrafluoroborate (0.168 g, 0.578 mmol). The vessel was purged with argon and heated to 100° C. for 5 hours. The mixture was cooled to RT, filtered through a pad of silica gel using EtOAc and concentrated. The crude was purified using normal phase silica gel chromatography eluting with 15-70% EtOAc/Hexanes. The product fractions were concentrated to yield 2-chloro-3-(1-trityl-1H-pyrazol-4-yl)pyridine as an off-white solid. MS m/z=422 [M+1]$^+$. Calc'd for $C_{27}H_{20}ClN_3$: 421.92.

Step 3. Preparation of 4-(3-(1-trityl-1H-pyrazol-4-yl)pyridin-2-yloxy)benzenamine In 4 separate microwave vessels were added equal amounts of the following (total/4): dissolved 4-aminophenol (0.054 g, 0.498 mmol) in 1-methyl-2-pyrrolidinone (4.7 mL), added cesium carbonate (0.309 g, 0.948 mmol). Each mixture was stirred at 20° C. for 5 minutes, after which was added 2-chloro-3-(1-trityl-1H-pyrazol-4-yl)pyridine (0.200 g, 0.474 mmol) and heated to 200° C. in the microwave for 6 minutes. The solutions were combined and extracted into EtOAc, washed 1×H$_2$O, 1×NaCl, dried with Mg$_2$SO$_4$, filtered through fritted funnel, and concentrated. The crude residue was purified by silica gel chromatography using 25-70% EtOAc/Hexanes. The product fraction was concentrated to yield 4-(3-(1-trityl-1H-pyrazol-4-yl)pyridin-2-yloxy)benzenamine as brown oil. MS m/z=495 [M+1]$^+$. Calc'd for $C_{33}H_{26}N_4O$: 494.59.

Step 4. Preparation of 4-(3-(1H-pyrazol-4-yl)pyridin-2-yloxy)benzenamine

In a 25 mL sealed tube, was added 4-(3-(1-trityl-1H-pyrazol-4-yl)pyridin-2-yloxy)benzenamine (0.150 g, 0.303 mmol), trifluoroacetic acid (0.23 mL, 3.0 mmol), and methanol (1.0 mL). The mixture was stirred at 80° C. for 36 hours. The mixture was concentrated. The residue was extracted into EtOAc, washed 1×NaHCO$_3$, 1×NaCl, and the organic layers were combined and dried over Mg$_2$SO$_4$, filtered through fritted funnel and concentrated to yield 4-(3-(1H-pyrazol-4-yl)pyridin-2-yloxy)benzenamine as dark brown waxy solid. MS m/z=253 [M+1]$^+$. Calc'd for $C_{14}H_{12}N_4O$: 252.27.

Example 33

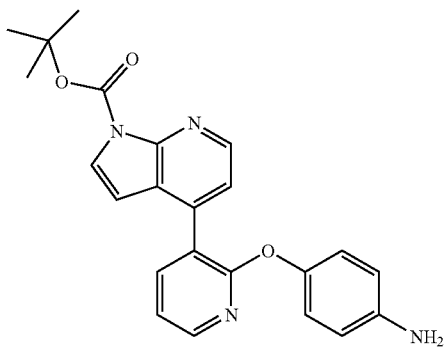

Synthesis of tert-butyl 4-(2-(4-aminophenoxy)pyridin-3-yl)-1H-pyrrolo[2,3-b]pyridine-1-carboxylate Step 1. Preparation of tert-Butyl 4-chloro-1H-pyrrolo[2,3-b]pyridine-1-carboxylate To a solution of 4-chloro-1H-pyrrolo[2,3-b]pyridine (3.00 g, 19.7 mmol), N,N-dimethylpyridin-4-amine (1.20 g, 9.83 mmol), dichloromethane (67.8 mL) was added di-tert-butyl dicarbonate (4.72 g, 21.6 mmol). The resulting mixture was stirred at RT under nitrogen. After 18 h, LC-MS showed only product (m/z=527, [M+Na]$^+$). The reaction mixture was diluted with CH$_2$Cl$_2$, washed with saturated sodium bicarbonate, and washed with brine. The organic phase was dried over magnesium sulfate, filtered, and concentrated. The crude was purified using an ISCO column chromatography on silica gel eluting with 90:10 Hex:EtOAc. The product fractions wre collected, concentrated and the oil was placed in the vacuum oven overnight to removed EtOAc. White solids, tert-butyl 4-chloro-1H-pyrrolo[2,3-b]pyridine-1-carboxylate were formed slowly under vacuum. MS m/z=527 [Dimer+Na]$^+$. Calcd for $C_{12}H_{13}ClN_2O_2$: 252.07.

Step 2. Preparation of 4-(3-Bromopyridin-2-yloxy)benzenamine

3-Bromo-2-chloropyridine (10.3 g, 53.4 mmol), 4-aminophenol (7.00 g, 64.1 mmol), cesium carbonate (34.8 g, 107 mmol), and DMSO (53 ml, 53.4 mmol) were added into a sealed tube. The tube was capped and placed in a preheated oil bath at 130° C. After 16 h, LC-MS showed mainly product. While the reaction mixture was stirring and cooling in ice-water, water was added to induce the product to precipitate out of the solution. A gray solid was obtained, washed with water, dried under vacuum at rt. MS m/z=265 [M+1]$^+$. Calcd for $C_{11}HgBrN_2O$: 263.99.

Step 3. Preparation of 4-(3-(4,4,5,5-Tetramethyl-1,3,2-dioxaborolan-2-yl)pyridin-2-yloxy)benzenamine Into a sealed tube was added 4-(3-bromopyridin-2-yloxy)benzenamine (5.38 g, 20.0 mmol), 1,4-dioxane (101 ml, 20.0 mmol), and potassium acetate (6.00 g, 61.0 mmol). The tube was purged with argon. Then PdCl$_2$(DPPF) (0.700 g, 1.00 mmol) and 4,4,5,5-tetramethyl-2-(4,4,5,5-tetramethyl-1,3,2-dioxaborolan-2-yl)-1,3,2-dioxaborolane (13.0 g, 53.0 mmol) were added. The reaction mixture was stirred for 0.5 h at RT until a deep brown solution was formed. The reaction tube was then placed in a preheated oil bath at 85° C. After 18 h, LC-MS confirmed that the reaction was completed. The reaction was cooled to RT and passed through a pad of celite eluting with the EtOAc, to remove the black impurities. The filtrate was concentrated to give a brown oil, which was placed under vacuum over the weekend. The oil became solid product 4-(3-(4,4,5,5-tetramethyl-1,3,2-dioxaborolan-2-yl)pyridin-2-yloxy)benzenamine. MS m/z=313 [M+1]$^+$. Calcd for $C_{17}H_{21}BN_2O_3$: 312.16.

Step 4. Preparation of tert-Butyl 4-(2-(4-aminophenoxy)pyridin-3-yl)-1H-pyrrolo[2,3-b]pyridine-1-carboxylate In an argon-purged sealed tube, tert-butyl 4-chloro-1H-pyrrolo[2,3-b]pyridine-1-carboxylate (2.77 g, 11.0 mmol), 4-(3-(4,4,5,5-tetramethyl-1,3,2-dioxaborolan-2-yl)pyridin-2-yloxy)benzenamine (5.14 g, 16.5 mmol), sodium carbonate (3.49 g, 32.9 mmol), 1,4-dioxane (32.3 mL), water (11.7 mL) were added. The reaction was stirred at rt for 5 min. Then palladium acetate (0.246 g, 1.10 mmol) and tri-t-butylphosphonium tetrafluororoborate (0.637 g, 2.19 mmol) were added. The tube was sealed and heated to 100° C. After 1 h 45 min, the reaction was monitored and found to be complete. The reaction mixture was cooled to rt and passed through a pad of celite, washing with EtOAc. The filtrate was dried over MgSO$_4$, filtered, and concentrated. The crude product was purified by column chromatography on 120 g silica gel column using DCM and 95:05 DCM:(90:10:1 DCM:MeOH:NH₄OH) to flush out the nonpolar spots, then 80:20 DCM:(90:10:1 DCM:MeOH:NH₄OH) to collect the Boc-product. A viscous brown oil was obtained. After setting the oil at rt for several hours, small amounts of crystalline colonies were formed. The oil was cooled to 0° C. and light yellow solid precipitated out after adding small amounts of hexanes and a little bit of ether in addition to scratching the wall of the flash with a spatula. The light yellow solid was filtered, washed with cold hexanes, and dried under vacuum. This solid, tert-butyl 4-(2-(4-aminophenoxy)pyridin-3-yl)-1H-pyrrolo[2,3-b]pyridine-1-carboxylate was obtained. MS m/z=403 [M+1]⁺. Calcd for $C_{23}H_{22}N_4O_3$: 402.17.

Example 34

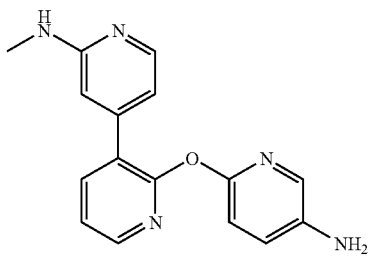

Synthesis of 4-(2-(5-Aminopyridin-2-yloxy)pyridin-3-yl)-N-methylpyridin-2-amine

In a microwave vial, 5-aminopyridin-2-ol (125 mg, 1.14 mmol) was dissolved in DMSO (0.910 mL, 0.228 mmol) and cesium carbonate (445 mg, 1.37 mmol) was added. The vial was capped with a septum and the reaction was stirred at RT for 25 minutes until a paste was formed. Then 4-(2-chloro-pyridin-3-yl)-N-methylpyridin-2-amine (50 mg, 0.23 mmol) was added and the vial was sealed and heated to 180° C. in Personal Chemistry Microwave for 15 min. The mixture was extracted with EtOAc, organic layers were washed with brine, dried over MgSO₄, filtered, and concentrated. The product was purified by column chromatography on silica gel using 60:40 DCM:(90:10:1 DCM:MeOH:NH₄OH to flush out top spots, then 50:50 DCM:(90:10:1 DCM:MeOH:NH₄OH) to collect the product. Green solid, 4-(2-(5-aminopyridin-2-yloxy)pyridin-3-yl)-N-methylpyridin-2-amine was obtained. MS m/z 294 [M+1]⁺. Calcd for $C_{16}H_{15}N_5O$: 293.13.

Example 35

Synthesis of tert-butyl 4-(2-(4-aminophenoxy)pyridin-3-yl)picolinoyl(methyl)carbamate Step 1. Preparation of tert-Butyl 4-chloropicolinoyl(methyl)carbamate The title compound was made following the procedure disclosed in the following references: (a) Marino, J. P.; Rubio, M. B.; Cao, G.; de Dios, A. J. Am. Chem. Soc. 2002, 124, 13398. (b) Diaz, D. D.; Finn, M. G. Org. Lett. 2004, 6, 43. (c) Padwa, A.; Brodney, M. A.; Lynch, S. M.; Rashatasakhon, P.; Wang, Q.; Zhang, H. J. Org. Chem. 2004, 69, 3735). As described, a solution of 4-chloro-N-methylpicolinamide (1.00 g, 5.86 mmol) in THF (11.7 ml, 5.86 mmol) was cooled to −78° C. Then n-BuLi (2.36 mL, 5.86 mmol) in THF was added dropwise at −78° C. The resulting thick yellow supension was stirred at −78° C. for 30 min, then warmed to 0° C., stirred at this temperature for 10 min, and cooled back down to −78° C. Di-tert-butyl dicarbonate (2.30 mg, 10.6 mmol) in 5 mL of THF was added dropwise. The reaction was stirred at −78° C. for 0.5 h and at 0° C. for 20 min, and warmed to RT for 10 min. After 2 days, LC-MS showed 1:1 Prod:SM. The reaction extracted with EtOAc, and the organic layers were washed with brine, dried over MgSO₄, filtered, and concentrated. The product was purified by column chromatography using silica gel eluting with 80:20 Hex:EtOAc. Tert-butyl 4-chloropicolinoyl(methyl)carbamate was collected as light yellow solid. MS m/z=563 [Dimer+Na]⁺. Calcd for $C_{12}H_{15}ClN_2O_3$: 270.08.

Step 2. Preparation of tert-Butyl 4-(2-(4-aminophenoxy)pyridin-3-yl)picolinoyl(methyl)carbamate In an argon-purged sealed tube, tert-butyl 4-chloropicolinoyl(methyl)carbamate (50 mg, 0.19 mmol), 4-(3-(4,4,5,5-tetramethyl-1,3,2-dioxaborolan-2-yl)pyridin-2-yloxy)benzenamine (173 mg, 0.554 mmol), sodium carbonate (59 mg, 0.55 mmol), palladium acetate (4.0 mg, 0.018 mmol), and tri-t-butylphosphonium tetrafluororoborate (11 mg, 0.037 mmol) were added followed by 1,4-dioxane (0.543 mL, 0.185 mmol) and water (0.196 mL, 0.185 mmol). The mixture was stirred at rt for 5 min, then the tube was sealed and placed in a preheated oil bath at 100° C. After 2.5 h, the product was extracted with EtOAc, washed with brine, dried over MgSO₄ and concentrated. The crude product was purified by silica gel chromatography on an ISCO column eluting with 80:20 DCM:(90:10:1 DCM:MeOH:NH₄OH). A brown oil was obtained which was mainly product, tert-butyl 4-(2-(4-aminophenoxy)pyridin-3-yl)picolinoyl(methyl)carbamate. MS m/z=421 [M+1]⁺. Calcd for $C_{23}H_{24}N_4O_4$: 420.18.

Example 36

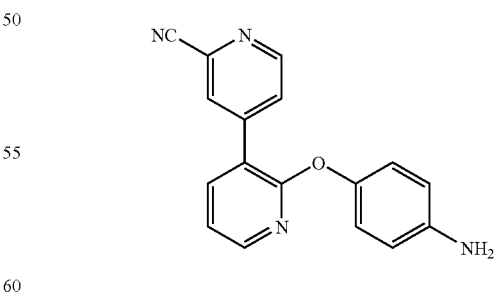

Synthesis of 4-(2-(4-aminophenoxy)pyridin-3-yl)picolinonitrile

In an argon-purged sealed tube, 4-bromopicolinonitrile (500 mg, 2.73 mmol), 4-(3-(4,4,5,5-tetramethyl-1,3,2-dioxaborolan-2-yl)pyridin-2-yloxy)benzenamine (2.56 g, 8.20

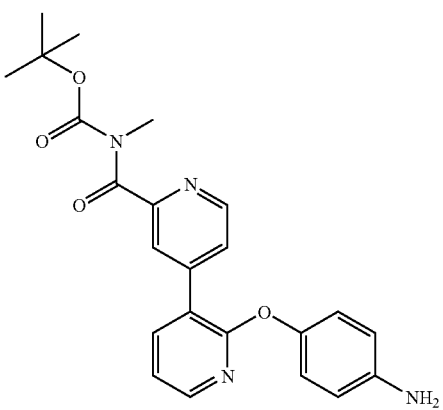

mmol), sodium carbonate (869 mg, 8.20 mmol), palladium acetate (61 mg, 273 μmol), and tri-t-butylphosphonium tetrafluoroborate (159 mg, 546 μmol) were added followed by 1,4-dioxane (8.04 ml, 2.73 mmol) and water (2.90 ml, 2.73 mmol). The reaction was stirred at RT for 5 min. The tube was sealed and placed in a preheated oil bath at 100° C. After 2 h, LC-MS showed product at 1.321 min. The product was extracted with EtOAc, washed with brine, dried over MgSO$_4$ and concentrated. The title compound was purified by silica gel chromatography on an ISCO column eluting with 80:20 DCM:(90:10:1 DCM:MeOH:NH$_4$OH), to obtain an off white solid. MS m/z=289 [M+1]$^+$. Calcd for C$_{17}$H$_{12}$N$_4$O: 288.10.

Example 37

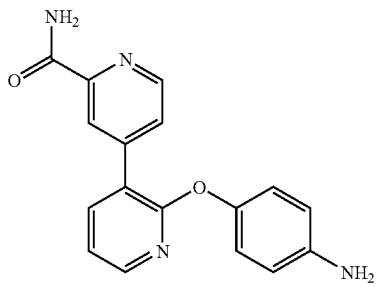

Synthesis of 4-(2-(4-aminophenoxy)pyridin-3-yl)picolinamide

The title compound was prepared according to the reference: Katritzky, A. R.; Pilarski, B.; Urogdi, L. *Synthesis* 1989, 949. As described, a solution of 4-(2-(4-aminophenoxy)pyridin-3-yl)picolinonitrile (764 mg, 2.65 mmol) in DMSO (0.883 mL, 2.65 mmol) was cooled to 0° C. 2.7 mL of 30% Hydrogen peroxide in water was added followed by potassium carbonate (37 mg, 0.27 mmol). The solution became a thick, milky white suspension. The mixture was warmed to rt. After 10 min, 1 mL of H$_2$O$_2$ and 20 mg of K$_2$CO$_3$ were added. After 20 min, LC-MS showed that the reaction was completed. The white solid was filtered off and washed with water. The product was dried under vacuum, to afford 4-(2-(4-aminophenoxy)pyridin-3-yl)picolinamide. MS m/z=307 [M+1]$^+$. Calcd for C$_{17}$H$_{14}$N$_4$O$_2$: 306.11.

Example 38

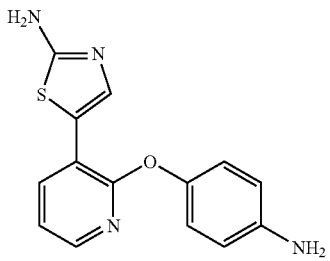

Synthesis of 5-(2-(4-aminophenoxy)pyridin-3-yl)thiazol-2-amine

In a 20 mL sealed tube was added dioxane (1.0 mL), purged solvent with nitrogen for 5 minutes and the tube was sealed. 4-(3-(4,4,5,5-tetramethyl-1,3,2-dioxaborolan-2-yl)pyridin-2-yloxy)benzenamine (0.144 g, 0.462 mmol), 5-bromothiazol-2-amine hydrobromide (0.100 g, 0.385 mmol), 2.0M aqueous sodium carbonate (0.385 mL) was added and the tube was purged flask with nitrogen, and again sealed. Tris(dibenzylideneacetone)dipalladium (0) (0.026 g, 0.029 mmol), tri-t-butylphosphonium tetrafluoroborate (0.025 g, 0.087 mmol) was added and the tube was purged with nitrogen, sealed and heated to 100° C. while stirring for 5 hours. The mixture was cooled to RT, passed through pad of silica, washing with 90:10:1 (CH$_2$Cl$_2$: MeOH: NH$_4$OH). The eluent was concentrated and the product was purified by silica gel chromatography eluting with 0-100% CH$_2$Cl$_2$:MeOH(90: 10)/CH$_2$Cl$_2$. The product fractions were concentrated to yield 5-(2-(4-aminophenoxy)pyridin-3-yl)thiazol-2-amine as tan solid. MS m/z=285[M+1]$^+$. Calc'd for C$_{14}$H$_{12}$N$_4$OS: 284.34.

Example 39

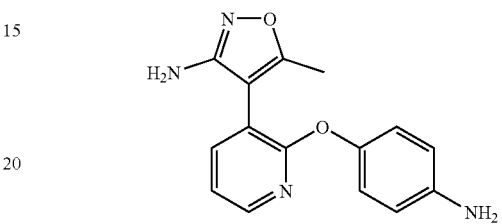

Synthesis of 4-(2-(4-aminophenoxy)pyridin-3-yl)-5-methylisoxazol-3-amine

In a 20 mL sealed tube was added dioxane (11.0 mL), which was purged with nitrogen for 5 minutes and the tube sealed. To this was added 3-amino-4-bromo-5-methylisoxazole (0.100 g, 0.565 mmol), 4-(3-(4,4,5,5-tetramethyl-1,3,2-dioxaborolan-2-yl)pyridin-2-yloxy)benzenamine (0.265 g, 0.847 mmol), 2.0M aqueous sodium carbonate (0.565 mL, 1.13 mmol) and the tube was purged with nitrogen and sealed. To the mixture was added tri-t-butylphosphonium tetrafluoroborate (0.037 g, 0.13 mmol), tris(dibenzylideneacetone)dipalladium (0) (0.039 g, 0.042 mmol) and the tube was purged with nitrogen, sealed and heated to 100° C. with stirring for 5 hours. The mixture was cooled to RT, passed through pad of silica, which was washed with 100% CH$_2$Cl$_2$: MeOH:NHOH (90:10:1)/CH$_2$Cl$_2$. The eluent was concentrated and purified on a Gilson reverse phase chromatography system. The product fractions were extracted into CH$_2$Cl$_2$, washed 1× saturated NaHCO$_3$, 1×H$_2$O, dried with Na$_2$SO$_4$, filtered through fritted funnel and concentrated to yield 4-(2-(4-aminophenoxy)pyridin-3-yl)-5-methylisoxazol-3-amine as light yellow solid. MS m/z=283[M+1]$^+$. Calc'd for C$_{15}$H$_{14}$N$_4$O$_2$: 282.30.

The following intermediates and compounds were made using intermediates made by methods described in the examples above.

Example 40

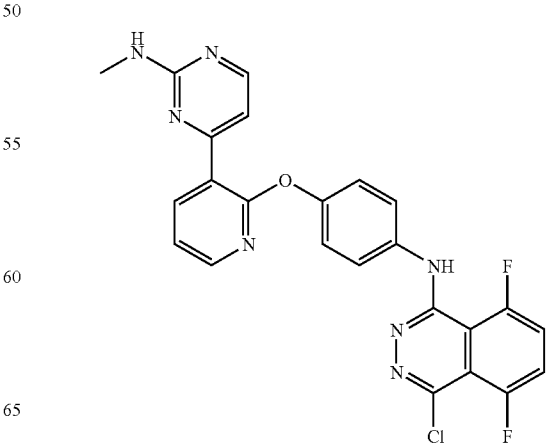

Synthesis of 4-chloro-5,8-difluoro-N-(4-(3-(2-(methylamino)pyrimidin-4-yl)pyridin-2-yloxy)phenyl)phthalazin-1-amine To 4-(2-(4-aminophenoxy)pyridin-3-yl)-N-methylpyrimidin-2-amine (0.100 g, 0.34 mmol) and 1,4-dichloro-5,8-difluorophthalazine (0.096 g, 0.41 mmol) was added tBuOH (1.0 mL). The resulting mixture was heated to 100° C. in a sealed tube for 45 min. The reaction was diluted with diethyl ether and the resulting solids were filtered and triturated with EtOAc. The solids were dried to yield 4-chloro-5,8-difluoro-N-(4-(3-(2-(methylamino)pyrimidin-4-yl)pyridin-2-yloxy)phenyl)phthalazin-1-amine as a dark gray solid. MS m/z=492 [M+H]$^+$. Calc'd for $C_{24}H_{16}ClF_2N_7O$: 491.89.

Example 41

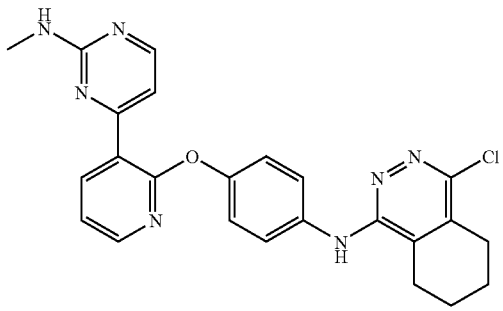

Synthesis of 4-chloro-N-(4-(3-(2-(methylamino)pyrimidin-4-yl)pyridin-2-yloxy)phenyl)-5,6,7,8-tetrahydrophthalazin-1-amine A slurry of 1,4-dichloro-5,6,7,8-tetrahydrophthalazine (1.66 g, 8.18 mmol) and 4-(2-(4-aminophenoxy)pyridin-3-yl)-N-methylpyrimidin-2-amine (2.00 g, 6.82 mmol) in 14 mL 2-BuOH was heated in a sealed pressure vessel to 110° C. The reaction became a thick mass that eventually became a stirring suspension over about 30 min. After 4 h, the reaction was cooled to ambient temperature, and the material was partitioned between 2N NaOH and EtOAc. The aqueous layer was extracted once with EtOAc. The organic layers were dried over anhyd. sodium sulfate, filtered, and concentrated to yield a brown solid. This solid was dissolved in MeOH/MC and adsorbed onto 10 g silica gel, dried, and purified by chromatography (0-100% EtOAc/DCM) to give 4-chloro-N-(4-(3-(2-(methylamino)pyrimidin-4-yl)pyridin-2-yloxy)phenyl)-5,6,7,8-tetrahydrophthalazin-1-amine as an off-white solid. MS m/z=460 [M+H]$^+$. Calc'd for $C_{24}H_{22}ClN_7O$: 459.9.

Example 41-A

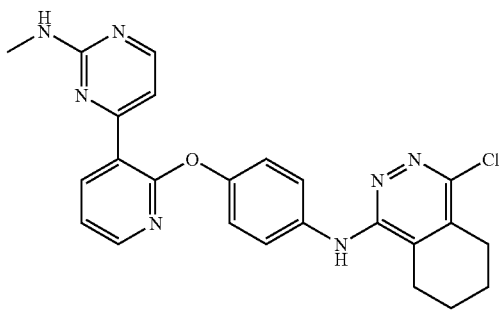

Synthesis of 4-chloro-N-(4-(3-(2-(methylamino)pyrimidin-4-yl)pyridin-2-yloxy)phenyl)-5,6,7,8-tetrahydrophthalazin-1-amine A resealable reaction tube was charged with 1,4-dichloro-5,6,7,8-tetrahydrophthalazine (0.050 g, 0.246 mmol), 4-(2-(4-aminophenoxy)pyridin-3-yl)-N-methylpyrimidin-2-amine (0.072 g, 0.246 mmol), tris(dibenzylideneacetone)dipalladium (0) (0.011 g, 0.012 mmol), 2-dicyclohexylphosphino-2',6'-dimethoxy-1,1'-biphenyl (0.020 g, 0.049 mmol), and sodium tert-butoxide (0.033 g, 0.345 mmol). The vial was purged with nitrogen for several minutes, followed by addition of 0.50 mL of toluene. The vial was capped and heated to 150° C. for 16 h. The reaction mixture was allowed to cool and was filtered through a plug of Celite, rinsing with dichloromethane. The filtrate was concentrated, and the crude material was purified by reverse phase chromatography, Gilson, 5-95% acetonitrile/H$_2$O/0.1% TFA over 14 min. The product-containing fractions were combined, brought to basic pH by addition of 2M Na$_2$CO$_3$ and extracted with dichloromethane. The organic portion was dried with MgSO$_4$, filtered, and concentrated to give 4-chloro-N-(4-(3-(2-(methylamino)pyrimidin-4-yl)pyridin-2-yloxy)phenyl)-5,6,7,8-tetrahydrophthalazin-1-amine as a light brown solid. MS m/z=460 [M+H]$^+$. Calc'd for $C_{24}H_{22}ClN_7O$: 459.93.

Example Method A1

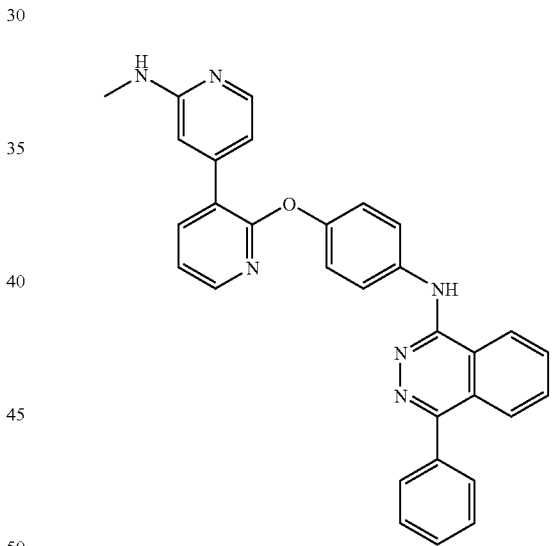

Synthesis of N-(4-(3-(2-(methylamino)pyridin-4-yl)pyridin-2-yloxy)phenyl)-4-phenylphthalazin-1-amine To 4-(2-(4-aminophenoxy)pyridin-3-yl)-N-methylpyrimidin-2-amine (0.070 g, 0.24 mmol) and 1-chloro-4-phenylphthalazine (0.048 g, 0.20 mmol) was added tBuOH (1.0 mL). The resulting mixture was heated at 100° C. in a sealed tube for 16 hours. The reaction was diluted with diethyl ether and saturated sodium carbonate and vigorously shaken. The resulting solids were filtered and washed with water, diethyl ether and air dried to yield N-(4-(3-(2-(methylamino)pyridin-4-yl)pyridin-2-yloxy)phenyl)-4-phenyphthalazin-1-amine as an off-white solid. MS m/z=497 [M+H]$^+$. Calc'd for $C_{31}H_{24}N_6O$: 496.58.

Example Method A2

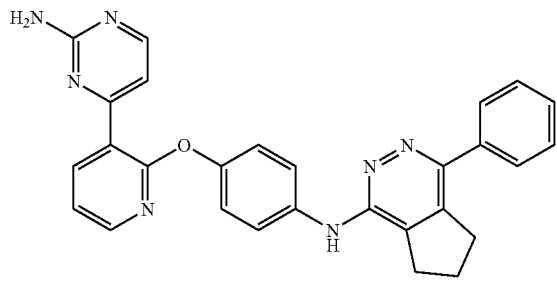

Synthesis of N-(4-(3-(2-aminopyrimidin-4-yl)pyridin-2-yloxy)phenyl)-4-phenyl-6,7-dihydro-5H-cyclopenta[d]pyridazin-1-amine A slurry of 4-(2-(4-aminophenoxy)pyrimidin-3-yl)pyrimidin-2-amine (0.15 g, 0.54 mmol), 1-chloro-4-phenyl-6,7-dihydro-5H-cyclopenta[d]pyridazine (0.113 g, 0.49 mmol), 2,2,2-trifluoroacetic acid (0.11 ml, 1.5 mmol) in 2 mL 2-BuOH was heated in a sealed tube to 110° C. The reaction became a thick orange mixture. After 2-3 h, the reaction was cooled, and partitioned between EtOAc and 2N NaOH. The organic layer was dried over anhyd. sodium sulfate, filtered, and concentrated. The solid was adsorbed onto silica gel from MeOH/DCM, and dried, and purified by silica gel chromatography (0-80% 90/10 DCM/MeOH in DCM to give 80 mg of impure material. This was further purified by reverse-phase HPLC, (ACN/H2O+0.1% TFA) to give N-(4-(3-(2-aminopyrimidin-4-yl)pyridin-2-yloxy)phenyl)-4-phenyl-6,7-dihydro-5H-cyclopenta[d]pyridazin-1-amine as a white solid. MS m/z=474 [M+H]$^+$. Calc'd for $C_{28}H_{23}N_7O$: 473.5.

Example Method A3

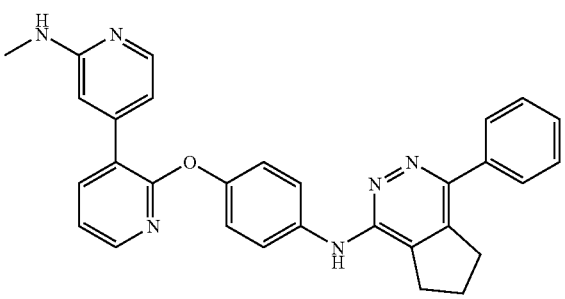

Synthesis of N-(4-(3-(2-(methylamino)pyridin-4-yl)pyridin-2-yloxy)phenyl)-4 phenyl-6,7-dihydro-5H-cyclopenta[d]pyridazin-1-amine A resealable reaction tube was charged with tris(dibenzylideneacetone)dipalladium (0) (0.012 g, 0.013 mmol), 2-dicyclohexylphosphino-2',6'-dimethoxy-1,1'-biphenyl (0.021 g, 0.051 mmol), 4-(2-(4-aminophenoxy)pyridin-3-yl)-N-methylpyridin-2-amine (0.075 g, 0.257 mmol), 1-chloro-4-phenyl-6,7-dihydro-5H-cyclopenta[d]pyridazine (0.059 g, 0.257 mmol), and sodium tert-butoxide (0.035 g, 0.359 mmol). This mixture was purged with nitrogen for several minutes, followed by addition of 0.780 mL of toluene. The vial was capped and heated at 100° C. for 1.5 h. Upon cooling, ethyl acetate was added and a precipitate formed. After filtration and washing with EtOAc, the crude material was purified by ISCO silica gel chromatography (90/10/1 DCM/MeOH/NH4OH, 12 g column), to provide N-(4-(3-(2-(methylamino)pyridin-4-yl)pyridin-2-yloxy)phenyl)-4-phenyl-6,7-dihydro-5H-cyclopenta[d]pyridazin-1-amine as a tan solid. MS m/z=487 [M+H]$^+$. Calc'd for $C_{30}H_{26}N_6O$: 486.57.

Example Method B1

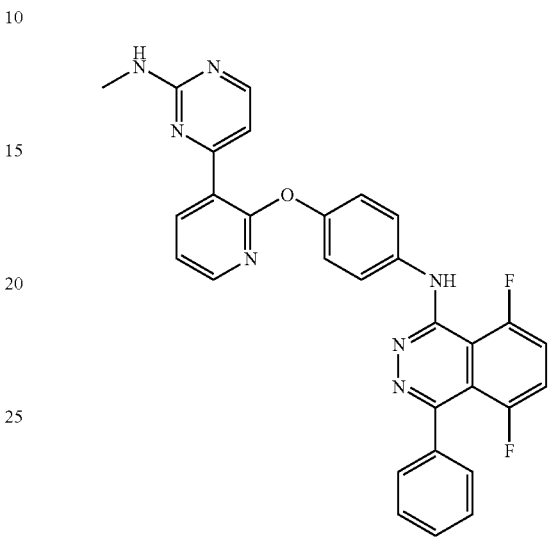

Synthesis of 5,8-difluoro-N-(4-(3-(2-(methylamino)pyrimidin-4-yl)pyridin-2-yloxy)phenyl)-4-phenylphthalazin-1-amine To phenylboronic acid (0.030 g, 0.24 mmol), 1,1'-bis(diphenylphosphino)ferrocene-palladium dichloride (0.0060 g, 0.0081 mmol) and 4-chloro-5,8-difluoro-N-(4-(3-(2-(methylamino)pyrimidin-4-yl)pyridin-2-yloxy)phenyl)phthalazin-1-amine (0.080 g, 0.16 mmol) was added dioxane (0.35 mL) and sodium carbonate (2.0 M, aqueous) (0.16 ml, 0.33 mmol). The resulting mixture was heated to 85° C. in a sealed tube for 60 minutes. The reaction was diluted with EtOAc and water, and the layers were separated and the organic layers were dried over sodium sulfate, filtered and concentrated. The crude was purified by ISCO silica gel chromatography (20-100% EtOAc/hexanes; 40 g column). Concentrated product fractions to yield 5,8-difluoro-N-(4-(3-(2-(methylamino)pyrimidin-4-yl)pyridin-2-yloxy)phenyl)-4-phenylphthalazin-1-amine as an off-white solid. MS m/z=534 [M+H]$^+$. Calc'd for $C_{30}H_{21}F_2N_7O$: 533.54.

Example Method B2

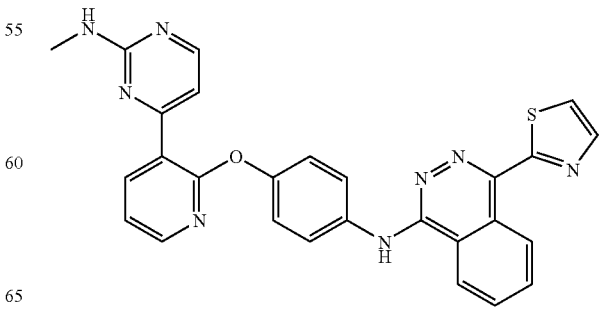

Synthesis of N-(4-(3-(2-(methylamino)pyrimidin-4-yl)pyridin-2-yloxy)phenyl)-4-(thiazol-2-yl)phthalazin-1-amine A resealable pressure tube, purged with argon, was charged with 4-chloro-N-(4-(3-(2-(methylamino)pyrimidin-4-yl)pyridin-2-yloxy)phenyl)phthalazin-1-amine (150 mg, 0.329 mmol), tetrakis(triphenylphosphine)palladium (38 mg, 0.033 mmol), and 2-(tributylstannyl)thiazole (0.207 mL, 0.658 mmol). This mixture was purged with argon for 10 minutes, followed by addition of toluene (1.6 ml, 0.2 M). Tube was sealed and mixture heated to 110° C. overnight. Next day LC/MS shows completion of reaction. The reaction was stopped, cooled to RT and concentrated under reduced pressure to a brown residue. This residue was purified by Gilson reverse phase chromatography (10% to 90% $CH_3CN/H_2O/$ 0.1% TFA). The product-containing fractions were combined, basified by addition of aq. $NaHCO_3$ and extracted with ethyl acetate. The organic portion was dried with $Na_2SO_4$, filtered, and concentrated to afford pure N-(4-(3-(2-(methylamino)pyrimidin-4-yl)pyridin-2-yloxy)phenyl)-4-(thiazol-2-yl)phthalazin-1-amine as a yellow solid. MS m/z=505 $[M+H]^+$. Calc'd for $C_{27}H_{20}N_8OS$: 504.57.

Example Method B3

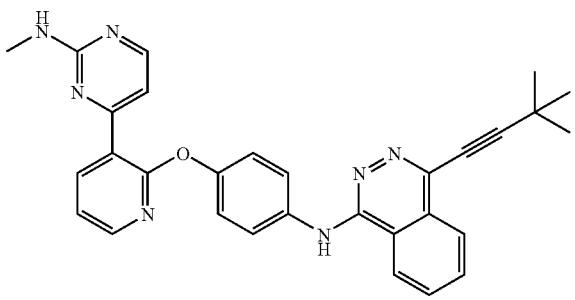

Synthesis of 4-(3,3-dimethylbut-1-ynyl)-N-(4-(3-(2-(methylamino)pyrimidin-4-yl)pyridin-2-yloxy)phenyl)phthalazin-1-amine A resealable pressure tube, purged with argon, was charged with 4-chloro-N-(4-(3-(2-(methylamino)pyrimidin-4-yl)pyridin-2-yloxy)phenyl)phthalazin-1-amine (150 mg, 0.329 mmol), bis(triphenylphosphine)palladium(II) chloride (14 mg, 0.020 mmol), copper(I) iodide (3.8 mg, 0.020 mmol), and 3,3-dimethyl-1-butyne (0.101 mL, 0.823 mmol). This mixture was purged with argon for 10 minutes, followed by addition of acetonitrile (3.3 ml, 0.1 M). The pressure tube was sealed and the mixture inside heated to 90° C. for 16 hrs. The next day, the reaction was stopped, cooled to RT, diluted with dichloromethane and filtered over a plug of celite. Filtrate was concentrated to afford a brown residue, which was purified by Gilson reverse phase chromatography (10% to 90% $CH_3CN/$ $H_2O$/0.1% TFA). The product-containing fractions were combined, basified by addition of aq. $NaHCO_3$ and extracted with ethyl acetate. The organic portion was dried with $Na_2SO_4$, filtered, and concentrated to afford pure 4-(3,3-dimethylbut-1-ynyl)-N-(4-(3-(2-(methylamino)pyrimidin-4-yl) pyridin-2-yloxy)phenyl)phthalazin-1-amine as a yellow solid. MS m/z=502 $[M+H]^+$. Calc'd for $C_{30}H_{27}N_7O$: 501.58.

Example Method B4

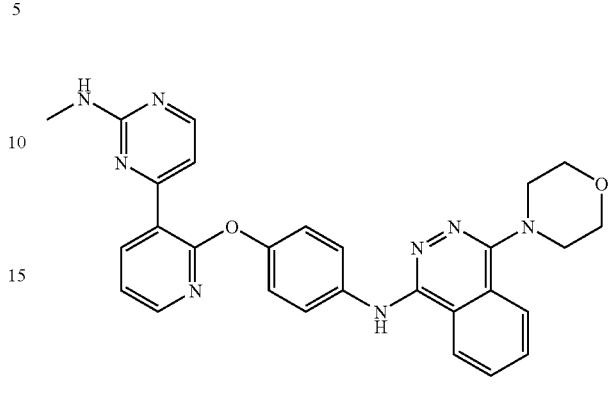

Synthesis of N-(4-(3-(2-(methylamino)pyrimidin-4-yl)pyridin-2-yloxy)phenyl)-4-morpholinophthalazin-1-amine To a resealable tube was added 4-chloro-N-(4-(3-(2-(methylamino)pyrimidin-4-yl)pyridin-2-yloxy)phenyl)phthalazin-1-amine (120 mg, 0.263 mmol) and DMSO (0.526 mL, 0.5 M). To this solution was added morpholine (0.689 mL, 7.89 mmol) and TEA (0.037 mL, 0.26 mmol), and the reaction mixture was heated at 100° C. for 48 h. The reaction was cooled and concentrated under reduced pressure. The crude residue was dissolved in dichloromethane and purified by Biotage column chromatography on silica gel (1%-5% MeOH/Dichloromethane); which provided pure N-(4-(3-(2-(methylamino)pyrimidin-4-yl)pyridin-2-yloxy)phenyl)-4-morpholinophthalazin-1-amine as a yellow solid. MS m/z=507 $[M+H]^+$. Calc'd for $C_{28}H_{26}N_8O_2$: 506.56.

Example Method B5

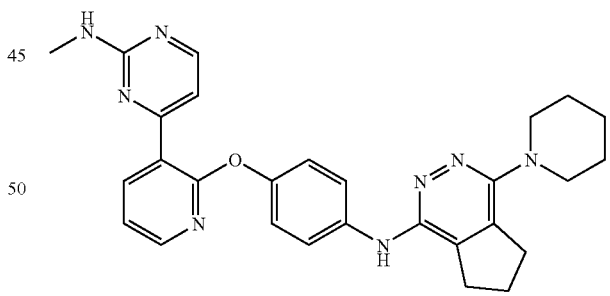

Synthesis of N-(4-(3-(2-(methylamino)pyrimidin-4-yl)pyridin-2-yloxy)phenyl)-4-(piperidin-1-yl)-6,7-dihydro-5H-cyclopenta[d]pyridazin-1-amine To a mixture of 4-chloro-N-(4-(3-(2-(methylamino)pyrimidin-4-yl)pyridin-2-yloxy)phenyl)-6,7-dihydro-5H-cyclopenta[d]pyridazin-1-amine (0.200 g, 0.449 mmol) and piperidine (0.310 ml, 3.14 mmol) in 2 mL 2-butanol was added TFA (0.173 ml, 2.24 mmol). The reaction became slightly homogeneous and then solid. The solid was heated to 125° C. for 24 h, showing a small amount of conversion. The reaction was heated to 135° C. for 3 days. The brown, homogeneous reaction was allowed to cool, and was diluted with 2N NaOH, water, and EtOAc. The organic layer was dried over anhydrous sodium sulfate, filtered, and concentrated. The resulting solid was adsorbed onto 2 g silica gel and purified by chromatography (0-100% 90/10 DCM/MeOH in DCM) to give N-(4-(3-(2-(methylamino)pyrimidin-4-yl)pyridin-2-yloxy)phenyl)-4-(piperidin-1-yl)-6,7-dihydro-5H-cyclopenta[d]pyridazin-1-amine as an off-white solid. MS m/z=495 [M+H]$^+$. Calc'd for $C_{28}H_{30}N_8O$: 494.6.

Example Method B6

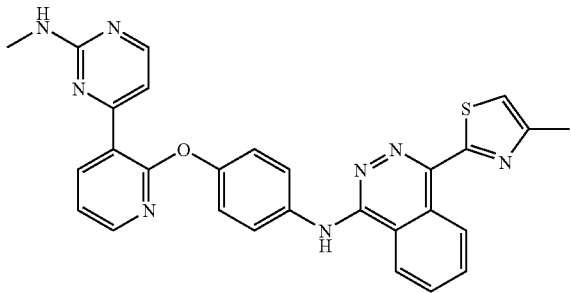

Synthesis of N-(4-(3-(2-(methylamino)pyrimidin-4-yl)pyridin-2-yloxy)phenyl)-4-(4-methylthiazol-2-yl)phthalazin-1-amine A dry 25 ml round bottom flask under nitrogen was charged with 2.5 M nBuLi in Hexanes (0.420 ml, 1.06 mmol); which was diluted with THF (1 ml). This was cooled to −78° C. and 4-methylthiazole (100 mg, 1.01 mmol) dissolved in 2 ml of THF was added slowly via syringe. This was stirred at −78° C. for 2 hours, slowly warmed up to −10° C. and stirred at this temperature for 0.5 hour. Reaction cooled back to −78° C. and 0.5M zinc(II) chloride in THF (3.03 ml, 1.51 mmol) added via syringe. Reaction stirred at −78° C. for 0.5 hour then at room temperature for 1 hour. At this time, 4-chloro-N-(4-(3-(2-(methylamino)pyrimidin-4-yl)pyridin-2-yloxy)phenyl)phthalazin-1-amine (115 mg, 0.250 mmol) and Pd(PPh$_3$)$_4$ (58 mg, 0.05 mmol) added and reaction stirred under nitrogen at 65° C. for 48 hours. Reaction stopped, cooled to room temperature, diluted with aq. EDTA/NaHCO$_3$ solution. This was extracted with ethyl acetate. Organic portion was dried with Na$_2$SO$_4$, filtered, and concentrated to give light brown residue. This was purified by Gilson reverse phase chromatography (10% to 90% CH$_3$CN/H$_2$O/0.1% TFA). The product-containing fractions were combined, basified by addition of Aq. NaHCO$_3$ and extracted with ethyl acetate. The organic portion was dried with Na$_2$SO$_4$, filtered, concentrated to afford pure N-(4-(3-(2-(methylamino)pyrimidin-4-yl)pyridin-2-yloxy)phenyl)-4-(4-methylthiazol-2-yl)phthalazin-1-amine as a yellow solid. MS m/z=519 [M+H]$^+$. Calc'd for $C_{28}H_{22}N_8OS$: 518.59.

Example Method B7

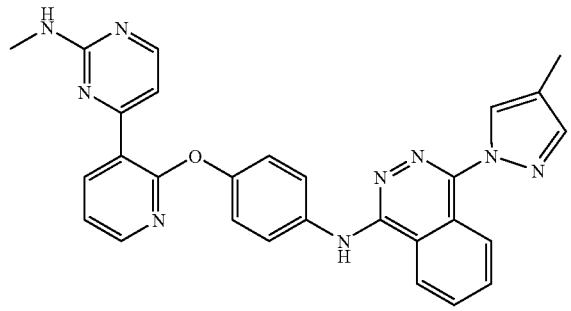

Synthesis of 4-(4-methyl-1H-pyrazol-1-yl)-N-(4-(3-(2-(methylamino)pyrimidin-4-yl)pyridin-2-yloxy)phenyl)phthalazin-1-amine A dry resealable pressure bottle, under nitrogen, was charged with 4-methylpyrazole (0.086 ml, 1.05 mmol). To this was added THF (1.3 ml, 0.2 M) and reaction mixture cooled to 0° C. 60% wt sodium hydride in mineral oil (44.0 mg, 1.10 mmol) was added slowly. Reaction mixture stirred at 0° C. for 15 minutes and 4-chloro-N-(4-(3-(2-(methylamino)pyrimidin-4-yl)pyridin-2-yloxy)phenyl)phthalazin-1-amine (120 mg, 0.260 mmol) added slowly. Reaction kept at 0° C. for 10 minutes, then warmed up slowly to room temperature and placed in an oil bath. Reaction heated to 65° C. and stirred at this temperature overnight. Reaction mixture was cooled to 0° C. and diluted with water, and extracted with EtOAc. The organic layer was collected, dried over Na$_2$SO$_4$ and concentrated to afford an orange residue, which was purified by Gilson reverse phase chromatography (10% to 90% CH$_3$CN/H$_2$O/0.1% TFA). The product-containing fractions were combined, basified by addition of aq. NaHCO$_3$ and extracted with ethyl acetate. The organic portion was dried with Na$_2$SO$_4$, filtered, and concentrated to afford pure 4-(4-methyl-1H-pyrazol-1-yl)-N-(4-(3-(2-(methylamino)pyrimidin-4-yl)pyridin-2-yloxy)phenyl)phthalazin-1-amine as a yellow solid. MS m/z=502 [M+H]$^+$. Calc'd for $C_{28}H_{23}N_9O$: 501.54.

Example Method C

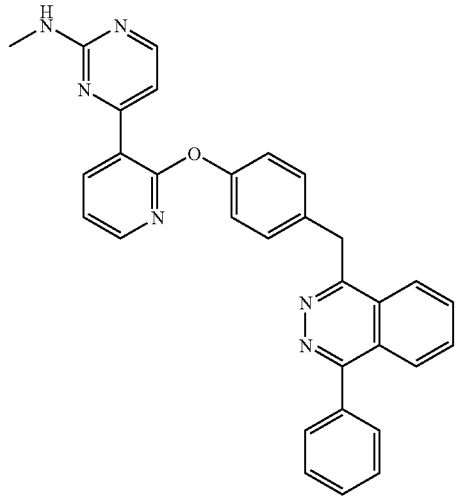

Synthesis of N-methyl-4-(2-(4-((4-phenylphthalazin-1-yl)methyl)phenoxy)pyridin-3-yl)pyrimidin-2-amine To a mixture of 4-(2-chloropyridin-3-yl)-N-methylpyrimidin-2-amine (0.0500 g, 0.23 mmol), 4-((4-phenylphthalazin-1-yl)methyl)phenol (0.071 g, 0.23 mmol) and cesium carbonate (0.15 g, 0.45 mmol) was added DMSO (0.5 mL). The resulting mixture was heated to 130° C. in a sealed tube for 15 hours, then diluted with EtOAc and extracted with saturated sodium bicarbonate. The organic layer was dried over sodium sulfate, filtered and concentrated. The crude concentrate was purified by Gilson reverse-phase HPLC (0.1% TFA in ACN/water; 15-95% ACN; 40 mL/min). Diluted product with DCM and extracted with saturated sodium bicarbonate. Dried organics over sodium sulfate, filtered and concentrated. Lyophilized concentrate to obtained N-methyl-4-(2-(4-((4-phenylphthalazin-1-yl)methyl)phenoxy)pyridin-3-yl)pyrimidin-2-amine as a white solid. MS m/z=497 [M+H]$^+$. Calc'd for $C_{31}H_{24}N_6O$: 496.58.

Example Method D

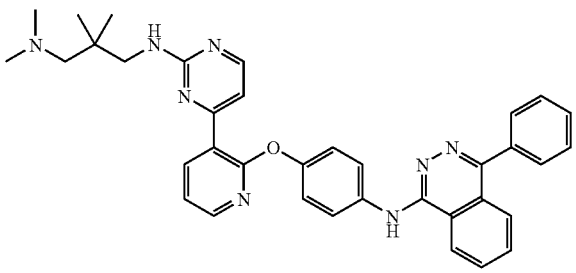

Synthesis of N-(4-(3-(2-(3-(dimethylamino)-2,2-dimethylpropylamino)pyrimidin-4-yl)pyridin-2-yloxy)phenyl)-4-phenylphthalazin-1-amine Step 1. Preparation of 4-(3-(2-(methylthio)pyrimidin-4-yl)pyridin-2-yloxy)benzenamine A resealable pressure bottle was charged with 4-(2-chloropyridin-3-yl)-2-(methylthio)pyrimidine (6.00 g, 25.2 mmol), 4-aminophenol (2.89 g, 26.5 mmol), and cesium carbonate (16.4 g, 50.5 mmol). These reagents were suspended in DMSO (50.5 ml, 0.50 M). The vessel was sealed and heated to 130° C. for 48 hrs. Reaction mixture was allowed to cool to RT, diluted with water and extracted with EtOAc. The organic layer was collected, dried with $Na_2SO_4$, filtered, and concentrated to give a light brown residue, which was purified by silica gel chromatography (ISCO, 10% to 50% Ethyl Acetate/Hexanes) to afford clean material as light yellow solid. MS m/z=311 [M+H]$^+$. Calc'd for $C_{16}H_{14}N_4OS$: 310.37.

Step 2. Preparation of N-(4-(3-(2-(methylthio)pyrimidin-4-yl)pyridin-2-yloxy)phenyl)-4-phenylphthalazin-1-amine A resealable pressure bottle was charged with 4-(3-(2-(methylthio)pyrimidin-4-yl)pyridin-2-yloxy)benzenamine (1.78 g, 5.74 mmol), 1-chloro-4-phenylphthalazine (1.38 g, 5.74 mmol) and suspended in butan-2-ol (28.7 ml, 0.20 M) under nitrogen. The vessel was sealed and heated to 100° C. for 6 hrs. The reaction mixture was allowed to cool to RT, upon which a precipitate formed. The precipitate was filtered and washed with dichloromethane, collected and dried under high vacuum to provide the HCl salt of N-(4-(3-(2-(methylthio)pyrimidin-4-yl)pyridin-2-yloxy)phenyl)-4-phenylphthalazin-1-amine as a light yellow solid. MS m/z=515 [M+H]$^+$. Calc'd for $C_{30}H_{22}N_6OS$: 514.60.

Step 3. Preparation of N-(4-(3-(2-(methylsulfonyl)pyrimidin-4-yl)pyridin-2-yloxy)phenyl)-4-phenylphthalazin-1-amine A 100 ml dried round bottom flask was charged with N-(4-(3-(2-(methylthio)pyrimidin-4-yl)pyridin-2-yloxy)phenyl)-4-phenylphthalazin-1-amine hydrochloride (1.25 g, 2.27 mmol) and sonicated in methanol (20.6 ml, 0.11 M) for 20 minutes. To this was added oxone (4.18 g, 6.81 mmol) and the mixture was stirred at RT for 2 days. The mixture was cooled to 0° C. and basified with aq. $NaHCO_3$. The solids were filtered, washed with water, and dried under high vacuum to provide N-(4-(3-(2-(methylsulfonyl)pyrimidin-4-yl)pyridin-2-yloxy)phenyl)-4-phenylphthalazin-1-amine as a light yellow solid. MS m/z=547 [M+H]$^+$. Calc'd for $C_{30}H_{22}N_6O_3S$: 546.60.

Step 4. Preparation of N-(4-(3-(2-(3-(dimethylamino)-2,2-dimethylpropylamino)pyrimidin-4-yl)pyridin-2-yloxy)phenyl)-4-phenylphthalazin-1-amine A resealable pressure vial was charged with N-(4-(3-(2-(methylsulfonyl)pyrimidin-4-yl)pyridin-2-yloxy)phenyl)-4-phenylphthalazin-1-amine (100 mg, 0.180 mmol) and N1,N1,2,2-tetramethylpropane-1,3-diamine (0.12 ml, 0.73 mmol) and DMSO (1.2 ml, 0.15 M). The reaction vessel was sealed and the mixture was stirred at 70° C. for 16 hrs. The reaction was cooled to RT and diluted with 3 ml of DMSO. The solution was purified by Gilson reverse phase chromatography (10% to 90% $CH_3CN/H_2O/0.1\%$ TFA). The product-containing fractions were combined, basified by addition of aq. $NaHCO_3$ and extracted with ethyl acetate. The organic portion was dried with $Na_2SO_4$, filtered, and concentrated to afford pure N-(4-(3-(2-(3-(dimethylamino)-2,2-dimethylpropylamino)pyrimidin-4-yl)pyridin-2-yloxy)phenyl)-4-phenylphthalazin-1-amine as a yellow solid. MS m/z=597 [M+H]$^+$. Calc'd for $C_{36}H_{36}N_8O$: 596.72.

The following compounds (Examples 42-240) in Table I were made, as noted in table I, by one of the exemplified methods A1, A2, A3, B1, B2, B3, B4, B5, B6, B7, C or D described above. The MS data represent the mass (M+H$^+$) found for that example.

TABLE 1

| Ex. No. | Name | Formula | MS Data | Method |
|---|---|---|---|---|
| 42 | N-methyl-N-(4-((3-(2-(methylamino)-4-pyrimidinyl)-2-pyridinyl)oxy) phenyl)-4-phenyl-1-phthalazinamine | $C_{31}H_{25}N_7O$ | 512 | A1 |
| 43 | N-(4-((3-(2-(methylamino)-4-pyrimidinyl)-2-pyridinyl)oxy) phenyl)-4-(2-pyridinyl)-1-phthalazinamine | $C_{29}H_{22}N_8O$ | 499 | A1 |
| 44 | N-(6-((3-(2-amino-4-pyrimidinyl)-2-pyridinyl)oxy)-3-pyridinyl)-4-(2-pyridinyl)-1-phthalazinamine | $C_{27}H_{19}N_9O$ | 486 | A1 |
| 45 | N-(4-(3,4'-bipyridin-2-yloxy)phenyl)-4-phenyl-1-phthalazinamine | $C_{30}H_{21}N_5O$ | 468 | A1 |
| 46 | N-(3-methyl-4-((3-(2-(methylamino)-4-pyrimidinyl)-2-pyridinyl)oxy) phenyl)-1-isoquinolinamine | $C_{26}H_{22}N_6O$ | 435 | A1 |
| 47 | N-(3-methyl-4-((3-(2-(methylamino)-4-pyrimidinyl)-2-pyridinyl)oxy) phenyl)-2-quinolinamine | $C_{26}H_{22}N_6O$ | 435 | A1 |

TABLE 1-continued

| Ex. No. | Name | Formula | MS Data | Method |
|---|---|---|---|---|
| 48 | 4-(3,5-dimethyl-1H-pyrazol-1-yl)-N-(4-((3-(2-(methylamino)-4-pyrimidinyl)-2-pyridinyl)oxy)phenyl)-1-phthalazinamine | $C_{29}H_{25}N_9O$ | 516 | A1 |
| 49 | N-(4-((3-(2-(methylamino)-4-pyrimidinyl)-2-pyridinyl)oxy) phenyl)-4-(2-thienyl)-1-phthalazinamine | $C_{28}H_{21}N_7OS$ | 504 | A1 |
| 50 | 4-phenyl-N-(4-((3-(4-pyrimidinyl)-2-pyridinyl)oxy)phenyl)-1-phthalazinamine | $C_{29}H_{20}N_6O$ | 469 | A1 |
| 51 | N-(4-((3-(5-fluoro-2-(methylamino)-4-pyrimidinyl)-2-pyridinyl)oxy) phenyl)-4-(1-piperidinyl)-1-phthalazinamine | $C_{29}H_{27}FN_8O$ | 523 | A1 |
| 52 | 2-((4-(((4-(4-fluorophenyl)-1-phthalazinyl)amino)phenyl)oxy)-N-methyl-3,4'-bipyridin-2'-amine | $C_{31}H_{23}FN_6O$ | 515 | A1 |
| 53 | 4-(4-fluorophenyl)-N-(4-((3-(1H-pyrrolo[2,3-b]pyridin-4-yl)-2-pyridinyl)oxy)phenyl)-1-phthalazinamine | $C_{32}H_{21}FN_6O$ | 525 | A1 |
| 54 | 4-(4-fluorophenyl)-N-(4-((3-(1H-pyrazolo[3,4-b]pyridin-4-yl)-2-pyridinyl)oxy)phenyl)-1-phthalazinamine | $C_{31}H_{20}FN_7O$ | 526 | A1 |
| 55 | N-(4-((3-(1H-pyrazolo[3,4-b]pyridin-4-yl)-2-pyridinyl)oxy)phenyl)-4-(2-thienyl)-1-phthalazinamine | $C_{29}H_{19}N_7OS$ | 514 | A1 |
| 56 | 4-phenyl-N-(4-((3-(1H-pyrazolo[3,4-b]pyridin-4-yl)-2-pyridinyl)oxy) phenyl)-1-phthalazinamine | $C_{31}H_{21}N_7O$ | 508 | A1 |
| 57 | 4-(4-methyl-2-thienyl)-N-(4-((3-(1H-pyrazolo[3,4-b]pyridin-4-yl)-2-pyridinyl)oxy)phenyl)-1-phthalazinamine | $C_{30}H_{21}N_7OS$ | 528 | A1 |
| 58 | 4-(1-piperidinyl)-N-(4-((3-(1H-pyrazolo[3,4-b]pyridin-4-yl)-2-pyridinyl)oxy)phenyl)-1-phthalazinamine | $C_{30}H_{26}N_8O$ | 515 | A1 |
| 59 | N-(4-(3-(2-aminopyrimidin-4-yl)pyridin-2-yloxy)phenyl)-4-phenylthieno[3,2-d]pyridazin-7-amine | $C_{27}H_{19}N_7OS$ | 490 | A1 |
| 60 | 2-((5-((4-(4-fluorophenyl)-1-phthalazinyl)amino)-2-pyridinyl) oxy)-N-methyl-3,4'-bipyridin-2'-amine | $C_{30}H_{22}FN_7O$ | 516 | A1 |
| 61 | 4-phenyl-N-(4-((3-(1H-pyrrolo[2,3-b]pyridin-4-yl)-2-pyridinyl)oxy) phenyl)-1-phthalazinamine | $C_{32}H_{22}N_6O$ | 527 | A1 |
| 62 | N-(cyclopropylmethyl)-2-((4-(((4-phenyl-1-phthalazinyl)amino) phenyl)oxy)-3,4'-bipyridin-2'-amine | $C_{34}H_{28}N_6O$ | 557 | A1 |
| 63 | 4-(4-methyl-2-thienyl)-N-(4-((3-(1H-pyrrolo[2,3-b]pyridin-4-yl)-2-pyridinyl)oxy)phenyl)-1-phthalazinamine | $C_{31}H_{22}N_6OS$ | 527 | A1 |
| 64 | 4-(3-chlorophenyl)-N-(4-((3-(1H-pyrrolo[2,3-b]pyridin-4-yl)-2-pyridinyl)oxy)phenyl)-1-phthalazinamine | $C_{32}H_{21}ClN_6O$ | 541 | A1 |
| 65 | N-methyl-2-((4-(((4-phenyl-1-phthalazinyl)amino)phenyl)oxy)-3,4'-bipyridine-2'-carboxamide | $C_{32}H_{24}N_6O_2$ | 525 | A1 |
| 66 | 4-(2-(4-(4-phenylphthalazin-1-ylamino)phenoxy)pyridin-3-yl) picolinamide | $C_{31}H_{22}N_6O_2$ | 511 | A1 |
| 67 | N-(4-((3-(2-amino-4-pyrimidinyl)-2-pyridinyl)oxy)phenyl)-4-(1-piperidinyl)-1-phthalazinamine | $C_{28}H_{26}N_8O$ | 491 | A1 |
| 68 | N-(6-((3-(2-(methylamino)-4-pyrimidinyl)-2-pyridinyl)oxy)-3-pyridinyl)-4-(1-piperidinyl)-1-phthalazinamine | $C_{28}H_{27}N_9O$ | 506 | A1 |
| 69 | N-methyl-2-((4-((4-(1-piperidinyl)-1-phthalazinyl)amino)phenyl)oxy)-3,4'-bipyridin-2'-amine | $C_{30}H_{29}N_7O$ | 504 | A1 |
| 70 | N-methyl-2-((4-((4-(4-methylphenyl)-1-phthalazinyl) amino)phenyl)oxy)-3,4'-bipyridin-2'-amine | $C_{32}H_{26}N_6O$ | 511 | A1 |
| 71 | N-(3-fluoro-4-((3-(2-(methylamino)-4-pyrimidinyl)-2-pyridinyl)oxy)phenyl)-4-(1-piperidinyl)-1-phthalazinamine | $C_{29}H_{27}FN_8O$ | 523 | A1 |
| 72 | N-(6-((3-(2-amino-4-pyrimidinyl)-2-pyridinyl)oxy)-3-pyridinyl)-4-(4-fluorophenyl)-1-phthalazinamine | $C_{28}H_{19}FN_8O$ | 503 | A1 |
| 73 | N-(6-((3-(2-amino-4-pyrimidinyl)-2-pyridinyl)oxy)-3-pyridinyl)-4-(2-thienyl)-1-phthalazinamine | $C_{26}H_{18}N_8OS$ | 491 | A1 |
| 74 | 2-((2-fluoro-4-(((4-(4-fluorophenyl)-1-phthalazinyl)amino)phenyl)oxy)-N-methyl-3,4'-bipyridin-2'-amine | $C_{31}H_{22}F_2N_6O$ | 533 | A1 |
| 75 | N-(4-((3-(4-(methylamino)-1,3,5-triazin-2-yl)-2-pyridinyl) oxy) phenyl)-4-(4-methylphenyl)-1-phthalazinamine | $C_{30}H_{24}N_8O$ | 513 | A1 |

TABLE 1-continued

| Ex. No. | Name | Formula | MS Data | Method |
|---|---|---|---|---|
| 76 | N-(4-((3-(2-amino-4-pyrimidinyl)-2-pyridinyl)oxy)phenyl)-4-(4-fluorophenyl)-1-phthalazinamine | $C_{29}H_{20}FN_7O$ | 502 | A1 |
| 77 | 4-(4-fluorophenyl)-N-(4-((3-(4-(methylamino)-1,3,5-triazin-2-yl)-2-pyridinyl)oxy)phenyl)-1-phthalazinamine | $C_{29}H_{21}FN_8O$ | 517 | A1 |
| 78 | N-(4-((3-(2-amino-4-pyrimidinyl)-2-pyridinyl)oxy)-3-fluorophenyl)-4-(4-fluorophenyl)-1-phthalazinamine | $C_{29}H_{19}F_2N_7O$ | 520 | A1 |
| 79 | N-(4-((5-chloro-3-(2-(methylamino)-4-pyrimidinyl)-2-pyridinyl)oxy) phenyl)-4-(4-fluorophenyl)-1-phthalazinamine | $C_{30}H_{21}ClFN_7O$ | 550 | A1 |
| 80 | N-(4-((3-(4-(methylamino)-1,3,5-triazin-2-yl)-2-pyridinyl) oxy)phenyl)-4-(2-thienyl)-1-phthalazinamine | $C_{27}H_{20}N_8OS$ | 505 | A1 |
| 81 | N-(6-((3-(2-amino-4-pyrimidinyl)-2-pyridinyl)oxy)-3-pyridinyl)-4-phenyl-1-phthalazinamine | $C_{28}H_{20}N_8O$ | 485 | A1 |
| 82 | N-(4-((3-(2-amino-4-pyrimidinyl)-2-pyridinyl)oxy)phenyl)-4-phenyl-1-phthalazinamine | $C_{29}H_{21}N_7O$ | 484 | A1 |
| 83 | 4-(4-fluorophenyl)-N-(4-((3-(4-pyrimidinyl)-2-pyridinyl)oxy)phenyl)-1-phthalazinamine | $C_{29}H_{19}FN_6O$ | 487 | A1 |
| 84 | 4-(4-chlorophenyl)-N-(4-((3-(4-pyrimidinyl)-2-pyridinyl)oxy)phenyl)-1-phthalazinamine | $C_{29}H_{19}ClN_6O$ | 503 | A1 |
| 85 | N-(4-((3-(3-amino-5-methyl-4-isoxazolyl)-2-pyridinyl)oxy)phenyl)-4-phenyl-1-phthalazinamine | $C_{29}H_{22}N_6O_2$ | 487 | A1 |
| 86 | N-(4-(3-(2-(methylamino)pyrimidin-4-yl)pyridin-2-ylthio)phenyl)-4-phenylphthalazin-1-amine | $C_{30}H_{23}N_7S$ | 514 | A1 |
| 87 | 4-(3,4-dimethylphenyl)-N-(4-((3-(2-(methylamino)-4-pyrimidinyl)-2-pyridinyl)oxy)phenyl)-1-phthalazinamine | $C_{32}H_{27}N_7O$ | 526 | A1 |
| 88 | N-(4-((3-(2-(methylamino)-4-pyrimidinyl)-2-pyridinyl)oxy)phenyl)-4-(1-piperidinyl)-1-phthalazinamine | $C_{29}H_{28}N_8O$ | 505 | A1 |
| 89 | 4-chloro-N-(4-((3-(2-(methylamino)-4-pyrimidinyl)-2-pyridinyl)oxy)phenyl)-1-phthalazinamine | $C_{24}H_{18}ClN_7O$ | 456 | A1 |
| 90 | N-(4-((3-(2-amino-4-pyrimidinyl)-2-pyridinyl)oxy)phenyl)-4-(3-thienyl)-1-phthalazinamine | $C_{27}H_{19}N_7OS$ | 490 | A1 |
| 91 | N-methyl-2-((4-((4-(3-thienyl)-1-phthalazinyl)amino)phenyl)oxy)-3,4'-bipyridin-2'-amine | $C_{29}H_{22}N_6OS$ | 503 | A1 |
| 92 | N-(6-((3-(2-(methylamino)-4-pyrimidinyl)-2-pyridinyl)oxy)-3-pyridinyl)-4-(3-thienyl)-1-phthalazinamine | $C_{27}H_{20}N_8OS$ | 505 | A1 |
| 93 | N-(4-((3-(4-pyrimidinyl)-2-pyridinyl) oxy)phenyl)-4-(3-thienyl)-1-phthalazinamine | $C_{27}H_{18}N_6OS$ | 475 | A1 |
| 94 | N-(3-fluoro-4-((3-(2-(methylamino)-4-pyrimidinyl)-2-pyridinyl)oxy)phenyl)-4-phenyl-1-phthalazinamine | $C_{30}H_{22}FN_7O$ | 516 | A1 |
| 95 | N-(4-((3-(2-amino-4-pyrimidinyl)-2-pyridinyl)oxy)phenyl)-4-(4-methyl-2-thienyl)-1-phthalazinamine | $C_{28}H_{21}N_7OS$ | 504 | A1 |
| 96 | N-(4-((3-(4-amino-1,3,5-triazin-2-yl)-2-pyridinyl)oxy)phenyl)-4-(4-fluorophenyl)-1-phthalazinamine | $C_{28}H_{19}FN_8O$ | 503 | A1 |
| 97 | N-(4-((3-(4-amino-1,3,5-triazin-2-yl)-2-pyridinyl)oxy)phenyl)-4-phenyl-1-phthalazinamine | $C_{28}H_{20}N_8O$ | 485 | A1 |
| 98 | N-(4-((3-(2-amino-4-pyrimidinyl)-2-pyridinyl)oxy)phenyl)-4-(4-methyl-1,3-thiazol-2-yl)-1-phthalazinamine | $C_{27}H_{20}N_8OS$ | 505 | A1 |
| 99 | N-(4-(3-(2-aminopyridin-4-yl)pyridin-2-yloxy)phenyl)-4-phenylphthalazin-1-amine | $C_{30}H_{22}N_6O$ | 483 | A1 |
| 100 | 2-((4-((4-(5-methyl-2-thienyl)-1-phthalazinyl)amino)phenyl)oxy)-3,4'-bipyridin-2'-amine | $C_{29}H_{22}N_6OS$ | 503 | A1 |
| 101 | 2-((4-((4-(4-methyl-2-thienyl)-1-phthalazinyl)amino)phenyl)oxy)-3,4'-bipyridin-2'-amine | $C_{29}H_{22}N_6OS$ | 503 | A1 |
| 102 | N-(4-((3-(2-(methylamino)-4-pyrimidinyl)-2-pyridinyl)oxy)phenyl)-6-phenyl-3-pyridazinamine | $C_{26}H_{21}N_7O$ | 448 | A2 |
| 103 | 5-methyl-N-(4-((3-(2-(methylamino)-4-pyrimidinyl)-2-pyridinyl)oxy)phenyl)-6-phenyl-3-pyridazinamine | $C_{27}H_{23}N_7O$ | 462 | A2 |
| 104 | N-methyl-2-((4-((4-phenyl-5,6,7,8-tetrahydro-1-phthalazinyl) amino) phenyl)oxy)-3,4'-bipyridin-2'-amine | $C_{31}H_{28}N_6O$ | 501 | A2 |

TABLE 1-continued

| Ex. No. | Name | Formula | MS Data | Method |
|---|---|---|---|---|
| 105 | N-(6-((3-(2-(methylamino)-4-pyrimidinyl)-2-pyridinyl)oxy)-3-pyridinyl)-4-phenyl-5,6,7,8-tetrahydro-1-phthalazinamine | $C_{29}H_{26}N_8O$ | 503 | A2 |
| 106 | 6-ethyl-N-(4-((3-(2-(methylamino)-4-pyrimidinyl)-2-pyridinyl)oxy) phenyl)-5-phenyl-3-pyridazinamine | $C_{28}H_{25}N_7O$ | 476 | A2 |
| 107 | N-(4-((3-(2-(methylamino)-4-pyrimidinyl)-2-pyridinyl)oxy) phenyl)-6-phenyl-4,5-diazatricyclo[6.2.2.0~2,7~]dodeca-2,4,6-trien-3-amine | $C_{32}H_{29}N_7O$ | 528 | A2 |
| 108 | N-(6-((3-(2-(methylamino)-4-pyrimidinyl)-2-pyridinyl)oxy)-3-pyridinyl)-4-phenyl-6,7-dihydro-5H-cyclopenta[d]pyridazin-1-amine | $C_{28}H_{24}N_8O$ | 489 | A2 |
| 109 | N-(4-((3-(2-(methylamino)-4-pyrimidinyl)-2-pyridinyl)oxy)phenyl)-6-(1-piperidinyl)-3-pyridazinamine | $C_{25}H_{26}N_8O$ | 455 | A2 |
| 110 | 6-(1-azepanyl)-N-(4-((3-(2-(methylamino)-4-pyrimidinyl)-2-pyridinyl)oxy)phenyl)-3-pyridazinamine | $C_{26}H_{28}N_8O$ | 469 | A2 |
| 111 | N-(4-((3-(2-amino-4-pyrimidinyl)-2-pyridinyl)oxy)phenyl)-4-phenyl-5,6,7,8-tetrahydro-1-phthalazinamine | $C_{29}H_{25}N_7O$ | 488 | A2 |
| 112 | N-(3-fluoro-4-((3-(2-(methylamino)-4-pyrimidinyl)-2-pyridinyl)oxy)phenyl)-4-phenyl-5,6,7,8-tetrahydro-1-phthalazinamine | $C_{30}H_{26}FN_7O$ | 520 | A2 |
| 113 | N-(6-((3-(2-amino-4-pyrimidinyl)-2-pyridinyl)oxy)-3-pyridinyl)-4-phenyl-5,6,7,8-tetrahydro-1-phthalazinamine | $C_{28}H_{24}N_8O$ | 489 | A2 |
| 114 | N-(4-((3-(2-amino-4-pyrimidinyl)-2-pyridinyl)oxy)-3-fluorophenyl)-4-phenyl-5,6,7,8-tetrahydro-1-phthalazinamine | $C_{29}H_{24}FN_7O$ | 506 | A2 |
| 115 | N-(6-((3-(2-amino-4-pyrimidinyl)-2-pyridinyl)oxy)-3-pyridinyl)-4-phenyl-6,7-dihydro-5H-cyclopenta[d]pyridazin-1-amine | $C_{27}H_{22}N_8O$ | 475 | A2 |
| 116 | 2-((4-((4-phenyl-6,7-dihydro-5H-cyclopenta[d]pyridazin-1-yl) amino)phenyl)oxy)-3,4'-bipyridin-2'-amine | $C_{29}H_{24}N_6O$ | 473 | A2 |
| 117 | 2-((4-((4-(4-methyl-2-thienyl)-6,7-dihydro-5H-cyclopenta[d] pyridazin-1-yl)amino)phenyl)oxy)-3,4'-bipyridin-2'-amine | $C_{28}H_{24}N_6OS$ | 493 | A2 |
| 118 | N-(4-((3-(2-amino-4-pyrimidinyl)-2-pyridinyl)oxy)phenyl)-5-methyl-6-phenyl-3-pyridazinamine | $C_{26}H_{21}N_7O$ | 448 | A2 |
| 119 | N-(4-((3-(2-amino-4-pyrimidinyl)-2-pyridinyl)oxy)phenyl)-4-methyl-6-phenyl-3-pyridazinamine | $C_{26}H_{21}N_7O$ | 448 | A2 |
| 120 | N-methyl-2-((5-((4-phenyl-6,7-dihydro-5H-cyclopenta[d]pyridazin-1-yl)amino)-2-pyridinyl)oxy)-3,4'-bipyridin-2'-amine | $C_{29}H_{25}N_7O$ | 488 | A3 |
| 121 | N-methyl-4-(2-((4-(2-pyridinylamino) phenyl)oxy)-3-pyridinyl)-2-pyrimidinamine | $C_{21}H_{18}N_6O$ | 371 | A3 |
| 122 | N-(4-((3-(2-(methylamino)-4-pyrimidinyl)-2-pyridinyl)oxy) phenyl)-4-(4-methyl-2-thienyl)-6,7-dihydro-5H-cyclopenta[d] pyridazin-1-amine | $C_{28}H_{25}N_7OS$ | 508 | A3 |
| 123 | N-(4-((3-(2-(methylamino)-4-pyrimidinyl)-2-pyridinyl)oxy) phenyl)-4-phenyl-5,6,7,8-tetrahydro-1-phthalazinamine | $C_{30}H_{27}N_7O$ | 502 | B1 |
| 124 | N-(4-((3-(2-(methylamino)-4-pyrimidinyl)-2-pyridinyl)oxy) phenyl)-4,5-bis((methyloxy)methyl)-6-phenyl-3-pyridazinamine | $C_{30}H_{29}N_7O_3$ | 536 | B1 |
| 125 | N-(4-(3,4'-bipyridin-2-yloxy)phenyl)-4-(4-methyl-2-thienyl)-1-phthalazinamine | $C_{29}H_{21}N_5OS$ | 488 | B1 |
| 126 | N-(4-(3,4'-bipyridin-2-yloxy)phenyl)-4-(5-methyl-2-thienyl)-1-phthalazinamine | $C_{29}H_{21}N_5OS$ | 488 | B1 |
| 127 | N-(4-(3,4'-bipyridin-2-yloxy)phenyl)-4-(5-chloro-2-thienyl)-1-phthalazinamine | $C_{28}H_{18}ClN_5OS$ | 508 | B1 |
| 128 | N-(4-((3-(2-(methylamino)-4-pyrimidinyl)-2-pyridinyl)oxy)phenyl)-4-phenyl-1-isoquinolinamine | $C_{31}H_{24}N_6O$ | 497 | B1 |
| 129 | 4-(4-fluorophenyl)-N-(4-((3-(2-(methylamino)-4-pyrimidinyl)-2-pyridinyl)oxy)phenyl)-1-isoquinolinamine | $C_{31}H_{23}FN_6O$ | 515 | B1 |
| 130 | N-(4-((3-(2-(methylamino)-4-pyrimidinyl)-2-pyridinyl)oxy)phenyl)-4-(2-thienyl)-1-isoquinolinamine | $C_{29}H_{22}N_6OS$ | 503 | B1 |
| 131 | N-(4-((3-(2-(methylamino)-4-pyrimidinyl)-2-pyridinyl)oxy) phenyl)-4-(3-thienyl)-1-isoquinolinamine | $C_{29}H_{22}N_6OS$ | 503 | B1 |

TABLE 1-continued

| Ex. No. | Name | Formula | MS Data | Method |
|---|---|---|---|---|
| 132 | 4-(2-fluorophenyl)-N-(4-((3-(2-(methylamino)-4-pyrimidinyl)-2-pyridinyl)oxy)phenyl)-1-isoquinolinamine | $C_{31}H_{23}FN_6O$ | 515 | B1 |
| 133 | 4-(3,4-dimethylphenyl)-N-(4-((3-(2-(methylamino)-4-pyrimidinyl)-2-pyridinyl)oxy)phenyl)-1-isoquinolinamine | $C_{33}H_{28}N_6O$ | 525 | B1 |
| 134 | N-(4-((3-(2-(methylamino)-4-pyrimidinyl)-2-pyridinyl)oxy) phenyl)-4-(4-methyl-2-thienyl)-1-phthalazinamine | $C_{29}H_{23}N_7OS$ | 518 | B1 |
| 135 | N-(4-((3-(2-(methylamino)-4-pyrimidinyl)-2-pyridinyl)oxy) phenyl)-4-(5-methyl-2-thienyl)-1-phthalazinamine | $C_{29}H_{23}N_7OS$ | 518 | B1 |
| 136 | 4-(3-chloro-4-fluorophenyl)-N-(4-((3-(2-(methylamino)-4-pyrimidinyl)-2-pyridinyl)oxy)phenyl)-1-phthalazinamine | $C_{30}H_{21}ClFN_7O$ | 550 | B1 |
| 137 | 4-(3-chloro-4-fluorophenyl)-N-(4-((3-(2-(methylamino)-4-pyrimidinyl)-2-pyridinyl)oxy)phenyl)-5,6,7,8-tetrahydro-1-phthalazinamine | $C_{30}H_{25}ClFN_7O$ | 554 | B1 |
| 138 | 4-(3,5-bis(trifluoromethyl) phenyl)-N-(4-((3-(2-(methylamino)-4-pyrimidinyl)-2-pyridinyl)oxy)phenyl)-1-phthalazinamine | $C_{32}H_{21}F_6N_7O$ | 634 | B1 |
| 139 | 4-(3,5-bis(trifluoromethyl) phenyl)-N-(4-((3-(2-(methylamino)-4-pyrimidinyl)-2-pyridinyl)oxy)phenyl)-5,6,7,8-tetrahydro-1-phthalazinamine | $C_{32}H_{25}F_6N_7O$ | 638 | B1 |
| 140 | N-(4-((3-(2-(methylamino)-4-pyrimidinyl)-2-pyridinyl)oxy) phenyl)-4-(3-(trifluoromethyl)phenyl)-1-phthalazinamine | $C_{31}H_{22}F_3N_7O$ | 566 | B1 |
| 141 | N-(4-((3-(2-(methylamino)-4-pyrimidinyl)-2-pyridinyl)oxy) phenyl)-4-(3-(trifluoromethyl)phenyl)-5,6,7,8-tetrahydro-1-phthalazinamine | $C_{31}H_{26}F_3N_7O$ | 570 | B1 |
| 142 | N-(4-((3-(2-(methylamino)-4-pyrimidinyl)-2-pyridinyl)oxy) phenyl)-4-(4-(trifluoromethyl)phenyl)-1-phthalazinamine | $C_{31}H_{22}F_3N_7O$ | 566 | B1 |
| 143 | N-(4-((3-(2-(methylamino)-4-pyrimidinyl)-2-pyridinyl)oxy) phenyl)-4-(4-(trifluoromethyl)phenyl)-5,6,7,8-tetrahydro-1-phthalazinamine | $C_{31}H_{26}F_3N_7O$ | 570 | B1 |
| 144 | 4-cyclopropyl-N-(4-((3-(2-(methylamino)-4-pyrimidinyl)-2-pyridinyl)oxy)phenyl)-1-isoquinolinamine | $C_{28}H_{24}N_6O$ | 461 | B1 |
| 145 | 4-(3-chlorophenyl)-N-(4-((3-(2-(methylamino)-4-pyrimidinyl)-2-pyridinyl)oxy)phenyl)-1-isoquinolinamine | $C_{31}H_{23}ClN_6O$ | 531 | B1 |
| 146 | N-(4-((3-(2-(methylamino)-4-pyrimidinyl)-2-pyridinyl)oxy) phenyl)-4-(3-pyridinyl)-1-isoquinolinamine | $C_{30}H_{23}N_7O$ | 498 | B1 |
| 147 | N-(4-((3-(2-amino-4-pyrimidinyl)-2-pyridinyl)oxy)phenyl)-4,5-dimethyl-6-(4-methyl-2-thienyl)-3-pyridazinamine | $C_{26}H_{23}N_7OS$ | 482 | B1 |
| 148 | N-(4-((3-(2-amino-4-pyrimidinyl)-2-pyridinyl)oxy)phenyl)-4,5-dimethyl-6-phenyl-3-pyridazinamine | $C_{27}H_{23}N_7O$ | 462 | B1 |
| 149 | N-(3-fluoro-4-((3-(2-(methylamino)-4-pyrimidinyl)-2-pyridinyl)oxy) phenyl)-4-phenyl-1-isoquinolinamine | $C_{31}H_{23}FN_6O$ | 515 | B1 |
| 150 | N-(4-((3-(2-amino-4-pyrimidinyl)-2-pyridinyl)oxy)phenyl)-4-phenyl-1-isoquinolinamine | $C_{30}H_{22}N_6O$ | 483 | B1 |
| 151 | 4-(4-methyl-2-thienyl)-N-(4-((3-(4-pyrimidinyl)-2-pyridinyl)oxy)phenyl)-1-phthalazinamine | $C_{28}H_{20}N_6OS$ | 489 | B1 |
| 152 | 4-(5-methyl-2-thienyl)-N-(4-((3-(4-pyrimidinyl)-2-pyridinyl)oxy)phenyl)-1-phthalazinamine | $C_{28}H_{20}N_6OS$ | 489 | B1 |
| 153 | 4-(4-methyl-2-thienyl)-N-(4-((3-(4-pyrimidinyl)-2-pyridinyl)oxy)phenyl)-1-phthalazinamine | $C_{28}H_{20}N_6OS$ | 489 | B1 |
| 154 | 4-(5-methyl-2-thienyl)-N-(4-((3-(4-pyrimidinyl)-2-pyridinyl)oxy)phenyl)-1-phthalazmaine | $C_{28}H_{20}N_6OS$ | 489 | B1 |
| 155 | 5-(4-chlorophenyl)-N-(4-((3-(2-(methylamino)-4-pyrimidinyl)-2-pyridinyl)oxy)phenyl)pyrido[2,3-d]pyridazin-8-amine | $C_{29}H_{21}ClN_8O$ | 533 | B1 |
| 156 | N-(4-((3-(2-amino-4-pyrimidinyl)-2-pyridinyl)oxy)phenyl)-6-(4-fluorophenyl)-4,5-dimethyl-3-pyridazinamine | $C_{27}H_{22}FN_7O$ | 480 | B1 |
| 157 | N-(4-((3-(2-(methylamino)-4-pyrimidinyl)-2-pyridinyl)oxy)phenyl)-6-(2-methylphenyl)-3-pyridazinamine | $C_{27}H_{23}N_7O$ | 462 | B1 |
| 158 | N-methyl-2-((5-((4-(4-methyl-2-thienyl)-1-phthalazinyl)amino)-2-pyridinyl)oxy)-3,4'-bipyridin-2'-amine | $C_{29}H_{23}N_7OS$ | 518 | B1 |

TABLE 1-continued

| Ex. No. | Name | Formula | MS Data | Method |
|---|---|---|---|---|
| 159 | 2-((5-((4-(3-chlorophenyl)-1-phthalazinyl)amino)-2-pyridinyl)oxy)-N-methyl-3,4'-bipyridin-2'-amine | $C_{30}H_{22}ClN_7O$ | 532 | B1 |
| 160 | N-(4-((3-(2-(methylamino)-4-pyrimidinyl)-2-pyridinyl)oxy)phenyl)-8-(4-methyl-2-thienyl)pyrazino[2,3-d]pyridazin-5-amine | $C_{27}H_{21}N_9OS$ | 520 | B1 |
| 161 | N-methyl-2-((5-((4-(5-methyl-2-thienyl)-1-phthalazinyl)amino)-2-pyridinyl)oxy)-3,4'-bipyridin-2'-amine | $C_{29}H_{23}N_7OS$ | 518 | B1 |
| 162 | 4-(5-methyl-2-thienyl)-N-(4-((3-(1H-pyrrolo[2,3-b]pyridin-4-yl)-2-pyridinyl)oxy)phenyl)-1-phthalazinamine | $C_{31}H_{22}N_6OS$ | 527 | B1 |
| 163 | 2-((5-((4-(5-chloro-2-thienyl)-1-phthalazinyl)amino)-2-pyridinyl)oxy)-N-methyl-3,4'-bipyridin-2'-amine | $C_{28}H_{20}ClN_7OS$ | 538 | B1 |
| 164 | N-(4-((3-(2-amino-4-pyrimidinyl)-2-pyridinyl)oxy)phenyl)-6,7-difluoro-4-(4-methyl-2-thienyl)-1-phthalazinamine | $C_{28}H_{19}F_2N_7OS$ | 540 | B1 |
| 165 | 4-(4-fluorophenyl)-N-(4-((3-(2-(methylamino)-4-pyrimidinyl)-2-pyridinyl)oxy)phenyl)-1-phthalazinamine | $C_{30}H_{22}FN_7O$ | 516 | B1 |
| 166 | N-(4-((3-(2-(methylamino)-4-pyrimidinyl)-2-pyridinyl)oxy)phenyl)-4-phenyl-1-phthalazinamine | $C_{30}H_{23}N_7O$ | 498 | B1 |
| 167 | N-(4-((3-(2-(methylamino)-4-pyrimidinyl)-2-pyridinyl)oxy)phenyl)-4-(3-thienyl)-1-phthalazinamine | $C_{28}H_{21}N_7OS$ | 504 | B1 |
| 168 | 4-(2-fluorophenyl)-N-(4-((3-(2-(methylamino)-4-pyrimidinyl)-2-pyridinyl)oxy)phenyl)-1-phthalazinamine | $C_{30}H_{22}FN_7O$ | 516 | B1 |
| 169 | N-(4-((3-(2-(methylamino)-4-pyrimidinyl)-2-pyridinyl)oxy)phenyl)-4-(2-(trifluoromethyl)phenyl)-1-phthalazinamine | $C_{31}H_{22}F_3N_7O$ | 566 | B1 |
| 170 | 4-(2-chlorophenyl)-N-(4-((3-(2-(methylamino)-4-pyrimidinyl)-2-pyridinyl)oxy)phenyl)-1-phthalazinamine | $C_{30}H_{22}ClN_7O$ | 532 | B1 |
| 171 | N-(4-((3-(2-(methylamino)-4-pyrimidinyl)-2-pyridinyl)oxy)phenyl)-4-(3-pyridinyl)-1-phthalazinamine | $C_{29}H_{22}N_8O$ | 499 | B1 |
| 172 | N-(4-((3-(2-(methylamino)-4-pyrimidinyl)-2-pyridinyl)oxy)phenyl)-4-(4-pyridinyl)-1-phthalazinamine | $C_{29}H_{22}N_8O$ | 499 | B1 |
| 173 | N-(4-((3-(2-(methylamino)-4-pyrimidinyl)-2-pyridinyl)oxy)phenyl)-4-(3-(methyloxy)phenyl)-5,6,7,8-tetrahydro-1-phthalazinamine | $C_{31}H_{29}N_7O_2$ | 532 | B1 |
| 174 | N-(4-((3-(2-(methylamino)-4-pyrimidinyl)-2-pyridinyl)oxy)phenyl)-4-(4-(methyloxy)phenyl)-5,6,7,8-tetrahydro-1-phthalazinamine | $C_{31}H_{29}N_7O_2$ | 532 | B1 |
| 175 | N-(4-((3-(2-(methylamino)-4-pyrimidinyl)-2-pyridinyl)oxy)phenyl)-4-(3-methylphenyl)-5,6,7,8-tetrahydro-1-phthalazinamine | $C_{31}H_{29}N_7O$ | 516 | B1 |
| 176 | N-(4-((3-(2-(methylamino)-4-pyrimidinyl)-2-pyridinyl)oxy)phenyl)-4-(4-methylphenyl)-5,6,7,8-tetrahydro-1-phthalazinamine | $C_{31}H_{29}N_7O$ | 516 | B1 |
| 177 | N-(4-((3-(2-(methylamino)-4-pyrimidinyl)-2-pyridinyl)oxy)phenyl)-4-(3-thienyl)-5,6,7,8-tetrahydro-1-phthalazinamine | $C_{28}H_{25}N_7OS$ | 508 | B1 |
| 178 | 4-(3,4-dimethylphenyl)-N-(4-((3-(2-(methylamino)-4-pyrimidinyl)-2-pyridinyl)oxy)phenyl)-5,6,7,8-tetrahydro-1-phthalazinamine | $C_{32}H_{31}N_7O$ | 530 | B1 |
| 179 | N-(4-((3-(2-(methylamino)-4-pyrimidinyl)-2-pyridinyl)oxy)phenyl)-4-(3-methylphenyl)-1-phthalazinamine | $C_{31}H_{25}N_7O$ | 512 | B1 |
| 180 | N-(4-((3-(2-(methylamino)-4-pyrimidinyl)-2-pyridinyl)oxy)phenyl)-4-(4-methylphenyl)-1-phthalazinamine | $C_{31}H_{25}N_7O$ | 512 | B1 |
| 181 | 4-(3,4-dimethylphenyl)-N-(3-fluoro-4-((3-(2-(methylamino)-4-pyrimidinyl)-2-pyridinyl)oxy)phenyl)-1-phthalazinamine | $C_{32}H_{26}FN_7O$ | 544 | B1 |
| 182 | N-(4-((3-(2-(methylamino)-4-pyrimidinyl)-2-pyridinyl)oxy)phenyl)-4-phenyl-6,7-dihydro-5H-cyclopenta[d]pyridazin-1-amine | $C_{29}H_{25}N_7O$ | 488 | B1 |
| 183 | 4-(3,5-dimethylphenyl)-N-(4-((3-(2-(methylamino)-4-pyrimidinyl)-2-pyridinyl)oxy)phenyl)-1-phthalazinamine | $C_{32}H_{27}N_7O$ | 526 | B1 |
| 184 | 4-(3,5-dimethylphenyl)-N-(4-((3-(2-(methylamino)-4-pyrimidinyl)-2-pyridinyl)oxy)phenyl)-5,6,7,8-tetrahydro-1-phthalazinamine | $C_{32}H_{31}N_7O$ | 530 | B1 |

TABLE 1-continued

| Ex. No. | Name | Formula | MS Data | Method |
|---|---|---|---|---|
| 185 | N-(4-((3-(2-(methylamino)-4-pyrimidinyl)-2-pyridinyl)oxy)phenyl)-4-(5-methyl-2-thienyl)-5,6,7,8-tetrahydro-1-phthalazinamine | $C_{29}H_{27}N_7OS$ | 522 | B1 |
| 186 | N-(4-((3-(2-(methylamino)-4-pyrimidinyl)-2-pyridinyl)oxy)phenyl)-4-(2-(methyloxy)phenyl)-5,6,7,8-tetrahydro-1-phthalazinamine | $C_{31}H_{29}N_7O_2$ | 532 | B1 |
| 187 | N-(4-((3-(2-(methylamino)-4-pyrimidinyl)-2-pyridinyl)oxy)phenyl)-4-(2-thienyl)-5,6,7,8-tetrahydro-1-phthalazinamine | $C_{28}H_{25}N_7OS$ | 508 | B1 |
| 188 | 3-(4-((4-((3-(2-(methylamino)-4-pyrimidinyl)-2-pyridinyl)oxy)phenyl)amino)-5,6,7,8-tetrahydro-1-phthalazinyl)benzonitrile | $C_{31}H_{26}N_8O$ | 527 | B1 |
| 189 | 4-(4-((4-((3-(2-(methylamino)-4-pyrimidinyl)-2-pyridinyl)oxy)phenyl)amino)-5,6,7,8-tetrahydro-1-phthalazinyl)benzonitrile | $C_{31}H_{26}N_8O$ | 527 | B1 |
| 190 | 4-(4-fluorophenyl)-N-(4-((3-(2-(methylamino)-4-pyrimidinyl)-2-pyridinyl)oxy)phenyl)-5,6,7,8-tetrahydro-1-phthalazinamine | $C_{30}H_{26}FN_7O$ | 520 | B1 |
| 191 | N-(4-((3-(2-(methylamino)-4-pyrimidinyl)-2-pyridinyl)oxy)phenyl)-4-(2-methylphenyl)-1-phthalazinamine | $C_{31}H_{25}N_7O$ | 512 | B1 |
| 192 | N-(4-((3-(2-(methylamino)-4-pyrimidinyl)-2-pyridinyl)oxy)phenyl)-4-(2-methylphenyl)-5,6,7,8-tetrahydro-1-phthalazinamine | $C_{31}H_{29}N_7O$ | 516 | B1 |
| 193 | 4-(3-chlorophenyl)-N-(4-((3-(2-(methylamino)-4-pyrimidinyl)-2-pyridinyl)oxy)phenyl)-5,6,7,8-tetrahydro-1-phthalazinamine | $C_{30}H_{26}ClN_7O$ | 536 | B1 |
| 194 | 4-(4-chlorophenyl)-N-(4-((3-(2-(methylamino)-4-pyrimidinyl)-2-pyridinyl)oxy)phenyl)-5,6,7,8-tetrahydro-1-phthalazinamine | $C_{30}H_{26}ClN_7O$ | 536 | B1 |
| 195 | 4-(3-chlorophenyl)-N-(4-((3-(2-(methylamino)-4-pyrimidinyl)-2-pyridinyl)oxy)phenyl)-1-phthalazinamine | $C_{30}H_{22}ClN_7O$ | 532 | B1 |
| 196 | 4-(4-chlorophenyl)-N-(4-((3-(2-(methylamino)-4-pyrimidinyl)-2-pyridinyl)oxy)phenyl)-1-phthalazinamine | $C_{30}H_{22}ClN_7O$ | 532 | B1 |
| 197 | N-(4-((3-(2-(methylamino)-4-pyrimidinyl)-2-pyridinyl)oxy)phenyl)-4-(4-methyl-2-thienyl)-5,6,7,8-tetrahydro-1-phthalazinamine | $C_{29}H_{27}N_7OS$ | 522 | B1 |
| 198 | 4-(4-fluoro-1-piperidinyl)-N-(4-((3-(2-(methylamino)-4-pyrimidinyl)-2-pyridinyl)oxy)phenyl)-1-phthalazinamine | $C_{29}H_{27}FN_8O$ | 523 | B1 |
| 199 | 4-(3-fluorophenyl)-N-(4-((3-(2-(methylamino)-4-pyrimidinyl)-2-pyridinyl)oxy)phenyl)-1-phthalazinamine | $C_{30}H_{22}FN_7O$ | 516 | B1 |
| 200 | 4-(3,4-difluorophenyl)-N-(4-((3-(2-(methylamino)-4-pyrimidinyl)-2-pyridinyl)oxy)phenyl)-1-phthalazinamine | $C_{30}H_{21}F_2N_7O$ | 534 | B1 |
| 201 | 4-(3,4-dichlorophenyl)-N-(4-((3-(2-(methylamino)-4-pyrimidinyl)-2-pyridinyl)oxy)phenyl)-1-phthalazinamine | $C_{30}H_{21}Cl_2N_7O$ | 566 | B1 |
| 202 | 2-((4-((4-(4-chlorophenyl)-1-phthalazinyl)amino)phenyl)oxy)-N-methyl-3,4'-bipyridin-2'-amine | $C_{31}H_{23}ClN_6O$ | 531 | B1 |
| 203 | 2-((4-((4-(3-chloro-4-fluorophenyl)-1-phthalazinyl)amino)phenyl)oxy)-N-methyl-3,4'-bipyridin-2'-amine | $C_{31}H_{22}ClFN_6O$ | 549 | B1 |
| 204 | 4-(3-chlorophenyl)-N-(4-((3-(2-(methylamino)-4-pyrimidinyl)-2-pyridinyl)oxy)phenyl)-6,7-dihydro-5H-cyclopenta[d]pyridazin-1-amine | $C_{29}H_{24}ClN_7O$ | 522 | B1 |
| 205 | 2-((4-((4-(3-chlorophenyl)-1-phthalazinyl)amino)phenyl)oxy)-N-methyl-3,4'-bipyridin-2'-amine | $C_{31}H_{23}ClN_6O$ | 531 | B1 |
| 206 | 4-(3,4-dichlorophenyl)-N-(4-((3-(2-(methylamino)-4-pyrimidinyl)-2-pyridinyl)oxy)phenyl)-5,6,7,8-tetrahydro-1-phthalazinamine | $C_{30}H_{25}Cl_2N_7O$ | 570 | B1 |
| 207 | N-methyl-2-((4-((4-(4-methyl-2-thienyl)-1-phthalazinyl)amino)phenyl) oxy)-3,4'-bipyridin-2'-amine | $C_{30}H_{24}N_6OS$ | 517 | B1 |
| 208 | N-methyl-2-((4-((4-(5-methyl-2-thienyl)-1-phthalazinyl)amino)phenyl) oxy)-3,4'-bipyridin-2'-amine | $C_{30}H_{24}N_6OS$ | 517 | B1 |
| 209 | 4-(5-chloro-2-thienyl)-N-(4-((3-(2-(methylamino)-4-pyrimidinyl)-2-pyridinyl)oxy)phenyl)-1-phthalazinamine | $C_{28}H_{20}ClN_7OS$ | 538 | B1 |

TABLE 1-continued

| Ex. No. | Name | Formula | MS Data | Method |
|---|---|---|---|---|
| 210 | 4-(5-chloro-2-thienyl)-N-(4-((3-(2-(methylamino)-4-pyrimidinyl)-2-pyridinyl)oxy)phenyl)-5,6,7,8-tetrahydro-1-phthalazinamine | $C_{28}H_{24}ClN_7OS$ | 542 | B1 |
| 211 | N-(4-((3-(2-amino-4-pyrimidinyl)-2-pyridinyl)oxy)phenyl)-4-(3-pyridinyl)-1-phthalazinamine | $C_{28}H_{20}N_8O$ | 485 | B1 |
| 212 | N-(4-((3-(2-amino-4-pyrimidinyl)-2-pyridinyl)oxy)phenyl)-4-(2-thienyl)-1-phthalazinamine | $C_{27}H_{19}N_7OS$ | 490 | B1 |
| 213 | N-(4-((3-(2-amino-4-pyrimidinyl)-2-pyridinyl)oxy)phenyl)-4-(5-methyl-2-thienyl)-1-phthalazinamine | $C_{28}H_{21}N_7OS$ | 504 | B1 |
| 214 | N-(6-((3-(2-amino-4-pyrimidinyl)-2-pyridinyl)oxy)-3-pyridinyl)-4-(4-methyl-2-thienyl)-1-phthalazinamine | $C_{27}H_{20}N_8OS$ | 505 | B1 |
| 215 | N-(4-((3-(2-((3-(4-methyl-1-piperazinyl)propyl)amino)-4-pyrimidinyl)-2-pyridinyl)oxy)phenyl)-4-(4-methyl-2-thienyl)-1-phthalazinamine | $C_{36}H_{37}N_9OS$ | 644 | B1 |
| 216 | 4-(1-benzothien-3-yl)-N-(4-((3-(2-(methylamino)-4-pyrimidinyl)-2-pyridinyl)oxy)phenyl)-1-phthalazinamine | $C_{32}H_{23}N_7OS$ | 554 | B1 |
| 217 | 4-(1-benzothien-2-yl)-N-(4-((3-(2-(methylamino)-4-pyrimidinyl)-2-pyridinyl)oxy)phenyl)-1-phthalazinamine | $C_{32}H_{23}N_7OS$ | 554 | B1 |
| 218 | 4-(1H-indol-5-yl)-N-(4-((3-(2-(methylamino)-4-pyrimidinyl)-2-pyridinyl)oxy)phenyl)-1-phthalazinamine | $C_{32}H_{24}N_8O$ | 537 | B1 |
| 219 | 4-(1-benzothien-3-yl)-N-(4-((3-(2-(methylamino)-4-pyrimidinyl)-2-pyridinyl)oxy)phenyl)-5,6,7,8-tetrahydro-1-phthalazinamine | $C_{32}H_{27}N_7OS$ | 558 | B1 |
| 220 | 4-(1-benzothien-2-yl)-N-(4-((3-(2-(methylamino)-4-pyrimidinyl)-2-pyridinyl)oxy)phenyl)-5,6,7,8-tetrahydro-1-phthalazinamine | $C_{32}H_{27}N_7OS$ | 558 | B1 |
| 221 | 4-(4-chlorophenyl)-N-(4-((3-(2-(methylamino)-4-pyrimidinyl)-2-pyridinyl)oxy)phenyl)-6,7-dihydro-5H-cyclopenta[d]pyridazin-1-amine | $C_{29}H_{24}ClN_7O$ | 522 | B1 |
| 222 | N-(4-((3-(2-(methylamino)-4-pyrimidinyl)-2-pyridinyl)oxy)phenyl)-4-(2-pyridinyl)-5,6,7,8-tetrahydro-1-phthalazinamine | $C_{29}H_{26}N_8O$ | 503 | B2 |
| 223 | 4-(cyclopropylethynyl)-N-(4-((3-(2-(methylamino)-4-pyrimidinyl)-2-pyridinyl)oxy)phenyl)-1-phthalazinamine | $C_{29}H_{23}N_7O$ | 486 | B3 |
| 224 | N-(4-((3-(2-(methylamino)-4-pyrimidinyl)-2-pyridinyl)oxy)phenyl)-4-(4-methyl-1-piperazinyl)-1-phthalazinamine | $C_{29}H_{29}N_9O$ | 520 | B4 |
| 225 | N-(4-((3-(2-(methylamino)-4-pyrimidinyl)-2-pyridinyl)oxy)phenyl)-4-(1-pyrrolidinyl)-1-phthalazinamine | $C_{28}H_{26}N_8O$ | 491 | B4 |
| 226 | 4-(1-azepanyl)-N-(4-((3-(2-(methylamino)-4-pyrimidinyl)-2-pyridinyl)oxy)phenyl)-1-phthalazinamine | $C_{30}H_{30}N_8O$ | 519 | B4 |
| 227 | N-(4-((3-(2-(methylamino)-4-pyrimidinyl)-2-pyridinyl)oxy)phenyl)-4-(3-methyl-1-piperidinyl)-1-phthalazinamine | $C_{30}H_{30}N_8O$ | 519 | B4 |
| 228 | N-(4-((3-(2-amino-4-pyrimidinyl)-2-pyridinyl)oxy)phenyl)-4-(4-methyl-1-piperazinyl)-1-phthalazinamine | $C_{28}H_{27}N_9O$ | 506 | B4 |
| 229 | 4-(4-ethyl-1-piperazinyl)-N-(4-((3-(2-(methylamino)-4-pyrimidinyl)-2-pyridinyl)oxy)phenyl)-1-phthalazinamine | $C_{30}H_{31}N_9O$ | 534 | B4 |
| 230 | N-(4-((3-(2-(methylamino)-4-pyrimidinyl)-2-pyridinyl)oxy)phenyl)-4-(4-(1-methylethyl)-1-piperazinyl)-1-phthalazinamine | $C_{31}H_{33}N_9O$ | 548 | B4 |
| 231 | N-(4-((3-(2-(methylamino)-4-pyrimidinyl)-2-pyridinyl)oxy)phenyl)-4-(1-piperidinyl)-5,6,7,8-tetrahydro-1-phthalazinamine | $C_{29}H_{32}N_8O$ | 509 | B5 |
| 232 | N-(4-((3-(2-(methylamino)-4-pyrimidinyl)-2-pyridinyl)oxy)phenyl)-4-(5-methyl-1,3-thiazol-2-yl)-1-phthalazinamine | $C_{28}H_{22}N_8OS$ | 519 | B6 |
| 233 | N-(4-((3-(2-amino-4-pyrimidinyl)-2-pyridinyl)oxy)phenyl)-4-(5-methyl-1,3-thiazol-2-yl)-1-phthalazinamine | $C_{27}H_{20}N_8OS$ | 505 | B6 |
| 234 | 4-(1H-imidazol-1-yl)-N-(4-((3-(2-(methylamino)-4-pyrimidinyl)-2-pyridinyl)oxy)phenyl)-1-phthalazinamine | $C_{27}H_{21}N_9O$ | 488 | B7 |

TABLE 1-continued

| Ex. No. | Name | Formula | MS Data | Method |
|---|---|---|---|---|
| 235 | N-(4-((3-(2-(methylamino)-4-pyrimidinyl)-2-pyridinyl)oxy)phenyl)-4-(1H-pyrazol-1-yl)-1-phthalazinamine | $C_{27}H_{21}N_9O$ | 488 | B7 |
| 236 | N-(4-((3-(2-amino-4-pyrimidinyl)-2-pyridinyl)oxy)phenyl)-4-(4-methyl-1H-pyrazol-1-yl)-1-phthalazinamine | $C_{27}H_{21}N_9O$ | 488 | B7 |
| 237 | N-methyl-2-((4-((4-phenyl-1-phthalazinyl)methyl)phenyl)oxy)-3,4'-bipyridin-2'-amine | $C_{32}H_{25}N_5O$ | 496 | C |
| 238 | N-(4-((3-(5-amino-1H-pyrazol-4-yl)-2-pyridinyl)oxy)phenyl)-4-phenyl-1-phthalazinamine | $C_{28}H_{21}N_7O$ | 472 | C |
| 239 | N-(4-(3-(2-(2-(dimethylamino)ethylamino)pyrimidin-4-yl)pyridin-2-yloxy)phenyl)-4-phenylphthalazin-1-amine | $C_{33}H_{30}N_8O$ | 555 | D |
| 240 | N-(4-(3-(2-(3-(diethylamino)propylamino)pyrimidin-4-yl)pyridin-2-yloxy)phenyl)-4-phenylphthalazin-1-amine | $C_{36}H_{36}N_8O$ | 597 | D |

Example Method E

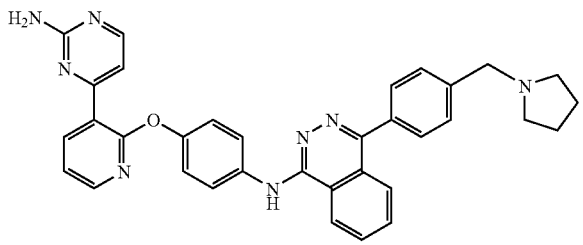

Synthesis of N-(4-(3-(2-aminopyrimidin-4-yl)pyridin-2-yloxy)phenyl)-4-(4-(pyrrolidin-1-ylmethyl)phenyl)phthalazin-1-amine A 25 mL RBF under nitrogen was charged with 4-(4-(4-(3-(2-aminopyrimidin-4-yl)pyridin-2-yloxy)phenylamino)phthalazin-1-yl)benzaldehyde (90 mg, 0.18 mmol), pyrrolidine (125 mg, 1.8 mmol) and MeOH (3.5 mL, 0.05 M). HOAc was added (0.02 mL, 0.36 mmol) and the reaction mixture was stirred at RT for 2 hrs. The reaction mixture was cooled to 0° C. and sodium triacetoxyborohydride (186 mg, 0.90 mmol) was added portionwise. The mixture was stirred at RT overnight, then cooled to 0° C. and basified with aqueous sodium bicarbonate and the product was extracted into DCM. The organic layers were collected, dried over sodium sulfate, filtered and concentrated to give brown residue. The crude residue was purified by Gilson reverse phase liquid chromatography (5%-85% $CH_3CN/H_2O+0.1\%$ TFA). Product-containing fractions were combined and basified with aqueous sodium bicarbonate. This was extracted with EtOAc, dried over sodium sulfate, filtered, concentrated under reduced pressure, and dried under high vacuum to afford N-(4-(3-(2-aminopyrimidin-4-yl)pyridin-2-yloxy)phenyl)-4-(4-(pyrrolidin-1-ylmethyl)phenyl)phthalazin-1-amine as a light yellow solid. MS m/z=567 [M+H]$^+$. Calc'd for $C_{34}H_{30}N_8O$: 566.7.

Example Method F

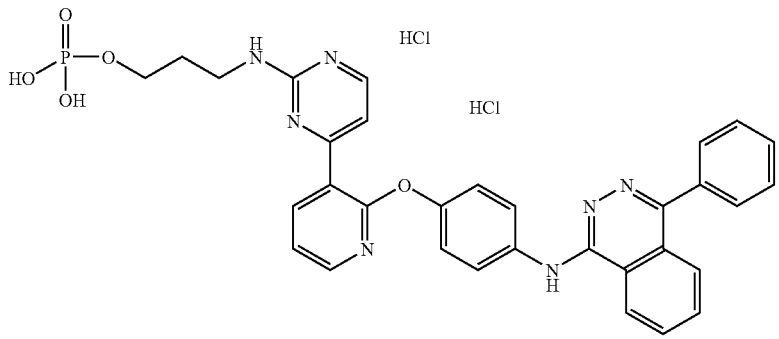

Synthesis of 3-(4-(2-(4-(4-phenylphthalazin-1-ylamino)phenoxy)pyridin-3-yl)pyrimidin-2-ylamino)propyl dihydrogen phosphate dihydrochloride Step 1: Preparation of di-tert-butyl 3-(4-(2-(4-(4-phenylphthalazin-1-ylamino)phenoxy)pyridin-3-yl)pyrimidin-2-ylamino)propyl phosphate A 15 mL RBF under nitrogen was charged with 3-(4-(2-(4-(4-phenylphthalazin-1-ylamino)phenoxy)pyridin-3-yl)pyrimidin-2-ylamino)propan-1-ol (130 mg, 0.24 mmol) in DMA (1.2 mL, 0.24 mmol). To this was added di-tert-butyl diethylphosphoramidite (0.14 mL, 0.57 mmol) and 1H-tetrazole (1.1 mL, 0.49 mmol). The reaction mixture was stirred at RT for 2 hrs, then cooled to −5° C. and hydrogen peroxide -30 wt. % in water (0.05 mL, 0.51 mmol) added slowly via syringe. The reaction was warmed up to RT and stirred for 2 hrs. The reaction was cooled back to −5° C. and quenched with saturated aqueous solution of sodium thiosulfate. The product was extracted into EtOAc, and the organic layer was collected, dried over sodium sulfate and concentrated to afford a crude yellow residue. The residue was purified by ISCO silica gel chromatography (2-5% MeOH/DCM), and the purified fractions were further purified by Gilson RPLC in system (15%-85% CH$_3$CN/H$_2$O/0.1% TFA) to afford di-tert-butyl 3-(4-(2-(4-(4-phenylphthalazin-1-ylamino)phenoxy)pyridin-3-yl)pyrimidin-2-ylamino)propyl phosphate. MS m/z=734 [M+H]$^+$. Calc'd for C$_{40}$H$_{44}$N$_7$O$_5$P: 733.8.

Step 2: Preparation of 3-(4-(2-(4-(4-phenylphthalazin-1-ylamino)phenoxy)pyridin-3-yl)pyrimidin-2-ylamino)propyl dihydrogen phosphate dihydrochloride To a solution of di-tert-butyl 3-(4-(2-(4-(4-phenylphthalazin-1-ylamino)phenoxy)pyridin-3-yl)pyrimidin-2-ylamino)propyl phosphate (95 mg, 0.13 mmol) in 1,4-dioxane (3.7 ml, 0.04 M) under nitrogen was added 4M HCl in Dioxane (0.23 mL, 0.91 mmol). Reaction stirred at RT for 18 hrs. The mixture appeared heterogeneous, and the solids were filtered, washed with dioxane and ether, and dried under reduced pressure to afford 3-(4-(2-(4-(4-phenylphthalazin-1-ylamino)phenoxy)pyridin-3-yl)pyrimidin-2-ylamino)propyl dihydrogen phosphate dihydrochloride as a yellow solid. Mass of the title compound was obtained as the free base: MS m/z=622 [M+H]$^+$. Calc'd for C$_{32}$H$_{30}$Cl$_2$N$_7$O$_5$P: 621.6.

The following additional exemplary compounds should further assist in understanding the scope of the invention.

Example 241

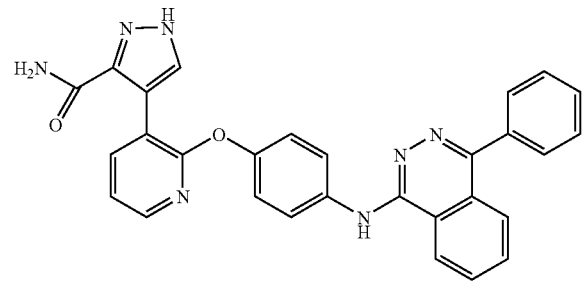

Synthesis of 4-(2-(4-(4-phenylphthalazin-1-ylamino)phenoxy)pyridin-3-yl)-1H-pyrazole-3-carboxamide Step 1. Preparation of tert-butyl 4-bromo-3-cyano-1H-pyrazole-1-carboxylate In a 20 mL sealed tube was dissolved 4-bromo-1 h-pyrazole-3-carbonitrile (1.0 g, 5.8 mmol) in THF (10 mL). The mixture was cooled to 0° C., upon which NaH (60% in mineral oil; 0.42 g, 12 mmol) was added, and stirred for 5 minutes. To the mixture was added di-tert-butyl dicarbonate (2.5 g, 12 mmol) and the mixture was stirred at 0° C. for 3 h, then quenched with water, extracted into EtOAc, and the organic layer was washed 1×H$_2$O, 1× saturated NaCl, dried with Na$_2$SO$_4$, filtered through fritted funnel and concentrated. The crude material was purified by normal phase silica gel chromatography using 10-100% EtOAc/Hexanes. The product was concentrated to yield tert-butyl 4-bromo-3-cyano-1H-pyrazole-1-carboxylate as light yellow solid.

Step 2. Preparation of 4-(2-(4-aminophenoxy)pyridin-3-yl)-1H-pyrazole-3-carbonitrile Dioxane (2.0 mL) was added to a 20 mL sealed tube. The tube was purged with nitrogen for 5 minutes. To this was added tert-butyl 4-bromo-3-cyano-1H-pyrazole-1-carboxylate (0.100 g, 0.368 mmol), 4-(3-(4,4,5,5-tetramethyl-1,3,2-dioxaborolan-2-yl)pyridin-2-yloxy)benzenamine (0.229 g, 0.735 mmol), and sodium carbonate (2.0 M in water) (0.667 mL). Palladium(II) acetate (0.008 g, 0.037 mmol) and tri-t-butylphosphonium tetrafluoroborate (0.021 g, 0.074 mmol) was added and the tube was purged with nitrogen, sealed, and heated to 100° C. for 17 hours. The reaction was cooled to RT, concentrated and passed through a pad of silica with the aid of 90:10:1 (CH$_2$Cl$_2$:MeOH:NH$_4$OH). The eluent was concentrated to yield 4-(2-(4-aminophenoxy)pyridin-3-yl)-1H-pyrazole-3-carbonitrile as light brown solid. MS m/z=278 [M+1]$^+$. Calc'd for C$_{15}$H$_{11}$N$_5$O: 277.28.

Step 3. Preparation of 4-(2-(4-(4-phenylphthalazin-1-ylamino)phenoxy)pyridin-3-yl)-1H-pyrazole-3-carbonitrile In a 20-mL sealed tube was dissolved 4-(2-(4-aminophenoxy)pyridin-3-yl)-1H-pyrazole-3-carbonitrile (0.120 g, 0.433 mmol) in t-BuOH (1.0 mL). Then 1-chloro-4-phenylphthalazine (0.104 g, 0.433 mmol) was added and the mixture was stirred at 100° C. for 3 days. The reaction was cooled to RT, concentrated and purified on a Gilson reverse phase chromatography system. The title compound was extracted into CH$_2$Cl$_2$ washed 1× saturated NaHCO$_3$, 1×H$_2$O, dried over Na$_2$SO$_4$, filtered through fritted funnel and concentrated. The title compound was further purified by silica gel chromatography using 10-100% EtOAc/Hexanes to afford 4-(2-(4-(4-phenylphthalazin-1-ylamino)phenoxy)pyridin-3-yl)-1H-pyrazole-3-carbonitrile as light yellow solid. MS m/z=482 [M+1]$^+$. Calc'd for C$_{29}$H$_{19}$N$_7$O: 481.51.

Step 4. Preparation of 4-(2-(4-(4-phenylphthalazin-1-ylamino)phenoxy)pyridin-3-yl)-1H-pyrazole-3-carboxamide In a 20-mL sealed tube was dissolved 4-(2-(4-(4-phenylphthalazin-1-ylamino)phenoxy)pyridin-3-yl)-1H-pyrazole-3-carbonitrile (0.070 g, 0.145 mmol) in DMSO (1.0 mL). To this was added potassium carbonate (0.024 g, 0.174 mmol) and hydrogen peroxide (0.445 mL, 14.5 mmol) and the mixture was stirred at 20° C. for 3 days and quenched with water. The product was extracted into EtOAc, washed 1× saturated NaHCO$_3$, 1×H$_2$O, dried over Na$_2$SO$_4$, filtered through fritted funnel and concentrated. The title compound was purified using a Gilson reverse phase liquid chromatography system. The product fractions were extracted into CH$_2$Cl$_2$. The organic layers were washed organics 1× saturated NaHCO$_3$, 1×H$_2$O, dried with Na$_2$SO$_4$, filtered through fritted funnel and concentrated to yield 4-(2-(4-(4-phenylphthalazin-1-ylamino)phenoxy)pyridin-3-yl)-1H-pyrazole-3-carboxamide as light yellow solid. MS m/z=500 [M+1]$^+$. Calc'd for C$_{29}$H$_{21}$N$_7$O$_2$: 499.52.

Example 242

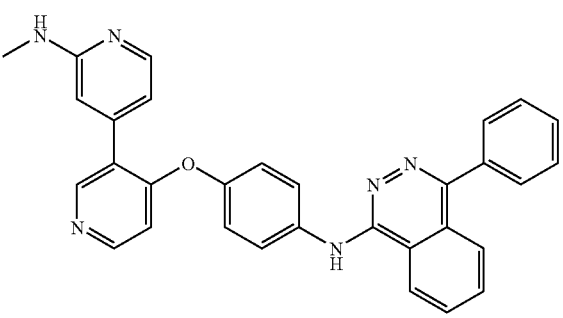

Synthesis of N-(4-(3-(2-(methylamino)pyridin-4-yl)pyridin-4-yloxy)phenyl)-4-phenylphthalazin-1-amine Step 1. Preparation of 4-(4-phenylphthalazin-1-ylamino)phenol A pressure bottle was charged with 4-aminophenol (0.453 g, 0.416 mmol), 1-chloro-4-phenylphthalazine (1.00 g, 0.416 mmol) and 16.8 mL of benzene. The bottle was sealed and heated to 100° C. for 25 h. The reaction mixture was concentrated. The crude material was dissolved in methanol and was purified by Gilson reverse phase liquid chromatography, 5-75% ACN/H$_2$O/0.1% TFA over 14 min. The product-containing fractions were combined, brought to basic pH by addition of 1M NaHCO$_3$, and extracted with dichloromethane. The organic portion was dried with MgSO$_4$, filtered and concentrated to provide 4-(4-phenylphthalazin-1-ylamino)phenol as a yellow solid. MS m/z=314 [M+H]$^+$. Calc'd for C$_{20}$H$_{15}$N$_3$O: 313.35.

Step 2. Preparation of N-(4-(3-bromopyridin-4-yloxyy)phenyl)-4-phenylphthalazin-1-amine A resealable reaction tube was charged with cesium carbonate (0.873 g, 0.268 mmol), 3-bromo-4-chloropyridine hydrochloride (0.205 g, 0.894 mmol) and 4-(4-phenylphthalazin-1-ylamino)phenol (0.280 g, 0.894 mmol) and purged with nitrogen for several minutes. 1.8 mL of DMSO was added, the tube was sealed, and the reaction mixture was heated to 130° C. for 3 h. Upon cooling the mixture was diluted with EtOAc and washed with water. The aqueous portion was extracted with EtOAc, and the combined organic portions were dried with MgSO$_4$ and concentrated. N-(4-(3-bromopyridin-4-yloxy)phenyl)-4-phenylphthalazin-1-amine was isolated as an orange solid. MS m/z=470 [M+H]$^+$. Calc'd for C$_{25}$H$_{17}$BrN$_4$O: 469.33.

Step 3. Preparation of N-(4-(3-(2-fluoropyridin-4-yl)pyridin-4-yloxy)phenyl)-4-phenylphthalazin-1-amine A resealable reaction tube was charged with tri-tert-butylphosphonium tetrafluoroborate (0.024 g, 0.082 mmol), palladium (II) acetate (0.009 g, 0.041 mmol), 2-fluoropyridine-4-boronic acid (0.086 g, 0.614 mmol) and N-(4-(3-bromopyridin-4-yloxy)phenyl)-4-phenylphthalazin-1-amine (0.192 mg, 0.409 mmol) and was purged with nitrogen for several minutes. 1.2 mL of dioxane and 2.0 M aqueous sodium carbonate (0.614 mL, 0.123 mmol) were added, the tube was sealed, and the reaction mixture was heated to 100° C. for 48 h. The mixture was diluted with EtOAc and washed with water. The organic portion was dried with MgSO$_4$ and concentrated. Purification by Gilson reverse phase liquid chromatography (5-70% ACN/water/0.1% TFA over 14 min) provided N-(4-(3-(2-fluoropyridin-4-yl)pyridin-4-yloxy)phenyl)-4-phenylphthalazin-1-amine as a mixture with the hydrodehalogenation product of N-(4-(3-bromopyridin-4-yloxy)phenyl)-4-phenylphthalazin-1-amine.

Step 4. Preparation of N-(4-(3-(2-(methylamino)pyridin-4-yl)pyridin-4-yloxy)phenyl)-4-phenylphthalazin-1-amine A high pressure steel bomb was charged with N-(4-(3-(2-fluoropyridin-4-yl)pyridin-4-yloxy)phenyl)-4-phenylphthalazin-1-amine (0.115 g, 0.237 mmol), potassium carbonate (0.049 g, 0.355 mol) and 3.0 mL of THF. The bomb was sealed, cooled to 0° C. and pressurized with methylamine gas. The reaction mixture was allowed to warm to RT, and heated at 80° C. for 45 h. Upon cooling, the reaction mixture was filtered through a fritted funnel, washed with MeOH, and concentrated. This mixture was purified by silica gel chromatography, (ISCO, 40 g column 0-10% MeOH/dichloromethane) to provide N-(4-(3-(2-(methylamino)pyridin-4-yl)pyridin-4-yloxy)phenyl)-4-phenylphthalazin-1-amine as a light yellow solid. MS m/z=497 [M+H]$^+$. Calc'd for C$_{31}$H$_{24}$N$_6$O: 496.56.

Example 243

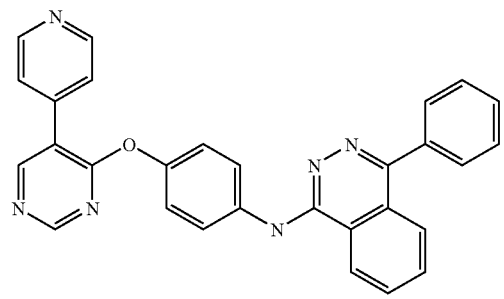

Synthesis of 4-phenyl-N-(4-(5(pyridin-4-yl)pyrimidin-4-yloxy)phenyl)phthalazin-1-amine Step 1. Preparation of 5-iodopyrimidin-4-ol The title compound was prepared following the literature reference: Chem. Pharm. Bull. 1986, 34, 2719-2714. As described therein, to a light yellow solution of pyrimidin-4-ol (10.0 g, 104 mmol) in sodium hydride 6.0 M (23.1 ml, 139 mmol) and water (77 mL) was added iodine (26.4 g, 104 mmol). The mixture was heated to 80° C., with an air-cooled condenser, and became quite thick after 5 min. After 30 min, the mixture was easy to stir and red/purplish in color. The reaction was heated overnight, then cooled and neutralized by a small amount of AcOH. The precipitate was collected by filtration, rinsed with 1090 mL water, and was dried in vacuo to give 5-iodopyrimidin-4-ol as a tan solid. MS m/z=223 [M+H]$^+$. Calc'd for C$_4$H$_3$IN$_2$O: 222.0.

Step 2. Preparation of 4-chloro-5-iodopyrimidine

A mixture of 5-iodopyrimidin-4-ol (14.9 g, 67.1 mmol) in phosphorous oxychloride (25.0 ml, 268 mmol) with a water-cooled reflux condenser fitted with a drying tube was heated to reflux in a 135° C. bath for 3 h. The purple solution was cooled until warm and poured onto ice with swirling. The ice-cold mixture was basified with 6N NaOH, with addition of ice to maintain the cool temperature. The resulting brown precipitate was collected by filtration, rinsed with water, and dried in vacuo to give 4-chloro-5-iodopyrimidine as an orange solid. MS m/z=241 [M+H]$^+$. Calc'd for C$_4$H$_2$ClIN$_2$: 240.4.

Step 3. Preparation of N-(4-(5-iodopyrimidin-4-yloxy)phenyl)-4-phenylphthalazin-1-amime To a brown mixture of cesium carbonate (2.79 g, 8.58 mmol) and 4-(4-phenylphthalazin-1-ylamino)phenol hydrochloride (1.00 g, 2.86 mmol) in 10 mL DMSO was added 4-chloro-5-iodopyrimidine (0.687 g, 2.86 mmol). The reaction was allowed to stir at RT for 1 h. The reaction was heated to and maintained at 70° C. overnight. The reaction was cooled and diluted with water. The solid was filtered and dried in vacuo to give N-(4-(5-iodopyrimidin-4-yloxy)phenyl)-4-phenylphthalazin-1-amine as a gray solid. MS m/z=518 [M+H]$^+$. Calc'd for C$_{24}$H$_{16}$IN$_5$O: 517.3.

Step 4. Preparation of 4-phenyl-N-(4-(5-(pyridin-4-yl)pyrimidin-4-yloxy)phenyl)phthalazin-1-amine A slurry of 4-pyridylboronic acid (0.0950 g, 0.773 mmol), 1,1'-bis(diphenylphosphino)ferrocene-palladium dichloride (0.0141 g, 0.0193 mmol), and N-(4-(5-iodopyrimidin-4-yloxy)phenyl)-4-phenylphthalazin-1-amine (0.200 g, 0.387 mmol) and sodium carbonate 2.0 M in H$_2$O (0.387 ml, 0.773 mmol) in 1.5 mL dioxane was flushed with nitrogen, sealed, and heated to 80° C. The reaction became dark and solids dissolved after 1 h. After 3 h, the reaction was judged complete. The reaction was cooled and diluted with DCM and water. The resulting aqueous emulsion was extracted 4×DCM. The combined organics were dried over anhyd sodium sulfate, filtered, and concentrated in vacuo. The material was adsorbed onto 1.8 g silica gel from MeOH/DCM, dried, and purified by silica gel chromatography (0-60-100% 90/10 DCM/MeOH in DCM) to give 4-phenyl-N-(4-(5-(pyridin-4-yl)pyrimidin-4-yloxy)phenyl)phthalazin-1-amine as a tan solid. MS m/z=469 [M+H]$^+$. Calc'd for C$_{29}$H$_{20}$N$_6$O: 468.5.

Example 244

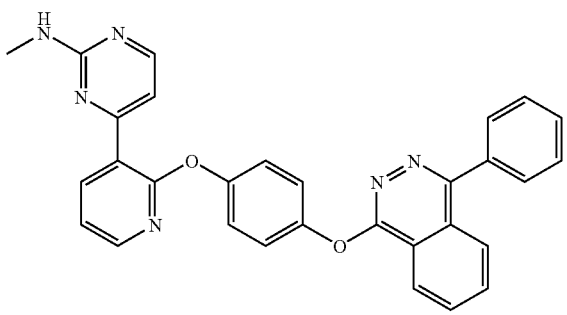

Synthesis of N-methyl-4-(2-(4-(4-phenylphthalazin-1-yloxy)phenoxy)pyridin-3-yl)pyrimidin-2-amine Step 1. Preparation of N-methyl-4-(2-(4-(4,4,5,5-tetramethyl-1,3,2-dioxaborolan-2-yl)phenoxy)pyridin-3-yl)pyrimidin-2-amine 1,1'-Bis(diphenylphosphino)ferrocene-palladium dichloride (0.0453 g, 0.0618 mmol), bis(pinacolato)diboron (0.330 g, 1.30 mmol), 4-(2-(4-iodophenoxy)pyridin-3-yl)-N-methylpyrimidin-2-amine (0.500 g, 1.24 mmol), and potassium acetate (0.243 g, 2.47 mmol) were combined in a sealed tube under nitrogen. 5 mL Dioxane was added, and the orange mixture was sealed and heated to and maintained at 75° C. After 5 h, a trace of desired product was evident by LCMS. The reaction was heated to 100° C., overnight. The temperature was raised to 120° C. After 16 h, the reaction was filtered through celite, rinsing with EtOAc, and concentrated in vacuo to a dark oil, which was purified by silica gel chromatography (50-100% EtOAc/hexanes) to give N-methyl-4-(2-(4-(4,4,5,5-tetramethyl-1,3,2-dioxaborolan-2-yl)phenoxy)pyridin-3-yl)pyrimidin-2-amine. MS m/z=405 [M+H]$^+$. Calc'd for C$_{22}$H$_{25}$BN$_4$O$_3$: 404.3.

Step 2. Preparation of 4-(3-(2-(methylamino)pyrimidin-4-yl)pyridin-2-yloxy)phenol To a solution of N-methyl-4-(2-(4-(4,4,5,5-tetramethyl-1,3,2-dioxaborolan-2-yl)phenoxy)pyridin-3-yl)pyrimidin-2-amine (0.414 g, 1.02 mmol) in 2 mL EtOH at 0° C. was added hydrogen peroxide, 30 wt. % solution in water (0.984 ml, 10.2 mmol). The reaction was allowed to warm to ambient temperature. After 1 h, the reaction was diluted with DCM, and the layers were separated. The aqueous layer was extracted with 5% MeOH/DCM. The combined organics were dried over anhydrous sodium sulfate, filtered, and concentrated in vacuo. The residue was purified by silica gel chromatography, (EtOAc/hexanes) to give 4-(3-(2-(methylamino)pyrimidin-4-yl)pyridin-2-yloxy)phenol as a white solid. MS m/z=295 [M+H]$^+$. Calc'd for C$_{16}$H$_{14}$N$_4$O$_2$: 294.3.

Step 3. Preparation of N-methyl-4-(2-(4-(4-phenylphthalazin-1-yloxy)phenoxy)pyridin-3-yl)pyrimidin-2-amine A mixture of 1-chloro-4-phenylphthalazine (0.0900 g, 0.374 mmol), 4-(3-(2-(methylamino)pyrimidin-4-yl)pyridin-2-yloxy)phenol (0.110 g, 0.374 mmol), and potassium carbonate (0.129 g, 0.934 mmol) in 1 mL DMSO was heated in a sealed tube for 1 h. Upon cooling, a white precipitate formed. The material was partitioned between water and DCM. The organic layer was dried over sodium sulfate, filtered, and concentrated in vacuo to give a crude solid, which was suspended in MeOH, sonicated, filtered and dried to give N-methyl-4-(2-(4-(4-phenylphthalazin-1-yloxy)phenoxy)pyridin-3-yl)pyrimidin-2-amine as a white solid. MS m/z=499 [M+H]$^+$. Calc'd for C$_{30}$H$_{22}$N$_6$O$_2$: 498.5.

Example 245

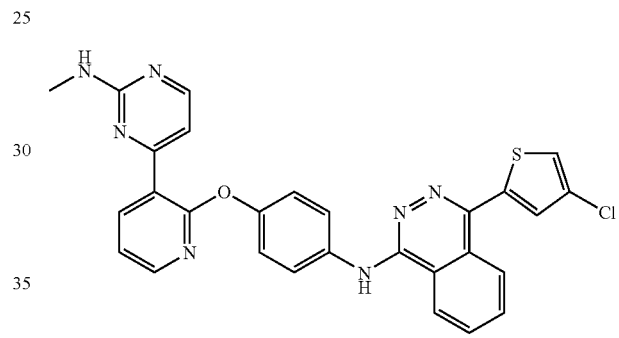

Synthesis of 4-(4-chlorothiophen-2-yl)-N-(4-(3-(2-(methylamino)pyrimidin-4-yl)pyridin-2-yloxy)phenyl)phthalazin-1-amine Step 1. Preparation of (3-chlorothiophen-2-yl)trimethylsilane The title compound was prepared according to the procedure described in WO9412505. To a solution of 3-chlorothiophene (7.00 g, 59.0 mmol) in 60 mL anhydrous THF under nitrogen was added n-butyllithium, 2.5 M in hexanes (23.6 ml, 59.0 mmol) dropwise from a plastic syringe over 15 min. The reaction became cloudy with a white ppt. The reaction was allowed to stir for 40 min, at which point trimethylsilyl chloride (8.24 ml, 64.9 mmol) was added dropwise via syringe over 5 min. The mixture was allowed to stir for 10 min, and was then warmed to 0° C. for 10 min, and 7 mL water and 35 mL brine were added. The mixture was diluted with EtOAc, and the layers separated. The aqueous layer was extracted once with EtOAc. The combined organics were dried over anhydrous sodium sulfate, filtered, and concentrated in vacuo to give (3-chlorothiophen-2-yl)trimethylsilane as a yellow oil.

Step 2. Preparation of 4-chloro-5-(trimethylsilyl)thiophen-2-ylboronic acid

To a solution of diisopropyl amine (1.8 ml, 13 mmol) at 0° C. in 50 mL anhdrous THF under nitrogen was added butyllithium, 2.5 M in hexanes (4.6 ml, 12 mmol). The solution was allowed to stir 5 min and then was cooled to −78° C.

(3-Chlorothiophen-2-yl)trimethylsilane (2.0 g, 10 mmol) in 5 mL THF at RT was added slowly via cannula, dropwise, over about 10 min. The resulting solution was allowed to stir for 30 min, at which point trimethyl borate (2.4 ml, 21 mmol) was added dropwise. The solution was allowed to stir for 1 h, and was then warmed to 0° C. and quenched by the addition of 25 mL of 2NHCl, and warmed to ambient temperature with stirring. The mixture was extracted three times with DCM, and the combined organics were dried over anhydrous sodium sulfate, filtered, and concentrated in vacuo to give a semisolid. Purification by silica gel chromatography, (0-40% EtOAc/hexanes) provided 4-chloro-5-(trimethylsilyl)thiophen-2-ylboronic acid as an off-white solid.

Step 3. Preparation of 4-(4-chlorothiophen-2-yl)-N-(4-(3-(2-(methylamino)pyrimidin-4-yl)pyridin-2-yloxy)phenyl)phthalazin-1-amine 1,1'-Bis(diphenylphosphino)ferrocene-palladium dichloride (0.0401 g, 0.0548 mmol), 4-chloro-5-(trimethylsilyl)thiophen-2-ylboronic acid (0.161 g, 0.685 mmol), 4-chloro-N-(4-(3-(2-(methylamino)pyrimidin-4-yl)pyridin-2-yloxy)phenyl)phthalazin-1-amine (0.250 g, 0.548 mmol), sodium carbonate 2M in $H_2O$ (0.548 ml, 1.10 mmol) in 3 mL dioxane was heated in a sealed tube to 90° C. After 3 h 0.75 equiv boronic acid was added and the reaction was heated for 16 h. The reaction was cooled to ambient temperature and partitioned between EtOAc and 1N NaOH. The aqueous layer was extracted 3× with EtOAc. The combined organics were dried over anhydrous sodium sulfate, filtered, and concentrated in vacuo. The resulting oil was purified by silica gel chromatography (0-100% EtOAc/DCM) to give a to give a mixture of 4-(4-chloro-5-(trimethylsilyl)thiophen-2-yl)-N-(4-(3-(2-(methylamino)pyrimidin-4-yl)pyridin-2-yloxy)phenyl)phthalazin-1-amine and 4-(4-chlorothiophen-2-yl)-N-(4-(3-(2-(methylamino)pyrimidin-4-yl)pyridin-2-yloxy)phenyl)phthalazin-1-amine as a yellow oil. This material was taken up in 2.5 mL THF and water (0.061 ml, 3.4 mmol) was added, followed by tetrabutylammonium fluoride, 1.0 M in THF (0.45 ml, 0.45 mmol). The reaction was stirred for 16 h, and was then diluted with EtOAc/brine. The organic layer was dried over anhydrous sodium sulfate, filtered, and concentrated to a yellow oil. 4 mL MeOH was added, producing a yellow solution, and this was sonicated for several minutes until a thick precipitate formed. Additional methanol was added, and the mixture was filtered. The precipitate was rinsed with 2×MeOH and dried in vacuo to give 4-(4-chlorothiophen-2-yl)-N-(4-(3-(2-(methylamino)pyrimidin-4-yl)pyridin-2-yloxy)phenyl)phthalazin-1-amine as a yellow solid. MS m/z=538 [M+H]$^+$. Calc'd for $C_{28}H_{20}ClN_7OS$: 538.0.

The following compounds (Examples 246-460) in Table II were made, as noted in table I, by one of the exemplified methods A1, A2, A3, B1, B2, B3, B4, B5, B6, B7, C or D described above. The MS data represent the mass (M+H$^+$) found for that example.

TABLE II

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 246 | N-(4-((3-(2-amino-4-pyrimidinyl)-2-pyridinyl)oxy)phenyl)-4,6-diphenyl-3-pyridazinamine | + | +++ | + | 510 | A2 |
| 247 | 2-(4-(4-((4-((3-(2-amino-4-pyrimidinyl)-2-pyridinyl)oxy)phenyl)amino)-1-phthalazinyl)phenyl)ethanol | 0.0198 | 0.0042 | 0.3348 | 528 | A1 |
| 248 | N-(5-((3-(2-(methylamino)-4-pyrimidinyl)-2-pyridinyl)oxy)-2-pyridinyl)-4-phenyl-1-phthalazinamine | 0.1488 | 0.0110 | 0.4647 | 499 | A4 |
| 249 | (4-(4-((4-((3-(2-amino-4-pyrimidinyl)-2-pyridinyl)oxy)phenyl)amino)-1-phthalazinyl)phenyl)methanol | +++ | +++ | ++ | 514 | A1 |
| 250 | N-(4-((3-(2-amino-4-pyrimidinyl)-2-pyridinyl)oxy)phenyl)-4-phenylfuro[2,3-d]pyridazin-7-amine | 0.0303 | 0.0199 | 0.175 | 474 | A2 |
| 251 | N-(4-((3-(2-amino-4-pyrimidinyl)-2-pyridinyl)oxy)phenyl)-4-(3-methyl-5-isothiazolyl)-1-phthalazinamine | 0.0160 | 0.0004 | | 505 | A1 |
| 252 | 4-phenyl-N-(4-((2-(4-pyridinyl)phenyl)oxy)phenyl)-1-phthalazinamine | 0.1663 | 0.6600 | | 467 | A1 |
| 253 | N-(4-((3-(2-amino-4-pyrimidinyl)-2-pyridinyl)oxy)phenyl)-4-(2,6-bis(methyloxy)phenyl)-1-phthalazinamine | 2.3246 | 0.4724 | | 544 | A1 |
| 254 | N-(4-((2-(2-amino-4-pyrimidinyl)phenyl)oxy)phenyl)-4-phenyl-1-phthalazinamine | +++ | +++ | | 483 | A1 |
| 255 | N-(3-(6-(methylamino)-4-pyrimidinyl)-2-pyridinyl)-N'-(4-phenyl-1-phthalazinyl)-1,4-benzenediamine | ++ | +++ | | 497 | C |
| 256 | (1R)-1-(4-(4-((4-((3-(2-amino-4-pyrimidinyl)-2-pyridinyl)oxy)phenyl)amino)-1-phthalazinyl)phenyl)ethanol | 0.1493 | 0.0018 | | 528 | A2 |
| 257 | (1S)-1-(4-(4-((4-((3-(2-amino-4-pyrimidinyl)-2-pyridinyl)oxy)phenyl)amino)-1-phthalazinyl)phenyl)ethanol | +++ | +++ | | 528 | A2 |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 258 | N-(4-((3-(2-amino-4-pyrimidinyl)-2-pyridinyl)oxy)phenyl)-4-((1S,4S)-5-methyl-2,5-diazabicyclo[2.2.1]hept-2-yl)-1-phthalazinamine | + | ++ | | 518 | A2 |
| 259 | N-(4-((3-(2-amino-4-pyrimidinyl)-2-pyridinyl)oxy)phenyl)-4,5-dimethyl-6-(4-methyl-2-thienyl)-3-pyridazinamine | 0.0059 | 0.0028 | 0.0417 | 482 | B1 |
| 260 | N-(4-((3-(2-amino-4-pyrimidinyl)-2-pyridinyl)oxy)phenyl)-4-phenyl-1-isoquinolinamine | 0.0330 | 0.0148 | 0.2281 | 483 | B1 |
| 261 | 4-phenyl-N-(4-((3-(4-pyridinyl)-2-pyrazinyl)oxy)phenyl)-1-phthalazinamine | ++ | ++ | + | 469 | A1 |
| 262 | N-(4-((3-(2-amino-4-pyrimidinyl)-2-pyridinyl)oxy)phenyl)-4-(4-methyl-2-thienyl)-1-isoquinolinamine | 0.0348 | 0.0158 | 0.3339 | 503 | B1 |
| 263 | 3-((4-((3-(2-amino-4-pyrimidinyl)-2-pyridinyl)oxy)phenyl)amino)-6-phenyl-4-pyridazinol | + | + | + | 450 | A2 |
| 264 | N-(4-(3,4'-bipyridin-2-yloxy)phenyl)-5-bromo-3-methyl-2-pyridinamine | | + | + | 434 | A2 |
| 265 | N-(4-((3-(2-amino-4-pyrimidinyl)-2-pyridinyl)oxy)phenyl)-4-(4-chlorophenyl)-1-isoquinolinamine | +++ | +++ | | 517 | B1 |
| 266 | N-(6-((3-(2-amino-4-pyrimidinyl)-2-pyridinyl)oxy)-3-pyridinyl)-4-phenyl-1-isoquinolinamine | +++ | +++ | | 484 | B1 |
| 267 | 4-phenyl-N-(6-((3-(2-((3-(1-piperidinyl)propyl)amino)-4-pyrimidinyl)-2-pyridinyl)oxy)-3-pyridinyl)-1-phthalazinamine | 0.0964 | 0.0104 | | 610 | D |
| 268 | N-(4-((3-(1H-imidazol-1-yl)-2-pyridinyl)oxy)phenyl)-4-phenyl-1-phthalazinamine | + | + | | 457 | A1 |
| 269 | N-(6-((3-(2-amino-4-pyrimidinyl)-2-pyridinyl)oxy)-3-pyridinyl)-4-(1-methylethyl)-1-phthalazinamine | ++ | +++ | | 451 | A1 |
| 270 | N-(6-((3-(2-amino-4-pyrimidinyl)-2-pyridinyl)oxy)-3-pyridinyl)-4-(6-methyl-2-pyridinyl)-1-phthalazinamine | +++ | +++ | | 500 | A1 |
| 271 | N-(4-((3-(2-amino-4-pyrimidinyl)-2-pyridinyl)oxy)phenyl)-4-(6-methyl-2-pyridinyl)-1-phthalazinamine | 0.0243 | 0.0010 | | 499 | A1 |
| 272 | N-(4-((3-(2-amino-4-pyrimidinyl)-2-pyridinyl)oxy)phenyl)-4-cyclohexyl-1-phthalazinamine | 0.0197 | 0.0055 | | 490 | A1 |
| 273 | N-(4-((3-(2-amino-4-pyrimidinyl)-2-pyridinyl)oxy)phenyl)-4-(1-methylethyl)-1-phthalazinamine | ++ | +++ | | 450 | A1 |
| 274 | N-(6-((3-(2-amino-4-pyrimidinyl)-2-pyridinyl)oxy)-3-pyridinyl)-4-cyclohexyl-1-phthalazinamine | +++ | +++ | +++ | 491 | A1 |
| 275 | N-(4-((3-(2-((3-(4-methyl-1-piperazinyl)propyl)amino)-4-pyrimidinyl)-2-pyridinyl)oxy)phenyl)-4-(6-methyl-2-pyridinyl)-1-phthalazinamine | 0.0949 | 0.0134 | | 639 | D |
| 276 | 4-(6-methyl-2-pyridinyl)-N-(4-((3-(2-((3-(1-piperidinyl)propyl)amino)-4-pyrimidinyl)-2-pyridinyl)oxy)phenyl)-1-phthalazinamine | ++ | +++ | | 624 | D |
| 277 | 4-(6-methyl-2-pyridinyl)-N-(4-((3-(2-((3-(1-piperazinyl)propyl)amino)-4-pyrimidinyl)-2-pyridinyl)oxy)phenyl)-1-phthalazinamine | 0.1258 | 0.0027 | | 625 | D |
| 278 | N-(4-((3-(2-amino-4-pyrimidinyl)-2-pyridinyl)oxy)phenyl)-4-(3-fluoro-1-piperidinyl)-1-phthalazinamine | 0.0299 | 0.0074 | 0.2822 | 509 | B4 |
| 279 | N-(3-(4-methyl-1-piperazinyl)propyl)-2-((4-((4-phenyl-1-phthalazinyl)amino)phenyl)oxy)-3,4'-bipyridin-2'-amine | ++ | +++ | ++ | 624 | A1 |
| 280 | 4-methyl-N-(6-((3-(2-((3-(4-methyl-1-piperazinyl)propyl)amino)-4-pyrimidinyl)-2-pyridinyl)oxy)-3-pyridinyl)-6-phenyl-3-pyridazinamine | +++ | +++ | ++ | 590 | D |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 281 | 4-(2-((4-((4-phenyl-1-phthalazinyl)amino)phenyl)oxy)-3-pyridinyl)-1,3-dihydro-2H-pyrrolo[2,3-b]pyridin-2-one | 0.0204 | 0.0061 | 0.1704 | 523 | A1 |
| 282 | 4-(2-((4-((4-methyl-6-phenyl-3-pyridazinyl)amino)phenyl)oxy)-3-pyridinyl)-1,3-dihydro-2H-pyrrolo[2,3-b]pyridin-2-one | +++ | +++ | ++ | 487 | A2 |
| 283 | 4-phenyl-N-(4-((3-(5,6,7,8-tetrahydro-1,8-naphthyridin-4-yl)-2-pyridinyl)oxy)phenyl)-1-phthalazinamine | + | ++ | | 523 | A1 |
| 284 | 4-(4-methyl-1,3-thiazol-2-yl)-N-(4-((3-(5,6,7,8-tetrahydro-1,8-naphthyridin-4-yl)-2-pyridinyl)oxy)phenyl)-1-phthalazinamine | 0.1670 | 0.1906 | | 544 | A1 |
| 285 | 4-methyl-6-phenyl-N-(4-((3-(5,6,7,8-tetrahydro-1,8-naphthyridin-4-yl)-2-pyridinyl)oxy)phenyl)-3-pyridazinamine | + | ++ | | 487 | A2 |
| 286 | 4-methyl-6-(4-methyl-1,3-thiazol-2-yl)-N-(4-((3-(5,6,7,8-tetrahydro-1,8-naphthyridin-4-yl)-2-pyridinyl)oxy)phenyl)-3-pyridazinamine | | + | | 508 | A2 |
| 287 | N-(4-((3-(2,3-dihydro-1H-pyrrolo[2,3-b]pyridin-4-yl)-2-pyridinyl)oxy)phenyl)-4-phenyl-1-phthalazinamine | 0.0833 | 0.0103 | | 509 | A1 |
| 288 | N-(4-((3-(2,3-dihydro-1H-pyrrolol[2,3-b]pyridin-4-yl)-2-pyridinyl)oxy)phenyl)-4-(4-methyl-1,3-thiazol-2-yl)-1-phthalazinamine | +++ | + | | 530 | A2 |
| 289 | N-(6-((3-(2-amino-4-pyrimidinyl)-2-pyridinyl)oxy)-3-pyridinyl)-4-(5-methyl-2-pyridinyl)-1-phthalazinamine | 0.0241 | 0.0019 | | 500 | A1 |
| 290 | N-(2-(2-(2-(((4-(methyloxy)phenyl)methyl)amino)-4-pyridinyl)phenyl)oxy)-5-pyrimidinyl)-4-phenyl-1-phthalazinamine | | + | | 604 | D |
| 291 | N-(4-((3-(5-fluoro-2-((3-(4-methyl-1-piperazinyl)propyl)amino)-4-pyrimidinyl)-2-pyridinyl)oxy)phenyl)-4-phenyl-1-phthalazinamine | 0.0157 | 0.0030 | | 642 | D |
| 292 | N-(4-((3-(2-amino-4-pyrimidinyl)-2-pyridinyl)oxy)phenyl)-4-(6-(methyloxy)-2-pyridinyl)-1-phthalazinamine | +++ | +++ | | 515 | A1 |
| 293 | N-(6-((3-(2-amino-4-pyrimidinyl)-2-pyridinyl)oxy)-3-pyridinyl)-4-(6-(methyloxy)-2-pyridinyl)-1-phthalazinamine | +++ | +++ | | 516 | A1 |
| 294 | N-(4-((3-(2-(1-azetidinyl)-4-pyrimidinyl)-2-pyridinyl)oxy)phenyl)-4-phenyl-1-phthalazinamine | | +++ | | 524 | D |
| 295 | N-(4-((3-(2-((3-(1-azetidinyl)propyl)amino)-4-pyrimidinyl)-2-pyridinyl)oxy)phenyl)-4-phenyl-1-phthalazinamine | ++ | +++ | | 581 | D |
| 296 | (6-(4-((4-((3-(2-amino-4-pyrimidinyl)-2-pyridinyl)oxy)phenyl)amino)-1-phthalazinyl)-2-pyridinyl)methyl acetate | +++ | +++ | | 557 | A1 |
| 297 | (6-(4-((4-((3-(2-amino-4-pyrimidinyl)-2-pyridinyl)oxy)phenyl)amino)-1-phthalazinyl)-2-pyridinyl)methanol | +++ | +++ | | 515 | A1 |
| 298 | N-(4-((3-(2-amino-4-pyrimidinyl)-2-pyridinyl)oxy)phenyl)-4-(6-((methyloxy)methyl)-2-pyridinyl)-1-phthalazinamine | +++ | +++ | | 530 | A1 |
| 299 | N-(4-((3-(2-amino-4-pyrimidinyl)-2-pyridinyl)oxy)phenyl)-4-(3-((dimethylamino)methyl)phenyl)-1-phthalazinamine | ++ | +++ | + | 541 | A2 |
| 300 | N-(4-((3-(3-methyl-1H-pyrazol-4-yl)-2-pyridinyl)oxy)phenyl)-4-phenyl-1-phthalazinamine | ++ | ++ | ++ | 471 | A1 |
| 301 | N-(4-((3-(3-amino-1H-pyrazol-4-yl)-2-pyridinyl)oxy)phenyl)-4-(4-methylphenyl)-1-phthalazinamine | 0.0055 | 0.0031 | 0.1664 | 486 | A1 |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 302 | N-(4-((3-(3-amino-1H-pyrazol-4-yl)-2-pyridinyl)oxy)phenyl)-4-methyl-6-phenyl-3-pyridazinamine | +++ | +++ | + | 436 | A2 |
| 303 | N-(4-((3-(3-amino-1H-pyrazol-4-yl)-2-pyridinyl)oxy)phenyl)-4-(phenylmethyl)-1-phthalazinamine | 0.0032 | 0.0166 | 0.7287 | 486 | A1 |
| 304 | N-(4-((3-(3-amino-1H-pyrazol-4-yl)-2-pyridinyl)oxy)phenyl)-4-phenylthieno[2,3-d]pyridazin-7-amine | 0.0164 | 0.0687 | 0.7884 | 478 | A1 |
| 305 | (3-(4-((4-((3-(3-amino-1H-pyrazol-4-yl)-2-pyridinyl)oxy)phenyl)amino)-1-phthalazinyl)phenyl)methanol | +++ | +++ | + | 502 | A1 |
| 306 | N-(4-((3-(3-amino-1H-pyrazol-4-yl)-2-pyridinyl)oxy)phenyl)-4-(4-chlorophenyl)-1-phthalazinamine | +++ | +++ | ++ | 506 | A1 |
| 307 | N-(4-((3-(3-amino-1H-pyrazol-4-yl)-2-pyridinyl)oxy)phenyl)-4-(4-methyl-2-thienyl)-1-phthalazinamine | +++ | +++ | ++ | 492 | A1 |
| 308 | N-(4-((3-(3-amino-1H-pyrazol-4-yl)-2-pyridinyl)oxy)phenyl)-4-phenyl-5,6,7,8-tetrahydro-1-phthalazinamine | +++ | +++ | + | 476 | A2 |
| 309 | N-(4-((3-(3-amino-1H-pyrazol-4-yl)-2-pyridinyl)oxy)phenyl)-4-(4-methyl-1,3-thiazol-2-yl)-1-phthalazinamine | +++ | +++ | + | 493 | A1 |
| 310 | N-(4-((3-(2-(hydroxyamino)-4-pyrimidinyl)-2-pyridinyl)oxy)phenyl)-4-phenyl-1-phthalazinamine | +++ | +++ | | 500 | A1 |
| 311 | N-(5-(3,4'-bipyridin-2-yloxy)-2-pyrimidinyl)-4-phenyl-1-phthalazinamine | + | + | | 470 | A3 |
| 312 | N-(4-((3-(3-amino-1H-pyrazol-4-yl)-2-pyridinyl)oxy)-3-fluorophenyl)-4-(4-methyl-1,3-thiazol-2-yl)-1-phthalazinamine | +++ | +++ | | 511 | A1 |
| 313 | N-(6-((3-(2-amino-4-pyrimidinyl)-2-pyridinyl)oxy)-3-pyridinyl)-4-phenylthieno[2,3-d]pyridazin-7-amine | +++ | +++ | | 491 | A1 |
| 314 | N-(4-((3-(3-amino-1H-pyrazol-4-yl)-2-pyridinyl)oxy)-3-fluorophenyl)-4-phenyl-1-phthalazinamine | 0.0045 | 0.0024 | | 490 | A1 |
| 315 | N-(6-((3-(2-amino-4-pyrimidinyl)-2-pyridinyl)oxy)-3-pyridinyl)-4-(4-chlorophenyl)-1-phthalazinamine | +++ | +++ | | 519 | A1 |
| 316 | N-(4-((3-(2-amino-4-pyrimidinyl)-2-pyridinyl)oxy)phenyl)-4-(3-(methylsulfonyl)phenyl)-1-phthalazinamine | +++ | +++ | | 562 | A1 |
| 317 | N-(4-((3-(3-amino-1H-pyrazol-4-yl)-2-pyridinyl)oxy)phenyl)-4-(3-(methyloxy)phenyl)-1-phthalazinamine | +++ | +++ | | 502 | A1 |
| 318 | N-(6-((3-(2-amino-4-pyrimidinyl)-2-pyridinyl)oxy)-3-pyridinyl)-4-(3-(methylsulfonyl)phenyl)-1-phthalazinamine | 0.0238 | 0.0056 | | 563 | A1 |
| 319 | N-(6-((3-(2-amino-4-pyrimidinyl)-2-pyridinyl)oxy)-3-pyridinyl)-4-(4-(methyloxy)phenyl)-1-phthalazinamine | +++ | +++ | | 515 | A1 |
| 320 | N-(4-((3-(2-amino-4-pyrimidinyl)-2-pyridinyl)oxy)phenyl)-4-(4-(methyloxy)phenyl)-1-phthalazinamine | +++ | +++ | | 514 | A1 |
| 321 | N-(4-((3-(2-amino-4-pyrimidinyl)-2-pyridinyl)oxy)phenyl)-4-(4-(ethyloxy)phenyl)-1-phthalazinamine | +++ | +++ | | 528 | A1 |
| 322 | N-(4-((3-(2-amino-4-pyrimidinyl)-2-pyridinyl)oxy)phenyl)-4-(2-(ethyloxy)phenyl)-1-phthalazinamine | +++ | +++ | | 528 | A1 |
| 323 | N-(4-(3-(2-((3-(4-methyl-1-piperazinyl)propyl)amino)-4-pyrimidinyl)-2-pyridinyl)oxy)phenyl)-4-(2-pyridinyl)-1-phthalazinamine | ++ | +++ | | 625 | D |
| 324 | N-(4-((3-(2-((3-(3-(dimethylamino)-1-pyrrolidinyl)propyl)amino)-4-pyrimidinyl)-2-pyridinyl)oxy)phenyl)-4-phenyl-1-phthalazinamine | +++ | +++ | | 638 | D |
| 325 | 4-(2-((4-((4-phenyl-1-phthalazinyl)amino)phenyl)oxy)-3-pyridinyl)-2-pyrimidinol | + | | | 485 | D |

TABLE II-continued

| Ex. No. | Name | AurA/TP X2_IC50_IP (Avg) | AurB_IC50_IP (Avg) | pHH3 EC50_IP (Avg) | MS Data | Method |
|---|---|---|---|---|---|---|
| 326 | N-(4-((3-(2-((3-(2,6-dimethyl-4-morpholinyl)propyl)amino)-4-pyrimidinyl)-2-pyridinyl)oxy)phenyl)-4-phenyl-1-phthalazinamine | +++ | +++ |  | 639 | D |
| 327 | N-(4-2-((4-((4-phenyl-1-phthalazinyl)amino)phenyl)oxy)-3-pyridinyl)-2-pyrimidinyl)-beta-alanine | ++ | + |  | 556 | D |
| 328 | N-(4-((3-(2-((3-((2S,5S)-2,5-dimethyl-4-morpholinyl)propyl)amino)-4-pyrimidinyl)-2-pyridinyl)oxy)phenyl)-4-phenyl-1-phthalazinamine | 0.0650 | 0.0043 |  | 639 | D |
| 329 | 1-(3-(4-((4-((3-(2-amino-4-pyrimidinyl)-2-pyridinyl)oxy)phenyl)amino)-1-phthalazinyl)phenyl)ethanone |  |  |  | 526 | A1 |
| 330 | N-(4-((3-(2-amino-4-pyrimidinyl)-2-pyridinyl)oxy)phenyl)-4-(4-methyl-1,3-thiazol-2-yl)-1-phthalazinamine | +++ | +++ | +++ | 505 | A1 |
| 331 | N-(4-((3-(2-amino-4-pyrimidinyl)-2-pyridinyl)oxy)phenyl)-4-(4-methyl-2-thienyl)-1-phthalazinamine | +++ | +++ | +++ | 504 | A1 |
| 332 | N-(6-((3-(2-amino-4-pyrimidinyl)-2-pyridinyl)oxy)-3-pyridinyl)-4-(4-methyl-2-thienyl)-1-phthalazmamine | 0.0052 | 0.0016 | 0.0033 | 505 | B1 |
| 333 | N-(4-((3-(2-((3-(4-methyl-1-piperazinyl)propyl)amino)-4-pyrimidinyl)-2-pyridinyl)oxy)phenyl)-4-phenyl-1-phthalazinamine | +++ | +++ | +++ | 624 | D |
| 334 | N-(4-((3-(2-amino-4-pyrimidinyl)-2-pyridinyl)oxy)phenyl)-4-methyl-6-(1-piperidinyl)-3-pyridazinamine | ++ | +++ | + | 455 | A2 |
| 335 | 4-phenyl-N-(4-((3-(2-((4-piperidinylmethyl)amino)-4-pyrimidinyl)-2-pyridinyl)oxy)phenyl)-1-phthalazinamine | + | ++ | + | 581 | D |
| 336 | N-(4-((3-(2-amino-4-pyrimidinyl)-2-pyridinyl)oxy)phenyl)-4-(4-((dimethylamino)methyl)phenyl)-1-phthalazinamine | + | ++ | + | 541 | E |
| 337 | 3-((4-(2-((4-((4-phenyl-1-phthalazinyl)amino)phenyl)oxy)-3-pyridinyl)-2-pyrimidinyl)amino)-1,2-propanediol | +++ | +++ | ++ | 558 | D |
| 338 | N,N-dimethyl-N'-(4-(2-((4-((4-phenyl-1-phthalazinyl)amino)phenyl)oxy)-3-pyridinyl)-2-pyrimidinyl)-1,4-butanediamine | +++ | +++ | +++ | 583 | D |
| 339 | 3-((4-(2-((4-((4-phenyl-1-phthalazinyl)amino)phenyl)oxy)-3-pyridinyl)-2-pyrimidinyl)amino)-1-propanol | +++ | +++ | ++ | 542 | D |
| 340 | 4-phenyl-N-(4-((3-(2-((3-(1-piperazinyl)propyl)amino)-4-pyrimidinyl)-2-pyridinyl)oxy)phenyl)-1-phthalazinamine | +++ | +++ | ++ | 610 | D |
| 341 | 2,2'-((3-((4-(2-((4-((4-phenyl-1-phthalazinyl)amino)phenyl)oxy)-3-pyridinyl)-2-pyrimidinyl)amino)propyl)imino)diethanol | ++ | +++ | ++ | 629 | D |
| 342 | (3-(4-((4-((3-(2-amino-4-pyrimidinyl)-2-pyridinyl)oxy)phenyl)amino)-1-phthalazinyl)phenyl)methanol | +++ | +++ | ++ | 514 | A1 |
| 343 | 3-(4-((4-((3-(2-amino-4-pyrimidinyl)-2-pyridinyl)oxy)phenyl)amino)-1-phthalazinyl)phenol | +++ | +++ | +++ | 500 | A1 |
| 344 | 3-(3-(4-((4-((3-(2-amino-4-pyrimidinyl)-2-pyridinyl)oxy)phenyl)amino)-1-phthalazinyl)phenyl)-1-propanol | +++ | +++ | +++ | 542 | A1 |
| 345 | 2-((4-((4-(4-methyl-1,3-thiazol-2-yl)-1-phthalazinyl)amino)phenyl)oxy)-3,4'-bipyridin-2'-amine | +++ | +++ | ++ | 504 | A1 |
| 346 | 1-(3-(4-((4-((3-(2-amino-4-pyrimidinyl)-2-pyridinyl)oxy)phenyl)amino)-1-phthalazinyl)phenyl)ethanol | +++ | +++ | ++ | 528 | A1 |

TABLE II-continued

| Ex. No. | Name | AurA/TP X2_IC50_IP (Avg) | AurB_IC50_IP (Avg) | pHH3 EC50_IP (Avg) | MS Data | Method |
|---|---|---|---|---|---|---|
| 347 | 2-(ethyl(4-((4-(2-((4-((4-phenyl-1-phthalazinyl)amino)phenyl)oxy)-3-pyridinyl)-2-pyrimidinyl)amino)butyl)amino)ethanol | +++ | +++ | +++ | 627 | D |
| 348 | 2-(ethyl(4-((4-(2-((4-((4-methyl-6-phenyl-3-pyridazinyl)amino)phenyl)oxy)-3-pyridinyl)-2-pyrimidinyl)amino)butyl)amino)ethanol | +++ | +++ | ++ | 591 | D |
| 349 | 2-(ethyl(3-((4-(2-((4-((4-phenyl-1-phthalazinyl)amino)phenyl)oxy)-3-pyridinyl)-2-pyrimidinyl)amino)propyl)amino)ethanol | ++ | +++ | ++ | 613 | D |
| 350 | 2-(ethyl(3-((4-(2-((4-((4-methyl-6-phenyl-3-pyridazinyl)amino)phenyl)oxy)-3-pyridinyl)-2-pyrimidinyl)amino)propyl)amino)ethanol | +++ | +++ | ++ | 577 | D |
| 351 | (3-(4-((4-((3-(2-amino-4-pyrimidinyl)-2-pyridinyl)oxy)phenyl)amino)-1-phthalazinyl)phenyl)methyl dihydrogen phosphate | ++ | +++ | | 594 | F |
| 352 | (1-(4-((4-((3-(2-amino-4-pyrimidinyl)-2-pyridinyl)oxy)phenyl)amino)-1-phthalazinyl)-3-piperidinyl)methanol | +++ | +++ | | 521 | A2 |
| 353 | (1-(4-((4-((3-(2-amino-4-pyrimidinyl)-2-pyridinyl)oxy)phenyl)amino)-1-phthalazinyl)-4-piperidinyl)methanol | | +++ | | 521 | A2 |
| 354 | 1-(4-((4-((3-(2-amino-4-pyrimidinyl)-2-pyridinyl)oxy)phenyl)amino)-1-phthalazinyl)-3-piperidinol | 0.0874 | 0.0259 | | 507 | A2 |
| 355 | 2-(3-(4-((4-((3-(2-amino-4-pyrimidinyl)-2-pyridinyl)oxy)phenyl)amino)-1-phthalazinyl)phenyl)ethanol | +++ | +++ | | 528 | A1 |
| 356 | N-(4-((3-(2-amino-4-pyrimidinyl)-2-pyridinyl)oxy)phenyl)-4-(2-pyridinyl)-1-phthalazinamine | +++ | +++ | | 485 | A1 |
| 357 | 2-(3-(4-((4-((3-(2-amino-4-pyrimidinyl)-2-pyridinyl)oxy)phenyl)amino)-1-phthalazinyl)phenyl)-2-propanol | +++ | +++ | | 542 | A1 |
| 358 | 1-(4-((4-((3-(2-amino-4-pyrimidinyl)-2-pyridinyl)oxy)phenyl)amino)-1-phthalazinyl)-4-piperidinol | + | +++ | | 507 | A1 |
| 359 | 3-((4-(2-((4-((4-methyl-1,3-thiazol-2-yl)-1-phthalazinyl)amino)phenyl)oxy)-3-pyridinyl)-2-pyrimidinyl)amino)-1-propanol | +++ | +++ | | 563 | A1 |
| 360 | (1S)-1-(3-(4-((4-((3-(2-amino-4-pyrimidinyl)-2-pyridinyl)oxy)phenyl)amino)-1-phthalazinyl)phenyl)ethanol | +++ | +++ | | 528 | A2 |
| 361 | (1R)-1-(3-(4-((4-((3-(2-amino-4-pyrimidinyl)-2-pyridinyl)oxy)phenyl)amino)-1-phthalazinyl)phenyl)ethanol | +++ | +++ | | 528 | A1 |
| 362 | 3-(3-(4-((4-((3-(2-amino-4-pyrimidinyl)-2-pyridinyl)oxy)phenyl)amino)-1-phthalazinyl)phenyl)propyl dihydrogen phosphate | +++ | +++ | | 622 | F |
| 363 | 3-(4-((6-((3-(2-amino-4-pyrimidinyl)-2-pyridinyl)oxy)-3-pyridinyl)amino)-1-phthalazinyl)phenol | +++ | +++ | | 501 | A1 |
| 364 | 2-(4-((4-((3-(2-amino-4-pyrimidinyl)-2-pyridinyl)oxy)phenyl)amino)-1-phthalazinyl)phenol | ++ | +++ | | 500 | A1 |
| 365 | 2-(4-((6-((3-(2-amino-4-pyrimidinyl)-2-pyridinyl)oxy)-3-pyridinyl)amino)-1-phthalazinyl)phenol | 0.0276 | 0.0113 | | 501 | A1 |
| 366 | 3-(4-((4-((3-(2-amino-4-pyrimidinyl)-2-pyridinyl)oxy)phenyl)amino)-1-phthalazinyl)phenyl dihydrogen phosphate | ++ | ++ | | 580 | F |
| 367 | 3-((4-(2-((5-((4-phenyl-1-phthalazinyl)amino)-2-pyridinyl)oxy)-3-pyridinyl)-2-pyrimidinyl)amino)-1-propanol | +++ | +++ | | 543 | A1 |
| 368 | 2-(4-((4-((3-(2-amino-4-pyrimidinyl)-2-pyridinyl)oxy)phenyl)amino)-1-phthalazinyl)phenyl dihydrogen phosphate | + | + | | 580 | F |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 369 | (1S)-1-(3-(4-((6-((3-(2-amino-4-pyrimidinyl)-2-pyridinyl)oxy)-3-pyridinyl)amino)-1-phthalazinyl)phenyl)ethanol | +++ | +++ | | 529 | A2 |
| 370 | (3-(6-((4-((3-(2-amino-4-pyrimidinyl)-2-pyridinyl)oxy)phenyl)amino)-5-methyl-3-pyridazinyl)phenyl)methanol | +++ | +++ | | 478 | A2 |
| 371 | 2-(4-((4-((2'-amino-3,4'-bipyridin-2-yl)oxy)phenyl)amino)-1-phthalazinyl)phenol | ++ | +++ | | 499 | A1 |
| 372 | N-(4-((3-(2-amino-4-pyrimidinyl)-2-pyridinyl)oxy)phenyl)-4-(2-fluoro-5-(methyloxy)phenyl)-1-phthalazinamine | +++ | +++ | | 532 | A1 |
| 373 | 3-(4-((4-((3-(2-amino-4-pyrimidinyl)-2-pyridinyl)oxy)phenyl)amino)-1-phthalazinyl)-4-fluorophenol | +++ | +++ | | 518 | A1 |
| 374 | N-(4-((3-(2-amino-4-pyrimidinyl)-2-pyridinyl)oxy)phenyl)-4-(3-((3-(dimethylamino)propyl)oxy)phenyl)-1-phthalazinamine | +++ | +++ | | 585 | A2 |
| 375 | (3-(4-((6-((3-(2-amino-4-pyrimidinyl)-2-pyridinyl)oxy)-3-pyridinyl)amino)-1-phthalazinyl)phenyl)methanol | +++ | +++ | | 515 | A1 |
| 376 | N-(6-((3-(2-amino-4-pyrimidinyl)-2-pyridinyl)oxy)-3-pyridinyl)-4-(2-fluoro-5-(methyloxy)phenyl)-1-phthalazinamine | +++ | +++ | | 533 | A1 |
| 377 | N-(4-((3-(2-amino-4-pyrimidinyl)-2-pyridinyl)oxy)phenyl)-4-(3-((trifluoromethyl)oxy)phenyl)-1-phthalazinamine | +++ | +++ | | 568 | A1 |
| 378 | N-(6-((3-(2-amino-4-pyrimidinyl)-2-pyridinyl)oxy)-3-pyridinyl)-4-(3-((trifluoromethyl)oxy)phenyl)-1-phthalazinamine | +++ | +++ | | 569 | A1 |
| 379 | 3-(4-((6-((3-(2-amino-4-pyrimidinyl)-2-pyridinyl)oxy)-3-pyridinyl)amino)-1-phthalazinyl)-4-fluorophenol | +++ | +++ | | 519 | A1 |
| 380 | N-(4-((3-(2-amino-4-pyrimidinyl)-2-pyridinyl)oxy)phenyl)-4-(5-fluoro-2-(methyloxy)phenyl)-1-phthalazinamine | +++ | +++ | | 532 | A1 |
| 381 | N-(6-((3-(2-amino-4-pyrimidinyl)-2-pyridinyl)oxy)-3-pyridinyl)-4-(5-fluoro-2-(methyloxy)phenyl)-1-phthalazinamine | ++ | +++ | | 533 | A1 |
| 382 | N-(4-((3-(2-amino-4-pyrimidinyl)-2-pyridinyl)oxy)phenyl)-4-(2-((trifluoromethyl)oxy)phenyl)-1-phthalazinamine | ++ | +++ | | 568 | A1 |
| 383 | N-(6-((3-(2-amino-4-pyrimidinyl)-2-pyridinyl)oxy)-3-pyridinyl)-4-(2-((trifluoromethyl)oxy)phenyl)-1-phthalazinamine | + | +++ | | 569 | A1 |
| 384 | (2-(4-((4-((3-(2-amino-4-pyrimidinyl)-2-pyridinyl)oxy)phenyl)amino)-1-phthalazinyl)phenyl)methanol | +++ | +++ | | 514 | A1 |
| 385 | (2-(4-((6-((3-(2-amino-4-pyrimidinyl)-2-pyridinyl)oxy)-3-pyridinyl)amino)-1-phthalazinyl)phenyl)methanol | ++ | +++ | | 515 | A1 |
| 386 | 2-(4-((4-((3-(2-amino-4-pyrimidinyl)-2-pyridinyl)oxy)phenyl)amino)-1-phthalazinyl)-4-fluorophenol | +++ | +++ | | 518 | A1 |
| 387 | 2-(4-((6-((3-(2-amino-4-pyrimidinyl)-2-pyridinyl)oxy)-3-pyridinyl)amino)-1-phthalazinyl)-4-fluorophenol | +++ | +++ | | 519 | A1 |
| 388 | N-(6-((3-(2-amino-4-pyrimidinyl)-2-pyridinyl)oxy)-3-pyridinyl)-4-(3-((3-(dimethylamino)propyl)oxy)phenyl)-1-phthalazinamine | ++ | +++ | | 586 | A2 |
| 389 | N-(6-((3-(2-((3-(4-methyl-1-piperazinyl)propyl)amino)-4-pyrimidinyl)-2-pyridinyl)oxy)-3-pyridinyl)-4-phenyl-1-phthalazinamine | +++ | +++ | | 625 | D |
| 390 | 4-phenyl-N-(6-((3-(2-((3-(1-piperazinyl)propyl)amino)-4-pyrimidinyl)-2-pyridinyl)oxy)-3-pyridinyl)-1-phthalazinamine | +++ | +++ | | 611 | D |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 391 | 2-(4-((6-((3-(2-amino-4-pyrimidinyl)-2-pyridinyl)oxy)-3-pyridinyl)amino)-1-phthalazinyl)phenyl dihydrogen phosphate | 1.5953 | 0.6409 | | 581 | F |
| 392 | 3-(4-((6-((3-(2-amino-4-pyrimidinyl)-2-pyridinyl)oxy)-3-pyridinyl)amino)-1-phthalazinyl)phenyl dihydrogen phosphate | + | + | | 581 | F |
| 393 | N-(4-((3-(2-amino-4-pyrimidinyl)-2-pyridinyl)oxy)phenyl)-4-(1-piperazinyl)-1-phthalazinamine | + | ++ | | 492 | B4 |
| 394 | N-(4-((3-(2-amino-4-pyrimidinyl)-2-pyridinyl)oxy)phenyl)-4-(hexahydropyrrolo[1,2-a]pyrazin-2(1H)-yl)-1-phthalazinamine | +++ | +++ | | 532 | B4 |
| 395 | N-(4-((3-(2-amino-4-pyrimidinyl)-2-pyridinyl)oxy)phenyl)-4-(3,4-dimethyl-1-piperazinyl)-1-phthalazinamine | +++ | +++ | | 520 | B4 |
| 396 | N-(4-((3-(2-amino-4-pyrimidinyl)-2-pyridinyl)oxy)phenyl)-4-(5-methyl-2-pyridinyl)-1-phthalazinamine | 0.0047 | 0.0008 | | 499 | A1 |
| 397 | N-(6-((3-(2-amino-4-pyrimidinyl)-2-pyridinyl)oxy)-3-pyridinyl)-4-(hexahydropyrrolo[1,2-a]pyrazin-2(1H)-yl)-1-phthalazinamine | +++ | +++ | | 533 | B4 |
| 398 | N-(4-((3-(2-amino-4-pyrimidinyl)-2-pyridinyl)oxy)phenyl)-4-((3S)-3-methyl-1-piperazinyl)-1-phthalazinamine | | ++ | | 506 | B4 |
| 399 | N-(4-((3-(2-amino-4-pyrimidinyl)-2-pyridinyl)oxy)phenyl)-4-((3R)-3-methyl-1-piperazinyl)-1-phthalazinamine | + | ++ | | 506 | B4 |
| 400 | N-(4-((3-(5-fluoro-2-((3-(1-piperazinyl)propyl)amino)-4-pyrimidinyl)-2-pyridinyl)oxy)phenyl)-4-phenyl-1-phthalazinamine | ++ | +++ | | 628 | D |
| 401 | N-(4-((3-(2-amino-4-pyrimidinyl)-2-pyridinyl)oxy)phenyl)-4-((8aS)-hexahydropyrrolo[1,2-a]pyrazin-2(1H)-yl)-1-phthalazinamine | +++ | +++ | | 532 | B4 |
| 402 | N-(6-((3-(2-amino-4-pyrimidinyl)-2-pyridinyl)oxy)-3-pyridinyl)-4-((8aS)-hexahydropyrrolo[1,2-a]pyrazin-2(1H)-yl)-1-phthalazinamine | +++ | +++ | | 533 | B4 |
| 403 | N-(4-((3-(5-fluoro-2-((3-(1-piperidinyl)propyl)amino)-4-pyrimidinyl)-2-pyridinyl)oxy)phenyl)-4-phenyl-1-phthalazinamine | +++ | +++ | | 627 | D |
| 404 | N-(4-((3-(2-amino-4-pyrimidinyl)-2-pyridinyl)oxy)phenyl)-4-(4-methyl-2-pyridinyl)-1-phthalazinamine | ++ | +++ | | 499 | A1 |
| 405 | N-(6-((3-(2-amino-4-pyrimidinyl)-2-pyridinyl)oxy)-3-pyridinyl)-4-(4-methyl-2-pyridinyl)-1-phthalazinamine | ++ | +++ | | 500 | A1 |
| 406 | N-(4-((3-(2-amino-4-pyrimidinyl)-2-pyridinyl)oxy)phenyl)-4-(octahydro-2H-pyrido[1,2-a]pyrazin-2-yl)-1-phthalazinamine | +++ | +++ | | 546 | B4 |
| 407 | N-(4-((3-(2-amino-4-pyrimidinyl)-2-pyridinyl)oxy)phenyl)-4-(5-methyl-1H-pyrazol-1-yl)-1-phthalazinamine | +++ | +++ | | 488 | B7 |
| 408 | N-(4-((3-(2-amino-4-pyrimidinyl)-2-pyridinyl)oxy)phenyl)-4-(3-methyl-1H-pyrazol-1-yl)-1-phthalazinamine | +++ | +++ | | 488 | B7 |
| 409 | N-(4-((3-(2-((3-(4-methyl-1-piperazinyl)propyl)amino)-4-pyrimidinyl)-2-pyridinyl)oxy)phenyl)-4-(4-methyl-2-pyridinyl)-1-phthalazinamine | ++ | +++ | | 639 | D |
| 410 | 4-(6-(methyloxy)-2-pyridinyl)-N-(4-((3-(2-((3-(4-methyl-1-piperazinyl)propyl)amino)-4-pyrimidinyl)-2-pyridinyl)oxy)phenyl)-1-phthalazinamine | +++ | +++ | | 655 | D |
| 411 | N-(4-((3-(2-((3-((3S)-3-methyl-1-piperazinyl)propyl)amino)-4-pyrimidinyl)-2-pyridinyl)oxy)phenyl)-4-phenyl-1-phthalazinamine | +++ | +++ | | 624 | D |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 412 | 4-(4-methyl-2-pyridinyl)-N-(4-((3-(2-((3-(4-morpholinyl)propyl)amino)-4-pyrimidinyl)-2-pyridinyl)oxy)phenyl)-1-phthalazinamine | ++ | +++ | | 626 | D |
| 413 | 2-(((3-(4-((4-((3-(2-amino-4-pyrimidinyl)-2-pyridinyl)oxy)phenyl)amino)-1-phthalazinyl)phenyl)methyl)amino)ethanol | | +++ | | 557 | A2 |
| 414 | N-(6-((3-(2-amino-4-pyrimidinyl)-2-pyridinyl)oxy)-3-pyridinyl)-4-(3-methyl-5-isothiazolyl)-1-phthalazinamine | | | | 506 | A1 |
| 415 | N-(6-((3-(2-amino-4-pyrimidinyl)-2-pyridinyl)oxy)-3-pyridinyl)-4-phenyl-1-phthalazinamine | +++ | +++ | +++ | 486 | A1 |
| 416 | 2-((4-((4-(4-methyl-2-thienyl)-1-phthalazinyl)amino)phenyl)oxy)-3,4'-bipyridin-2'-amine | 0.0541 | 0.0145 | 0.1338 | 504 | A1 |
| 417 | N-(4-(3,4'-bipyridin-2-yloxy)phenyl)-4-methyl-6-phenyl-3-pyridazinamine | +++ | +++ | + | 432 | A2 |
| 418 | 2-((4-((4-methyl-6-phenyl-3-pyridazinyl)amino)phenyl)oxy)-3,4'-bipyridin-2'-amine | +++ | +++ | ++ | 448 | A2 |
| 419 | 2-((4-((4-(4-methyl-6-(4-methyl-2-thienyl)-3-pyridazinyl)amino)phenyl)oxy)-3,4'-bipyridin-2'-amine | +++ | +++ | ++ | 468 | A2 |
| 420 | 2-((4-((4-ethyl-6-phenyl-3-pyridazinyl)amino)phenyl)oxy)-3,4'-bipyridin-2'-amine | 0.0568 | 0.0071 | 0.3140 | 462 | A2 |
| 421 | 3-((4-(2-((4-((4-phenyl-1-phthalazinyl)amino)phenyl)oxy)-3-pyridinyl)-2-pyrimidinyl)amino)-1-propanesulfonic acid | ++ | ++ | + | 607 | D |
| 422 | 4-methyl-N-(4-((3-(2-(((3-(4-methyl-1-piperazinyl)propyl)amino)-4-pyrimidinyl)-2-pyridinyl)oxy)phenyl)-6-phenyl-3-pyridazinamine | +++ | +++ | ++ | 589 | D |
| 423 | N,N-dimethyl-N'-(4-(2-((4-((4-methyl-6-phenyl-3-pyridazinyl)amino)phenyl)oxy)-3-pyridinyl)-2-pyrimidinyl)-1,4-butanediamine | +++ | +++ | ++ | 548 | D |
| 424 | 4-methyl-6-phenyl-N-(4-((3-(2-((3-(1-piperidinyl)propyl)amino)-4-pyrimidinyl)-2-pyridinyl)oxy)phenyl)-3-pyridazinamine | +++ | +++ | ++ | 574 | D |
| 425 | 4-methyl-6-phenyl-N-(4-((3-(2-(((3-(1-pyrrolidinyl)propyl)amino)-4-pyrimidinyl)-2-pyridinyl)oxy)phenyl)-3-pyridazinamine | +++ | +++ | ++ | 560 | D |
| 426 | N,N-diethyl-N'-(4-(2-((4-((4-methyl-6-phenyl-3-pyridazinyl)amino)phenyl)oxy)-3-pyridinyl)-2-pyrimidinyl)-1,3-propanediamine | +++ | +++ | ++ | 562 | D |
| 427 | 4-((4-(2-((4-((4-phenyl-1-phthalazinyl)amino)phenyl)oxy)-3-pyridinyl)-2-pyrimidinyl)amino)butanoic acid | +++ | +++ | + | 571 | D |
| 428 | N-(4-(3,4'-bipyridin-2-yloxy)phenyl)-4-methyl-6-(4-methyl-2-thienyl)-3-pyridazinamine | +++ | +++ | + | 453 | A2 |
| 429 | 3-((4-(2-((4-((4-methyl-6-phenyl-3-pyridazinyl)amino)phenyl)oxy)-3-pyridinyl)-2-pyrimidinyl)amino)-1-propanol | +++ | +++ | ++ | 507 | D |
| 430 | 4-((4-(2-((4-((4-methyl-6-phenyl-3-pyridazinyl)amino)phenyl)oxy)-3-pyridinyl)-2-pyrimidinyl)amino)butanoic acid | +++ | +++ | + | 535 | D |
| 431 | 2-((5-(((4-phenyl-1-phthalazinyl)amino)-2-pyridinyl)oxy)-3,4'-bipyridin-2'-amine | +++ | +++ | +++ | 485 | A1 |
| 432 | 2-((4-((4-phenyl-1-phthalazinyl)amino)phenyl)oxy)-3,4'-bipyridin-2'(1'H)-one | | + | + | 485 | A1 |
| 433 | 3-((4-((3-(2-amino-4-pyrimidinyl)-2-pyridinyl)oxy)phenyl)amino)-6-phenyl-4-pyridazinecarboxylic acid | + | + | + | 478 | A1 |
| 434 | 2-((4-((4-methyl-6-(4-methyl-1,3-thiazol-2-yl)-3-pyridazinyl)amino)phenyl)oxy)-3,4'-bipyridin-2'-amine | 0.0986 | 0.0095 | 1.000 | 469 | A2 |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 435 | N-(4-((3-(2-amino-4-pyrimidinyl)-2-pyridinyl)oxy)phenyl-4-ethyl-6-phenyl-3-pyridazinamine | +++ | +++ | | 463 | C |
| 436 | 2-((4-((4-phenyl-1-phthalazinyl)amino)phenyl)oxy)-3-(4-pyridinyl)benzonitrile | ++ | +++ | | 493 | A1 |
| 437 | N-(4-((3-(2-amino-4-pyrimidinyl)-2-pyridinyl)oxy)phenyl)-4-(2-(methyloxy)phenyl)-1-phthalazinamine | +++ | +++ | | 515 | A1 |
| 438 | N-(4-((3-(2-amino-4-pyrimidinyl)-2-pyridinyl)oxy)phenyl)-4-(3-(methyloxy)phenyl)-1-phthalazinamine | +++ | +++ | | 515 | A1 |
| 439 | N-(6-((3-(2-amino-4-pyrimidinyl)-2-pyridinyl)oxy)-3-pyridinyl)-4-ethyl-6-phenyl-3-pyridazinamine | +++ | +++ | | 464 | C |
| 440 | N-(6-((3-(2-amino-4-pyrimidinyl)-2-pyridinyl)oxy)-3-pyridinyl)-4-(2-(methyloxy)phenyl)-1-phthalazinamine | +++ | +++ | | 516 | A1 |
| 441 | 2-((4-((4-(3-(methyloxy)phenyl)-1-phthalazinyl)amino)phenyl)oxy)-3,4'-bipyridin-2'-amine | ++ | ++ | | 514 | A1 |
| 442 | 2-((4-((4-(2-(methyloxy)phenyl)-1-phthalazinyl)amino)phenyl)oxy)-3,4'-bipyridin-2'-amine | 0.3748 | 0.0330 | | 514 | A1 |
| 443 | N-(4-((3-(2-amino-4-pyrimidinyl)-2-pyridinyl)oxy)phenyl)-4-methyl-6-(3-(methyloxy)phenyl)-3-pyridazinamine | +++ | +++ | | 479 | A2 |
| 444 | 2-((5-((4-ethyl-6-phenyl-3-pyridazinyl)amino)-2-pyridinyl)oxy)-3,4'-bipyridin-2'-amine | ++ | +++ | | 463 | C |
| 445 | N-(4-((3-(2-amino-4-pyrimidinyl)-2-pyridinyl)oxy)phenyl)-6-phenyl-4-propyl-3-pyridazinamine | 0.0235 | 0.0031 | | 477 | A2 |
| 446 | N-(4-((3-(2-amino-4-pyrimidinyl)-2-pyridinyl)oxy)phenyl)-4-((methyloxy)methyl)-6-phenyl-3-pyridazinamine | +++ | +++ | | 479 | A2 |
| 447 | 2-((4-((4-phenyl-1-phthalazinyl)amino)phenyl)oxy)-3-(4-pyridinyl)phenol | | + | | 484 | A1 |
| 448 | N-(4-((2-(methyloxy)-6-(4-pyridinyl)phenyl)oxy)phenyl)-4-phenyl-1-phthalazinamine | 0.1101 | 0.0096 | | 498 | A1 |
| 449 | 4-ethyl-N-(6-((3-(2-((3-(4-methyl-1-piperazinyl)propyl)amino)-4-pyrimidinyl)-2-pyridinyl)oxy)-3-pyridinyl)-6-phenyl-3-pyridazinamine | +++ | +++ | | 604 | D |
| 450 | 4-ethyl-6-phenyl-N-(6-((3-(2-((3-(1-piperidinyl)propyl)amino)-4-pyrimidinyl)-2-pyridinyl)oxy)-3-pyridinyl)-3-pyridazinamine | + | +++ | | 589 | D |
| 451 | 4-ethyl-6-phenyl-N-(6-((3-(2-((3-(1-piperazinyl)propyl)amino)-4-pyrimidinyl)-2-pyridinyl)oxy)-3-pyridinyl)-3-pyridazinamine | ++ | +++ | | 590 | D |
| 452 | N-(4-((3-(2-((3-(3-fluoro-1-piperidinyl)propyl)amino)-4-pyrimidinyl)-2-pyridinyl)oxy)phenyl)-4-phenyl-1-phthalazinamine | +++ | +++ | | 628 | D |
| 453 | N-(4-((3-(2-((3-(3,3-difluoro-1-piperidinyl)propyl)amino)-4-pyrimidinyl)-2-pyridinyl)oxy)phenyl)-4-phenyl-1-phthalazinamine | +++ | +++ | | 646 | D |
| 454 | 4-(6-(methyloxy)-2-pyridinyl)-N-(4-((3-(2-((3-(1-piperidinyl)propyl)amino)-4-pyrimidinyl)-2-pyridinyl)oxy)phenyl)-1-phthalazinamine | +++ | +++ | | 641 | D |
| 455 | 4-(6-(methyloxy)-2-pyridinyl)-N-(4-((3-(2-((3-(1-pyrrolidinyl)propyl)amino)-4-pyrimidinyl)-2-pyridinyl)oxy)phenyl)-1-phthalazinamine | +++ | +++ | | 627 | D |
| 456 | 4-ethyl-N-(4-((3-(2-((3-(4-methyl-1-piperazinyl)propyl)amino)-4-pyrimidinyl)-2-pyridinyl)oxy)phenyl)-6-phenyl-3-pyridazinamine | +++ | +++ | | 603 | D |

TABLE II-continued

| Ex. No. | Name | AurA/TPX2_IC50_IP (Avg) | AurB_IC50_IP (Avg) | pHH3 EC50_IP (Avg) | MS Data | Method |
|---|---|---|---|---|---|---|
| 457 | 4-ethyl-6-phenyl-N-(4-((3-(2-((3-(1-piperazinyl)propyl)amino)-4-pyrimidinyl)-2-pyridinyl)oxy)phenyl)-3-pyridazinamine | +++ | +++ | | 589 | D |
| 458 | 4-ethyl-6-phenyl-N-(4-((3-(2-((3-(1-piperidinyl)propyl)amino)-4-pyrimidinyl)-2-pyridinyl)oxy)phenyl)-3-pyridazinamine | +++ | +++ | | 588 | D |
| 459 | 4-ethyl-6-phenyl-N-(4-((3-(2-((3-(1-pyrrolidinyl)propyl)amino)-4-pyrimidinyl)-2-pyridinyl)oxy)phenyl)-3-pyridazinamine | ++ | +++ | | 574 | D |
| 460 | 4-(6-(methyloxy)-2-pyridinyl)-N-(4-((3-(2-((3-(1-piperazinyl)propyl)amino)-4-pyrimidinyl)-2-pyridinyl)oxy)phenyl)-1-phthalazinamine | +++ | +++ | | 642 | D |

Preparations of the following additional intermediates and compounds of formulas I-III should further assist in appreciating the scope of the present invention.

Example 461

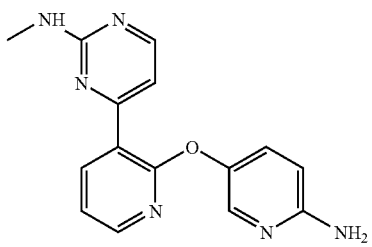

Synthesis of 4(2-(6-aminopyridin-3-yloxy)pyridin-3-yl)-N-methylpyrimidin-2-amine Step 1. Synthesis of 4-(2-(6-bromopyridin-3-yloxy)pyridin-3-yl)-N-methylpyrimidin-2-amine To a slurry of cesium carbonate (8.9 g, 27 mmol) and 6-bromopyridin-3-ol (2.6 g, 15 mmol) was added 4-(2-chloropyridin-3-yl)-N-methylpyrimidin-2-amine (3.0 g, 14 mmol). The reaction mixture was sealed and heated to 125° C. for 16 h. The mixture was cooled and diluted with water and the aqueous solution was extracted with DCM (3×75 mL). The combined organics were dried over anhydrous sodium sulfate, filtered, and concentrated in vacuo to give a brown oil, which was taken up in a little DCM and purified on an ISCO 120 g column, eluting with a gradient of 0-100% EtOAc/DCM, to afford 4-(2-(6-bromopyridin-3-yloxy)pyridin-3-yl)-N-methylpyrimidin-2-amine as an off-white solid. MS m/z=295 [M+H]⁺. Calc'd for $C_{15}H_{12}BrN_5O$: 358.2.

Step 2. 4-(2-(6-Aminopyridin-3-yloxy)pyridin-3-yl)-N-methylpyrimidin-2-amine

The title compound was prepared following the procedure described in Tet. Lett. 2001 42, 3251-3254. A slurry of 4-(2-(6-bromopyridin-3-yloxy)pyridin-3-yl)-N-methylpyrimidin-2-amine (2.42 g, 6.76 mmol) and copper(i) oxide (0.145 g, 1.01 mmol) in 35 mL ethylene glycol in a 25 mL stainless steel pressure vessel with stir bar was cooled to 0° C., and anhydrous ammonia was bubbled through for 15 min. The heterogeneous, reddish mixture was sealed, and heated to 100° C. in an oil bath overnight. The reaction was cooled to ambient temp and vented. The reaction was partitioned between water and DCM. The aqueous layer was extracted 4× with DCM. The combined organics were dried over anhydrous sodium sulfate, filtered, and concentrated in vacuo to give 2 g of a light yellow solid. This was further purified by adsorbing onto 10 g silica gel from MeOH/MC and purifying by silica gel chromatography, ISCO, 120 g, 40 min run, 0-70% 90/10 MC/MeOH in MC to provide 4-(2-(6-aminopyridin-3-yloxy)pyridin-3-yl)-N-methylpyrimidin-2-amine as a white solid. MS m/z=295 [M+H]⁺. Calc'd for $C_{15}H_{14}N_6O$: 294.3.

Example 462

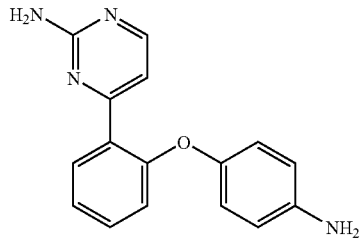

Synthesis of 4-(2-(4-aminophenoxy)phenyl)pyrimidin-2-amine

Step 1. Preparation of 4,4,5,5-tetramethyl-2-(2-(4-nitrophenoxy)phenyl)-1,3,2-dioxaborolane To a solution of 2-(4,4,5,5-tetramethyl-1,3,2-dioxaborolan-2-yl)phenol (2.00 g, 9.09 mmol) in DMF was added potassium carbonate (2.51 g, 18.2 mm, ol) and 1-fluoro-4-nitrobenzene (0.964 ml, 9.09 mmol). The reaction mixture was flushed with nitrogen, sealed, and heated to 120° C. After 18 h, water was added and the mixture was extracted 2× with EtOAc. The organic layer was dried over $Na_2SO_4$, filtered, and concentrated in vacuo, and the crude was purify by silica gel chromatography, eluting with 0-15% EtOAc/hexanes to give 4,4,5,5-tetramethyl-2-(2-(4-nitrophenoxy)phenyl)-1,3,2-dioxaborolane as a white solid. MS m/z=342 [M+1]⁺. Calc'd for $C_{18}H_2OBNO_5$: 341.17.

Step 2. Preparation of 4-(2-(4-nitrophenoxy)phenyl)pyrimidin-2-amine

The compound of step 1 (0.034 g, 0.054 mmol), potassium acetate (0.26 g, 2.7 mmol), 4,4,5,5-tetramethyl-2-(2-(4-nitrophenoxy)phenyl)-1,3,2-dioxaborolane (0.460 g, 1.3 mmol), and 4-chloropyrimidin-2-amine (0.17 g, 1.3 mmol) were combined in a sealed tube under nitrogen, to which 7 mL ACN and water (0.73 ml, 40 mmol) were added. The reaction was sealed and heated to 85° C. overnight. The reaction was diluted with DCM and water, and extracted 2× with DCM. The combined organics were dried over anhydrous sodium sulfate, filtered, and concentrated in vacuo. The resulting material was purified by silica gel chromatography (MeOH/DCM) to give 4-(2-(4-nitrophenoxy)phenyl)pyrimidin-2-amine as a white solid MS m/z=309 [M+H]$^+$. Calc'd for $C_{16}H_{12}N_4O_3$: 308.3.

Step 3. Preparation of 4-(2-(4-aminophenoxy)phenyl)pyrimidin-2-amine 4-(2-(4-nitrophenoxy)phenyl)pyrimidin-2-amine (0.280 g, 0.908 mmol) and palladium, 10 wt. % (dry basis) on activated carbon 50% water wet (0.193 g, 0.182 mmol) were combined under nitrogen and diluted with 5 mL MeOH. The atmosphere was replaced with hydrogen, and the mixture was stirred rapidly overnight. The reaction was flushed with nitrogen and was filtered through celite, rinsing with MeOH. Concentration in vacuo afforded 4-(2-(4-aminophenoxy)phenyl)pyrimidin-2-amine MS m/z=279 [M+H]$^+$. Calc'd for $C_{16}H_{14}N_4O$: 278.3.

Example 463

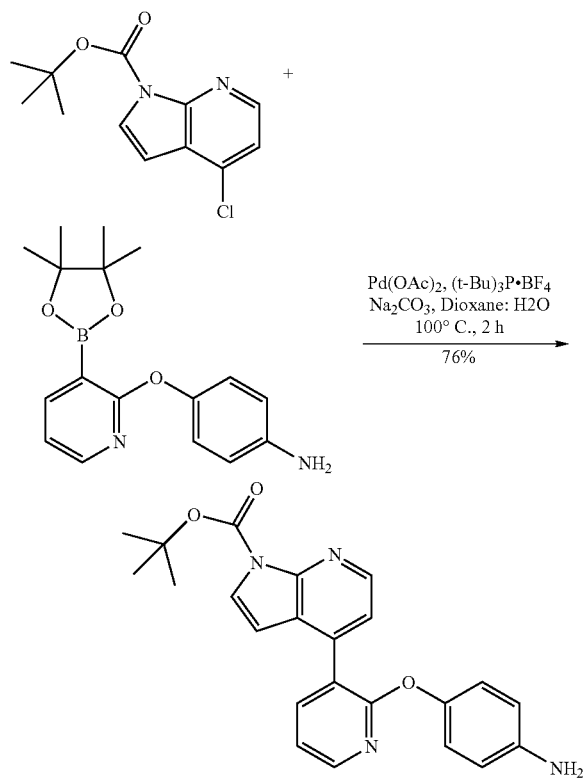

Synthesis of tert-Butyl 4-(2-(4-aminophenoxy)pyridin-3-yl)-1H-pyrrolo[2,3-b]pyridine-1-carboxylate In an argon-purged sealed tube, tert-butyl 4-chloro-1H-pyrrolo[2,3-b]pyridine-1-carboxylate (2.77 g, 11.0 mmol), 4-(3-(4,4,5,5-tetramethyl-1,3,2-dioxaborolan-2-yl)pyridin-2-yloxy)benzenamine (5.14 g, 16.5 mmol), sodium carbonate (3.49 g, 32.9 mmol), 1,4-dioxane (32.3 ml, 11.0 mmol), and water (11.7 ml, 11.0 mmol) were added. The tube was sealed, and the reaction was stirred at RT for 5 min. Palladium acetate (0.246 g, 1.10 mmol) and tri-t-butylphosphonium tetrafluoroborate (0.637 g, 2.19 mmol) were added, and the tube was sealed and heated to 100° C. After ~105 min, heating was stopped, the reaction mixture was cooled to RT and passed through a pad of celite with an aid of EtOAc. The filtrate was dried over $MgSO_4$, filtered, and concentrated. The crude product was purified by column chromatography on 120 g silica gel column using DCM and 95:05 DCM:(90:10:1 DCM:MeOH:$NH_4OH$) to flush out the nonpolar spots, then 80:20 DCM:(90:10:1 DCM:MeOH:$NH_4OH$) to collect the Boc-product. A viscous brown oil was obtained. After setting the oil at RT for several hours, crystals were formed. The oil was cooled to 0° C. and light yellow solid precipitated out after adding small amounts of hexanes and a little bit of ether in addition to scratching the wall of the flash with a spatula. The light yellow solid was filtered, washed with cold hexanes, and dried under vacuum. This solid, tert-butyl 4-(2-(4-aminophenoxy)pyridin-3-yl)-1H-pyrrolo[2,3-b]pyridine-1-carboxylate was mainly the product according to $^1$H NMR. MS Calcd for $C_{23}H_{22}N_4O_3$: [M]$^+$=402. Found: [M+H]$^+$=403.

Example 464

Synthesis of 3-(4-chlorophthalazin-1-yl)-N,N-dimethylprop-2-yn-1-amine

A resealable pressure bottle was charged with dichlorobis (triphenyl-phosphine)palladium(II) (106 mg, 0.15 mmol), N,N-dimethylprop-2-yn-1-amine (0.13 ml, 1.5 mmol), 1,4-dichlorophthalazine (300 mg, 1.5 mmol), copper(I) iodide (29 mg, 0.15 mmol), TEA (4.2 mL, 30.1 mmol), and ACN (15.0 mL, 0.1M). The vessel was sealed and the mixture was stirred at overnight at 90° C. Next day the reaction was cooled to RT, filtered over celite, and the filtrate was concentrated under reduced pressure to afford a brown residue, which was purified by ISCO silica gel chromatography (5%-7% of 90/10/1 DCM/MeOH/$NH_4OH$ to afford 3-(4-chlorophthalazin-1-yl)-N,N-dimethylprop-2-yn-1-amine. MS m/z=246 [M+1]$^+$. Calc'd for $C_{13}H_{12}ClN_3$: 245.7.

Example 465

Synthesis of 1-(4-chlorophthalazin-1-yl)piperidin-3-ol

A resealable pressure bottle was charged with potassium carbonate (273 mg, 2.0 mmol), 1,4-dichlorophthalazine (590 mg, 3.0 mmol), piperidin-3-ol (200 mg, 2.0 mmol) and methylsulfinylmethane (10 mL, 0.2M). The vessel was sealed and the mixture stirred at 90° C. for 24 hrs. Next day the reaction was cooled to RT and diluted with 5 ml of DMSO. The solution was purified by Gilson reverse phase liquid chromatography (10% to 90% $CH_3CN/H_2O$/0.1% TFA) to afford 1-(4-chlorophthalazin-1-yl)piperidin-3-ol. MS m/z 264 [M+1]$^+$. Calculated for $C_{13}H_{14}ClN_3O$: 263.7.

Example 466

Synthesis of 1-chloro-4-(4-methylthiazol-2-yl)phthalazine

Step 1. Preparation of 2-(4-methylthiazole-2-carbonyl)benzoic Acid

A dry 250 mL RBF under nitrogen was charged with THF (35.3 mL, 0.4 M), and cooled to −78° C., via dry ice bath in acetone. n-Butyllithium (6.3 mL, 15.8 mmol) was added via syringe. While keeping reaction mixture at −78° C., 4-methylthiazole (1.4 g, 15.1 mmol) in 40 mL of THF was added via addition funnel over 15 minutes. The reaction mixture was stirred at −78° C. for 2 hrs, allowed to warm up to 0° C. over half an hour, then cooled back to −78° C. and isobenzofuran-1,3-dione (3.4 g, 22.7 mmol) in 25 ml of THF rapidly added. The reaction was allowed to warm up to RT and stirred overnight. Reaction mixture was concentrated down to 30 mL, diluted with 60 mL of water, cooled to 0° C. and acidified with 6N HCl to pH4, and extracted with DCM (3×100 mL). The organic layers were combined, dried over sodium sulfate and concentrated to dryness under reduced pressure. The resulting residue was triturated with DCM to afford 2-(4-methylthiazole-2-carbonyl)benzoic acid. MS m/z=248 [M+H]$^+$. Calc'd for $C_{12}H_9NO_3S$: 247.3.

Step 2. Preparation of 4-(4-methylthiazol-2-yl)phthalazin-1(2H)-one

A RBF set up with stirring bar and reflux condenser was charged with 2-(4-methylthiazole-2-carbonyl)benzoic acid (1.9 g, 7.7 mmol), hydrazine (1.3 mL, 226.9 mmol), and ethanol (40 mL, 0.2 M) while kept under nitrogen atmosphere. The reaction mixture was stirred under reflux overnight, then cooled to RT. The resulting precipitate was filtered off and washed with DCM to afford 4-(4-methylthiazol-2-yl)phthalazin-1(2H)-one. MS m/z=244 [M+H]$^+$. Calc'd for $C_{12}H_9N_3OS$: 243.2.

Step 3. Preparation of 1-chloro-4-(4-methylthiazol-2-yl)phthalazine

A dry 50 mL RBF set up with stirring bar and reflux condenser was charged with 4-(4-methylthiazol-2-yl)phthalazin-1(2H)-one (1.6 g, 6.6 mmol) and phosphorus oxychloride (7.4 ml, 78.9 mmol). The mixture was stirred under reflux for 18 hrs, then poured onto ice while stirring vigorously. To the iced mixture was added 6N NaOH until pH=9. Stirring was continued vigorously until solids formed. The solids were filtered, washed with water and dried in oven to afford 1-chloro-4-(4-methylthiazol-2-yl)phthalazine. MS m/z=262 [M+H]$^+$. Calc'd for $C_{12}H_8ClN_3S$: 261.7.

Example 467

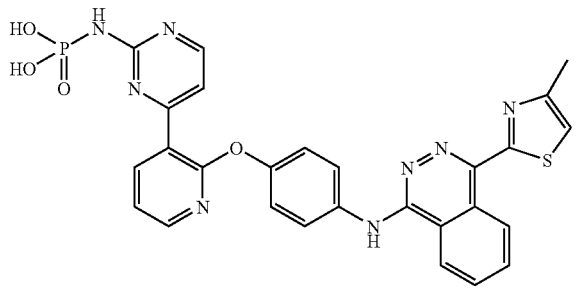

Synthesis of 4-(2-(4(4-(4-methylthiazol-2-yl)phthalazin-1-ylamino)phenoxy)pyridin-3-yl)pyrimidin-2-ylphosphoramidic acid dihydroiodide Step 1. To a yellow slurry of N-(4-(3-(2-aminopyrimidin-4-yl)pyridin-2-yloxy)phenyl)-4-(4-methylthiazol-2-yl)phthalazin-1-amine (0.335 g, 0.664 mmol) and tetrabenzyl pyrophosphate (0.501 g, 0.930 mmol) in 6.6 mL THF under nitrogen at 0° C. was added sodium bis(trimethylsilyl)amide 1 M in THF (2.32 ml, 2.32 mmol) dropwise over 3 min to give a deep red solution. The reaction was quenched with sat'd aq. NaHCO$_3$, and diluted with EtOAc. The organic layer was washed 3× with saturated aq. NaHCO$_3$, 1× brine, dried over anhydrous sodium sulfate, filtered, and concentrated in vacuo. The material was purified by silica gel chromatography, ISCO, 40 g, 50 min run, 0-60% 90/10 DCM/MeOH in DCM to give dibenzyl 4-(2-(4-(4-(4-methylthiazol-2-yl)phthalazin-1-ylamino)phenoxy)pyridin-3-yl)pyrimidin-2-ylphosphoramidate a yellow solid MS m/z 765 [M+H]$^+$. Calc'd for $C_{41}H_{33}N_8O_4PS$: 764.8.

Step 2. To a slightly cloudy mixture of dibenzyl 4-(2-(4-(4-(4-methylthiazol-2-yl)phthalazin-1-ylamino)phenoxy)pyridin-3-yl)pyrimidin-2-ylphosphoramidate (0.086 g, 0.11 mmol) in 3 mL 5:1 ACN/DCM was added iodotrimethylsilane (0.16 ml, 1.1 mmol) dropwise via syringe at ambient temperature under nitrogen. After 5 min, 0.6 mL MeOH was added and the stir bar was removed. The reaction was concentrated in vacuo and suspended in DCM and filtered. The resulting orange solid was collected and dried in vacuo to provide 4-(2-(4-(4-(4-methylthiazol-2-yl)phthalazin-1-ylamino)phenoxy)pyridin-3-yl)pyrimidin-2-ylphosphoramidic acid dihydroiodide as an orange solid. MS m/z=585 [M+H]$^+$. Calculated for $C_{27}H_{21}N_8O_4PS$: 584.6.

Example 468

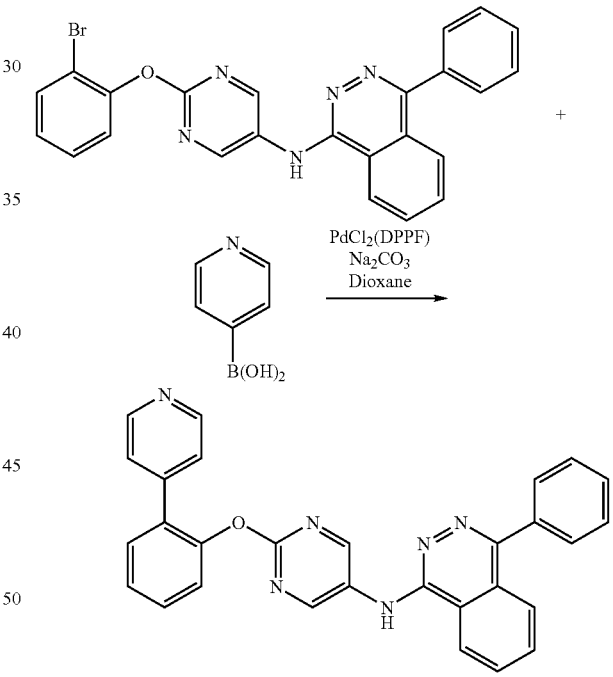

Step 1. 2-(2-Bromophenoxy)-5-nitropyrimidine

KH (6.29 g, 47.0 mmol, 30% in mineral oil) was washed with hexane under an argon atmosphere. Hexane was replaced with THF (62.7 ml, 18.8 mmol). The solution was cooled to 0° C. 2-Bromophenol (2.00 mL, 18.8 mmol) was added portion wise slowly at 0° C. The reaction was warmed to RT and a white suspension formed. After 15 min, the bubbling ceased and 2-chloro-5-nitropyrimidine (3.00 g, 18.8 mmol) was added portion wise at RT and a brown mixture formed. After 15 min, TLC showed the reaction to be complete and a new polar product formed. Water and/or alcoholic solvents were used in minimal quantities during reaction work up. The crude reaction material was passed through a pad of celite, washing with THF under a cover of nitrogen. Caution is recommended to not allow the celite pad to dry as KH is flammable and may ignite causing a fire. The wet celite cake was immediately transferred into a RBF containing THF. The excess KH was quenched with water slowly under argon atmosphere. The filtrate was concentrated to afford a yellow solid. $^1$H NMR showed mainly product, 2-(2-bromophenoxy)-5-nitropyrimidine. MS Calcd for $C_{10}H_6BrN_3O_3$: [M]$^+$=295; Found: [M+H]$^+$=296, [M+2H]$^+$=297.

Step 2. 2-(2-Bromophenox)pyrimidin-5-amine

To a solution of 2-(2-bromophenoxy)-5-nitropyrimidine (5.30 g, 17.9 mmol) in DMF (35.8 ml, 17.9 mmol) was added tin (II) chloride (17.0 g, 89.5 mmol) and water (4.48 ml, 17.9 mmol). The reaction was sonicated for 15 min and became deep red and exothermic in nature. The reaction was stirred at RT. After 4 h, the reaction was diluted with EtOAc, cooled to 0° C. and neutralized with 10% NaOH. Tin residue precipitated out of the solution. The reaction was diluted with EtOAc. The suspension was allowed to settle. The organic layer was decanted and passed through a fritted funnel. This procedure was repeated two more times to extract product into the organic layer. The organic layer, containing the product, was washed with brine, dried over MgSO$_4$, filtered, and concentrated. The product was purified by column chromatography on silica gel using 90:10 DCM:(90:10:1 DCM:MeOH:NH$_4$OH). Upon concentration of the product fractions, the resulting brown solid was dissolved/suspended in DCM, washed with water to remove the DMF, washed with brine, dried over MgSO$_4$, filtered, and concentrated. Yellow solid, 2-(2-bromophenoxy)pyrimidin-5-amine was obtained. MS Calc'd for $C_{10}H_8BrN_3O$: [M]$^+$=265. Found: [M+H]$^+$=266, [M+2H]$^+$=267.

Step 3. N-(2-(2-Bromophenoxy)pyrimidin-5-yl)-4-phenylphthalazin-1-amine 2-(2-Bromophenoxy)pyrimidin-5-amine (3.01 g, 11.3 mmol), 1-chloro-4-phenylphthalazine (2.72 g, 11.3 mmol), and butan-2-ol (56.6 ml, 11.3 mmol) were placed in a sealed tube. The reaction vessel was sealed and mixture heated to 120° C. After 1.5 h, LCMS showed mainly product as [M+H]$^+$=470 and a small amount of bromo starting material. 200 mg of phthalazine was added. After another 3.5 h, the reaction was cooled to RT. Hexane was added to allow a yellow solids to precipitate. The yellow solids were filtered and recrystallized with DCM and hexanes. The resulting dark brown solids were dried under vacuum overnight, affording the product, N-(2-(2-bromophenoxy)pyrimidin-5-yl)-4-phenylphthalazin-1-amine.

The filtrate was concentrated and the resulting residue purified by column chromatography on silica gel using 90:10 DCM:(90:10:1 DCM:MeOH:NHKOH). Product fractions were concentrated to afford a second crop of the title compound as a brown solid. MS Calc'd for $C_{24}H_{16}BrN_5O$: [M]$^+$=469; Found: [M+H]$^+$=470, [M+2H]$^+$=471.

Step 4. 4-Phenyl-N-(2-(2-(pyridin-4-yl)phenoxy)pyrimidin-5-yl)phthalazin-1-amine In an argon-purged sealed tube, N-(2-(2-bromophenoxy)pyrimidin-5-yl)-4-phenylphthalazin-1-amine (150 mg, 319 µmol), pyridin-4-ylboronic acid (157 mg, 1.27 µmol), Pd(DPPF)Cl$_2$ (47 mg, 64 µmol), sodium carbonate (239 µl, 478 µmol), and 1,4-dioxane (1.60 ml, 319 µmol) were added. The reaction was stirred at RT for 5 min. The tube was sealed and heated to 100° C. for 18 h. After 16 h, the reaction was cooled to RT, diluted with EtOAc and 10 mL of water. The product was extracted into EtOAc. The organic layer was washed with brine, dried over MgSO$_4$, filtered, and concentrated. The product was purified by column chromatography on silica gel using 60:40 DCM:(90:10:1 DCM:MeOH:NH$_4$OH). The resulting light brown solid was dissolved in 15 mL of DCM, the solvent were removed under vacuum, affording the title compound as a light brown solid. MS Calcd for $C_{29}H_{20}N_6O$: [M]$^+$=468. Found: [M+H]$^+$=469.

Example 469

Synthesis of N-(4-(3-(2-Amino-5-fluoropyrimidin-4-yl)pyridin-2-yloxy)phenyl)-4-phenylphthalazin-1-amine Step 1. N-(4-(3-(2-Chloro-5-fluoropyrimidin-4-yl)pyridin-2-yloxy)phenyl)-4-phenylphthalazin-1-amine Under an argon atmosphere, 2,4-dichloro-5-fluoropyrimidine (390 mg, 2.34 mmol) and 2-(4-(4-phenylphthalazin-1-ylamino)phenoxy)pyridin-3-ylboronic acid (1.01 g, 2.34 mmol) were dissolved in 1,2-dimethoxyethane (15.6 ml, 2.34 mmol) in a screw capped test tube. Sodium carbonate (4.67 ml, 9.34 mmol) was added followed by Pd(PPh$_3$)$_4$ (0.270 g, 0.234 mmol). The tube was purged with argon, sealed, and heated to 85° C. After 3 h, LCMS showed mostly product, a small amount of starting material left. 100 mg of Dichlorofluoropyrimidine was added, and the reaction was stirred overnight. After 22 h, LCMS showed complete conversion to product. Water was added. The product was extracted with DCM. The organic phase was dried over MgSO$_4$, filtered, and concentrated. Hexane was added to the residue. A tan solid precipitated and was filtered off with an aid of hexane. The product was purified using an ISCO column chromatography on silica gel eluting with 80:20 DCM:(90:10:1 DCM:MeOH:NHOH) and was obtained as a yellow solid, N-(4-(3-(2-chloro-5-fluoropyrimidin-4-yl)pyridin-2-yloxy)phenyl)-4-phenylphthalazin-1-amine (1.13 g, 93% yield). MS Calcd for $C_{29}H_{18}ClFN_6O$: [M]$^+$=520. Found: [M+1]$^+$=521.

Step 2. tert-Butyl 5-fluoro-4-(2-(4-(4-phenylphthalazin-1-ylamino)phenoxy)pyridin-3-yl)pyrimidin-2-ylcarbamate The title compound was prepared according to the procedure described in Garnier, E.; Andoux, J.; Pasquinet, E.; Suzenet, F.; Poullain, D.; Lebret, B.; Guillaumet, G. *J Org. Chem.* 2004, 69, 7809. Xantphos (281 mg, 486 µmol) and 1,4-dioxane (12151 µl, 2430 µmol) were added into a sealed tube. The tube was purged with argon, then palladium(II) acetate (55.0 mg, 243 µmol) was added. The mixture was stirred under argon for 10 min. In a separate sealed tube, N-(4-(3-(2-chloro-5-fluoropyrimidin-4-yl)pyridin-2-yloxy)phenyl)-4-phenylphthalazin-1-amine (1.27 mg, 2.43 mmol), tert-butyl carbamate (712 mg, 6.08 mmol), potassium carbonate (10.1 g, 72.9 mmol), and 1,4-dioxane (12.2 ml, 2.43 mmol) were added. Then Pd(OAc)$_2$/Xantphos solution was added via a syringe. The resulting mixture was heated to 110° C. under argon with vigorous stirring. After 3.5 h, LCMS showed mainly product at 1.793 min as [M+H]$^+$=602 and deBoc product at 1.602 min as [M+H]$^+$=502. The reaction was cooled to RT, diluted with DCM, passed through a pad of celite and silica gel (1 cm thick each) with an aid of DCM and a bit of MeOH. The filtrate was concentrated to afford tert-Butyl 5-fluoro-4-(2-(4-(4-phenylphthalazin-1-ylamino)phenoxy)pyridin-3-yl)pyrimidin-2-ylcarbamate, which was carried on without further purification. MS Calcd for $C_{34}H_{28}FN_7O_3$: [M]+=601. Found: [M+1]$^+$=602.

Step 3. N-(4-(3-(2-Amino-5-fluoropyrimidin-4-yl)pyridin-2-yloxy)phenyl)-4-phenylphthalazin-1-amine In a RBF, tert-butyl 5-fluoro-4-(2-(4-(4-phenylphthalazin-1-ylamino)phenoxy)pyridin-3-yl)pyrimidin-2-ylcarbamate (1.46 g, 2.43 mmol) was dissolved in DCM (4.86 ml, 2.43 mmol). TFA (749 µl, 9.72 mmol) was added at RT. The reaction was stirred at RT. After 20 min, LCMS showed mainly starting material. 1 mL of TFA was added and the reaction was allowed to stir at RT overnight. After 16 h, the reaction was concentrated and the residue dissolved in DCM. The solution was cooled to 0° C. and neutralized with 2N NaOH. At pH=5-7, the product as a white solid precipitated out. At pH>7, the product dissolves in DCM. The precipitate was filtered with aid of DCM. The solid product was set aside, while the filtrate was concentrated. The residue was diluted with a bit of DCM. Water was added. Ether was added and the whole solution was triturated to precipitate out additional product. The solid was filtered off with an aid of Et$_2$O. This crop was combined with the first crop of solid. The product was purified by column chromatography on 120 g silica gel using 70:30 DCM:(90:10:1 DCM:MeOH:NH$_4$OH). Fractions containing the product were combined, and concentrated, to afford an off white solid, which was triturated in Et$_2$O. The resulting yellow solid was filtered off with an aid of Et$_2$O and air dried. The solids were purified further via RPLC on the acidic Gilson Only fractions containing the product were combined, diluted with DCM, and washed with sat. NaHCO$_3$. The organic was dried over MgSO$_4$, filtered, and concentrated to afford N-(4-(3-(2-amino-5-fluoropyrimidin-4-yl)pyridin-2-yloxy)phenyl)-4-phenylphthalazin-1-amine. MS Calcd for C$_{29}$H$_{20}$FN$_7$O: [M]$^+$=501. Found: [M+1]$^+$=502.

Example 470

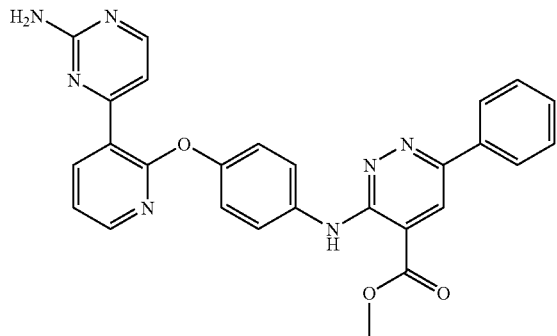

Synthesis of methyl 3-((4-((3-(2-amino-4-pyrimidinyl)-2-pyridinyl)oxy)phenyl)amino)-6-phenyl-4-pyridazinecarboxylate A RBF was charged with 4-(dimethylamino)pyridine (5.4 mg, 44 μmol), 3-(4-(3-(2-aminopyrimidin-4-yl)pyridin-2-yloxy)phenylamino)-6-phenylpyridazine-4-carboxylic acid (210 mg, 440 μmol), methanol (53 μl, 1319 μmol) and 1.3 mL DCM. The mixture was cooled to 0° C. and 1,3-dicyclohexylcarbodiimide (100 mg, 484 μmol) dissolved in 1.3 mL DCM was added. The heterogeneous mixture was allowed to warm to RT and stirred for 4 h. 1.3 mL of DMF was added and the reaction was stirred at RT for 72 h. The mixture was filtered through a pad of Celite, washing with DCM. The filtrate was concentrated twice from toluene to remove excess DMF. The crude material was purified by silica gel chromatography, 0-10% MeOH/dDCM. Further purification was done by reverse phase chromatography, Gilson, 5-75% acetonitrile/ 0.1% TFA over 14 min to provide methyl 3-(4-(3-(2-aminopyrimidin-4-yl)pyridin-2-yloxy)phenylamino)-6-phenylpyridazine-4-carboxylate cleanly as a bright yellow solid. MS m/z=492 [M+H]$^+$. Calc'd for C$_{27}$H$_{21}$N$_7$O$_3$: 491.50.

Example 471

Synthesis of 3-chloro-4-methoxy-6-phenylpyridazine 3,4-Dichloro-6-phenylpyridazine was synthesized from □-oxobenzenebutanoic acid and 1-(phenylmethyl)hydrazine in 2 steps according to a procedure by Sircar (Sircar, 1. *J. Het. Chem.* 1983, 20, 1473-1476.) 3,4-Dichloro-6-phenylpyridazine (100 mg, 0.44 mmol) was combined with sodium methoxide (1.1 mL of a 0.50M solution in methanol, 0.55 mmol, 1.25 equiv.) and methanol (296 μl, 1.5M) in a resealable tube and heated to 65° C. for 1 hour. The methanol was evaporated in vacuo, and water was added to the residue. The mixture was extracted with DCM, dried over K$_2$CO$_3$, filtered and concentrated in vacuo, to afford 3,4-dimethoxy-6-phenylpyridazine and 3-methoxy-4-chloro-6-phenylpyridazine, the title compound, as a solid.

Example 472

Synthesis of 7-chloro-4-phenylfuro[3,2-d]pyridazine

Step 1. N-tert-butylfuran-2-carboxamide

To a slurry of furan-2-carboxylic acid (10.0 g, 89 mmol) in 100 mL DCM at 0° C. under nitrogen was added DMF (0.069 ml, 0.89 mmol) and oxalyl chloride (9.9 ml, 112 mmol) slowly in small portions over 5 min. The reaction was allowed to warm to ambient temperature. After 3 h, the clear solution was concentrated in vacuo and the resulting oil was dissolved in 75 mL THF and cooled to 0° C. A solution of tert-butylamine (28 ml, 268 mmol) in 25 mL THF was added dropwise over 1 h. The bath was allowed to expire and the slurry was stirred over the weekend. The reaction was concentrated in vacuo and partitioned between 1N NaOH and DCM. The aqueous layer was extracted twice with DCM. The combined organic layers were concentrated in vacuo to give N-tert-butylfuran-2-carboxamide as a white solid. MS m/z=168 [M+H]$^+$. Calc'd for C$_9$H$_{13}$NO$_2$: 167.2.

Step 2. 3-benzoyl-N-tert-butylfuran-2-carboxamide

To a stirring solution of N-tert-butylfuran-2-carboxamide (1.8 ml, 12 mmol) in 100 mL DME under argon at −78° C. was added tert-butyllithium, 1.7 M solution in pentane (14 ml, 24 mmol) slowly dropwise over 5 min. The heterogeneous reaction mixture was allowed to stir 1 h, at which point a solution of N-tert-butylfuran-2-carboxamide (1.8 ml, 12 mmol) in 10 mL DME was added over 5 min, dropwise. After 15 min, the bath was removed and the reaction was allowed to warm to ambient temperature. The reaction was quenched by addition of saturated aqueous ammonium chloride, water, and EtOAc. The organic layer was dried over anhydrous sodium sulfate, filtered, and concentrated in vacuo. The resulting material was purified by silica gel chromatography, ISCO, 80 g, 0-40% EtOAc/hexanes over 33 min to give a semi-solid. This material was triturated 3x hexanes to give 3-benzoyl-N-tert-butylfuran-2-carboxamide as white crystals. MS m/z=272 [M+H]$^+$. Calc'd for C$_{16}$H$_{17}$NO$_3$: 271.3.

Step 3. 3-benzoylfuran-2-carboxylic Acid

To slurry of 3-benzoyl-N-tert-butylfuran-2-carboxamide (0.863 g, 3.18 mmol) in 4 mL dioxane and 3 mL water was added sulfuric acid (1.02 ml, 19.1 mmol). The mixture was sealed and heated to 120° C. for a total of 48 h. Additional 3.0 equiv H$_2$SO$_4$ was added, and the reaction was heated for 8 h. The reaction was cooled and partitioned between water and DCM. The aqueous layer was extracted with DCM (4×), and the combined organics were dried over anhydrous sodium sulfate, filtered, and concentrated in vacuo to give 3-benzoylfuran-2-carboxylic acid as a brown semi-solid. This material was carried on without further purification. MS m/z=217 [M+H]$^+$. Calc'd for $C_{12}H_8O_4$: 216.2.

Step 4. 4-Phenylfuro[3,2-d]pyridazin-7-ol

A brown solution of 3-benzoylfuran-2-carboxylic acid (0.770 g, 3.56 mmol) and anhydrous hydrazine (0.568 ml, 17.8 mmol) was heated to 100° C. in a sealed tube for approx. 72 h. The reaction was cooled, and diluted with sat'd aq. NH$_4$Cl and EtOAc. The organic layer was washed with sat'd aq. NH$_4$Cl and brine, and dried over anhydrous sodium sulfate, filtered, and concentrated in vacuo to give 4-phenylfuro[3,2-d]pyridazin-7-ol which was carried on without further purification. MS m/z=213 [M+H]$^+$. Calc'd for $C_{12}H_8N_2O_2$: 212.2.

Step 5. Chloro-4-phenylfuro[3,2-d]pyridazine

A slurry of 4-phenylfuro[3,2-d]pyridazin-7-ol (0.327 g, 1.5 mmol) and pyridine (0.38 ml, 4.6 mmol) in 5 mL POCl$_3$ was heated with a water-cooled reflux condenser with drying tube to 130° C. for 3 h. The brown solution was cooled and the reaction judged complete by LCMS. The reaction was poured onto ice with stirring. The solution was neutralized with 6 N NaOH and ice to control temperature. The resulting mixture was extracted into DCM (3×). The combined organic extracts were dried over anhydrous sodium sulfate, filtered, and concentrated in vacuo. The solid was adsorbed onto 2 g silica gel from DCM/MeOH and dried. The material was purified by silica gel chromatography, eluting with 0-20% EtOAc/DCM to give 7-chloro-4-phenylfuro[3,2-d]pyridazine as an off-white solid. MS m/z=231 [M+H]$^+$. Calc'd for $C_{12}H_7ClN_2O$: 230.7.

Example 473

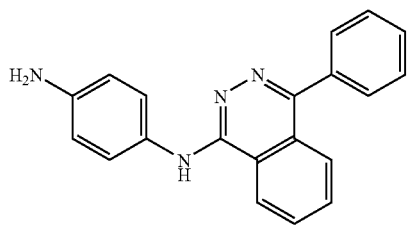

Synthesis of N1-(4-phenylphthalazin-1-yl)benzene-1,4-diamine

Benzene-1,4-diamine (0.337 g, 3.12 mmol) and 1-chloro-4-phenylphthalazine (0.500 g, 2.08 mmol) were treated with 7.5 mL 2-BuOH in a sealed tube and heated to 110° C. The reaction quickly became a solid, yellow mass. After several hours, the reaction was cooled and diluted with water. The slurry was then partitioned between DCM and 1N NaOH. The aqueous layer was extracted into DCM (2×). The combined organic layers were dried over anhydrous sodium sulfate, filtered, and concentrated in vacuo. The resulting material was purified by silica gel chromatography, ISCO, 40 g, 0-10% MeOH/MC to give N1-(4-phenylphthalazin-1-yl)benzene-1,4-diamine as an orange-brown solid. MS m/z=313 [M+H]$^+$. Calc'd for $C_{20}H_{16}N_4$: 312.4.

Example 474

Synthesis of 4-(3-Bromopyridin-2-yloxy)benzenamine

3-Bromo-2-chloropyridine (10.3 g, 53.4 mmol), 4-aminophenol (7.00 g, 64.1 mmol), cesium carbonate (34.8 g, 107 mmol), and DMSO (53 ml, 53.4 mmol) were added into a pressure tube. The tube was capped and placed in a preheated oil bath at 130° C. After 16 h, the reaction mixture was stirred and cooled in ice-water. Water was added slowly to the mixture and the product precipitated out as a gray solid. The solids were washed with water, dried under vacuum at RT to afford 4-(3-bromopyridin-2-yloxy)benzenamine. MS Calcd for C, H$_9$BrN$_2$O: [M]$^+$=264. Found [M+H]$^+$=265.

Example 475

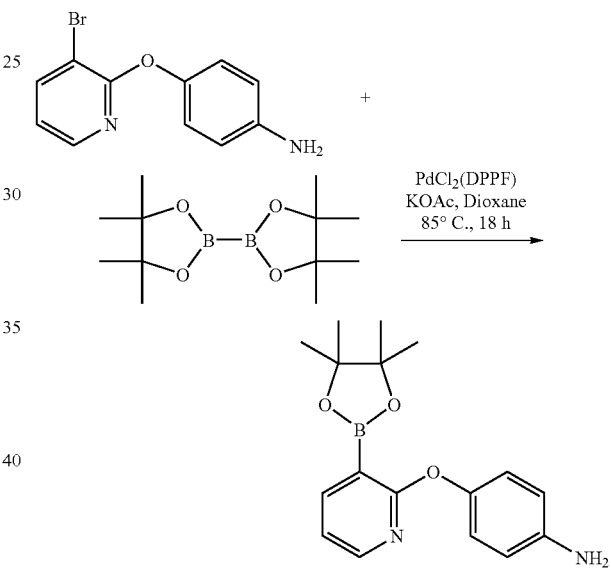

Synthesis of 4-(3-(4,4,5,5-Tetramethyl-1,3,2-dioxaborolan-2-yl)pyridin-2-yloxy)benzenamine Into a sealed tube was added 4-(3-bromopyridin-2-yloxy)benzenamine (5.38 g, 20.0 mmol), 1,4-dioxane (101 ml, 20.0 mmol), and potassium acetate (6.00 g, 61.0 mmol). The tube was purged with argon. Then PdCl$_2$(DPPF) (0.700 g, 1.00 mmol) and 4,4,5,5-tetramethyl-2-(4,4,5,5-tetramethyl-1,3,2-dioxaborolan-2-yl)-1,3,2-dioxaborolane (13.0 g, 53.0 mmol) were added. The reaction mixture was stirred for 0.5 h at rt until a deep brown solution was formed. The reaction tube was then placed in a preheated oil bath at 85° C. After 18 h, the reaction was cooled to rt and passed through a pad of celite with an aid of EtOAc to remove the black impurities. The filtrate was concentrated to give a brown oil. The oil was placed under vacuum over the weekend and became a solid of 4-(3-(4,4,5,5-tetramethyl-1,3,2-dioxaborolan-2-yl)pyridin-2-yloxy)benzenamine. MS Calcd for $C_{17}H_{21}BN_2O_3$: [M]$^+$=312. Found: [M+H]$^+$=313.

Example 476

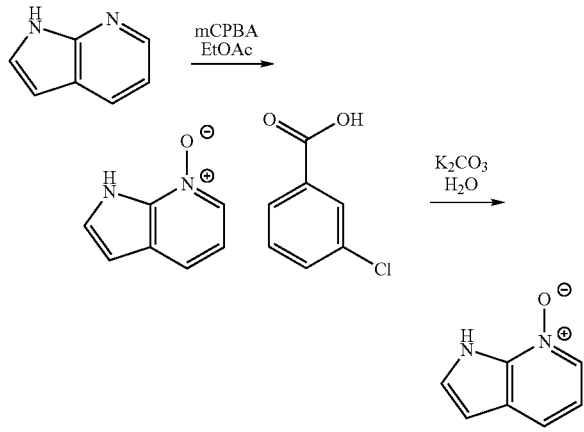

Synthesis of 1H-Pyrrolo[2,3-b]pyridine

The title compound was prepared according to the procedure described in WO2003082289A1. A solution of 1H-pyrrolo[2,3-b]pyridine (10.0 g, 84.6 mmol) in EtOAc (846 ml, 84.6 mmol) was cooled to 0° C. To the cold solution was added a solution of mCPBA (103 mmol, 23.1 g, 77% pure) in 53 mL of EtOAc over a period of 1.5 h. An additonal 100 mL of EtOAc was added to dilute the reaction. The residual of mCPBA was washed into the reaction mixture by an additional portion of EtOAc (25 mL). A lot of solid precipitated out of the solution. The resulting solution was warmed to rt, and allowed to stir at RT for 3 h. The reaction mixture was cooled to 0° C. and the resulting slurry was filtered to collect the N-oxide as the meta-chlorobenzoic acid salt. The solid was washed with additional EtOAc and dried under vacuum. The product, 1H-pyrrolo[2,3-b]pyridine 1-oxide salt of mCBA was obtained as light yellow solid. $^1$H NMR in deuterated MeOH indicated predominately the mCBA salt of the N-oxide.

The mCBA salt was treated with aqueous base to liberate the N-oxide. A slurry of the N-oxide mCBA salt (35.5 g, 265 mmol) in 149 mL of deionized water at 15° C. was treated with sufficient amount of aqueous solution containing 30% by weight of potassium carbonate (11.0 g, 79.4 mmol) to raise the pH of the slurry between 9.5 to 10.5. Additional water (74 mL) was added to the mixture while the temperature was maintained between 15° C. to rt for 2 h. The slurry was cooled to 0° C. for 5 h, and then filtered to recover the precipitate. The precipitate was washed with water and dried to afford the white N-oxide product, 1H-pyrrolo[2,3-b]pyridine 1-oxide. $^1$H NMR (Bruker, 400 MHz, CD$_3$OD) □: 8.23 (d, J=6.3 Hz, 1H), 7.94 (d, J=8.1 Hz, 1H), 7.52 (d, J=3.3 Hz, 1H), 7.22 (m, 1H), 6.71 (d, J=3.3 Hz, 1H).

Example 477

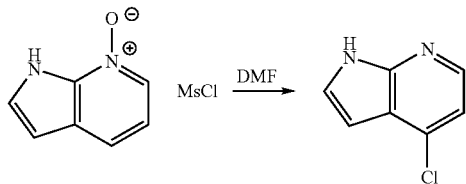

Synthesis of 4-Chloro-1H-pyrrolo[2,3-b]pyridine

The title compound was prepared according to the procedure described in WO2003082289A1. A solution of azaindole N-oxide (6.82 g, 51.0 mmol) in DMF (36.0 ml, 470 mmol) was heated to 50° C. Methanesulfonyl chloride (11.0 ml, 137 mmol) was added to the heated solution at such a rate as to maintain the reaction temperature at 65 to 75° C. The resulting mixture was heated at 68-77° C. until the reaction was judged complete by RPLC. The total reaction time was 4 hours. The reaction was cooled to rt and quenched with water (10 mL). The mixture was cooled to 5° C. 10 N NaOH solution was added to raise the pH of the solution to 7. The resulting slurry was warmed to rt, agitated for 1 h, and then filtered to collect the product. The product was washed with additional water and dried under vacuum. Rusty solid, 4-chloro-1H-pyrrolo[2,3-b]pyridine was collected. $^1$H NMR (Bruker, 400 MHz, DMSO-d$_6$) 12.0 (br s, 1H), 8.19 (d, J=5.4 Hz, 1H), 7.60 (t, J=3.0 Hz, 1H), 7.20 (d, J=5.0 Hz, 1H), 6.52 (d, J=3.0 Hz, 1H).

Example 478

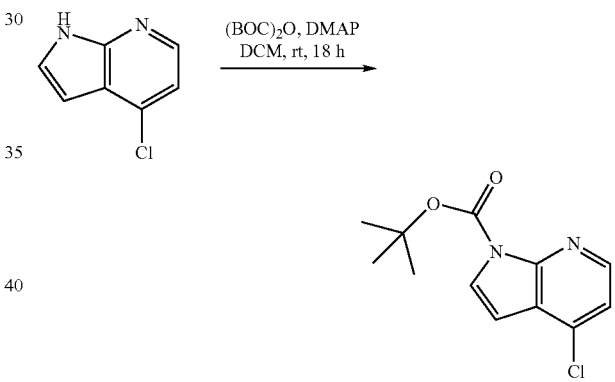

Synthesis of tert-Butyl 4-chloro-1H-pyrrolo[2,3-b]pyridine-1-carboxylate

To a solution of 4-chloro-1H-pyrrolo[2,3-b]pyridine (3.00 g, 19.7 mmol), N,N-dimethylpyridin-4-amine (1.20 g, 9.83 mmol), dichloromethane (67.8 ml, 19.7 mmol) was added di-tert-butyl dicarbonate (4.72 g, 21.6 mmol). The resulting mixture was stirred at rt under nitrogen. After 18 h, the reaction mixture was diluted with CH$_2$Cl$_2$, washed with saturated sodium bicarbonate, and washed with brine. The organic phase was dried over magnesium sulfate, filtered, and concentrated. Performing ISCO column chromatography on silica gel using 90:10 Hex:EtOAc afforded the product as a colorless oil. The oil was placed in the vacuum oven overnight to remove EtOAc. White solid, tert-butyl 4-chloro-1H-pyrrolo[2,3-b]pyridine-1-carboxylate formed slowly under vacuum. MS Calcd for C$_{12}$H$_{13}$ClN$_2$O$_2$: [M]$^+$=252. Found: [2M+Na]$^+$=527.

Example 479

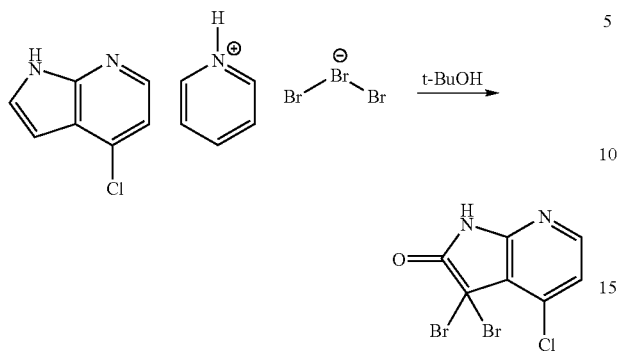

Synthesis of 3,3-Dibromo-4-chloro-1H-pyrrolo[2,3-b]pyridin-2(3H)-one

The title compound was prepared according to the procedure described in WO2001046196A1. To a stirred suspension of 4-chloro-1H-pyrrolo[2,3-b]pyridine (2.00 g, 13.1 mmol) in t-BuOH (131 ml, 13.1 mmol) was added pyridinium tribromide (14.1 g, 44.2 mmol) by small portions. The solution was stirred at rt for 2 h. After 3 h, LCMS showed product and mono brominated product. 5.00 g of pyridinium tribromide was added. After 1.5 h, LCMS showed mainly product and excess pyridinium tribromide. After another 0.5 h, water was added and the whole was diluted with EtOAc until all solids were dissolved. The product was extracted with EtOAc. The organic layer was washed with brine, dried over MgSO$_4$, filtered, and concentrated. Trituration of the crude product with hexanes gave an orange solid. $^1$H NMR confirmed the product, 3,3-dibromo-4-chloro-1H-pyrrolo[2,3-b]pyridin-2(3H)-one (4.07 g, 95% yield). The product was insoluble in DCM and CHCl$_3$. MS Calcd for C$_7$H$_3$Br$_2$ClN$_2$O: [M]$^+$=324. Found: [M+H]$^+$=325, [M+3H]$^+$=327.

Example 480

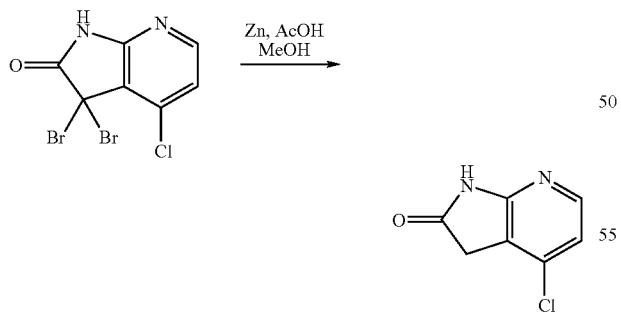

Synthesis of 4-Chloro-1H-pyrrolo[2,3-b]pyridin-2(3H)-one

The title compound was prepared according to the procedure described in WO2001046196A 1. A mixture of 3,3-dibromo-4-chloro-1H-pyrrolo[2,3-b]pyridin-2(3H)-one (4.07 g, 12.5 mmol), zinc dust (8.15 g, 125 mmol), AcOH (54.2 ml, 12.5 mmol), and MeOH (54.2 ml, 12.5 mmol) was stirred at rt. After 3 h, the reaction mixture was passed through a pad of celite with an aid of EtOAc. The filtrate was then diluted with brine. The whole was extracted with EtOAc. The organic layer was further washed with brine, dried over MgSO$_4$, filtered, concentrated. The product was purified by column chromatography on silica gel using 70:30 DCM:(90:10:1 DCM:MeOH:NHOH). Fractions containing the product were concentrated. White cotton-like solid, 4-chloro-1H-pyrrolo[2,3-b]pyridin-2(3H)-one was obtained. MS Calcd for C$_7$H$_5$ClN$_2$O: [M]$^+$=168. Found: [M+H]$^+$=169.

Example 481

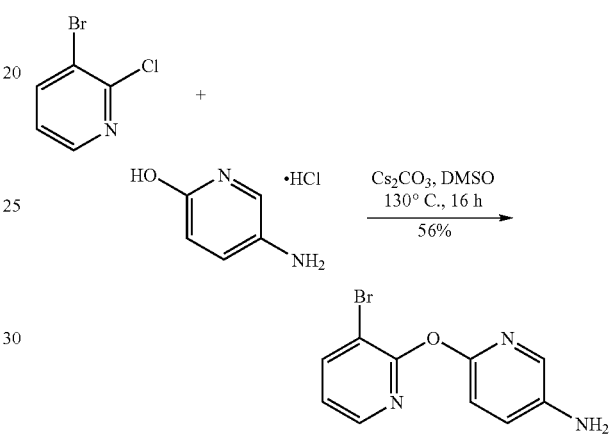

Synthesis of 6-(3-Bromopyridin-2-yloxy)pyridin-3-amine

3-Bromo-2-chloropyridine (7.27 g, 37.8 mmol), 5-aminopyridin-2-ol (4.99 g, 45.3 mmol), freshly ground cesium carbonate (36.9 g, 113 mmol), and DMSO (37.8 ml, 37.8 mmol) were added into a glass round bottom pressure vessel equipped with a stir bar. The vessel was sealed and placed in a preheated oil bath at 130° C. After 18 h, the reaction was diluted with EtOAc (4×250 mL) and the whole solution was sonicated. After the solid was settled, the top solution was decanted through a pad of celite and silica gel (each layer was 1 cm). This procedure was repeated for the salt residue which left in the flask to remove the product and DMSO from the salt. The filtrate was concentrated to give an oil which included the product and DMSO. The product was extracted with EtOAc (3×300 mL) and DCM (1×100 mL). The EtOAc and DCM layers were washed separately with a minimum amount of brine. The organic phases were dried separately over a minimum amount of MgSO$_4$. The MgSO$_4$ was filtered off and the filtrates were combined and concentrated. A wet, light green solid was obtained. The solid was triturated with hexanes. The solid was filtered off, collected, and dried under vacuum. The product, 6-(3-bromopyridin-2-yloxy)pyridin-3-amine was collected as tan solids. A second batch was obtained from the filtrate. The filtrate was concentrated to give an oil. The oil was purified by ISCO column chromatography using 90:10 DCM:(90:10:1 DCM:MeOH:NH$_4$OH). A light yellow solid, was obtained, dried under vacuum, and given a sample ID: A wet, green solid was obtained, dried under vacuum. MS Calcd for $C_{10}H_8BrN_3O$: $[M]^+=265$. Found $[M+1]^+=266$.

Example 482

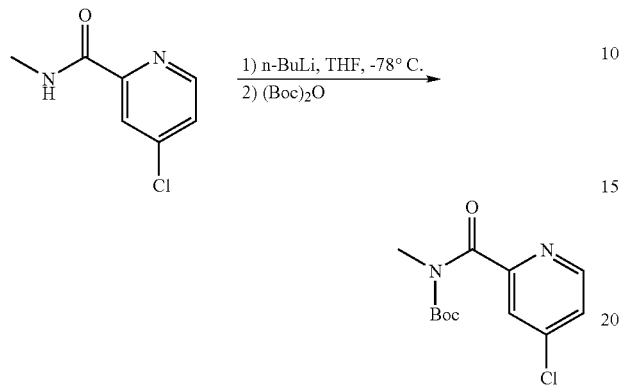

Synthesis of tert-Butyl 4-chloropicolinoyl(methyl)carbamate

The title compound was prepared according to the procedure described in references: Marino, J. P.; Rubio, M. B.; Cao, G.; de Dios, A. *J. Am. Chem. Soc.* 2002, 124, 13398. (b) Diaz, D. D.; Finn, M. G. *Org. Lett.* 2004, 6, 43. (c) Padwa, A.; Brodney, M. A.; Lynch, S. M.; Rashatasakhon, P.; Wang, Q.; Zhang, H. *J. Org. Chem.* 2004, 69, 3735). A solution of 4-chloro-N-methylpicolinamide (1.00 g, 5.86 mmol) in THF (11.7 ml, 5.86 mmol) was cooled to –78° C. Then n-BuLi (2345 µl, 5862 µmol) in THF was added dropwise at –78° C. A thick yellow suspension was formed in 5 min. The suspension was stirred at –78° C. for 30 min, then warmed to 0° C., stirred at this temperature for 10 min, and cooled back down to –78° C. Di-tert-butyl dicarbonate (2.30 mg, 10.6 mmol) in 5 mL of THF was added dropwise. The reaction was stirred at –78° C. for 0.5 h and at 0° C. for 20 min, and warmed to rt for 10 min. LCMS showed product at 2.231 min composed of $[M]^+$, $[M+Na]^+$, $[2M+Na]^+$; and starting material at 1.631 min in a ratio of 1:3. After 20 min, LCMS showed more product formed. The reaction was stirred at rt for 2 days. After 2 days, LCMS showed 1:1 Prod:SM. The reaction was stopped. The whole was extracted with EtOAc, washed with brine, dried over MgSO$_4$, filtered, and concentrated. The product was purified by performing column chromatography on silica gel using 80:20 Hex:EtOAc. $^1$H NMR showed mainly product. The product, tert-butyl 4-chloropicolinoyl (methyl)carbamate (849 mg, 54% yield) was collected as light yellow solid. MS Calculated for $C_{12}H_{15}ClN_2O_3$: $[M]^+=270$. Found $[2M+Na]^+=563$.

Example 483

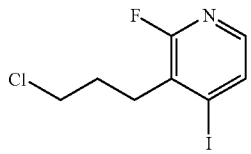

Synthesis of 3-(3-Chloropropyl)-2-fluoro-4-iodopyridine

To a –78° C. solution of 2-fluoro-3-iodopyridine (186 mg, 834 µmol) in tetrahydrofuran (4171 µl, 834 µmol) was added a solution of 2M LDA (500 µl, 1.00 mol) in heptane/THF at –78° C. After 1 h at –78° C., 1-chloro-3-iodopropane (512 mg, 2.50 mmol) in 0.5 mL of THF was added to the anion solution slowly at –78° C. After 30 min at –78° C., the reaction was warmed to rt and stirred overnight. The reaction was diluted with DCM, washed with brine, dried over MgSO$_4$, filtered, and concentrated. The residue was purified by performing a column chromatography on silica gel using 95:05 Hex:EtOAc. Fractions containing the product were concentrated. $^1$H NMR showed product, 3-(3-chloropropyl)-2-fluoro-4-iodopyridine. Light yellow liquid/solid mixture was collected. MS Calcd for $C_8H_8ClFIN$: $[M]^+=299$. Found: $[M+H]^+=300$. HRMS Calcd for $C_8H_8ClFIN$: $[M]^+=298.9447$. Found: $[M+H]^+=299.9752$. mp=24-25° C.

Example 484

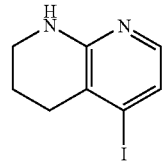

Synthesis of 5-Iodo-1,2,3,4-tetrahydro-1,8-naphthyridine 3-(3-Chloropropyl)-2-fluoro-4-iodopyridine (3.31 g, 11 mmol), ammonium hydroxide (71 mL, 20 ml, 553 mmol, 28.0-30.0%), ammonium acetate (12 g, 155 mmol), potassium iodide (3.9 g, 23 mmol), potassium carbonate (7.6 g, 55 mmol), and DMF (22 ml, 11 mmol) were added into a sealed tube. The tube was sealed and placed in an oil bath at 60° C. After 7 h, the reaction was cooled down to rt. Colorless crystals was formed. The reaction was diluted with EtOAc. The organic layer was extracted with EtOAc, washed with brine, dried over MgSO$_4$, filtered, and concentrated. The product was purified by column chromatography on silica gel using Hex and 70:30 Hex:EtOAc. A suspension was obtained. This suspension was diluted with DCM, washed with water to remove the DMF, washed with brine, dried over MgSO$_4$, filtered, and concentrated. Off white solid was obtained. $^1$H NMR was showed mainly product, 5-iodo-1,2,3,4-tetrahydro-1,8-naphthyridine. This material was carried to the next step. $^1$H NMR (400 MHz, CDCl$_3$) δ 7.46 (d, J=5.3 Hz, 1H), 7.01 (d, J=5.3 Hz, 1H), 4.90 (br s, 1H), 3.39. mp=117-118° C.

Example 485

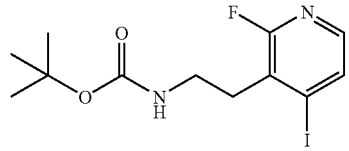

Synthesis of tert-Butyl 2-(2-fluoro-4-iodopyridin-3-yl)ethylcarbamate

To –78° C. solution of 2-fluoro-3-iodopyridine (7.61 g, 34.1 mmol) in tetrahydrofuran (171 ml, 34.1 mmol) was added a solution of 2M LDA (20.5 ml, 41.0 mmol) in heptane/THF at −78° C. After 1 h 20 min at −78° C., sulfamidate (9.90 g, 44.4 mmol) in 80 mL of THF was added to the anion solution slowly at −78° C. over 10 min. After 30 min, the reaction was warmed to rt and the reaction was stirred overnight. The solvent was evaporated and the residue was diluted with 70 mL of water and treated with 6 N HCl until the pH=1. After 1.5 h, an aliquot was removed, diluted with EtOAc, and neutralized with sat NaHCO$_3$. LCMS of the organic layer showed tert-butyl 2-(2-fluoro-4-iodopyridin-3-yl)ethylcarbamate at 2.250 min as [M+H]$^+$=367. After 2 h, the reaction was cooled to 0° C., 100 mL of DCM was added, and the whole was neutralized slowly with sat. NaHCO$_3$ and solid NaHCO$_3$ to pH=7. The product was extracted with DCM (3×100 mL). The organic layer was washed with brine, dried over MgSO$_4$, filtered and concentrated. The residue was purified by column chromatography on silica gel using 80:20 Hex:EtOAc to collect the product. Viscous yellow oil became a light tan solid. $^1$H NMR showed mainly product, tert-butyl 2-(2-fluoro-4-iodopyridin-3-yl)ethylcarbamate. MS Calcd for C$_{12}$H$_{16}$FIN$_2$O$_2$: [M]$^+$=366. Found: [M+H]$^+$=367. HRMS Calcd for C$_{12}$H$_{16}$FIN$_2$O$_2$: [M]$^+$=366.0313. Found: [M+H]$^+$=367.0324.

Example 486

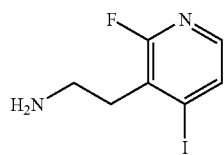

Synthesis of 2-(2-Fluoro-4-iodopyridin-3-yl)ethanamine

TFA (0.677 ml, 8.79 mmol) was added into a solution of tert-butyl 2-(2-fluoro-4-iodopyridin-3-yl)ethylcarbamate (1.61 g, 4.40 mmol) in DCM (6.28 ml, 4.40 mmol). After 4 h, LCMS showed mainly starting material. 1 mL of TFA was added. After 16 h, the reaction was diluted with DCM, neutralized with sat. NaHCO$_3$. The product was extracted with DCM. The organic layer was washed with brine, dried over MgSO$_4$, and concentrated to afford a creamy colored solid, 2-(2-fluoro-4-iodopyridin-3-yl)ethanamine. MS Calcd for C$_7$H$_8$FIN$_2$: [M]$^+$=266. Found: [M+H]$^+$=267. HRMS Calcd for C$_7$H$_8$FIN$_2$: [M+H]$^+$=266.9789. Found: [M+H]$^+$=266.9802.

Example 487

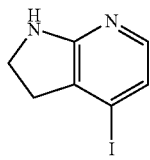

Synthesis of 4-Iodo-2,3-dihydro-1H-pyrrolo[2,3-b]pyridine 2-(2-Fluoro-4-iodopyridin-3-yl)ethanamine (666 mg, 2503 μmol), potassium carbonate (727 mg, 5.26 mmol), and DMF (5.00 ml, 2.50 mmol) were added into a sealed tube. The tube was sealed and placed in an oil bath at 60° C. After 23 h, the reaction was diluted with DCM, washed with brine, dried over MgSO$_4$, filtered, and concentrated. The residue was dissolved in 50 mL of DCM and washed with water (3×30 mL) to remove DMF. The organic layer was washed with brine, dried over MgSO$_4$, filtered, and concentrated. Dark orange solid (semi-liquid) was obtained. $^1$H NMR showed mainly desired cyclized product, 4-iodo-2,3-dihydro-1H-pyrrolo[2,3-b]pyridine. MS Calcd for C$_7$H$_7$IN$_2$: [M]$^+$=246. Found: [M+H]$^+$=247.

Example 488

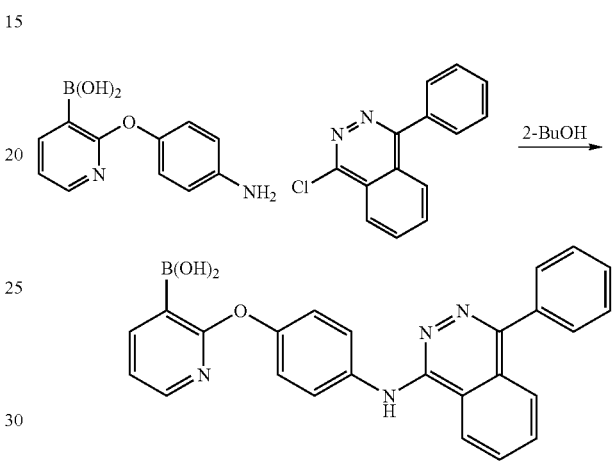

Synthesis of 2-(4-(4-Phenylphthalazin-1-ylamino) phenoxy)pyridin-3-ylboronic Acid 2-(4-Aminophenoxy)pyridin-3-ylboronic acid (478 mg, 2.08 mmol), 1-chloro-4-phenylphthalazine (500 mg, 2.08 mmol) and butan-2-ol (4.16 ml, 2.08 mmol) were placed in a sealed tube. The reaction vessel was sealed and the mixture heated to 100° C. After 1 h 45 min, the reaction was cooled to rt. Hexane was added and the precipitated tan solid was filtered off with hexanes. LCMS of the solids indicated product, 2-(4-(4-phenylphthalazin-1-ylamino)phenoxy)pyridin-3-ylboronic acid. MS Calculated for C$_{25}$H$_{19}$BN$_4$O: [M]$^+$=434. Found: [M+1]$^+$=435.

Example 489

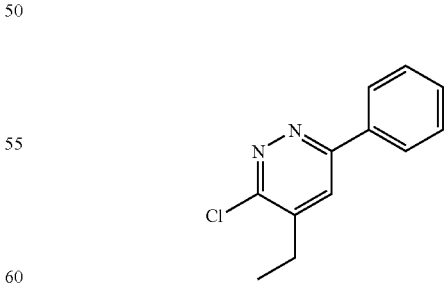

Synthesis of 3-chloro-4-ethyl-6-phenylpyridazine

A RBF was charged with 3-chloro-4-methyl-6-phenylpyridazine (5.0 g, 24 mmol) and 120 mL of THF under nitrogen, and the solution was cooled to −78° C. Lithium diisopropylamide, 2.0M in heptane/THF/ethylbenzene (15 ml, 29 mmol) was added and the mixture was stirred at −78° C. for 5 min, followed by RT for 1 h. The mixture was cooled to −78° C. and methyl iodide (1.8 ml, 29 mmol), which had been passed through a plug of basic alumina prior to use, was added dropwise. After stirring at −78° C. for 5 min, the reaction was stirred at RT for 0.5 h. Water was added to quench the reaction, and the mixture was concentrated and partitioned between dichloromethane and water. The layers were separated and the aqueous portion was extracted with additional DCM. The combined organics were dried with MgSO$_4$, filtered and concentrated. The crude material was purified by silica gel chromatography (100% DCM to 95/5 DCM/MeOH) to provide 3-chloro-4-ethyl-6-phenylpyridazine as a tan solid. MS m/z=219 [M+H]$^+$. Calc'd for $C_{12}H_{11}ClN_2$: 218.68.

Example 490

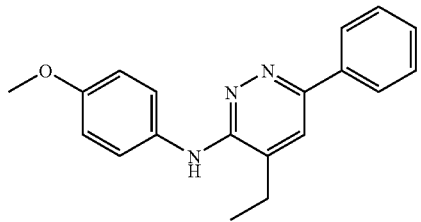

Synthesis of 4-ethyl-N-(4-methoxyphenyl)-6-phenylpyridazin-3-amine

A pressure bottle was charged with 3-chloro-4-ethyl-6-phenylpyridazine (1.00 g, 4.57 mmol), 1,4-anisidine (0.526 ml, 4.57 mmol), tris(dibenzylideneacetone)dipalladium (0) (0.105 g, 0.114 mmol), S-Phos (0.188 g, 0.457 mmol), sodium tert-butoxide (0.615 g, 6.40 mmol) and 13.8 mL of toluene. The bottle was sealed and the reaction mixture was heated 100° C. for 1 h. Upon cooling, the mixture was diluted with DCM and washed with water. The organic portion was dried with MgSO$_4$, filtered and concentrated. The crude material was purified by silica gel chromatography using 5% MeOH/DCM to provide 4-ethyl-N-(4-methoxyphenyl)-6-phenylpyridazin-3-amine as a tan solid. MS m/z=306 [M+H]$^+$. Calc'd for $C_{19}H_{19}N_3O$: 305.37.

Example 491

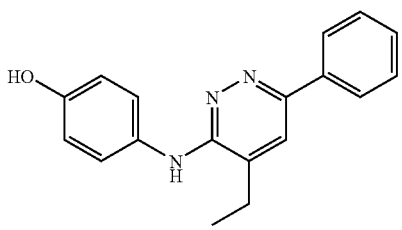

Synthesis of 4-(4-ethyl-6-phenylpyridazin-3-ylamino)phenol

A RBF was charged with 13.9 mL of 1:1 AcOH:HBr and 4-ethyl-N-(4-methoxyphenyl)-6-phenylpyridazin-3-amine (1.27 g, 4.16 mmol). The flask was fitted with a reflux condenser and was heated at 140° C. for 4 h. Upon cooling, the reaction mixture was poured into ice water and brought to neutral pH by careful addition of 2M aqueous Na$_2$CO$_3$. The resulting precipitate was filtered, washed with water and dried under vacuum to provide 4-(4-ethyl-6-phenylpyridazin-3-ylamino)phenol as a tan solid. MS m/z=292 [M+H]$^+$. Calc'd for $C_{18}H_{17}N_3O$: 291.35.

Example 492

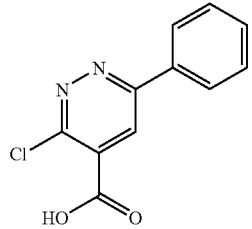

Synthesis of 3-Chloro-6-phenylpyridazine-carboxylic acid

A 250 mL RBF was charged with 56 mL of anhydrous THF, cooled to −78° C. and kept under nitrogen atmosphere. Butyllithium (2.5 M, 5770 μl, 14426 μmol) was added, followed by 2,2,6,6-tetramethylpiperidine (2656 μl, 15737 μmol). The mixture was warmed to 0° C., stirred at that temperature for 0.5 h, then re-cooled to −78° C. 3-chloro-6-phenylpyridazine (2.5 g, 13114 μmol) was dissolved in a separate pot in warm THF (~20 mL) and was added via syringe quickly and in portions to avoid precipitation. The mixture became dark red upon addition, and was stirred for 0.5 h at −78° C. Carbon dioxide (s) was added to a separate pot fitted with a drying tube and was connected to the reaction mixture via additional tubing. After exposure to carbon dioxide (g), the reaction mixture was stirred at −78° C. for 10 min. The reaction was quenched by addition of 25 mL 25% conc. HCl/THF and was allowed to warm to RT. The mixture was diluted with DCM and washed with water. The organic portion was washed with 1 M NaHCO$_3$ twice. The aqueous portion was carefully acidified with conc. HCl upon which the product crashed out. The solid was filtered, washed with water and dried to provide 3-chloro-6-phenylpyridazine-4-carboxylic acid. MS m/z=235 [M+H]$^+$. Calc'd for $C_{11}H_7ClN_2O_2$: 234.64.

The invention further provides methods for making compounds of Formulas I-III. For example, and in one embodiment, there is provided a method of making a compound of Formula I, the method comprising the step of reacting compound of Formula A

A

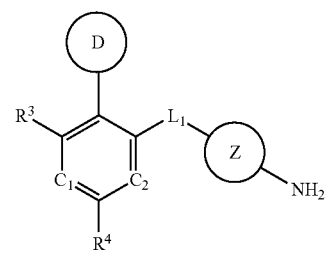

with a compound of Formula B

B

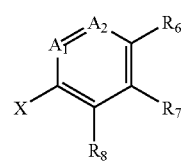

wherein $C^1$, $C^2$, D, $L^1$, Z and $R^{34}$ of compound of formula A and $A^1$, $A^2$ and $R^{6-8}$ of compound of formula B are as defined herein, and X is a halogen, to make a compound of Formula I. This method may also be used to make a compound of Formulas II and III.

While the examples described above provide processes for synthesizing compounds of Formulas I-III, other methods may be utilized to prepare such compounds. In the procedures described herein, the steps may be performed in an alternate order and may be preceded, or followed, by additional protection/deprotection steps as necessary.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Those of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosauren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

The procedures may further use appropriate reaction conditions, including inert solvents, additional reagents, such as bases (e.g., LDA, DWEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

All synthetic procedures described herein can be carried out either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further includes salt forms of compounds of Formulas I, II and III. Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

The invention further encompasses pro-drugs of compounds of Formulas I, II and III. For example, a phosphate group may be a pro-drug derivative of an alcohol group or an amine group, or an ester may be a pro-drug of a carboxylic acid functional group. See Example 476 herein for preparation of a phosphate group. Phosphate groups may be incorporated into desired compounds of Formulas I, II and III in order to improve upon in-vivo bioavailability and/or other pharmacokinetic or pharmacodynamic properties of the compound.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with chiral reagents, such as an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The synthetic chemistry transformations, as well as protecting group methodologies (protection and deprotection) described above and useful in synthesizing the inhibitor compounds described herein, are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Biological Evaluation

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention. Briefly, representative compounds of the invention were found to inhibit the activity of Aurora kinase selectively or non-selectively, at doses less than 25 µM. This activity demonstrates the utility of the compounds in the prophylaxis and treatment of cellular proliferative disorders, including cancer as described herein.

Aurora Kinase HTRF Assays

AuroraA-TPX2-Homogeneous Time Resolved Fluorescent (HTRF) Kinase Assay

The Aurora-A HTRF assay begins with Aurora-A in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The Aurora-A HTRF assay comprises 1 µL of compound in 100% DMSO, 20 µL of ATP and biotinylated PLK, and 20 µL of AuroraA-TPX2 KD GST for a final volume of 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

The following exemplary compounds 42-45, 48-58, 60-64, 67, 68, 70-84, 87-152, 155-162, 164-214 and 216-238 exhibited an average inhibitory activity of less than 10 μM ($IC_{50}$) in the Aurora kinase A HTRF assay. The following exemplary compounds 43-45, 48-52, 54-58, 60, 61, 63-64, 67, 68, 70-84, 87-90, 92-108, 110-120, 122-123, 125143, 145-152, 155-156, 158-162, 164-191, 193-214, 216-229, 231-233 and 235-238 exhibited an average inhibitory activity of less than 500 nM ($IC_{50}$) in the Aurora kinase A HTRF assay. Many of these Examples exhibited an average inhibitory activity of less than 100 nM ($IC_{50}$) in the Aurora kinase A HTRF assay. Examples Method F, 242-244, 468 and 469 each exhibited an average activity in the Aurora kinase A HTRF assay of less than or equal to 100 nM. Method E, Examples 241, 245 and 470 exhibited an average activity in the Aurora kinase A HTRF assay of less than or equal to 1.0 uM. Selected Examples 246-460 exhibited an average activity in the Aurora kinase A HTRF assay as follows:

"+" represents an activity ($IC_{50}$) in the range of 2.5 uM -500 nM;
"++" represents an activity ($IC_{50}$) in the range of 500-100 nM; and
"+++" represents an activity ($IC_{50}$) of less than or equal to 100 nM.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quentched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 μL of compound in 100% DMSO, 20 μL of ATP and biotinylated Histone H3, and 20 μL of AuroraB FL His for a final volume of 41 μL. The final concentration of Histone H3 is 0.1 μM. The final concentration of ATP is 23 μM (Km(app)=23 μM+/−2.6) and the final concentration of AuroraB is 400 pM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-His H3) at a final conc of 0.064 nM.

The assay plate is read in either a Discovery or a RubyStar. The eu-anti-His H3 is excited at 320 nm and emits at 615 nm to excite the SA-APC which in turn emits at 655 nm. The ratio of SA-APC at 655 nm (excited due to close proximity to the Eu-anti-H is H3 because of phosphorylation of the peptide) to free Eu-anti-His H3 at 615 nm will give substrate phosphorylation.

The following exemplary compounds 42-58, 60-65, 67-84 87-152, 155-162, 164-214 and 216-238 exhibited inhibitory activity of less than 10 μM ($K_i$) in the Aurora kinase B HTRF assay. The following exemplary compounds 42-52, 54-58, 60-61, 63-65, 67-84 87-152, 155-162, 164-214, 216-236 and 238 exhibited inhibitory activity of less than 500 nM ($IC_{50}$) in the Aurora kinase B HTRF assay. A vast majority of these Examples exhibited an average inhibitory activity of less than 200 nM ($IC_{50}$) in the Aurora kinase B HTRF assay. Examples Method F, 242-244, 468 and 469 each exhibited an average activity in the Aurora kinase B HTRF assay of less than or equal to 100 nM. Method E, Examples 241, 245 and 470 exhibited an average activity in the Aurora kinase B HTRF assay of less than or equal to 1.0 uM. Selected Examples 246-460 exhibited an average activity in the Aurora kinase B HTRF assay as follows:

"+" represents an activity ($IC_{50}$) in the range of 2.5 uM -500 nM;
"++" represents an activity ($IC_{50}$) in the range of 500-100 nM; and
"+++" represents an activity ($IC_{50}$) of less than or equal to 100 nM.

Aurora Kinase Cell-based Assays

HeLa Cell 1-hour Phospho-histone Assay

The purpose of this assay is to test the inhibitory effect of Aurora compounds with respect to phosphorylation of Histone H3 in the cellular context. HeLa cells ($9 \times 10^4$/well) are plated in black 96-well flat-bottom tissue culture plates and incubated for 40 hours prior to compound addition. Compounds are serially diluted in DMSO, followed by dilution into MEM containing 10 mM HEPES; 10 ul/well of diluted compounds are added to cells (0.5% DMSO final). Cells are incubated for 1 hour at 37° C. in 5% $CO_2$. Cells are then fixed with 3.7% formaldehyde for 10 minutes, washed with wash buffer (1% goat serum and 0.1% Tween 20 in PBS), then permeabilized with 0.5% Triton X in PBS for 15 minutes. After washing with wash buffer, cells are incubated with primary antibody (Upstate #06-507 anti-phospho-histone (Ser 10) antibody (pHH3) for 1 hour at 10 ug/ml. After 2 washes with wash buffer, cells are incubated with secondary antibody (Molecular Probes #A11034 goat anti-rabbit Alexa-488 for 1 hour at 1 ug/ml+Hoechst 33342 nuclear dye at 1 ug/ml (Molecular Probes). Cells are washed 2 times with wash buffer, and buffer replaced with PBS. Plates are scanned on the Cellomics Array Scan (6 fields, ~2000 cells/well) and % of cells that are pHH3 positive were calculated using the Cellomics algorithm. The following exemplary compounds 42-45, 48-52, 54-58, 60-65, 67-76, 78-84, 87-108, 111-120, 122, 123, 125-137, 140-143, 145-148, 150-156, 158-162, 164-168, 170-214, 216-233 and 235-238 exhibited inhibitory activity of less than 10 μM ($EC_{50}$) in the phospho-histone H3 assay. The following exemplary compounds 42-45, 49-52, 54-58, 60-61, 63-64, 67-68, 70-76, 78-84, 87-88, 90, 92, 94-101, 105, 107, 108, 111-117, 119, 120, 122, 123, 125-128, 130-132, 134-137, 140-143, 147-148, 150-151, 153-156, 158-159, 161-162, 164-168, 170-171, 173-176, 178-188, 190-191, 193-214, 216-228, 232-233, 235-236 and 238 exhibited inhibitory activity of less than 1 μM ($EC_{50}$) in the phospho-histone H3 assay. Many of these Examples exhibited inhibitory activity of less than 500 nM ($EC_{50}$) in the phospho-histone H3 assay Selected Examples 246-460 exhibited an average activity in the phospho-histone H3 assay as follows:

"+" represents an activity ($IC_{50}$) in the range of 2.5 uM-500 nM;

"++" represents an activity ($IC_{50}$) in the range of 500-100 nM; and

"+++" represents an activity ($IC_{50}$) of less than or equal to 100 nM.

Indications

The compounds of the invention have Aurora kinase modulatory activity in general, and inhibitory activity in particular. In one embodiment of the invention, there is provided a method of modulating Aurora kinase enzyme in a subject, the method comprising administering to the subject an effective dosage amount of a compound of a compound of Formulas I-III. As such, the compounds of the invention may be used to treat cellular proliferation disorders, including uncontrolled cell growth and aberrant cell cycle regulation. The compounds are also useful for treating disorders related to hyperproliferation of cells in normal tissue, including without limitation, non-tumor bearing and metastatic tissue. For example, one use may be to protect normal hair follicles from chemotherapy induced alopecia.

In addition, compounds of the invention are useful for, but not limited to, the prevention or treatment of cancer and other Aurora kinase-mediated diseases or disorders. For example, compounds of the invention would be useful for the treatment of various solid and hematologically derived tumors, such as carcinomas, including, without limitation, cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compound of the invention may also be used to treat chemotherapy-induced thrombocytopenia, since the compounds may increase platelet count be increasing the rate of megakaryocyte maturation.

The compounds would also be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the invention are also useful in the treatment of cardiovascular conditions such as atherosclerosis, restenosis, arteriosclerosis, vascular occlusion and carotid obstructive disease.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions, also referred to as medicaments, comprising the active compounds of Formulas I-III in association with one or more non-toxic, pharmaceutically-acceptable carriers and/or diluents and/or adjuvants (collectively referred to herein as "carrier" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy or with neoplastic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

Alternatively, the compounds of the invention may also be used in co-therapies with other anti-neoplastic agents, such as other kinase inhibitors including angiogenic agents such as VEGFR inhibitors, p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID'S, SOD mimics or $\alpha_v\beta_3$ inhibitors.

The foregoing is merely illustrative of the invention and is not intended to limit the invention to the disclosed compounds. Variations and changes, which are obvious to one skilled in the art, are intended to be within the scope and nature of the invention, which are defined in the appended claims. All mentioned references, patents, applications and publications, are hereby incorporated by reference in their entirety, as if here written.

What is claimed is:

1. A compound of Formula I:

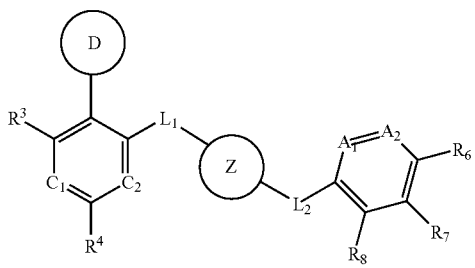

or a stereoisomer or pharmaceutically acceptable salt thereof, wherein
- each of $A^1$ and $A^2$, independently, is N or $CR^9$, provided that at least one of $A^1$ and $A^2$ is N;
- either $C^1$ is $CR^{10}$ and $C^2$ is N or $C^1$ is N and $C^2$ is CH;
- ring D is

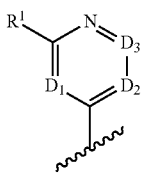

wherein $D^1$ is N or $CR^{11}$;
$D^2$ is N or $CR^{12}$;
$D^3$ is N or $CR^2$;
$R^1$ is H, $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$, wherein n is 0, 1, 2, 3 or 4;
$R^{1a}$ is H, CN or $C_{1-10}$alkyl;
alternatively $R^1$ taken together with either of $R^{11}$ and $R^{1a}$ and the carbon or nitrogen atoms to which they are attached form a partially or fully unsaturated 5- or 6-membered ring of carbon atoms optionally including 1-3 heteroatoms selected from O, N and S, and the ring optionally substituted independently with 1-3 substituents of oxo, $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$; and
$R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;
$L^1$ is $NR^3$, O, S, C(O), S(O), $SO_2$ or $CR^3R^3$;
$L^2$ is $NR^3$, O or S;
Z is phenyl, pyridyl, pyrimidinyl, pyridazinyl, pyazinyl, triazinyl, thienyl, furyl, pyrrolyl, pyrazolyl, imidazolyl, triazolyl, tetrazolyl, thiazolyl, thiadiazolyl, oxazolyl, oxadiazolyl, isoxazolyl, or isothiazolyl, each ring of which is optionally substituted independently with 1-5 substituents of $R^{15}$;
each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;
alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;
each $R^5$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;
each of $R^6$, $R^7$ and $R^8$, independently, is $R^{13}$, $R^{14}$ or $R^{15}$;
alternatively, either of $R^6$ or $R^8$, independently, taken together with $R^7$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;
each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;
$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2NR^{14}R^{15}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;
$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of $R^{15}$; and
$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

provided that (1) no more than one of $D^1$, $D^2$ and $D^3$ is N.

2. The compound of claim 1, or a stereoisomer or pharmaceutically acceptable salt thereof, wherein D is

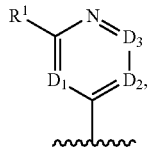

wherein $D^1$ is N, $D^2$ is $CR^{12}$ and $D^3$ is CH.

3. The compound of claim 1, or a stereoisomer or pharmaceutically acceptable salt thereof, wherein D is

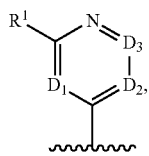

wherein $D^1$ is $CR^{11}$, $D^2$ is N and $D^3$ is CH.

4. The compound of claim 1, or a stereoisomer or pharmaceutically acceptable salt thereof, wherein
   $C^1$ is $CR^{10}$ and $R^{10}$ is H, halo, haloalkyl, haloalkoxyl, CN, OH, SH, $NO_2$, $NH_2$, acetyl, $C_{1-10}$-alkyl or $C_{1-10}$-alkoxyl;
   $C^2$ is N; and
   $R^2$ is H, halo, $NO_2$, CN, $C_{1-10}$alkyl or $C_{1-10}$alkoxyl.

5. The compound of claim 1, or a stereoisomer or pharmaceutically acceptable salt thereof, wherein
   $L^1$ is $NR^{15}$, O, $CHR^{15}$, S, C(O), S(O) or $SO_2$; and
   $R^2$ is H, halo, $NO_2$, CN, $C_{1-10}$alkyl or $C_{1-10}$alkoxyl.

6. The compound of claim 5, or a stereoisomer or pharmaceutically acceptable salt thereof, wherein
   $L^2$ is $NR^{15}$, O or S;
   each of $R^3$, $R^4$ and $R^9$, independently, is H; and
   $C^1$ is $CR^{10}$ and $C^2$ is N.

7. The compound of claim 6, or a stereoisomer or pharmaceutically acceptable salt thereof, wherein $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$.

8. The compound of claim 6, or a stereoisomer or pharmaceutically acceptable salt thereof, wherein
   each of $A^1$ and $A^2$, independently, is N; and
   $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thienyl, furyl, tetrahydrofuranyl, pyrrolyl, pyrazolyl, thienopyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of $R^{15}$.

9. A compound of claim 1 having a Formula II:

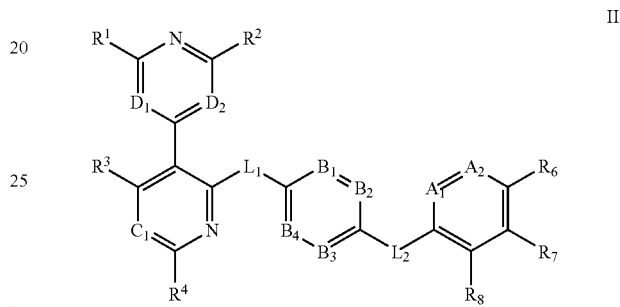

II or a stereoisomer or pharmaceutically acceptable salt thereof, wherein
   each of $A^1$ and $A^2$, independently, is N or $CR^9$, provided that at least one of $A^1$ and $A^2$ is N;
   each of $B^1$, $B^2$, $B^3$ and $B^4$, independently, is N or $CR^5$, provided that no more than two of $B^1$, $B^2$, $B^3$ and $B^4$ is N;
   $C^1$ is $CR^{10}$;
   $D^1$ is N or $CR^{11}$;
   $D^2$ is N or $CR^{12}$;
   $L^1$ is $NR^3$, O, S or $CR^3R^3$;
   $L^2$ is $NR^3$, O or S;
   $R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$;
   alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of oxo, $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$;
   $R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;
   each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;
   alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^6$ is $R^{13}$ or $R^{14}$;

each of $R^7$ and $R^8$, independently, is $R^{13}$, $R^{14}$ or $R^{15}$;

alternatively, $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of $R^{15}$;

$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 0, 1, 2, 3 or 4;

provided that no more than one of $D^1$ and $D^2$ is N.

10. The compound of claim 9, or a stereoisomer or pharmaceutically acceptable salt thereof, wherein each of $A^1$ and $A^2$, independently, is N;

each of $B^1$, $B^2$, $B^3$ and $B^4$, independently, is N or $CR^5$, provided that no more than one of $B^1$, $B^2$, $B^3$ and $B^4$ is N;

$C^1$ is $CR^{10}$;

$D^1$ is N or $CR^{11}$;

$D^2$ is N or $CR^{12}$;

$L^1$ is NH, O or S;

$L^2$ is NH, O or S; provided that both of $L^1$ and $L^2$ are not either O or S;

$R^1$ is H, halo, haloalkyl, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$alkoxyl, $C_{1-10}$, $NHR^{14}$, $NHR^{15}$, $OR^{15}$, $SR^{15}$ or $CH_2R^{15}$;

$R^2$ is H, halo, $NO_2$, CN, $C_{1-10}$alkyl or $C_{1-10}$alkoxyl;

each of $R^3$ and $R^4$, independently, is $SR^{15}$, $OR^{15}$, $NR^{14}R^{15}$, $NR^{15}R^{15}$, $C(O)R^{14}$, $C(O)R^{15}$ or $R^{15}$;

each $R^5$ is, independently, is $SR^{15}$, $OR^{15}$, $NR^{15}R^{15}$, $C(O)R^{15}$, $C(O)NR^{15}R^{15}$, $NR^{15}C(O)R^{15}$, $NR^{15}C(O)NR^{15}R^{15}$, $NR^{15}(COOR^{15})$, $S(O)_2R^{15}$, $S(O)_2NR^{15}$, $R^{15}NR^{15}S(O)_2NR^{15}R^{15}$, $NR^{15}S(O)_2R^{15}$, $NR15C(O)C(O)NR^{14}R^{15}$ or $R^{15}$;

$R^6$ is $R^{14}$;

each of $R^7$ and $R^8$, independently, is $R^{15}$;

alternatively, $R^7$ and $R^8$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$ or $R^{15}$; and each of $R^9$, $R^{10}$, $R^{11}$ and $R^{12}$, independently, is $R^{15}$.

11. The compound of claim 9 or a stereoisomer or pharmaceutically acceptable salt thereof, wherein, $R^1$ is $NR^{14}R^{15}$, $NR^{15}R^{15}$, $(CHR^{15})_nR^{14}$, $(CHR^{15})_nR^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of $R^{15}$;

$R^2$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

each of $R^3$ and $R^4$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

each $R^5$ is, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino;

$R^6$ is $R^{13}$ or $R^{14}$;

each of $R^7$ and $R^8$, independently, is $R^{15}$;

alternatively, $R^7$ and $R^8$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$; and each of $R^9$, $R^{10}$, $R^{11}$ and $R^{12}$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino.

12. The compound of claim 11 or a stereoisomer or pharmaceutically acceptable salt thereof, wherein,
each of $A^1$ and $A^2$, independently, is N; and
$R^7$ and $R^8$ taken together with the carbon atoms to which they are attached form a fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$.

13. The compound of claim 12 or a stereoisomer or pharmaceutically acceptable salt thereof, wherein $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thienyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of $R^{15}$.

14. The compound of claim 9, or a stereoisomer or pharmaceutically acceptable salt thereof, wherein,
$C^1$ is CH;
$D^1$ is N;
$D^2$ is $CR^{12}$ wherein $R^{12}$ is H, halo, $NO_2$, CN, $C_{1-10}$alkyl or $C_{1-10}$alkoxyl;
$L^1$ is NH, O or S;
$L^2$ is NH;
$R^1$ is H, halo, haloalkyl, acetyl, $C_{1-10}$-alkyl or $NHR^{15}$;
each of $R^2$, $R^3$ and $R^4$, independently, is H, halo, $C_{1-10}$alkyl or $C_{1-10}$alkoxyl;
$R^6$ is $R^{14}$; and
$R^7$ and $R^8$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$ or $R^{15}$.

15. A compound of Formula III:

III or a stereoisomer or pharmaceutically acceptable salt thereof, wherein
each of $A^1$ and $A^2$, independently, is N or $CR^9$, provided that at least one of $A^1$ and $A^2$ is N;
each of $B^1$, $B^2$, $B^3$ and $B^4$, independently, is N or $CR^5$, provided that no more than two of $B^1$, $B^2$, $B^3$ and $B^4$ is N;
$C^1$ is $CR^{10}$;
$L^1$ is O, S, C(O), S(O), $SO_2$ or $CR^3R^3$;
$L^2$ is $NR^3$, O or S;
$R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$;
alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-3 substituents of $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$;
$R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;
each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;
alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;
each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, OC(O) $R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;
$R^6$ is $R^{13}$ or $R^{14}$;
each of $R^7$ and $R^8$, independently, is $R^{13}$, $R^{14}$ or $R^{15}$;
alternatively, $R^7$ and $R^8$ taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;
each of $R^9$, $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;
$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

R$^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of R$^{15}$;

R$^{15}$ is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 0, 1, 2, 3 or 4.

16. The compound of claim 1, or a pharmaceutically acceptable salt thereof, selected from:

2-(4-(4-((4-((3-(2-amino-4-pyrimidinyl)-2-pyridinyl)oxy)phenyl)amino)1-phthalazinyl) phenyl)ethanol;

N-(5-((3-(2-(methylamino)-4-pyrimidinyl)-2-pyridinyl)oxy)-2-pyridinyl)-4-phenyl-1-phthalazinamine;

N-(4-((3-(2-amino-4-pyrimidinyl)-2-pyridinyl)oxy)phenyl)-4-phenylfuro[2,3-d]pyridazin-7-amine;

N-(4-((3-(2-amino-4-pyrimidinyl)-2-pyridinyl)oxy)phenyl)-4-(2,6-bis(methyloxy)phenyl)-1-phthalazinamine;

(1R)-1-(4-(4-((4-((3-(2-amino-4-pyrimidinyl)-2-pyridinyl)oxy)phenyl)amino)-1- phthalazinyl) phenyl)ethanol;

N-(4-((3-(2-amino-4-pyrimidinyl)-2-pyridinyl)oxy)phenyl)-4,5-dimethyl-6-(4-methyl-2-thienyl)-3-pyridazinamine;

N-(4-((3-(2-amino-4-pyrimidinyl)-2-pyridinyl)oxy)phenyl)-4-phenyl-1-isoquinolinamine;

N-(4-((3-(2-amino-4-pyrimidinyl)-2-pyridinyl)oxy)phenyl)-4-(4-methyl-2-thienyl)-1-isoquinolinamine;

4-phenyl-N-(6-((3-(2-((3-(1-piperidinyl)propyl)amino)-4-pyrimidinyl)-2-pyridinyl)oxy)-3-pyridinyl)1-phthalazinamine;

N-(4-((3-(2-amino-4-pyrimidinyl)-2-pyridinyl)oxy)phenyl)-4-cyclohexyl-1-phthalazinamine;

N-(4-((3-(2-((3-(4-methyl-1-piperazinyl)propyl)amino)-4-pyrimidinyl)-2-pyridinyl)oxy)phenyl)-4-(6-methyl-2-pyridinyl)-1-phthalazinamine;

4-(6-methyl-2-pyridinyl)-N-(4-((3-(2-((3-(1-piperazinyl)propyl)amino)-4-pyrimidinyl)-2-pyridinyl)oxy)phenyl)-1-phthalazinamine;

N-(4((3-(2-amino-4-pyrimidinyl)-2-pyridinyl)oxy)phenyl)-4-(3-fluoro-1-piperidinyl)-1-phthalazinamine;

4-(2-((4-((4-phenyl-1-phthalazinyl)amino)phenyl)oxy)-3-pyridinyl)-1,3-dihydro-2H-pyrrolo[2,3-b]pyridin-2-one;

4-(4-methyl-1,3-thiazol-2-yl)-N-(4-((3-(5,6,7,8-tetrahydro-1,8-naphthyridin-4-yl)-2-pyridinyl) oxy)phenyl)-1-phthalazinamine;

N-(4-((3-(2,3-dihydro-1H-pyrrolo[2,3-b]pyridin-4-yl)-2-pyridinyl)oxy)phenyl)-4-phenyl-1-phthalazinamine;

N-(6((3-(2-amino-4-pyrimidinyl)-2-pyridinyl)oxy)-3-pyridinyl)-4-(5-methyl-2-pyridinyl)-1-phthalazinamine;

N-(4-((3-(5-fluoro-2-((3-(4-methyl-1-piperazinyl)propyl)amino)-4-pyrimidinyl)-2-pyridinyl) oxy)phenyl)-4-phenyl-1-phthalazinamine;

N-(6((3-(2-amino-4-pyrimidinyl)-2-pyridinyl)oxy)-3-pyridinyl)-4-(3-(methylsulfonyl)phenyl)-1-phthalazinamine;

N-(4-((3-(2-((3-((2S,5S)-2,5-dimethyl-4-morpholinyl)propyl)amino)-4-pyrimidinyl)-2-pyridinyl) oxy)phenyl)-4-phenyl-1-phthalazinamine;

N-(6-((3-(2-amino-4-pyrimidinyl)-2-pyridinyl)oxy)-3-pyridinyl)-4-(4-methyl-2-thienyl)-1-phthalazinamine;

1-(4-((4-((3-(2-amino-4-pyrimidinyl)-2-pyridinyl)oxy)phenyl)amino)-1-phthalazinyl)-3- piperidinol;

2-(4-((6-((3-(2-amino-4-pyrimidinyl)-2-pyridinyl)oxy)-3-pyridinyl)amino)1- phthalazinyl) phenol;

2-(4-((6-((3-(2-amino-4-pyrimidinyl)-2-pyridinyl)oxy)-3-pyridinyl)amino)1-phthalazinyl)phenyl dihydrogen phosphate;

2-((4-((4-(4-methyl-2-thienyl)-1-phthalazinyl)amino)phenyl)oxy)-3,4'-bipyridin-2'-amine;

2-((4-((4-ethyl-6-phenyl-3-pyridazinyl)amino)phenyl)oxy)-3,4'-bipyridin-2'-amine;

2-((4-((4-methyl-6-(4-methyl-1,3-thiazol-2-yl)-3-pyridazinyl)amino)phenyl)oxy)-3,4'-bipyridin-2'-amine;

2-((4-((4-(2-(methyloxy)phenyl)-1-phthalazinyl)amino)phenyl)oxy)-3,4'-bipyridin-2'-amine;

N-(4-((3-(2-amino-4-pyrimidinyl)-2-pyridinyl)oxy)phenyl)-6-phenyl-4-propyl-3-pyridazinamine;

N-(4-((3-(2-amino-4-pyrimidinyl)-2-pyridinyl)oxy)phenyl)-4-(3-methyl-5-isothiazolyl)-1-phthalazinamine;

N-(4-((3-(2-amino-4-pyrimidinyl)-2-pyridinyl)oxy)phenyl)-4-(6-methyl-2-pyridinyl)-1-phthalazinamine;

N-(4-((3-(2-amino-4-pyrimidinyl)-2-pyridinyl)oxy)phenyl)-4-(4-methyl-2-thienyl)-1-phthalazinamine;

N-(4-((3-(2-amino-4-pyrimidinyl)-2-pyridinyl)oxy)phenyl)-4-(5-methyl-2-pyridinyl)-1-phthalazinamine; and N-(4-((3-(2-amino-4-pyrimidinyl)-2-pyridinyl)oxy)phenyl)-4-(3-methyl-1H-pyrazol-1-yl)-1-phthalazinamine.

17. A pharmaceutical composition comprising a pharmaceutically acceptable carrier and a dose effective amount of the compound of claim 9.

18. A pharmaceutical composition comprising a pharmaceutically acceptable carrier and a dose effective amount of a compound of claim 16.

19. A method of treating breast cancer, colon cancer, kidney cancer, liver cancer, non-small cell lung cancer, esophagus cancer, gall-bladder cancer, ovarian cancer, pancreatic cancer, stomach cancer, cervical cancer, thyroid cancer, prostate cancer, skin cancer or a combination thereof in a subject, the method comprising administering to the subject a dose effective amount of a compound selected from N-(4-((3-(2-amino-4-pyrimidinyl)-2-pyridinyl)oxy)phenyl)-4-(3-methyl-5-isothiazolyl)1-phthalazinamine, N-(4-((3-(2-amino-4-pyrimidinyl)-2-pyridinyl)oxy)phenyl)-4-(6-methyl-2-pyridinyl)1-phthalazinamine, N-(4-((3-(2-amino-4-pyrimidinyl)-2-pyridinyl)oxy)phenyl)-4-(4-methyl-2-thienyl)1-phthalazinamine, N-(4-((3-(2-amino-4- pyrimidinyl)-2-pyridinyl)oxy)phenyl)-4-(5-methyl-2-pyridinyl)1-phthalazinamine and N-(4-((3-(2-amino-4-pyrimidinyl)-2-pyridinyl)oxy)phenyl)-4-(3-methyl-1H-pyrazol-1-yl)-1-phthalazinamine, or a pharmaceutically acceptable salt thereof.

20. A method of making a compound of Formula I of claim 1, the method comprising the step of reacting compound of Formula A

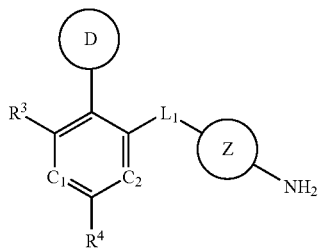

with a compound of Formula B

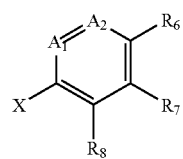

wherein $C^1$, $C^2$, D, $L^1$, Z and $R^{3-4}$ of compound of formula A and $A^1$, $A^2$ and $R^{6-8}$ of compound of formula B are as defined in claim 1, and X is a halogen, to make a compound of Formula I.

21. The compound of claim 9 having a Formula II

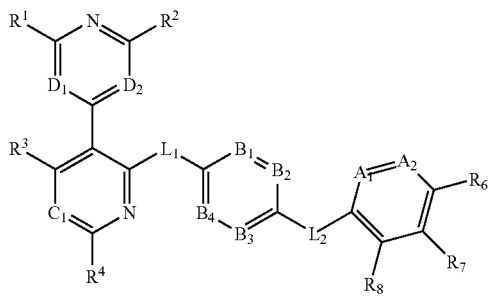

or a stereoisomer or pharmaceutically acceptable salt thereof, wherein
each of $A^1$ and $A^2$, independently, is N;
each of $B^1$, $B^2$, $B^3$ and $B^4$, independently, is $CR^5$, wherein each $R^5$, independently, is H, halo, haloalkyl, haloalkoxyl, CN, OH, SH, $NO_2$, $NH_2$, acetyl, $C_{1-4}$-alkyl, $C_{1-4}$-alkylamino-, $C_{1-4}$-alkoxyl or $C_{1-4}$-thioalkoxyl;
$C^1$ is CH;
$D^1$ is N;
$D^2$ is $CR^{12}$, wherein $R^{12}$ is H, F, CN, $CH_3$ or $-OCH_3$;
$L^1$ is O or S;
$L^2$ is $NR^{15}$, wherein $R^{15}$ is H or $CH_3$;
$R^1$ is $R^{15}$ wherein $R^{15}$ is $NH_2$, $C_{1-10}$alkylamino or $C_{1-10}$dialkylamino-;
$R^2$ is H;
each of $R^3$ and $R^4$, independently, is H;

$R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thienyl, furyl, tetrahydrofuranyl, pyrrolyl, pyrazolyl, thienopyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl or pyranyl, each of which is optionally substituted independently with 1-5 substituents of $R^{15}$;
$R^7$ and $R^8$ taken together with the carbon atoms to which they are attached form a phenyl, pyridine or pryimidine ring, the ring optionally substituted independently with 1-4 substituents of $R^{13}$, $R^{14}$ or $R^{15}$;
$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;
$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of $R^{15}$; and
$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl.

22. The compound of claim 21, or a stereoisomer or pharmaceutically acceptable salt thereof, wherein
each $R^5$, independently, is H, Cl, F, Br, I, $CF_3$, $CF_2CF_3$, $-OCF_3$, CN, OH, SH, $NO_2$, $NH_2$, $CH_3$, $CH_2CH_3$ or acetyl;
$D^2$ is $CR^{12}$, wherein $R^{12}$ is H;
$L^1$ is O;
$L^2$ is NH;
$R^1$ is $R^{15}$ wherein $R^{15}$ is $-NH_2$ or $-NHCH_3$;

R[6] is phenyl, pyridyl, pyrimidinyl, thienyl, furyl, tetrahydrofuranyl, pyrrolyl, pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, isothiazolinyl, pyrazolinyl, morpholinyl, piperidinyl, piperazinyl, cyclopropyl, cyclobutyl, azetidinyl, cyclopentyl, cyclohexyl, cycloheptyl or pyranyl, each of which is optionally substituted independently with 1-5 substituents of R[15];

R[7] and R[8] taken together with the carbon atoms to which they are attached form a phenyl optionally substituted independently with 1-4 substituents of R[13], R[14] or R[15];

R[13] is SR[14], OR[14], SR[15], OR[15], NR[14]R[15], NR[15]R[15], C(O)R[14], C(O)R[15], OC(O)R[14], OC(O)R[15], COOR[14], COOR[15], C(O)NR[14]R[15], C(O)NR[15]R[15], NR[15]C(O)R[14], NR[15]C(O)R[15], C(O)C(O)R[15], NR[15]C(O)NR[14]R[15], NR[15]C(O)NR[15]R[15], NR[15]C(O)C(O)R[15], NR[15](COOR[14]), NR[15](COOR[15]), NR[15]C(O)C(O)NR[14]R[15], NR[15]C(O)C(O)NR[15]R[15], S(O)$_2$R[14], S(O)$_2$R[15], S(O)$_2$NR[14]R[15], S(O)$_2$NR[15]R[15], NR[15]S(O)$_2$R[14], NR[15]S(O)$_2$R[15], NR[15]S(O)$_2$NR[14]R[15] or NR[15]S(O)$_2$NR[15]R[15];

R[14] is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-5 substituents of R[15]; and R[15] is H, halo, haloalkyl, haloalkoxyl, oxo, CN, OH, SH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl.

23. The compound of claim 22, or a stereoisomer or pharmaceutically acceptable salt thereof, wherein
each R[5], independently, is H, Cl, F, CF$_3$, —OCF$_3$, CN, OH, SH or CH$_3$; and
R[6] is phenyl, pyridyl, thiazol-2-yl, isothiazolyl, morpholinyl, piperidinyl, pyrazol-1-yl, imidazol-1-yl, thien-2-yl, thien-3-yl, cyclohexyl, piperazinyl, cyclopropyl, each of which is optionally substituted independently with 1-3 substituents of F, Cl, Br, CH$_3$, C$_2$H$_5$, —OCH$_3$, —CF$_3$, —SCH$_3$, —NHCH$_3$, CN, OH, NH$_2$ or acetyl.

24. The compound of claim 22, or a pharmaceutically acceptable salt thereof, wherein
each R[5], independently, is H; and
R[6] is phenyl, thiazol-2-yl, isothiazolyl, pyrazol-1-yl, imidazol-1-yl, thien-2-yl or thien-3-yl, each of which is optionally substituted independently with 1-3 substituents of F, Cl, Br, CH$_3$, C$_2$H$_5$, —OCH$_3$, —CF$_3$, —SCH$_3$, —NHCH$_3$, CN, OH, NH$_2$ or acetyl.

25. The compound of claim 24, or a pharmaceutically acceptable salt thereof, wherein R[6] is thien-2-yl or thien-3-yl, each of which is optionally substituted independently with 1-3 substituents of F, Cl, Br, CH$_3$, C$_2$H$_5$, —OCH$_3$, —CF$_3$, —SCH$_3$, —NHCH$_3$, CN, OH, NH$_2$ or acetyl.

26. A pharmaceutical composition comprising a pharmaceutically acceptable carrier and a dose effective amount of the compound, or a pharmaceutically acceptable salt thereof, of claim 25.

27. A method of treating breast cancer, colon cancer, kidney cancer, liver cancer, non-small cell lung cancer, esophagus cancer, gall-bladder cancer, ovarian cancer, pancreatic cancer, stomach cancer, cervical cancer, thyroid cancer, prostate cancer, skin cancer or a combination thereof in a subject, the method comprising administering to the subject a dose effective amount of the compound N-(4-((3-(2-amino-4-pyrimidinyl)-2-pyridinyl)oxy)phenyl)-4-(4-methyl-2-thienyl)-1-phthalazinamine, having the chemical structure of

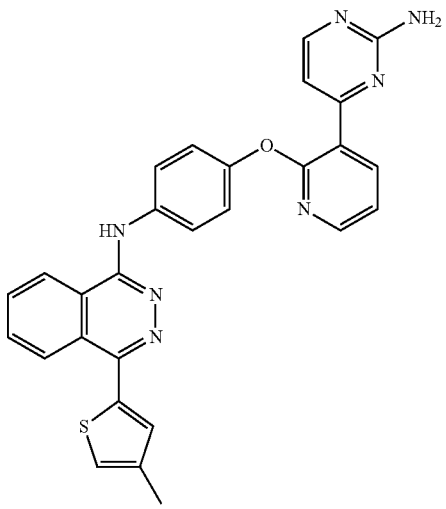

or a pharmaceutically acceptable salt thereof.

28. A method of treating breast cancer in a subject, the method comprising administering to the subject a dose effective amount of the compound having a chemical structure of

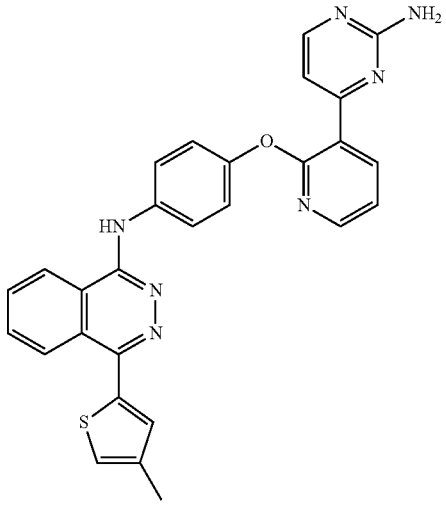

or a pharmaceutically acceptable salt thereof.

* * * * *